US011172939B2

(12) United States Patent
Donner et al.

(10) Patent No.: US 11,172,939 B2
(45) Date of Patent: Nov. 16, 2021

(54) SYSTEMS FOR AND METHODS OF PREPARING A SACROILIAC JOINT FOR FUSION

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 157 days.

(21) Appl. No.: 16/544,193

(22) Filed: Aug. 19, 2019

(65) Prior Publication Data

US 2020/0029979 A1    Jan. 30, 2020

Related U.S. Application Data

(63) Continuation-in-part of application No. 15/785,997, filed on Oct. 17, 2017, now Pat. No. 10,492,802,
(Continued)

(51) Int. Cl.
*A61B 17/88* (2006.01)
*A61B 17/16* (2006.01)
(Continued)

(52) U.S. Cl.
CPC ........ *A61B 17/1659* (2013.01); *A61B 17/144* (2016.11); *A61B 17/149* (2016.11);
(Continued)

(58) Field of Classification Search
CPC . A61B 17/1659; A61B 17/149; A61B 17/144; A61B 17/1604; A61B 17/1735;
(Continued)

(56) References Cited

U.S. PATENT DOCUMENTS

2009/0216238 A1*  8/2009  Stark ............... A61F 2/30988
                                                  606/96
2014/0135927 A1*  5/2014  Pavlov ............. A61B 17/7055
                                                  623/17.11
(Continued)

*Primary Examiner* — Eduardo C Robert
*Assistant Examiner* — David C Comstock
(74) *Attorney, Agent, or Firm* — Polsinelli PC; Joshua J. Pranckun; Samuel Wade Johnson

(57) ABSTRACT

A method of surgically preparing a sacroiliac joint comprising: a) approaching a sacroiliac joint space with a joint preparation tool comprising a cutting element including an exterior having an asymmetric cutting band such that the first side includes a first surface having a first texture and the second side includes a second surface having a second texture, the first and second textures being different such that the first texture is substantially smoother than the second texture; and b) delivering at least a portion of the cutting element non-transversely into the sacroiliac joint space for decortication, the cutting element being oriented in the sacroiliac joint space such that the first surface opposes the generally softer sacrum and the second surface opposes the generally harder ilium in order to more aggressively prepare the surface of the ilium while not over-preparing the sacrum to provide a robust biologic environment for intra-articular fusion.

27 Claims, 90 Drawing Sheets

Related U.S. Application Data which is a continuation-in-part of application No. 14/514,221, filed on Oct. 14, 2014, now Pat. No. 9,826,986, and a continuation-in-part of application No. 14/447,612, filed on Jul. 31, 2014, now Pat. No. 9,700,356, application No. 16/544,193, which is a continuation-in-part of application No. 15/662,045, filed on Jul. 27, 2017, now Pat. No. 10,383,664, which is a continuation-in-part of application No. 14/567,956, filed on Dec. 11, 2014, now Pat. No. 9,717,539, which is a continuation of application No. 14/514,221, filed on Oct. 14, 2014, now Pat. No. 9,826,986, said application No. 14/567,956 is a continuation-in-part of application No. 14/447,612, filed on Jul. 31, 2014, now Pat. No. 9,700,356, application No. 16/544,193, which is a continuation-in-part of application No. 15/418,633, filed on Jan. 27, 2017, now Pat. No. 10,433,880, which is a continuation-in-part of application No. 14/660,784, filed on Mar. 17, 2015, now Pat. No. 10,245,087, and a continuation-in-part of application No. PCT/US2014/030889, filed on Mar. 17, 2014, said application No. 14/660,784 is a continuation of application No. 14/514,221, filed on Oct. 14, 2014, now Pat. No. 9,826,986, and a continuation-in-part of application No. 14/447,612, filed on Jul. 31, 2014, now Pat. No. 9,700,356, and a continuation-in-part of application No. 14/567,956, filed on Dec. 11, 2014, now Pat. No. 9,717,539.

(60) Provisional application No. 61/891,330, filed on Oct. 15, 2013, provisional application No. 61/891,345, filed on Oct. 15, 2013, provisional application No. 61/912,494, filed on Dec. 5, 2013, provisional application No. 61/914,409, filed on Dec. 11, 2013, provisional application No. 61/954,594, filed on Mar. 17, 2014, provisional application No. 61/798,225, filed on Mar. 15, 2013, provisional application No. 61/859,134, filed on Jul. 26, 2013, provisional application No. 61/979,857, filed on Apr. 15, 2014, provisional application No. 61/955,126, filed on Mar. 18, 2014, provisional application No. 61/860,185, filed on Jul. 30, 2013.

(51) Int. Cl.
| | | |
|---|---|---|
| *A61B 17/17* | (2006.01) | |
| *A61B 17/68* | (2006.01) | |
| *A61B 17/14* | (2006.01) | |
| *A61F 2/30* | (2006.01) | |
| *A61B 17/15* | (2006.01) | |
| *A61B 17/92* | (2006.01) | |

(52) U.S. Cl.
CPC ...... *A61B 17/1604* (2013.01); *A61B 17/1735* (2013.01); *A61B 17/1739* (2013.01); *A61B 17/68* (2013.01); *A61B 17/15* (2013.01); *A61B 17/1757* (2013.01); *A61B 2017/922* (2013.01); *A61F 2002/30995* (2013.01)

(58) Field of Classification Search
CPC ..... A61B 17/1739; A61B 17/68; A61B 17/15; A61B 17/1757; A61B 2017/922; A61F 2002/30995
USPC ... 606/279, 80, 82, 83, 84, 85, 86 R, 87, 96, 606/98, 99, 100, 104, 86 A; 623/17.11, 623/18.11
See application file for complete search history.

(56) References Cited

U.S. PATENT DOCUMENTS

| | | | |
|---|---|---|---|
| 2014/0277460 A1* | 9/2014 | Schifano | ............... A61F 2/4455 623/17.11 |
| 2015/0112444 A1* | 4/2015 | Aksu | ..................... A61B 17/68 623/18.11 |

\* cited by examiner

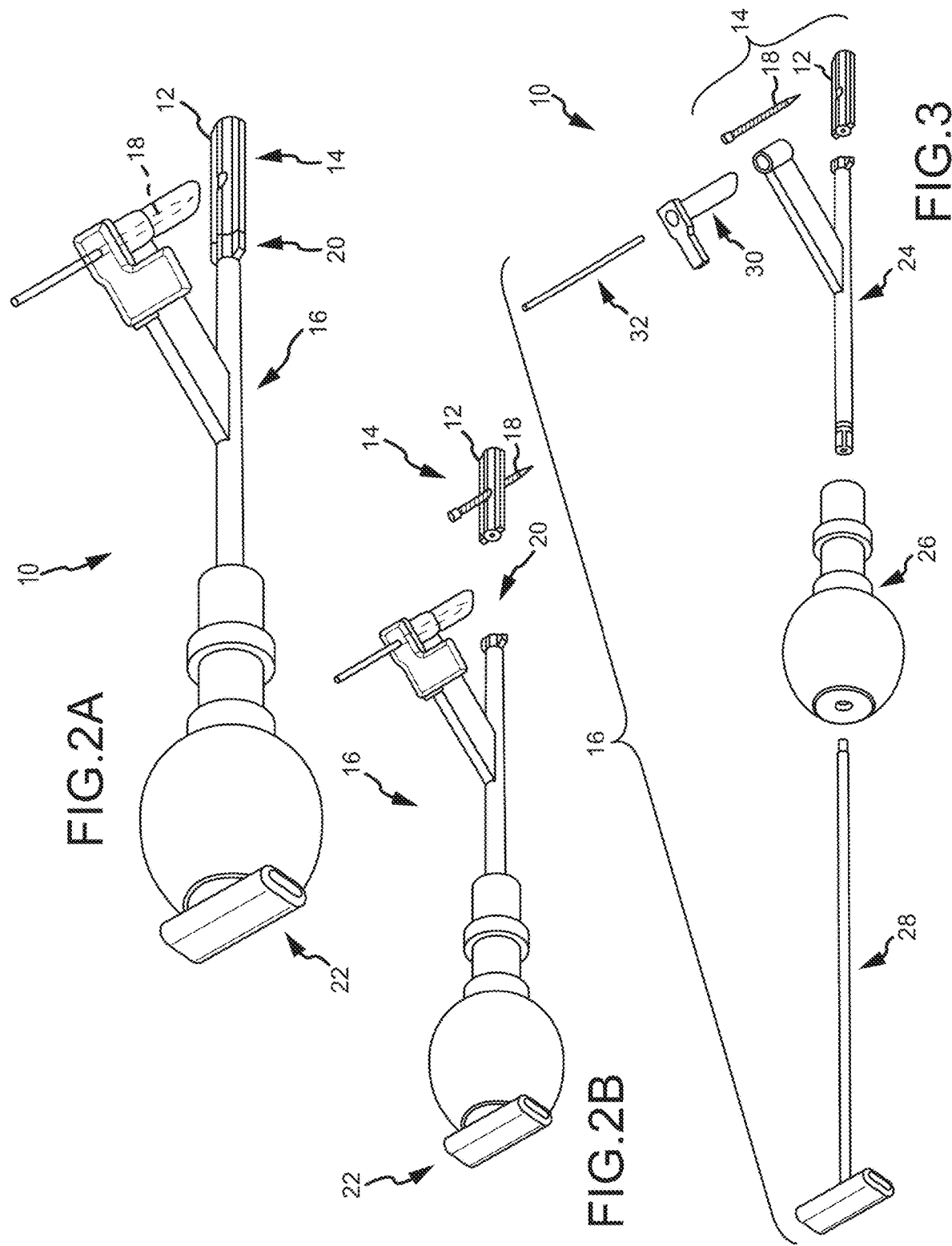

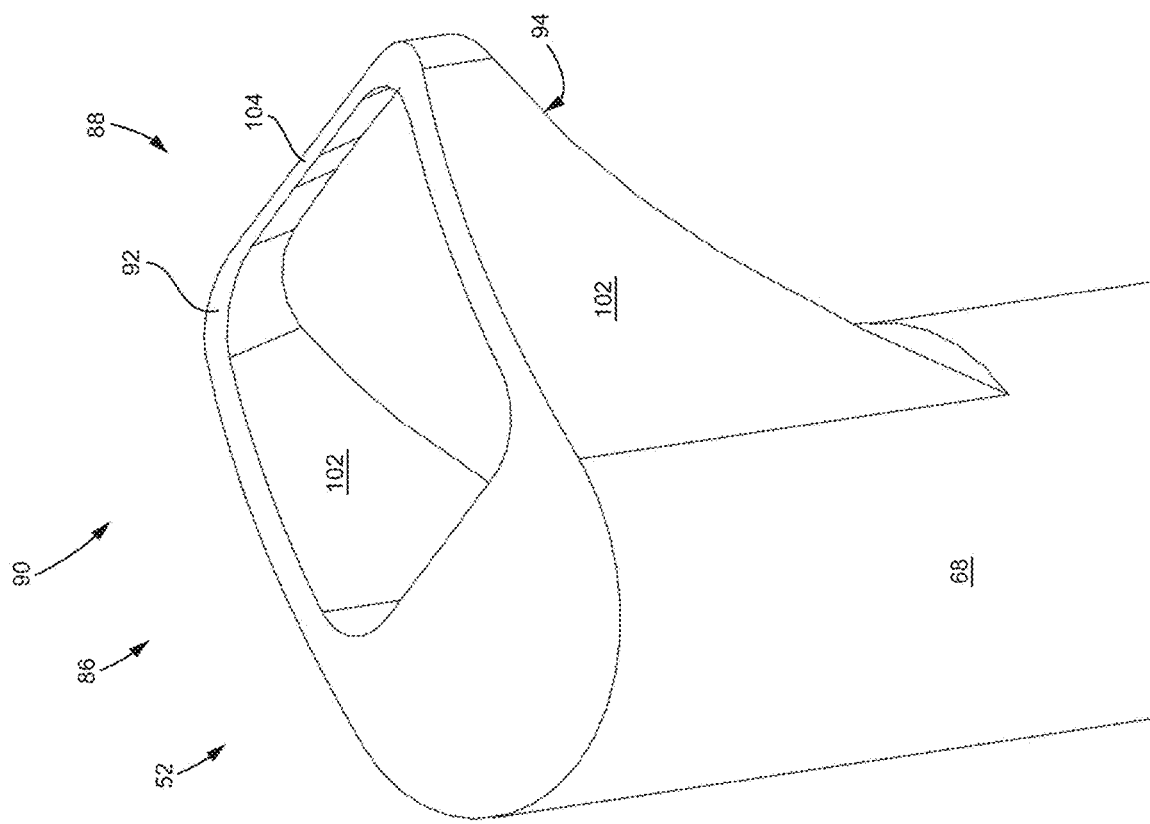
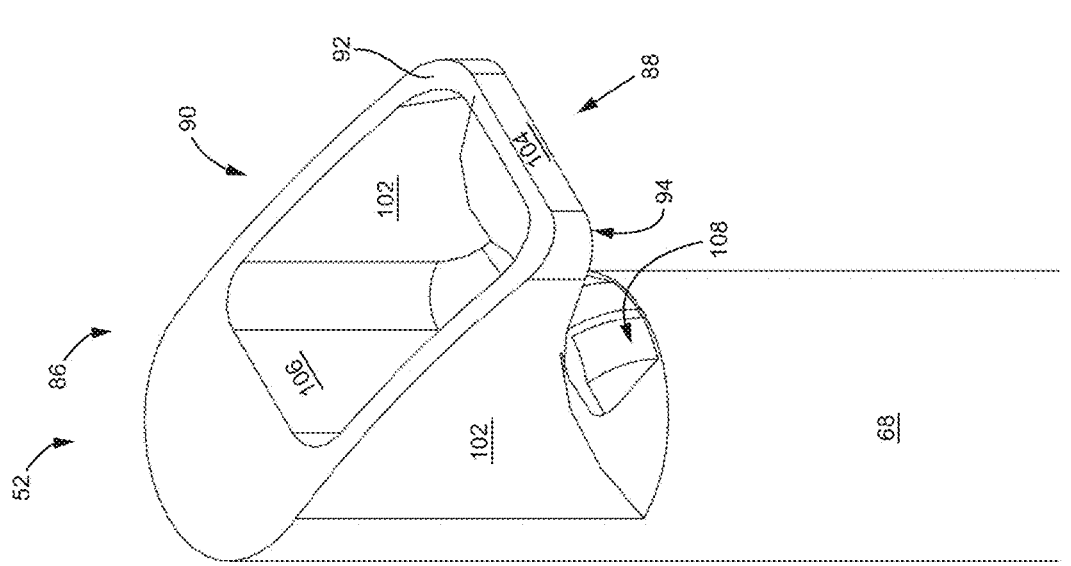

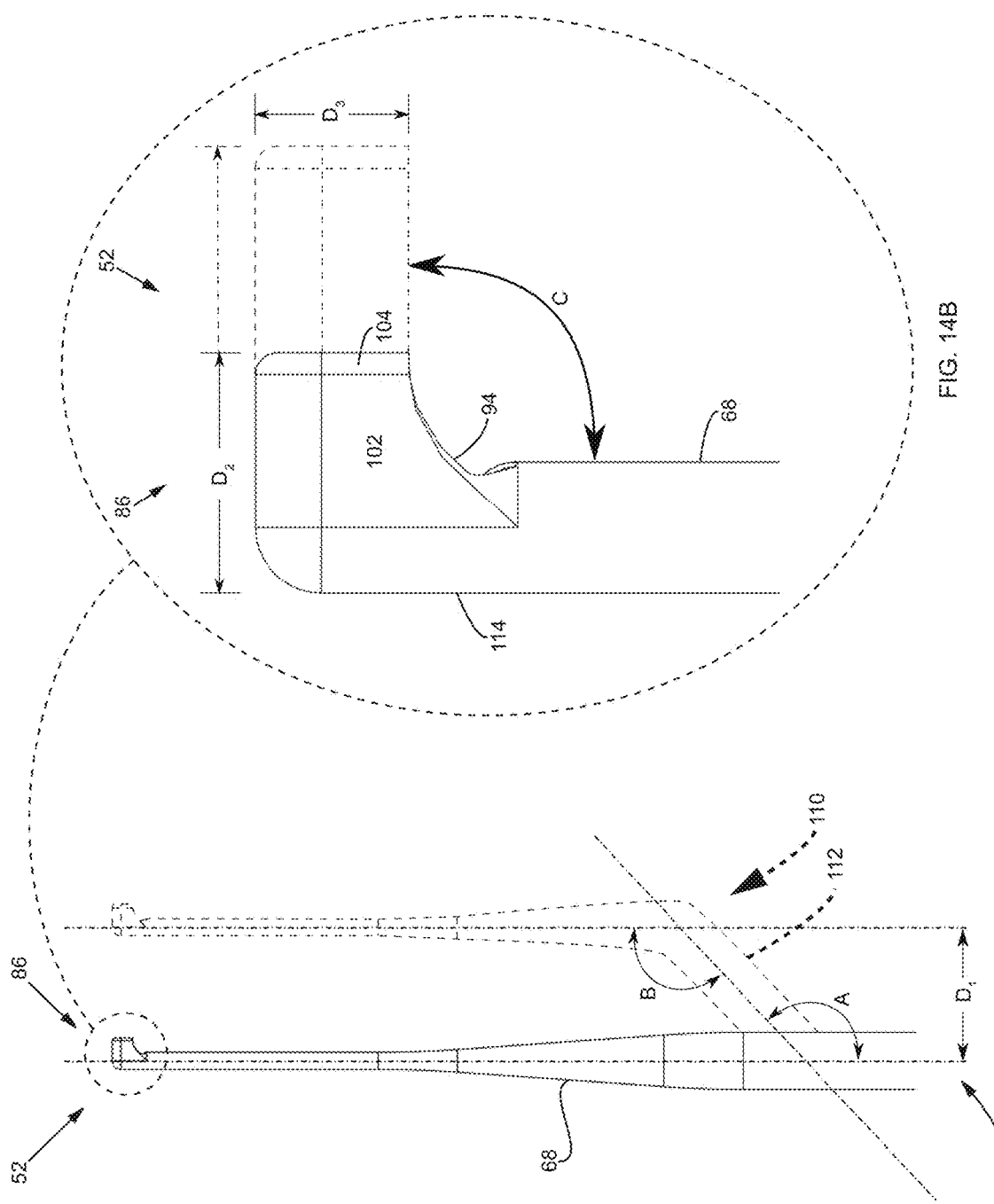

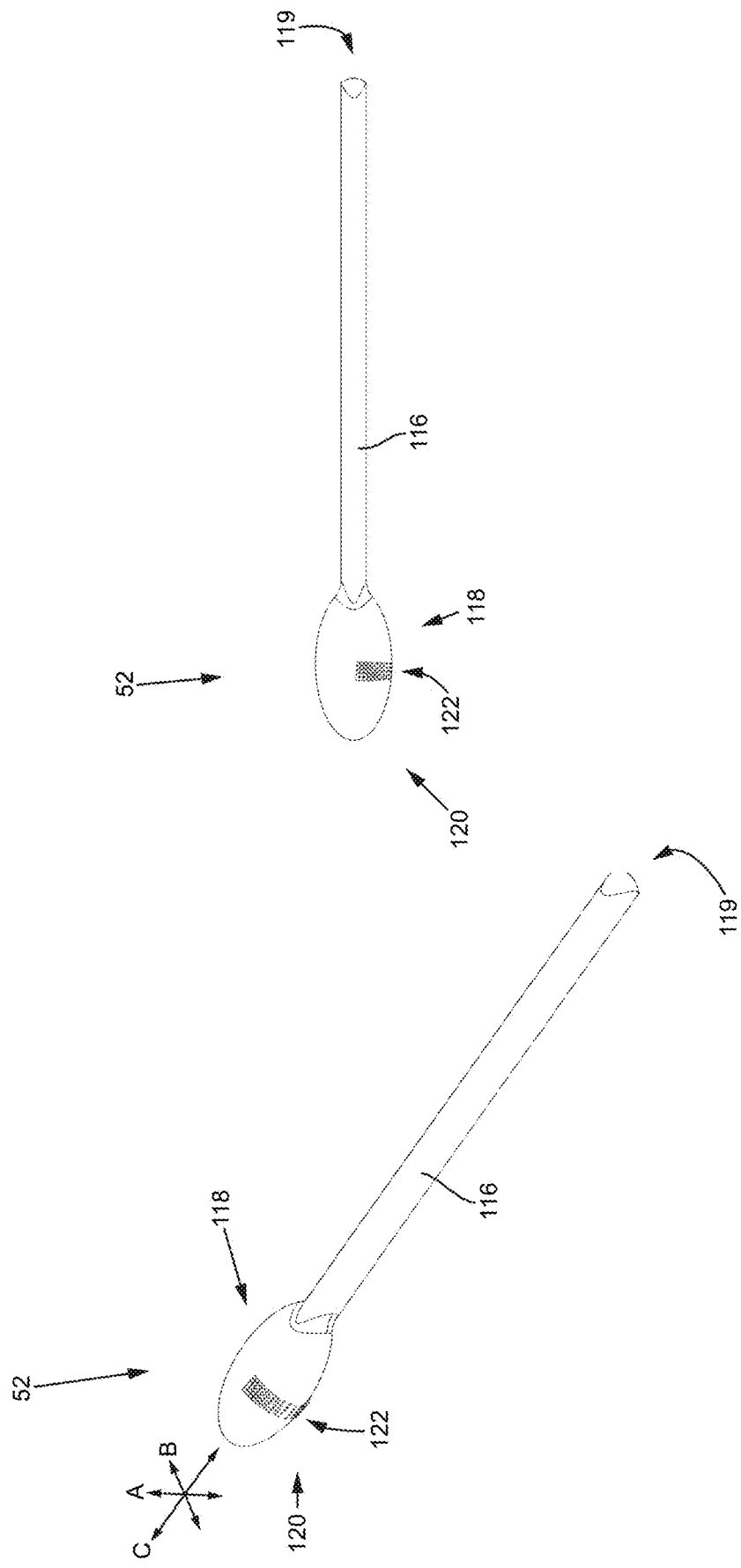

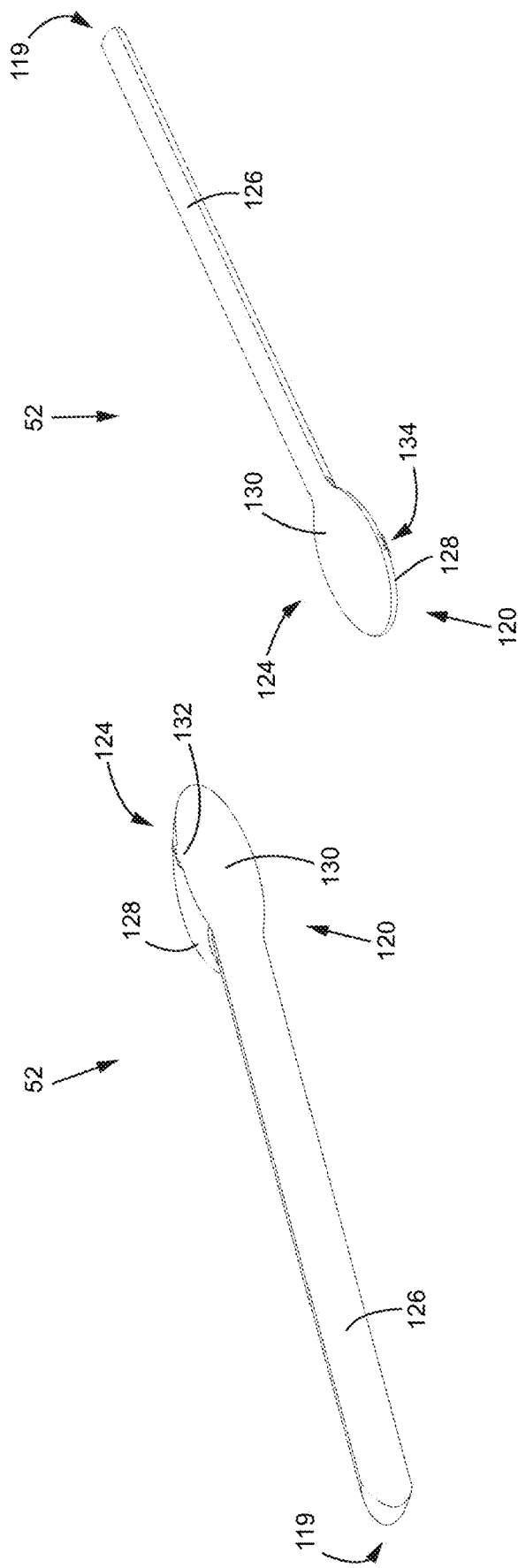

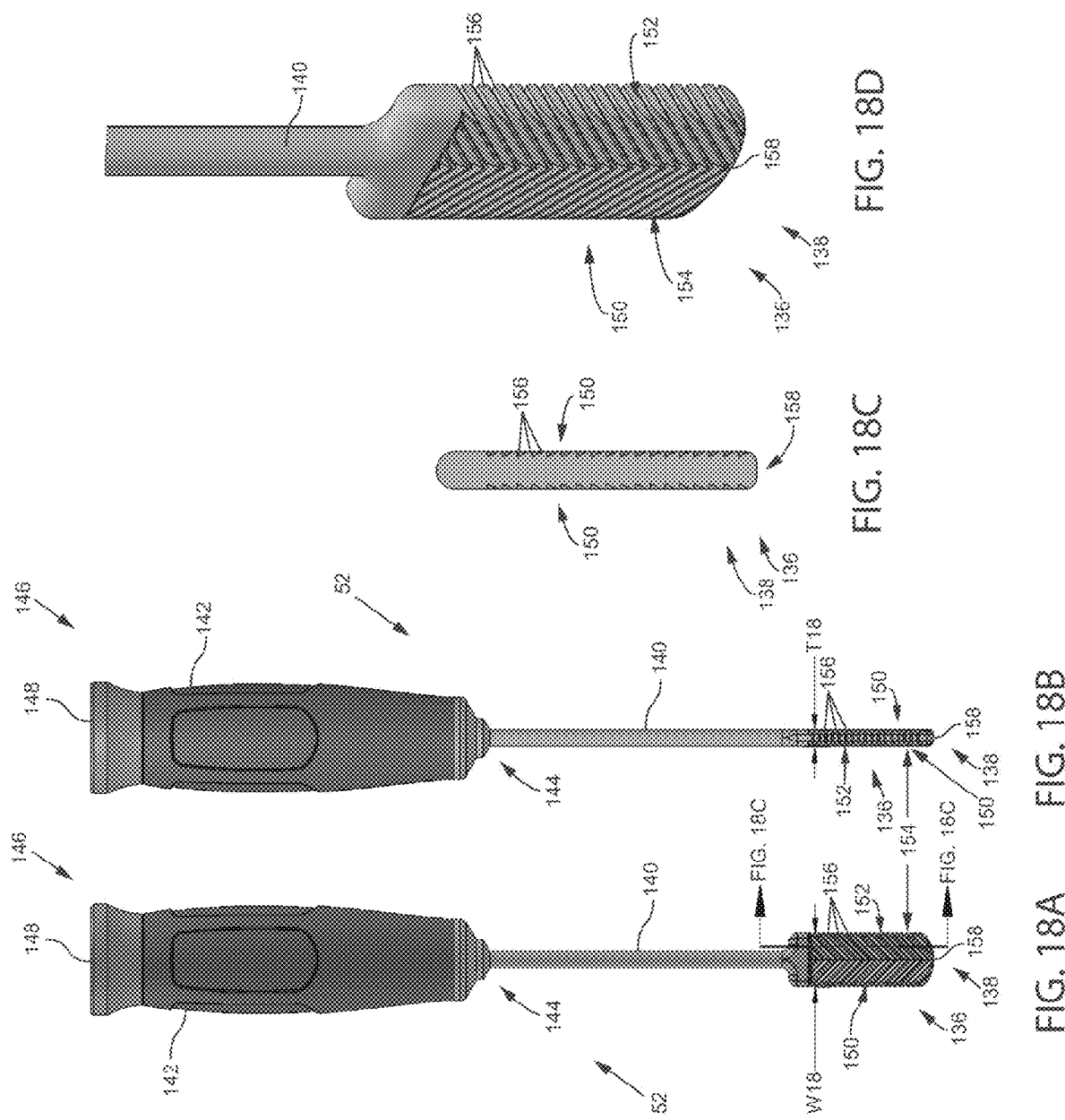

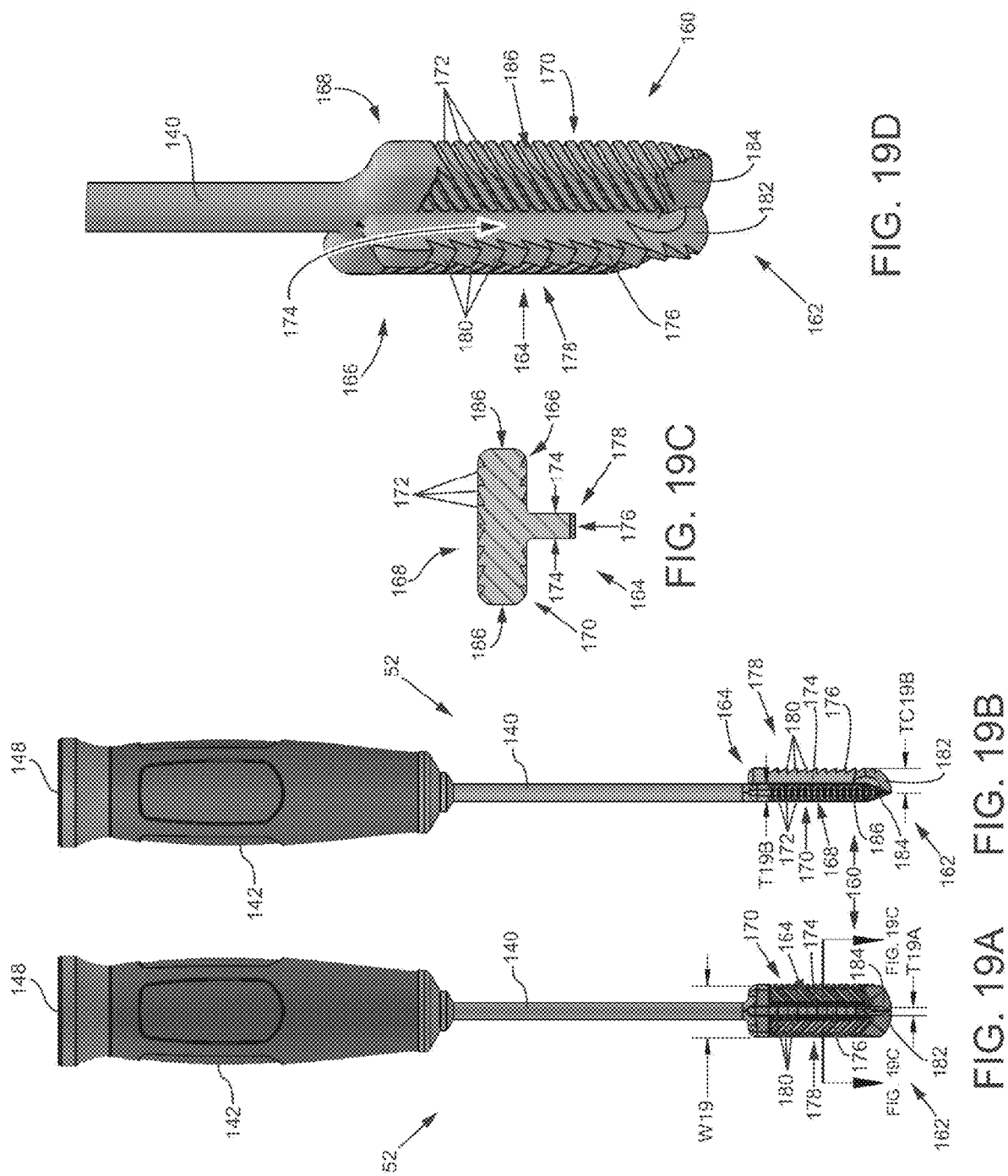

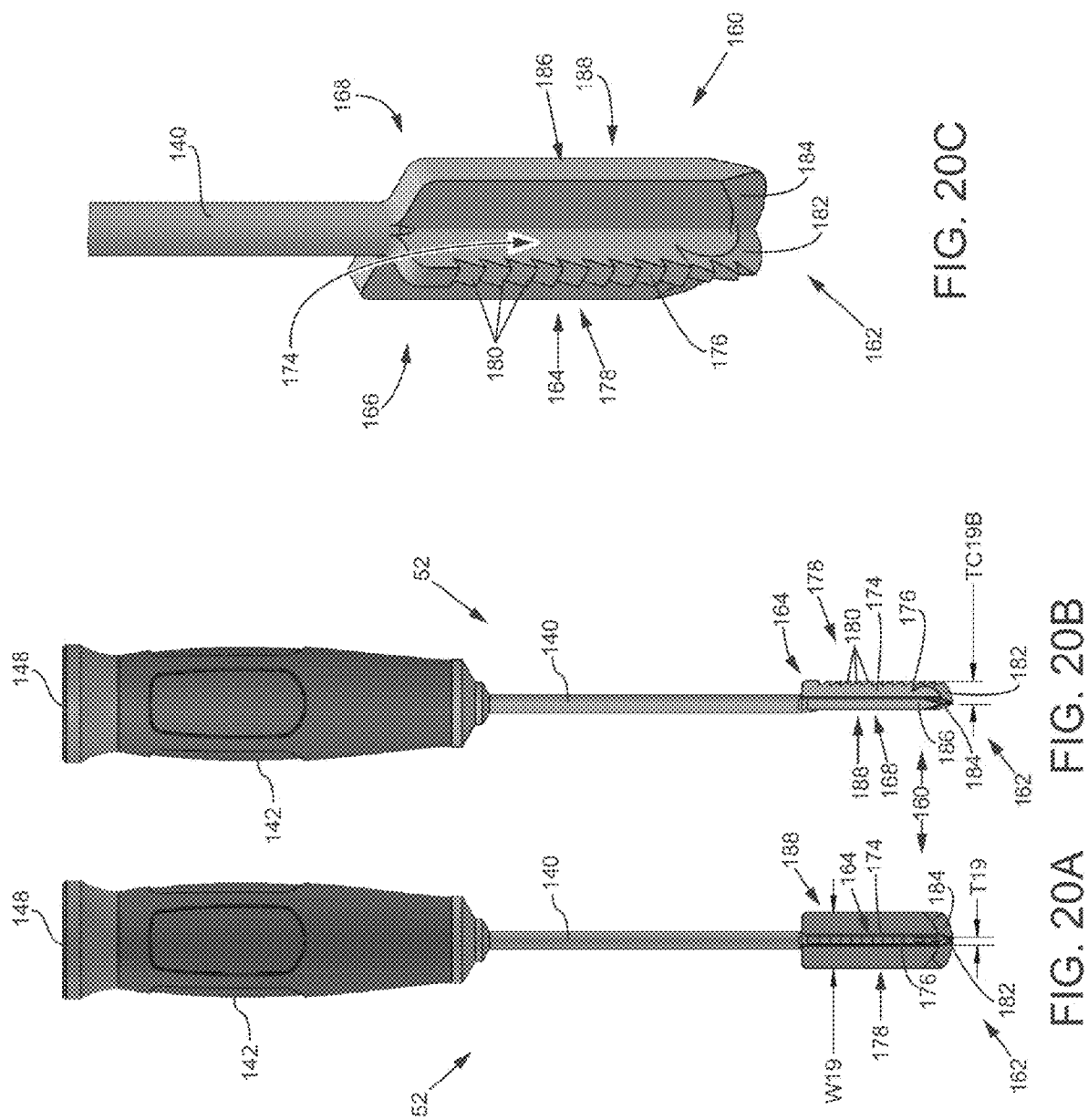

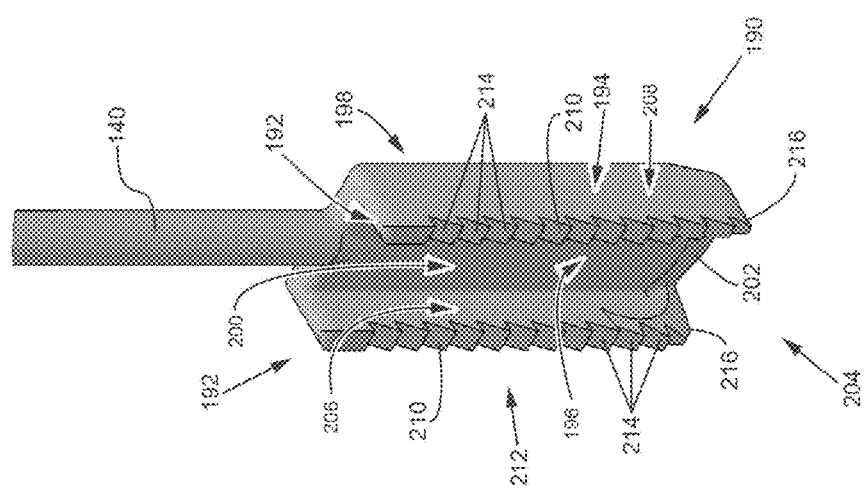
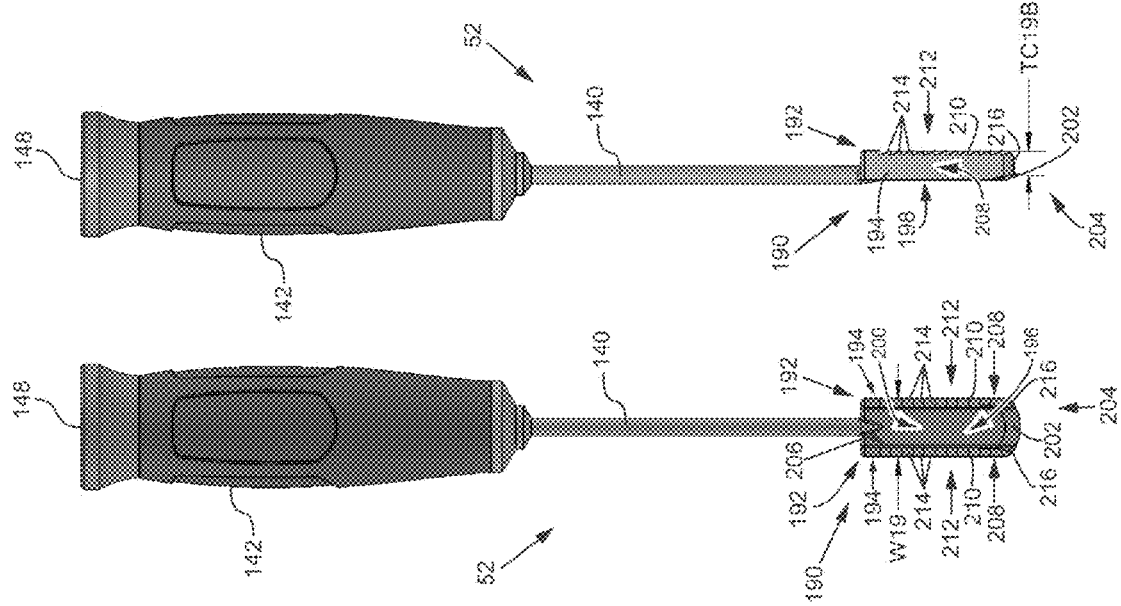
FIG. 21A  FIG. 21B  FIG. 21C

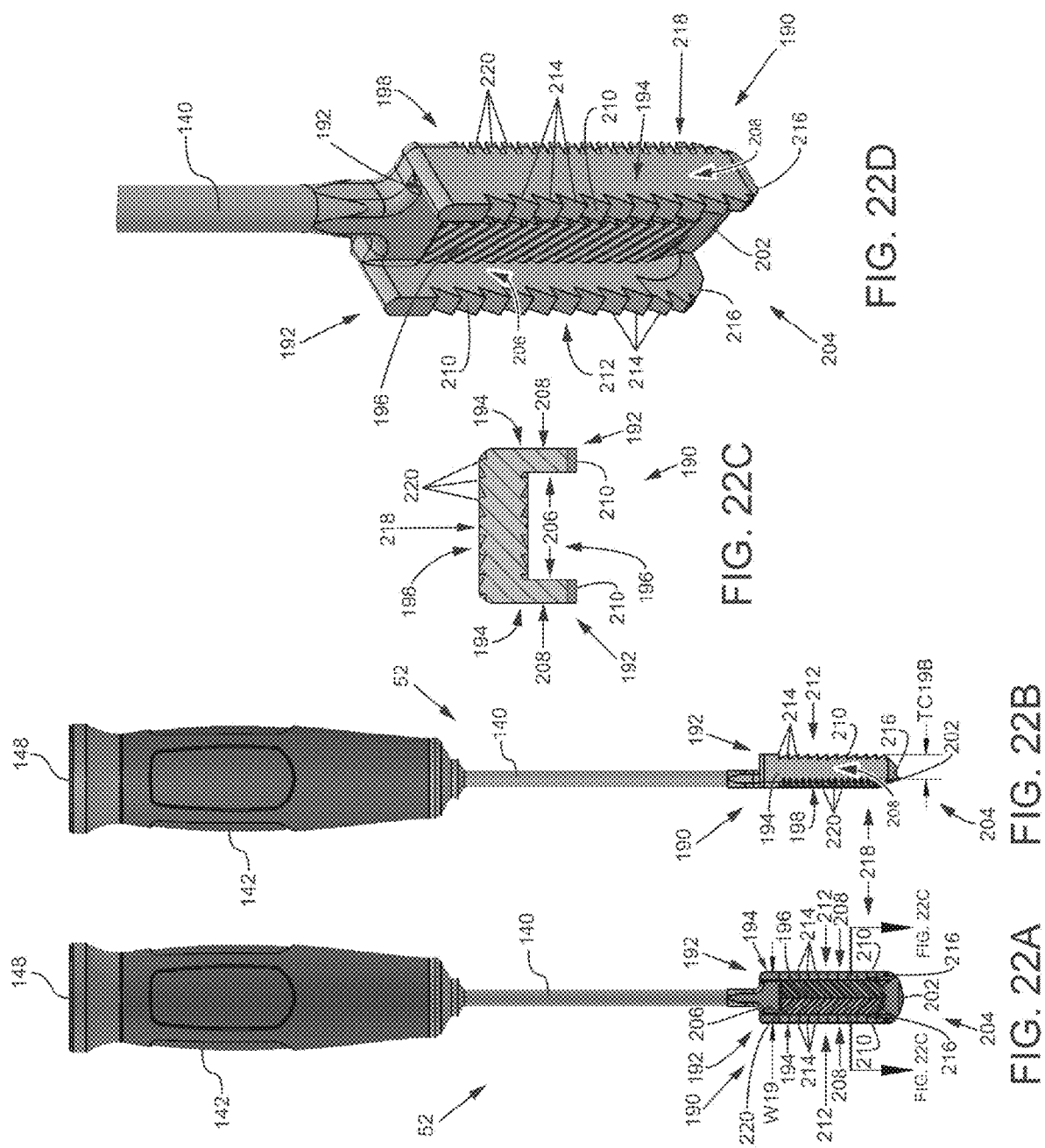

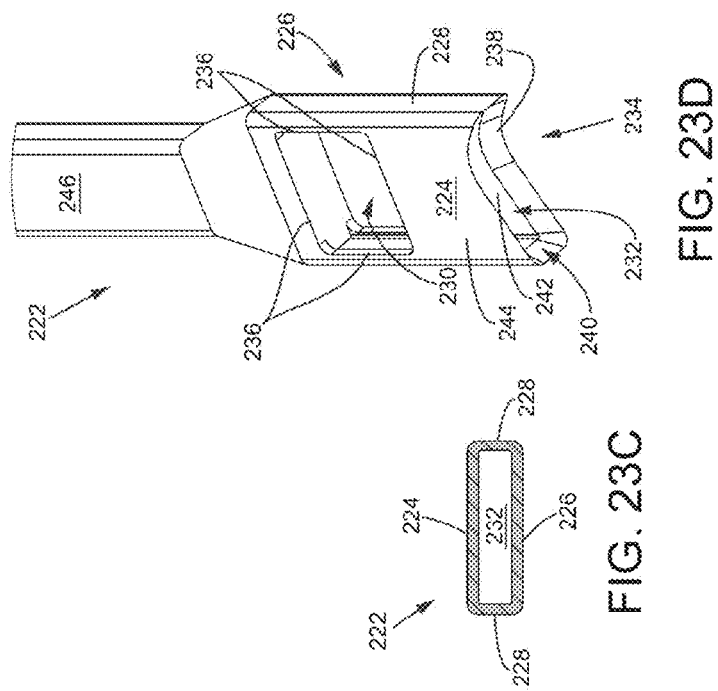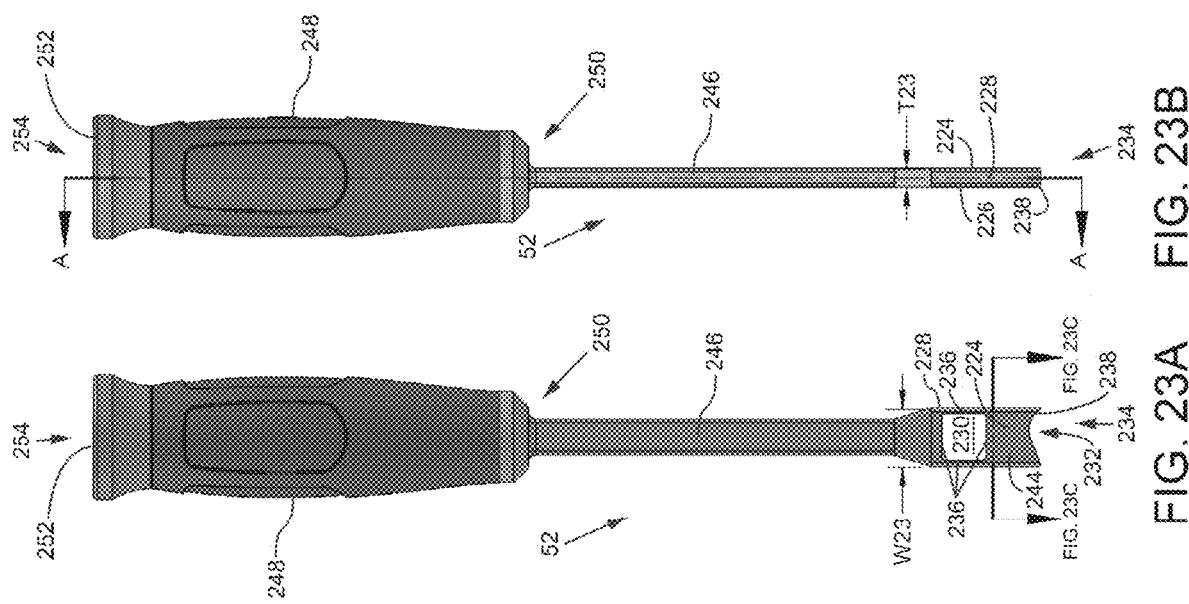

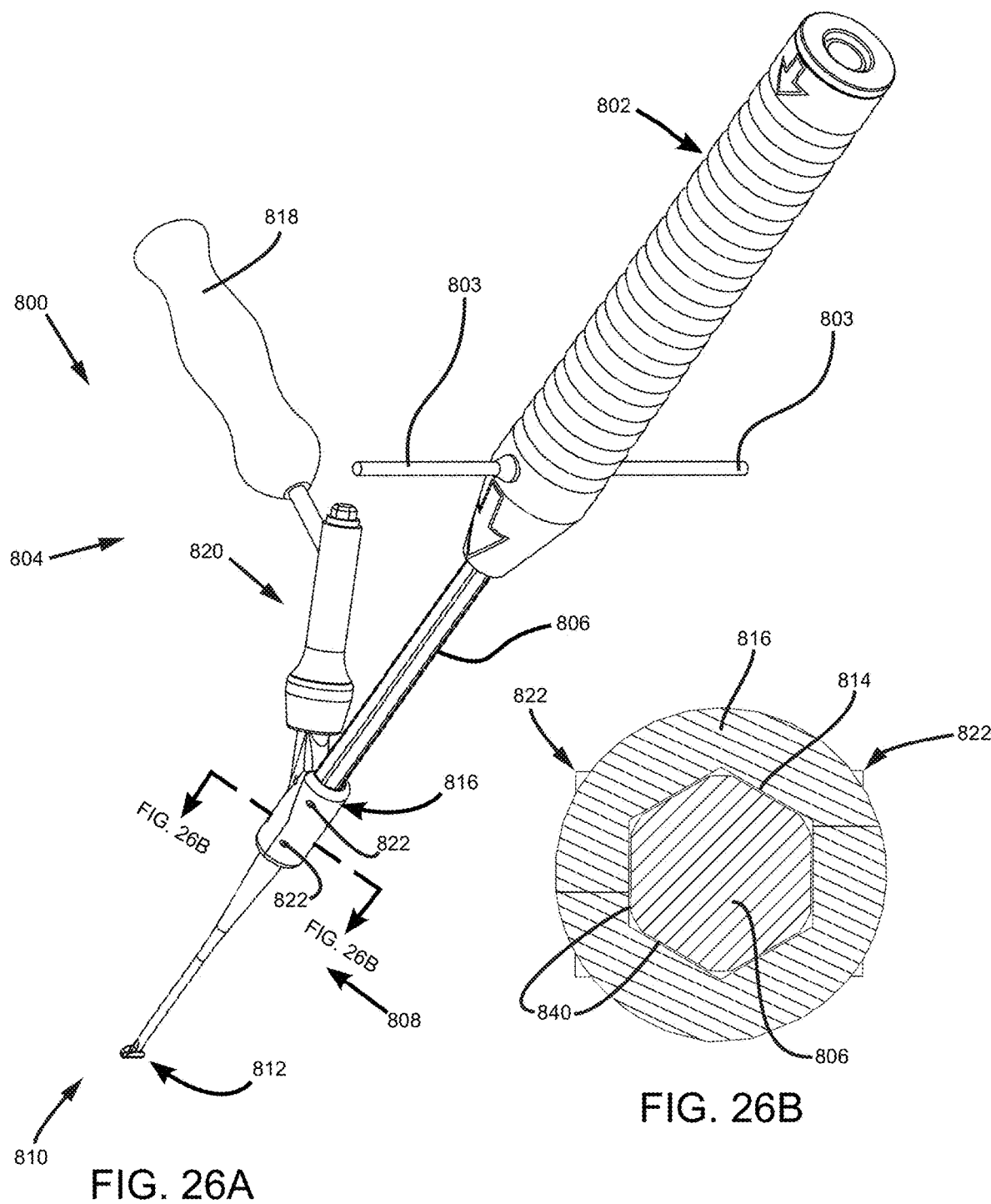

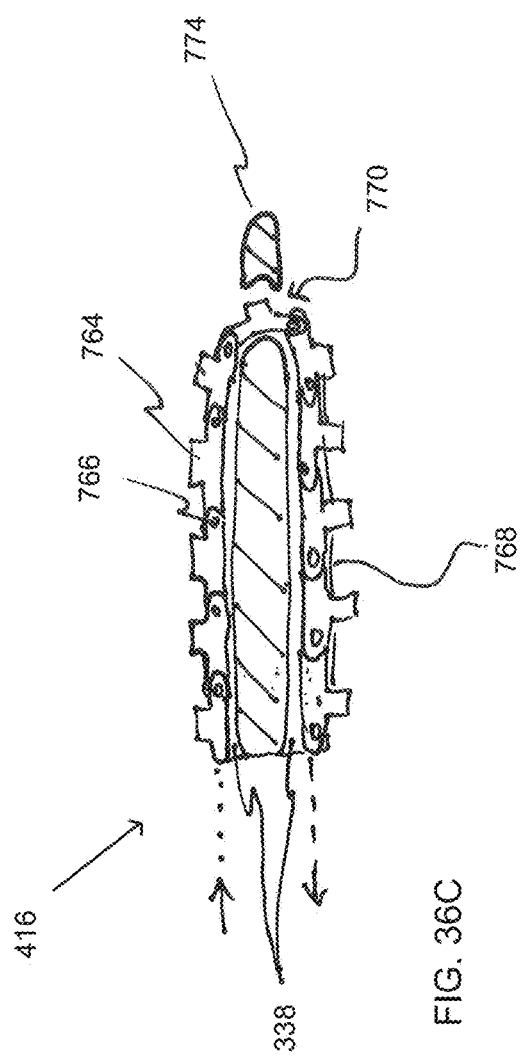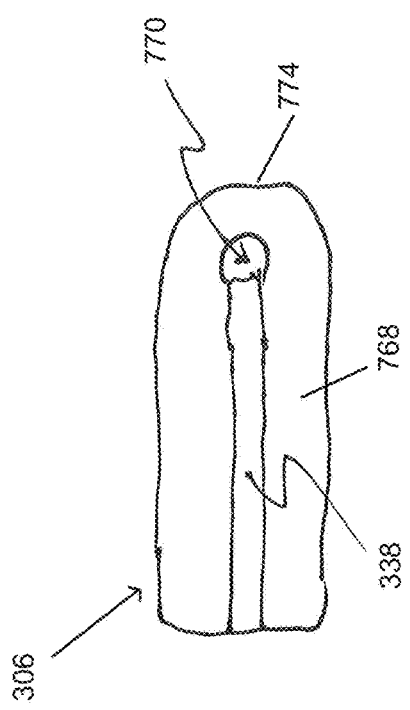
FIG. 36C
FIG. 36D

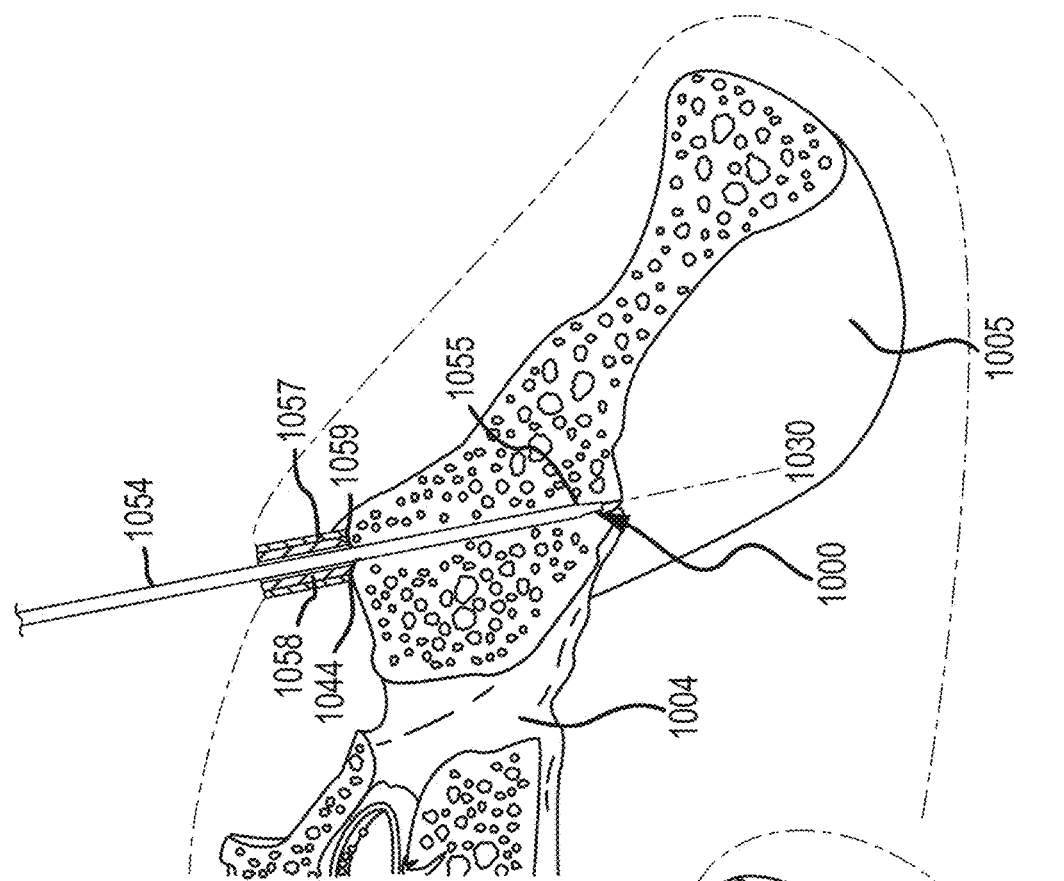
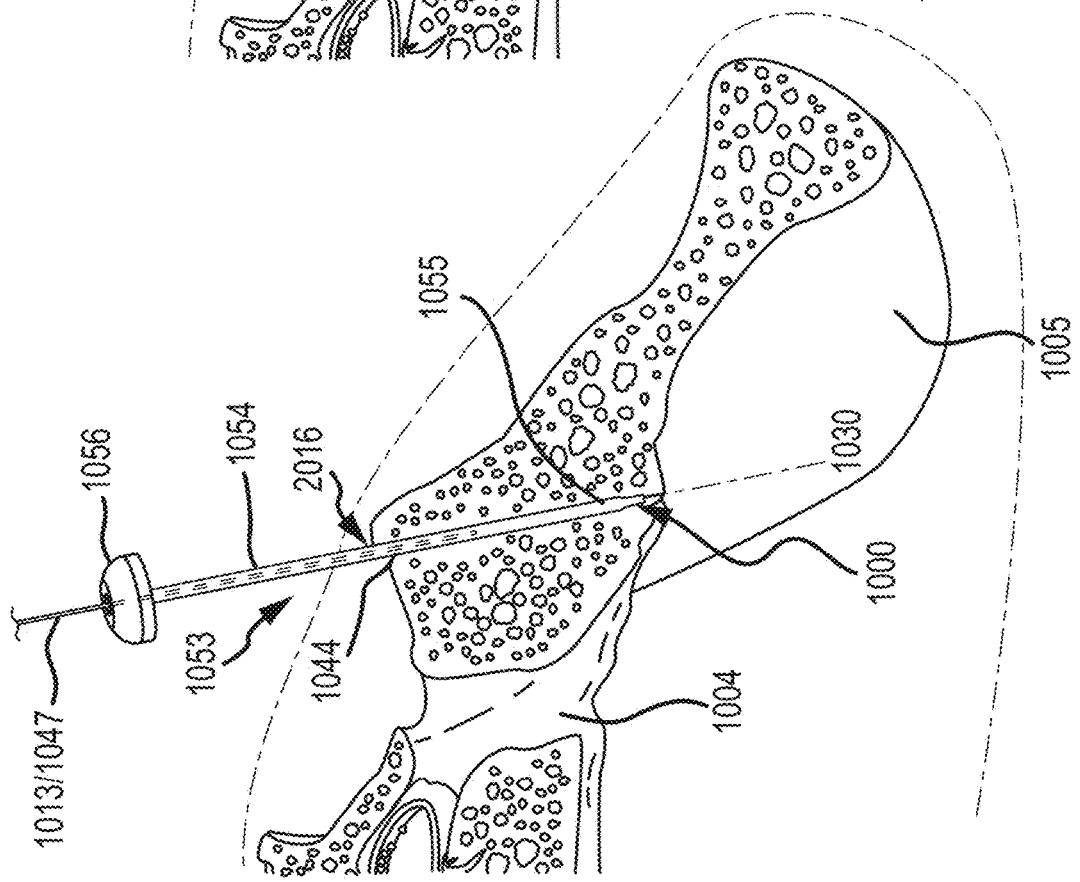

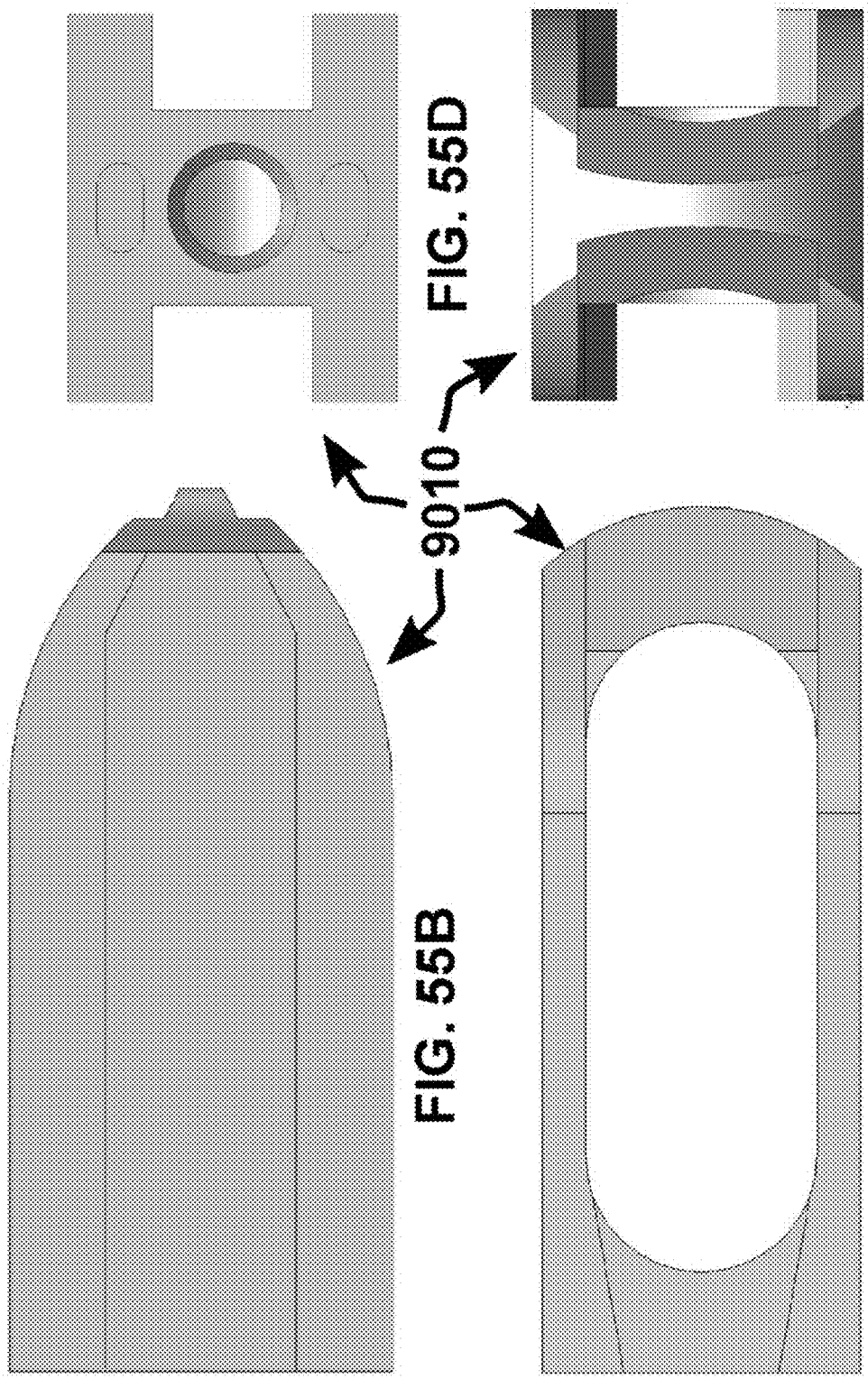

SYSTEMS FOR AND METHODS OF PREPARING A SACROILIAC JOINT FOR FUSION

CROSS REFERENCE TO RELATED APPLICATIONS

The present application is a continuation-in-part of U.S. patent application Ser. No. 15/785,997 filed Oct. 17, 2017, which application is a continuation of U.S. patent application Ser. No. 14/514,221, now U.S. Pat. No. 9,826,986, filed Oct. 14, 2014 ("the '221 application"). The '221 application claims priority under 35 U.S.C. § 119 to U.S. Provisional Patent Application 61/891,330, which was filed Oct. 15, 2013. The '221 application also claims priority under 35 U.S.C. § 119 to U.S. Provisional Patent Application 61/891,345, which was filed Oct. 15, 2013. The '221 application also claims priority under 35 U.S.C. § 119 to U.S. Provisional Patent Application 61/912,494, which was filed Dec. 5, 2013. The '221 application also claims priority under 35 U.S.C. § 119 to U.S. Provisional Patent Application 61/914,409, which was filed Dec. 11, 2013. The '221 application also claims priority under 35 U.S.C. § 119 to U.S. Provisional Patent Application 61/954,594, which was filed Mar. 17, 2014. The '221 application is also a continuation-in-part ("CIP") application of U.S. patent application Ser. No. 14/447,612 ("the '612 application"), now U.S. Pat. No. 9,700,356, which was filed Jul. 31, 2014. The '612 application claims priority under 35 U.S.C. § 119 to: 1) U.S. Provisional Patent Application 61/979,857, which was filed Apr. 15, 2014; 2) U.S. provisional application 61/955,126, which was filed Mar. 18, 2014; 3) U.S. Provisional Patent Application 61/914,409, which was filed Dec. 11, 2013; and 4) U.S. Provisional Patent Application 61/860,185, which was filed Jul. 30, 2013.

The present application is also a CIP of U.S. patent application Ser. No. 15/662,045 filed Jul. 27, 2017, which application is a continuation application of U.S. patent application Ser. No. 14/567,956 filed Dec. 11, 2014, now U.S. Pat. No. 9,717,539, which application claims priority under 35 U.S.C. § 119 to U.S. Provisional Patent Application 61/914,409, which was filed Dec. 11, 2013. U.S. patent application Ser. No. 14/567,956 is also a CIP application of U.S. patent application Ser. No. 14/514,221 ("the '221 application"), now U.S. Pat. No. 9,826,986, which was filed Oct. 14, 2014. The '221 application claims priority under 35 U.S.C. § 119 to: 1) U.S. Provisional Patent Application 61/891,330, which was filed Oct. 15, 2013; 2) U.S. Provisional Patent Application 61/891,345, which was filed Oct. 15, 2013; 3) U.S. Provisional Patent Application 61/912,494, which was filed Dec. 5, 2013; 4) U.S. Provisional Patent Application 61/914,409, which was filed Dec. 11, 2013; and 5) U.S. Provisional Patent Application 61/954,594, which was filed Mar. 17, 2014. U.S. patent application Ser. No. 14/567,956 is also a CIP application of U.S. patent application Ser. No. 14/447,612 ("the '612 application"), which was filed Jul. 31, 2014, now U.S. Pat. No. 9,700,356. The '612 application claims priority under 35 U.S.C. § 119 to: 1) U.S. Provisional Patent Application 61/979,857, which was filed Apr. 15, 2014; 2) U.S. provisional application 61/955,126, which was filed Mar. 18, 2014; 3) U.S. Provisional Patent Application 61/914,409, which was filed Dec. 11, 2013; and 4) U.S. Provisional Patent Application 61/860,185, which was filed Jul. 30, 2013.

The present application is also a CIP of U.S. patent application Ser. No. 15/418,633, filed Jan. 27, 2017, which application is a CIP of U.S. patent application Ser. No. 14/660,784 ("the '784 application"), now U.S. Pat. No. 10,245,087, filed on Mar. 17, 2015, which claims the benefit of U.S. Provisional Patent Application 61/954,594, filed on Mar. 17, 2014. The '784 application is also a CIP of International Application PCT/US2014/30889, filed on Mar. 17, 2014, which claims the benefit of U.S. Provisional Patent Application 61/798,225, filed on Mar. 15, 2013. International Application PCT/US2014/30889 further claims the benefit of U.S. Provisional Patent Application 61/859,134, filed on Jul. 26, 2013.

The '784 application is also a CIP of U.S. patent application Ser. No. 14/514,221 ("the '221 application"), now U.S. Pat. No. 9,826,986, filed on Oct. 14, 2014. The priority of the '221 application has been included in the previous paragraphs. The '784 application is also a CIP of U.S. patent application Ser. No. 14/447,612 ("the '612 application"), now U.S. Pat. No. 9,700,356, filed on Jul. 31, 2014. The priority of the '612 application has been included in the previous paragraphs. The '784 application is also a CIP of U.S. patent application Ser. No. 14/567,956 filed Dec. 11, 2014, now U.S. Pat. No. 9,717,539. The priority of the '956 application has been included in the previous paragraphs.

All of the aforementioned Patents and patent applications are hereby incorporated by reference in their entireties into the present application for all purposes.

TECHNICAL FIELD

Aspects of the present disclosure relate to medical apparatus and methods. More specifically, the present disclosure relates to devices and methods for preparing a sacroiliac joint for fusion.

BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods encompassing an anterior approach, a posterior approach, and a lateral approach with or without percutaneous screw or other type implant fixation. However, while each of these methods has been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint including the anterior approach, posterior approach, or lateral approach may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery.

A danger to open surgery using the anterior approach can be damage to the L5 nerve root, which lies approximately two centimeters medial to the sacroiliac joint or damage to the major blood vessels. Additionally and as seen in FIG. 1, which depicts a conventional fusion procedure (immobilization of the articular surfaces of the sacroiliac joint in relation to one another) on a sacroiliac joint 1, one or more screws or implants 2 are implanted transversely across the articular surfaces 3 and through the sacrum 4 and the ilium bones 5. That is, the joint 1 is immobilized by placement of a fusion device 2 transverse to or across a plane defined by articular surfaces 3 of the sacroiliac joint space.

Use of trans-sacroiliac and SI pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult, requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to mal-placement of implants leading to damage of surrounding structures. Additionally, these procedures are often performed without fusion of the sacroiliac joint, which does not remove the degenerative joint surface and thereby does not address the degenerative condition of the sacroiliac joint, which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen, which can be of relatively large dimension and which are subsequently broached with instruments, which can result in bone being impacted into the pelvis and neuroforamen.

The creation of the trans-sacroiliac bores and subsequent broaching of the bores requires a guide pin, which may be inadvertently advanced into the pelvis or sacral foramen, resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint, which may result in continued or recurrent pain requiring additional surgery.

Another substantial problem with conventional procedures can be that placement of posterior extra-articular distracting fusion implants and bone grafts may be inadequate with respect to removal of the articular surface or preparation of cortical bone, the implant structure and fixation of the sacroiliac joint. The conventional procedures may not remove sufficient amounts of the articular surfaces or cortical surfaces of the sacroiliac joint to relieve pain in the sacroiliac joint. The conventional implant structures may have insufficient or avoid engagement with the articular surfaces or cortical bone of the sacroiliac joint for adequate fixation or fusion. The failure to sufficiently stabilize and fuse the sacroiliac joint with the conventional implant structures and methods may result in a failure to relieve the condition of sacroiliac joint being treated. Additionally, conventional methods of driving apart a sacrum and ilium may lead to mal-alignment of the sacroiliac joint and increased pain.

Improvements to sacroiliac joint fusion involve systems and methods for non-transverse delivery of an implant into the sacroiliac joint are described in U.S. patent application Ser. No. 12/998,712, filed May 23, 2011 entitled SACROILIAC JOINT FIXATION FUSION SYSTEM; Ser. No. 13/236,411, filed Sep. 19, 2011 entitled SYSTEMS FOR AND METHODS OF FUSING A SACROILIAC JOINT; and Ser. No. 13/475,695, filed May 18, 2012, entitled SYSTEMS FOR AND METHODS OF FUSING A SACROILIAC JOINT; and Ser. No. 13/945,053, filed Jul. 18, 2013, entitled SYSTEMS FOR AND METHODS OF FUSING A SACROILIAC JOINT; and Ser. No. 13/946,790, filed Jul. 19, 2013, entitled SYSTEMS FOR AND METHODS OF FUSING A SACROILIAC JOINT; and Ser. No. 14/216,975, filed Mar. 17, 2014, entitled SYSTEMS AND METHODS FOR FUSING A SACROILIAC JOINT AND ANCHORING AN ORTHOPEDIC APPLIANCE; and Ser. No. 14/447,612, filed Jul. 31, 2014, entitled SYSTEMS FOR AND METHODS OF FUSING A SACROILIAC JOINT. All of application Ser. Nos. 12/998,712, 13/236,411, 13/475,695, 13/945,053, 13/946,790, 14/216,975, and 14/447,612 are herein incorporated by reference in their entirety. In certain instances, it may be desirable to prepare the surfaces of the sacroiliac joint prior to implantation of the fusion device, e.g., the intra-articular or extra-articular surfaces. While surgical preparation tools may exist for procedures in other areas of the body, tools for preparing the sacroiliac joint for fusion are lacking. Thus, the systems and methods discussed herein address the challenges in preparing the sacroiliac joint for fixation and fusion.

SUMMARY

One implementation of the present disclosure may take the form of a surgical preparation tool for preparing a sacroiliac joint having a sacrum and an ilium for a surgical procedure. In one embodiment, the tool may include a trial tool assembly and a cutting tool.

The trial tool assembly may include an implant trial at a distal end of the trial tool assembly and a trial shaft coupled to and extending proximally from the implant trial. The implant trial may include a body comprising a first length extending along a longitudinal axis from a proximal to a distal end, a top surface, a bottom surface generally opposite the top surface, a first side surface, and a second side surface generally opposite the first side surface. The implant trial may be configured to be delivered non-transversely into the sacroiliac joint such that the first top and first bottom surfaces oppose either the sacrum or the ilium.

The cutting tool of the surgical preparation tool may be configured to releasably and slidably couple with the trial tool assembly. The cutting tool may include a first cutting element at a distal end of the cutting tool and a cutting shaft extending proximally from the cutting element. The first cutting element may include a second length extending from a proximal to a distal end. The trial tool assembly is configured to guide the cutting tool during distal-proximal translation such that as the first cutting element distally advances relative to the implant trial, at least a portion of the first cutting element extends generally over and perpendicularly outward from the first side surface of the body of the implant trial.

Another implementation of the present disclosure may take the form of a surgical preparation tool for preparing a sacroiliac joint having a sacrum and an ilium for a surgical procedure. In one embodiment, the tool may include a trial tool assembly and a drill guide assembly.

The trial tool assembly may include an implant trial at a distal end of the trial tool assembly and a trial shaft coupled to and extending proximally from the implant trial. The implant trial may include a body comprising a first length extending along a longitudinal axis from a proximal to a distal end, a first top surface, a first bottom surface generally opposite the first top surface, and a thickness defined between the first top and first bottom surfaces. The implant trial may be configured to be delivered non-transversely into the sacroiliac joint such that the first top and first bottom surfaces oppose either the sacrum or the ilium.

The drill guide assembly may be configured to releasably and slidably couple with the trial tool assembly. The drill guide assembly may include a drill guide at a distal end of the cutting guide and a drill guide shaft extending proximally from the drill guide. The drill guide may include a first passageway that is configured to guide a drill bit during distal-proximal translation of the drill bit relative to the drill guide assembly. The trial tool assembly may be configured to guide the drill guide assembly during distal-proximal translation such that as the drill guide distally advances relative to the implant trial, the drill guide is positioned in an orientation to deliver the drill bit generally over at least a portion of the first top surface of the body of the implant trial.

Yet another implementation of the present disclosure may take the form of a method of surgically preparing a sacroiliac joint having a sacrum and an ilium for a surgical fusion procedure.

In one embodiment, the method may include approaching a sacroiliac joint space with a joint preparation tool that may include an implant trial assembly and a cutting tool. The implant trial assembly may include an implant trial at a distal end of the joint preparation tool and an implant trial shaft extending proximally from the implant trial. The implant trial may include a length extending from a proximal end to a distal end of the implant trial, a first top surface, and a first bottom surface generally opposite the first top surface. The cutting tool may be configured to releasably and slidably couple with the trial tool assembly. The cutting tool may include a cutting element at a distal end of the cutting tool and a cutting shaft extending proximally from the cutting element. The cutting element may include a second length extending from a proximal to a distal end, wherein the trial tool assembly is configured to guide the cutting tool during distal-proximal translation.

The method may also include delivering a portion of the implant trial non-transversely into the sacroiliac joint space. The implant trial may be oriented in the sacroiliac joint space such that the first top and bottom surfaces are generally coplanar with a joint plane of the sacroiliac joint space.

The method may further include causing the cutting tool to be distally driven relative to the trial tool assembly such that the cutting element makes a cut extending into the sacrum or the ilium.

Another implementation of the present disclosure may take the form of a surgical system for preparing a sacroiliac joint having a sacrum and an ilium for a surgical procedure. In one embodiment, the system may include a joint preparation tool and a first anchoring arm.

The joint preparation tool may include a rasping head at a distal end of the joint preparation tool, a shaft extending proximally from the rasping head, and a longitudinal axis extending from a proximal to a distal end of the joint preparation tool. The rasping head may include a length extending from a distal to a proximal end of the rasping head, a top surface, and a bottom surface opposite the top surface.

The first anchoring arm may include a proximal end and a distal end, where the distal end of the first anchoring arm may be configured to engage a proximal end of an anchor element, the first anchoring arm may be operably coupled to the joint preparation tool in an arrangement such that a longitudinal axis of the anchor element is generally transversely aligned with the longitudinal axis of the joint preparation tool when the distal end of the first anchoring arm is engaged with the proximal end of the anchor element, wherein the first anchoring arm is configured to deliver the anchor element across the sacroiliac joint according to the arrangement.

Another implementation of the present disclosure may take the form of a surgical preparation tool for preparing a sacroiliac joint having a sacrum and an ilium for a surgical procedure. In one embodiment, the tool may include a trial tool assembly and a cutting tool assembly.

The trial tool assembly may include an implant trial at a distal end of the trial tool assembly and a trial shaft coupled to and extending proximally from the implant trial. The implant trial may include a body comprising a first length extending along a longitudinal axis from a proximal to a distal end, a first top surface, a first bottom surface generally opposite the first top surface, and a thickness defined between the first top and first bottom surfaces. The implant trial may be configured to be delivered non-transversely into the sacroiliac joint such that the first top and first bottom surfaces oppose either the sacrum or the ilium.

The cutting tool may be configured to releasably and slidably couple with the trial tool assembly. The cutting tool may include a cutting element at a distal end of the cutting tool and a cutting shaft extending proximally from the cutting element. The cutting element may include a second length extending from a proximal to a distal end. The trial tool assembly may be configured to guide the cutting tool during distal-proximal translation such that as the cutting element distally advances relative to the implant trial, at least a portion of the cutting element extends generally over and perpendicularly outward from the first top surface of the body of the implant trial.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 2A is an isometric view of a first embodiment of a system for fusing a sacroiliac joint.

FIG. 2B is the same view as FIG. 2A, except the delivery tool and implant assembly are decoupled from each other.

FIG. 3 is the same view as FIG. 2A, except the system is exploded to better illustrate its components.

FIGS. 9A-9B are isometric views of a cutting element at a distal end of the tooling head.

FIG. 14A is a side view of the shaft of the tooling head and possible modifications.

FIG. 14B is a close-up side view of the distal end of the tooling head of FIG. 14A.

FIG. 15A is an isometric view of a tooling head with an ellipsoidal head.

FIG. 15B is a side view of the tooling head with the ellipsoidal head.

FIG. 16 is an isometric view of a tooling head with a bisected ellipsoidal head.

FIG. 17 is an isometric view of another tooling head with a bisected ellipsoidal head.

FIG. 18A is a front view of a tooling head with a planar rasping head.

FIG. 18B is a side view of the tooling head of FIG. 18A.

FIG. 18C is a side cross-sectional view of the planar rasping head.

FIG. 18D is a close-up isometric view of the planar rasping head.

FIG. 19A is a front view of a tooling head with a planar rasping head and a single perpendicularly extending cutting element.

FIG. 19B is a side view of the tooling head of FIG. 19A.

FIG. 19C is a side cross-sectional view of the planar rasping head and the single perpendicularly extending cutting element.

FIG. 19D is a close-up isometric view of the planar rasping head and the single perpendicularly extending cutting element.

FIG. 20A is a front view of a tooling head with a smooth planar head and a single perpendicularly extending cutting element.

FIG. 20B is a side view of the tooling head of FIG. 20A.

FIG. 20C is a close-up isometric view of the smooth planar head and the single perpendicularly extending cutting element.

FIG. 21A is a front view of a tooling head with a smooth planar head and a pair of perpendicularly extending cutting elements.

FIG. 21B is a side view of the tooling head of FIG. 21A.

FIG. 21C is a close-up isometric view of the smooth planar head and the pair of perpendicularly extending cutting elements.

FIG. 22A is a front view of a tooling head with a planar rasping head and a pair of perpendicularly extending cutting elements.

FIG. 22B is a side view of the tooling head of FIG. 22A.

FIG. 22C is a side cross-sectional view of the tooling head of FIG. 22A.

FIG. 22D is a close-up isometric view of the planar rasping head and the pair of perpendicularly extending cutting elements.

FIG. 23A is a front view of a tooling head with a box osteotome head.

FIG. 23B is a side view of the tooling head of FIG. 23A.

FIG. 23C is a cross-sectional view of the box osteotome head.

FIG. 23D is a bottom close-up isometric view of the box osteotome head.

FIG. 26A is an isometric view of a joint preparation tool with a translating and rotation inhibiting distal handle assembly.

FIG. 26B is a cross-sectional view of a coupler member and a shaft of a tooling head of the tool of FIG. 26A.

FIG. 36C is a side view of a cutting element formed of a chain of interconnected teeth.

FIG. 36D is a top view of an implant trial configured to guide the cutting element of FIG. 36C.

FIGS. 49A-49D are each a step in the methodology and illustrated as the same transverse cross section taken along a plane extending generally medial-lateral and generally anterior posterior.

FIG. 55A-55E depict, respectively, an isometric view, top view, side view, back view, and front view of a joint implant, in one embodiment. The side view being the same as an opposite side view, and the top view being the same as the bottom view.

DETAILED DESCRIPTION

Figure 1:
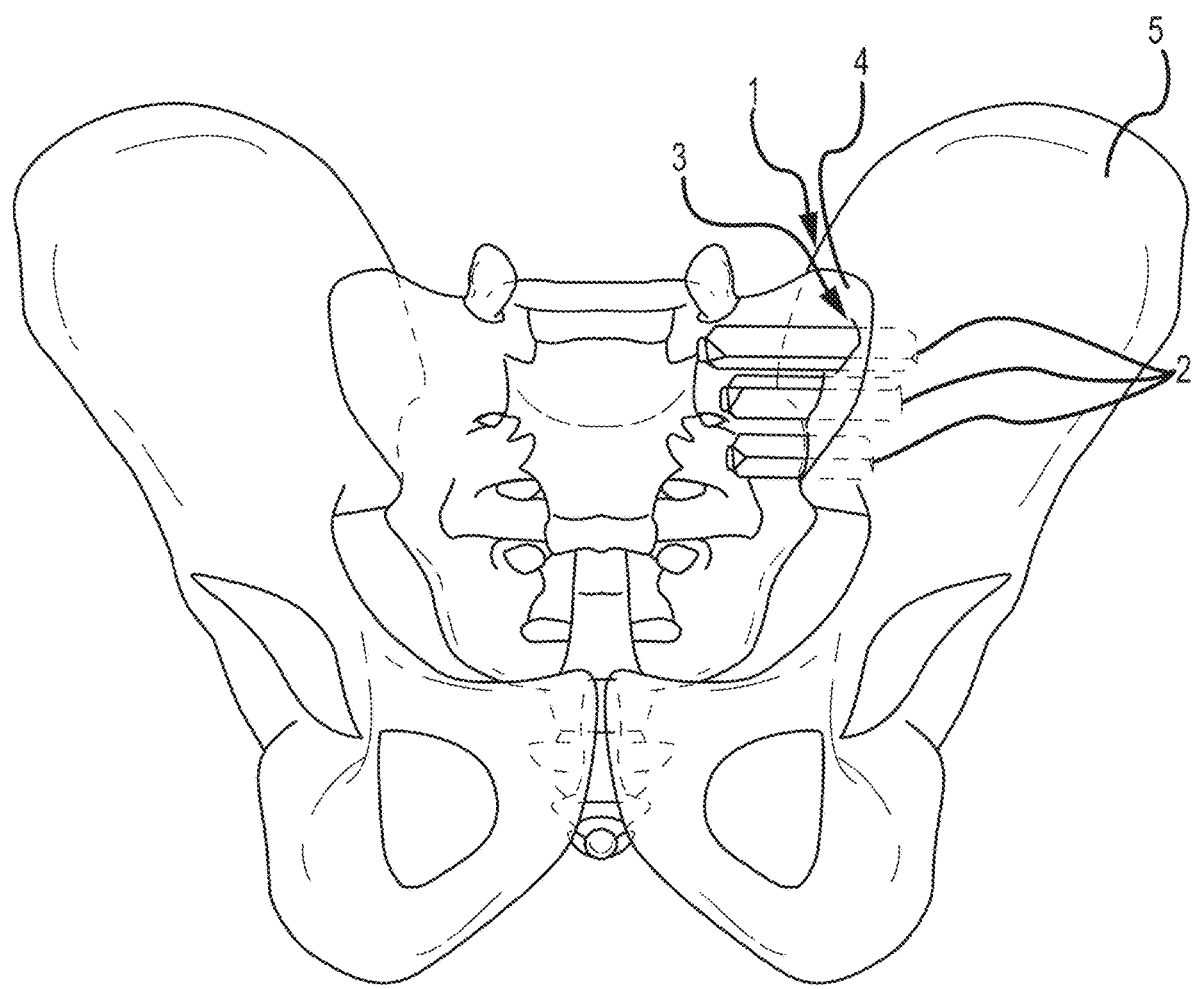
FIG. 1 is an anterior view of the pelvic region and a conventional method and device for stabilizing the sacroiliac joint.

The present application incorporates herein by reference the contents of each of the following applications in each application's entirety: U.S. patent application Ser. No. 14/127,119, entitled "Sacroiliac Joint Implant System," filed on Dec. 17, 2013; U.S. patent application Ser. No. 13/946,790, entitled "Systems for and Methods of Fusing a Sacroiliac Joint," filed on Jul. 19, 2013; International Application PCT/US2012/042823, entitled "Sacroiliac Joint Implant System," filed Jun. 15, 2012; U.S. patent application Ser. No. 13/475,695, entitled "Systems for and Methods of Fusing a Sacroiliac Joint," filed on May 18, 2012; U.S. patent application Ser. No. 13/236,411, entitled "Systems for and Methods of Fusing a Sacroiliac Joint," filed on Sep. 19, 2011; U.S. Provisional Patent Application 61/520,956, entitled "Sacroiliac Joint Implant System," filed on Jun. 17, 2011; U.S. patent application Ser. No. 12/998,712, entitled "Sacroiliac Joint Fixation Fusion System," filed on May 23, 2011; International Application PCT/US2011/000070, entitled "Sacroiliac Joint Fixation Fusion System," filed on Jan. 13, 2011; and U.S. Provisional Patent Application 61/335,947, entitled "Sacroiliac Joint Fusion System," filed on Jan. 13, 2010.

Implementations of the present disclosure involve a system for preparing a sacroiliac joint for fusion. In particular, the system may include a preparation tool for removing articular cartilage from the sacroiliac joint space, abrading of the articular surfaces to enhance boney fusion, and removal of portions of the cortical, subchondral or cancellous bone for implantation of a fusion device. The preparation tool may include an anchoring arm that is configured to direct an anchoring element for transverse delivery through the sacroiliac joint space. The anchor may be delivered into the joint space before, during, or after the joint space is prepared for implant delivery. Alternatively, an implant may not be delivered into the joint and instead, e.g., bone paste or slurry may be introduced into the prepared sacroiliac joint before or after anchor placement. And, the anchor may be delivered cranial, caudal, or in-line with the eventual placement of the implant. The preparation tool is configured to quickly, accurately and reliably prepare the joint space for insertion of an implant.

I. System for Fusion of the Sacroiliac Joint

To begin a detailed discussion of a system 10 for delivering an implant 12 into the sacroiliac joint, reference is made to FIGS. 2A-3. FIG. 2A is an isometric view of the system 10. FIG. 2B is the same view as FIG. 2A, except an implant assembly 14 of the system 10 is separated from a delivery tool 16 of the system 10. FIG. 3 is the same view as FIG. 2A, except the system 10 is shown exploded to better illustrate the components of the system 10.

As can be understood from FIGS. 2A and 2B, the system 10 includes a delivery tool 16 and an implant assembly 14 for implanting at the sacroiliac joint via the delivery tool 16, the implant assembly 14 being for fusing the sacroiliac joint. As indicated in FIG. 3, the implant assembly 14 includes an implant 12 and an anchor element 18 (e.g., a bone screw or other elongated body). As discussed below in greater detail, during the implantation of the implant assembly 14 at the sacroiliac joint, the implant 12 and anchor element 18 are supported by a distal end 20 of the delivery tool 16, as illustrated in FIG. 2A. The delivery tool 16 is used to deliver the implant 12 into the sacroiliac joint space. The delivery tool 16 is then used to cause the anchor element 18 to extend through the ilium, sacrum and implant 12 generally transverse to the sacroiliac joint and implant 12. The delivery tool 16 is then decoupled from the implanted implant assembly 14, as can be understood from FIG. 2B. As illustrated in FIG. 3, the delivery tool 16 further includes a proximal end 22 opposite the distal end 20, an arm assembly 24, a handle 26, an implant retainer 28, a sleeve 30 and a trocar or guidewire 32. While in the embodiment of FIGS. 2A-3, the delivery tool 16 is fixed and non-adjustable and configured to deliver the anchoring element 18 in a single orientation relative to the implant 12, the delivery tool 16 may be adjustable and configured to deliver the anchoring element 18 within a range of orientations relative to the implant 12 that will orient the anchoring element 18 either within a bore of the implant 12, or adjacent implant 12 as described in U.S. patent application Ser. No. 14/447,612, filed Jul. 31, 2014, entitled SYSTEMS FOR AND METHODS OF FUSING A SACROILIAC JOINT, which is hereby incorporated by reference in its entirety.

In particular embodiments, first and second articular faces of the implant 12 may be selected to match the contour of the joint space of the sacroiliac joint within which the implant 12 is to be inserted. For example, the sacral, medial or first articular face of the implant may be configured to be generally convex to match the contour of a sacral auricular boney surface or to match the contour of an extra-articular region of a sacrum (e.g., a sacral fossa). In one aspect and referring to portions of the anatomy shown FIG. 48C, the sacral, medial or first articular face of the implant 12 may be generally a surface negative of the articular surfaces 1016 of the extra-articular region 3007 and/or articular region 1044 of the sacrum 1004. As another example, the lateral, iliac or second articular face of the implant 12 may be configured to be generally concave to match the contour of an iliac auricular boney surface or to match the contour of an extra-articular region of an ilium (e.g., an iliac tuberosity). In one aspect, the lateral, iliac or second articular face of the implant 12 may be generally a surface negative of the articular surfaces 1016 of the extra-articular region 3007 and/or articular region 1044 of the ilium 1005.

Referring to FIGS. 54A-54E, in one embodiment the implant 9010 includes a first planar member 9012 extending a first top length of the implant and comprising a first planar top surface 9014 that extends between a first sacral side edge 9016 and a first ilium side edge 9018 that is opposite of and substantially parallel with the first sacral side edge, the side edges being substantially perpendicular to first planar top surface, the side edges extending the first top length of the implant and disposed a first thickness 9020 from a first bottom surface 9022 that is opposite the first planar top surface, the first planar top surface also extending between a substantially perpendicular proximal end edge 9024 and a tapered distal end edge 9026, the tapered distal edge including a sloped taper 9028 along the first thickness between the first planar top surface and the first bottom surface such that the first top length is shorter than a first bottom length that extends a length of the first bottom surface, the tapered distal edge also including an inward tapering 9030 of the side edges towards a distal end of the implant, the side edges including a taper 9032 at a proximal end of the implant such that the first thickness substantially linearly increases until the side edges meet with the proximal end edge.

The implant further includes a second planar member 9034 that is opposite the first planar member, the second planar member extending a second top length of the implant and comprising a second planar top surface 9036 that extends between a second sacral side edge 9038 and a second ilium side edge 9040 that is opposite of and substantially parallel with the second sacral side edge, the side edges being substantially perpendicular to the second planar top surface, the side edges extending the second top length of the implant and disposed a second thickness 9042 from a second bottom surface 9044 that is opposite the first planar top surface and opposed to the first bottom surface, the second planar top surface also extending between a substantially perpendicular proximal end edge 9046 and a tapered distal end edge 9048, the tapered distal edge including a sloped taper 9050 along the second thickness between the second planar top surface and the second bottom surface such that the second top length is shorter than a second bottom length that extends a length of the second bottom surface, the tapered distal edge also including an inward tapering 9052 of the side edges towards the distal end of the implant, the side edges including a taper 9054 at a proximal end of the implant such that the second thickness substantially linearly increases until the side edges meet with the proximal end edge.

The implant further includes a distal end member 9056 that couples the respective tapered distal end edges of the first planar member and the second planar member, the distal end member extending perpendicularly between the first planar member and the second planar member and including a distal front edge 9058, a proximal edge 9060 opposite the distal front edge, and a pair of distal end member side surfaces 9062 between the distal front edge and the proximal edge, the proximal edge including a width that is larger than a width of the distal front edge such that the pair of distal end member side surfaces tapers or narrows 9064 towards the distal front edge, the distal front edge including a distal most point 9066 that slopes toward each of the respective first planar top surface and the second planar top surface, the sloping of the distal front edge smoothly transitioning 9068 with the sloped taper between the first planar top surface and the first bottom surface as well as the sloped taper between the second planar top surface and the second bottom surface, the distal front edge and the proximal edge both defining radial curves 9069.

The implant further includes a proximal end member 9070 that couples the respective proximal end edges of the first planar member and the second planar member, the proximal end member including a proximal side 9072 that is in-line and parallel with the first and the second proximal end edge and a distal side 9074 that is opposite the proximal side, the distal side including a curve 9076 that is a mirror of the radial curve of the proximal edge of the distal end member, the proximal end member including an axial bore 9078 through the proximal end member, the proximal end member being slightly larger and including a similar shape to the axial bore, the axial bore being threaded and configured to mate with an implant insertion tool, wherein a bone graft or anchoring window 9080 is defined between the proximal edge of the distal end member and the distal side of the proximal end member, the window including a stadium shape that extends perpendicularly through a longitudinal axis of the implant, the window being adapted to receive bone graft or an anchoring element to anchor the implant to the articular surfaces.

In certain embodiments, the distal end member side edges and the proximal edge meet at a corner where the corner is perpendicular or rounded. Similarly, other meeting points between respective edges can be straight edges (e.g., perpendicular) or rounded.

In still other embodiments, among other figures, the first sacral side edge 9016 and the first ilium side edge 9018 taper inward from the proximal end 9024 to the distal end 9026 of the implant such that the first planar top surface 9014 and the second planar top surface 9016 defines a truncated isosceles triangle with the side edges forming sides of equal length.

While reference is made to the embodiment of the implant 9010 in FIGS. 54A-54E, the reference numerals are similarly applicable to the implant 9010 in FIGS. 55A-55E.

Figure 4:
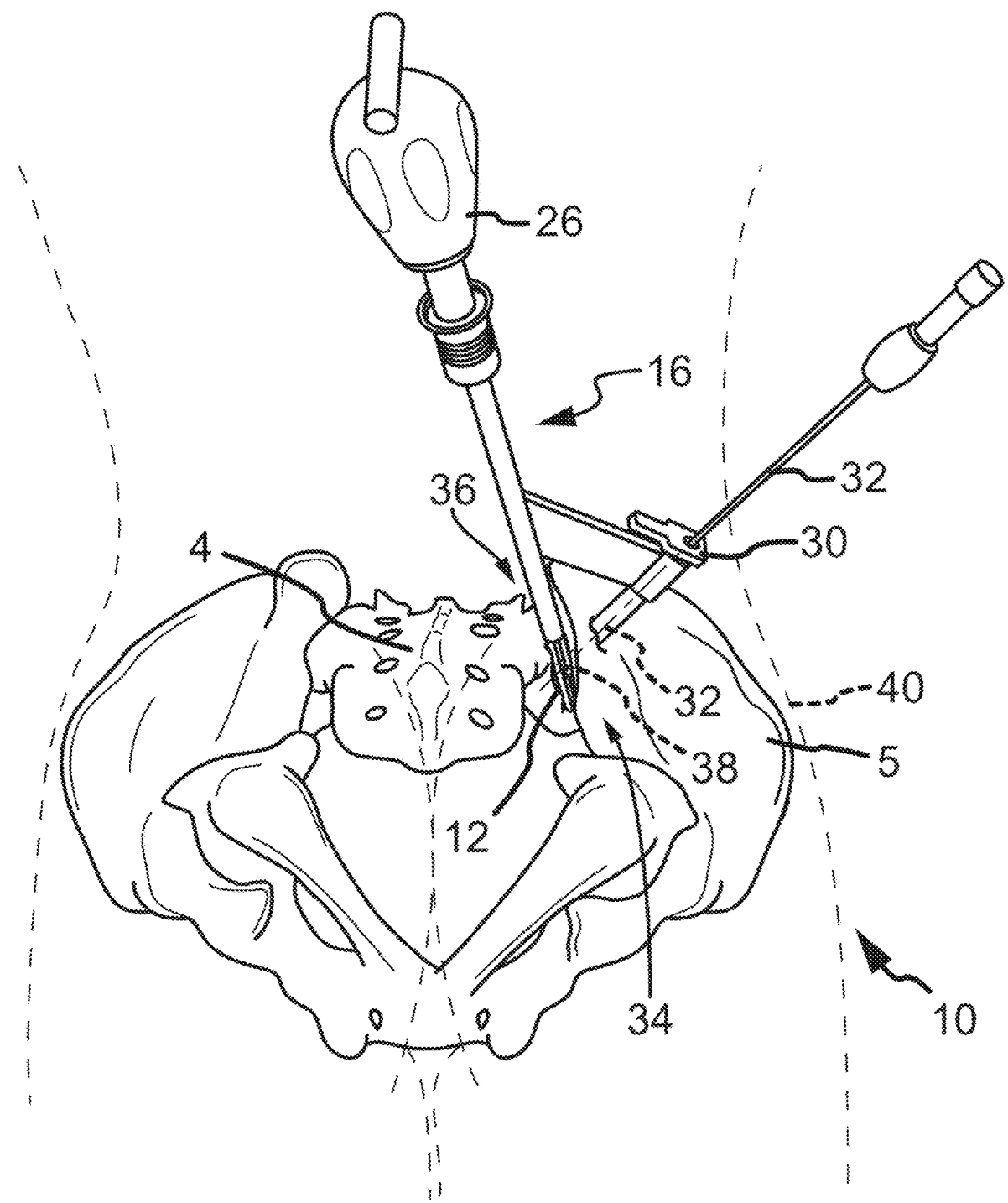
FIG. 4 is a posterior-inferior view of a sacroiliac joint with a patient body shown in broken line.
Figure 5:
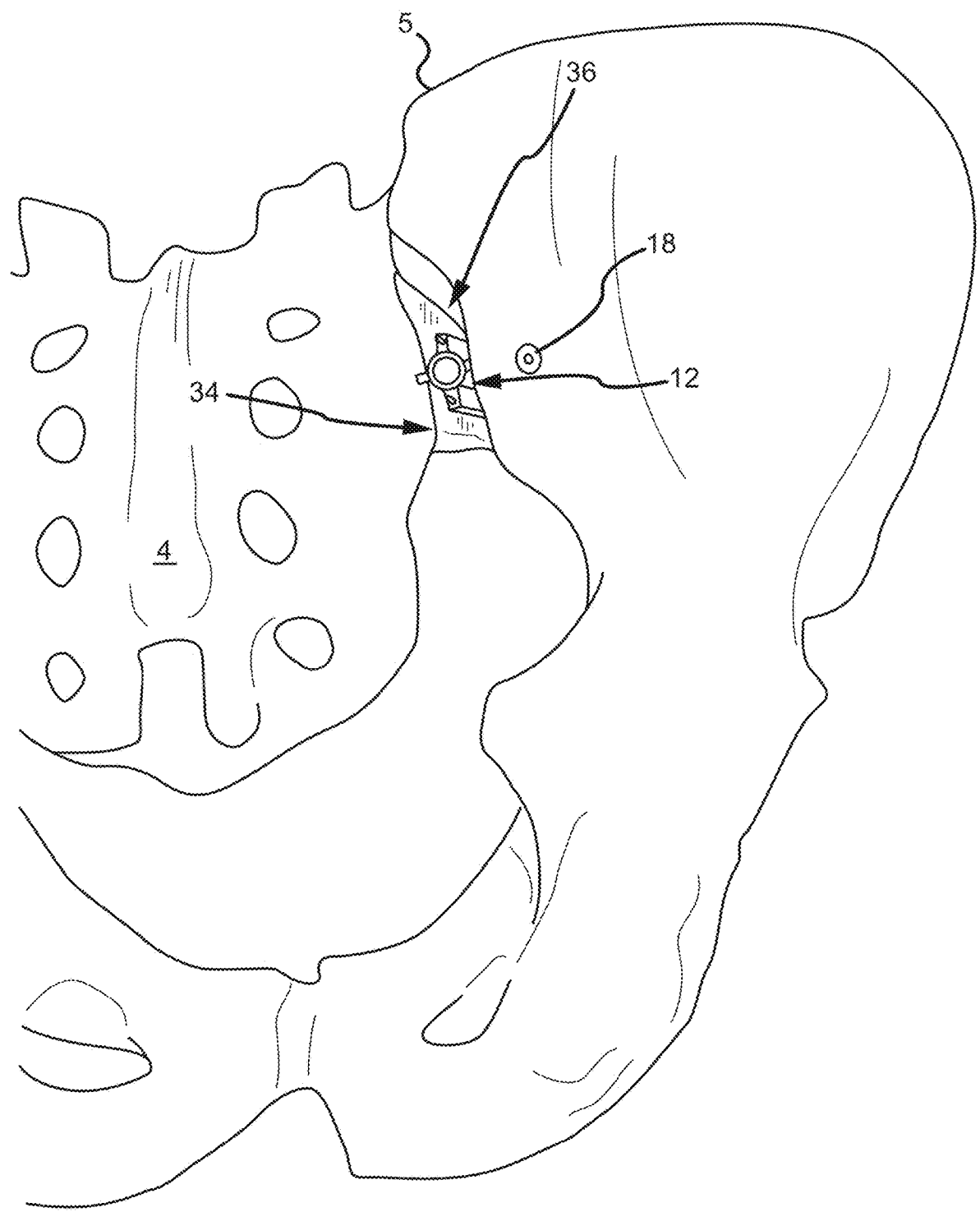
FIG. 5 is a close-up view of the implant and anchor element in the sacroiliac joint.

A system as described in FIGS. 2A-3 may be used in a surgical procedure via a posterior approach, as seen in FIGS. 4-5. As can be understood from FIG. 4, which is a posterior-inferior view of a sacroiliac joint 36 with a patient 40 shown in broken line, the delivery tool 16 is positioned to deliver the implant 12 into a caudal region 34 of the sacroiliac joint 36 and the anchoring element 18 through the ilium 5 and into the bore 38 of the implant 12. Referring to FIG. 5, the implant 12 and anchoring element 18 have been inserted into the caudal region 34 of the sacroiliac joint 36 and the delivery tool 16 has been removed.

Figure 48A:
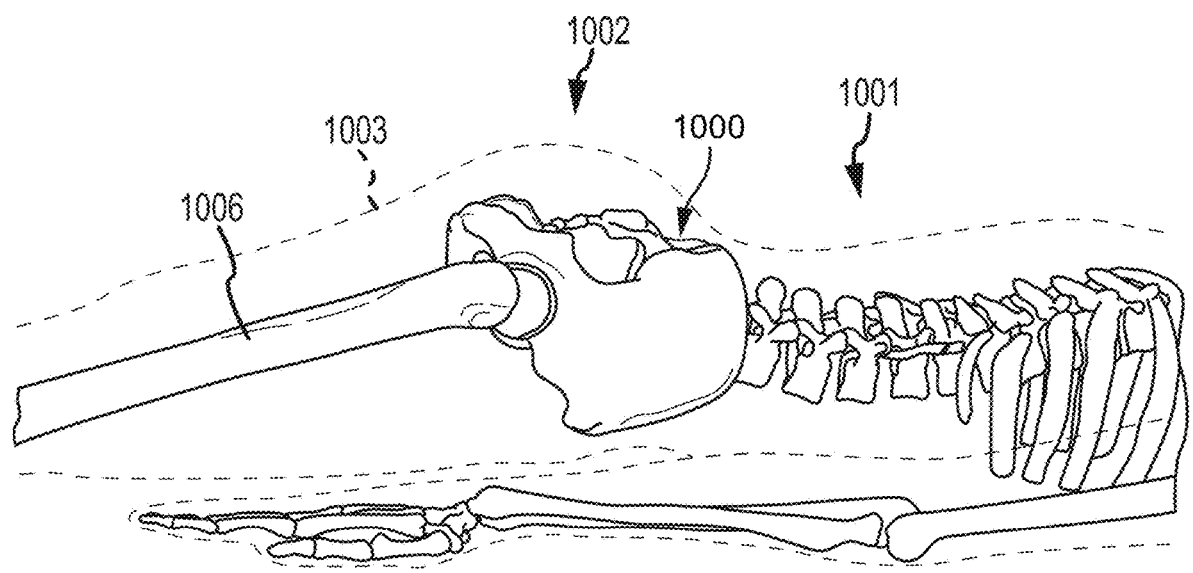
FIG. 48A is a right lateral view of a hip region of a patient lying in a prone position, wherein the soft tissue surrounding the skeletal structure of the patient is shown in dashed lines.
Figure 48B:
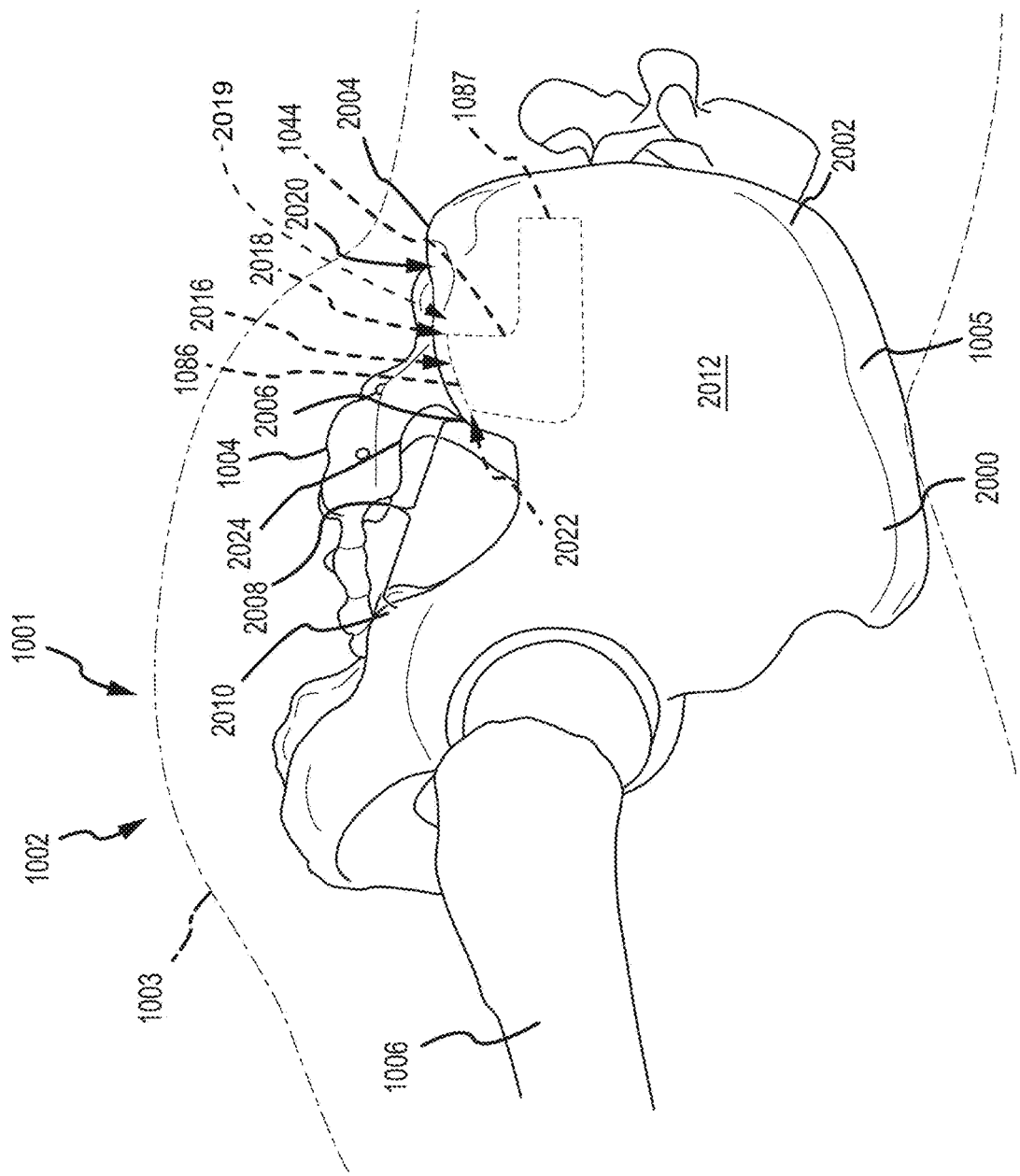
FIG. 48B is an enlarged view of the hip region of FIG. 48A.
Figure 48C:
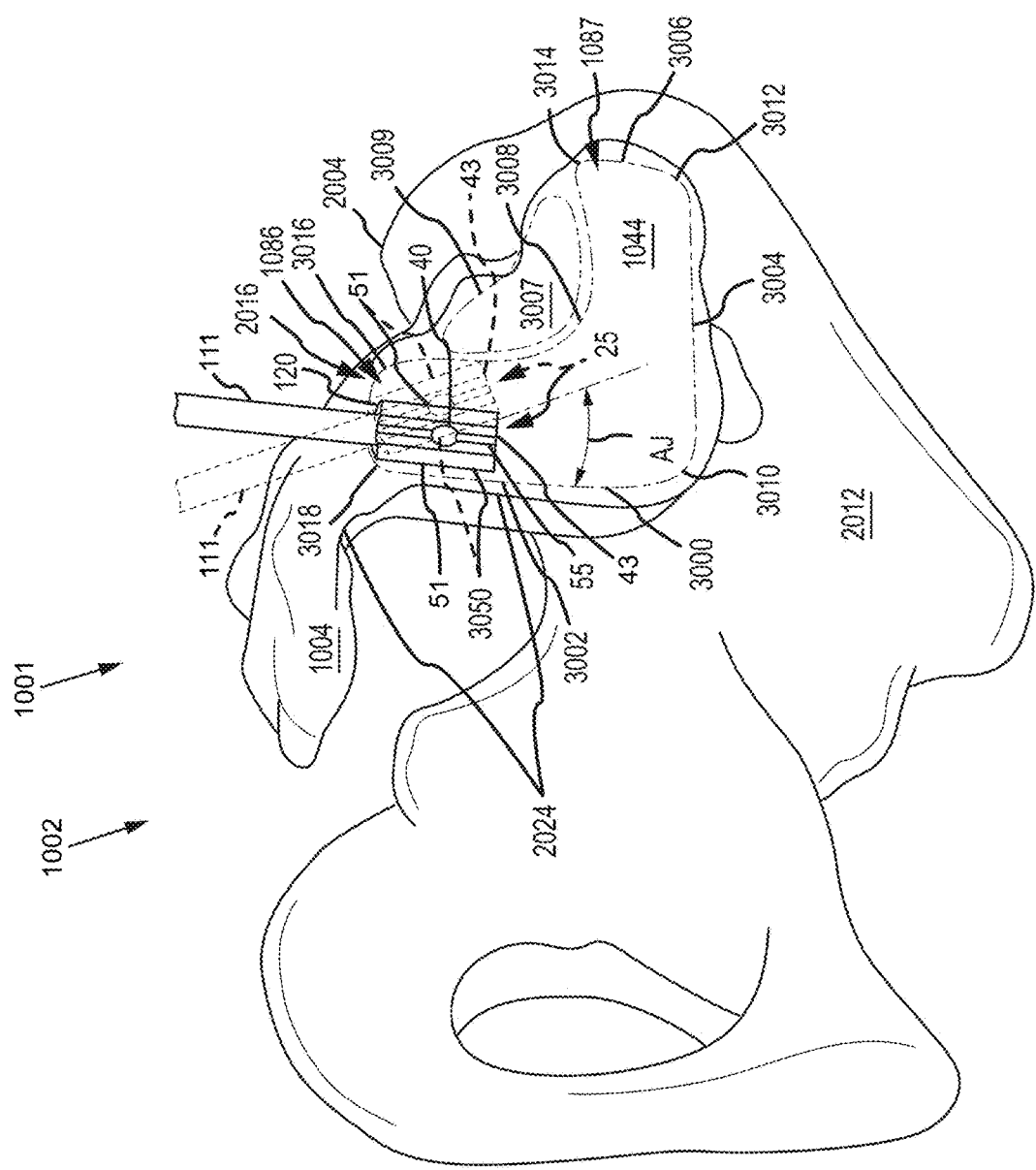
FIG. 48C is generally the same view as FIG. 48B, except that the ilium is removed to show the sacroiliac joint space boundary defined along the sacrum and an implant positioned for implantation within the joint space.

With further reference to the boney anatomy shown in FIG. 48C, a system as described herein may be used in a surgical procedure via an anterior approach (e.g., such that the surgical pathway includes traversing an anterior boundary segment 3004 and/or traversing an anterior-inferior corner 3010) and may further include positioning an implant into a sacroiliac joint such that: 1) the implant longitudinal axis a) is generally parallel to a sacroiliac joint inferior boundary segment 3002, or b) points towards a posterior superior iliac spine, or c) point towards a posterior inferior iliac spine, or d) points toward a sacroiliac extra-articular region; or, 2) the distal end of the implant generally lies within a) a caudal region of the sacroiliac joint articular region, or b) an extra-articular portion of the sacroiliac joint, or c) a cranial portion or cephalad region of the sacroiliac joint articular region.

Additionally, a system as described herein may be used in a surgical procedure via an approach which includes a surgical pathway which transverses a sacroiliac joint inferior boundary segment 3002, e.g., as described in U.S. patent application Ser. No. 13/945,053, filed Jul. 18, 2013, entitled SYSTEMS AND METHODS OF FUSING A SACROILIAC JOINT, which is hereby incorporated by reference in its entirety. A surgical procedure via this pathway may further include positioning an implant into a sacroiliac joint such that: 1) the implant longitudinal axis a) is transverse to a sacroiliac joint inferior boundary segment 3002, or b) points towards a posterior superior iliac spine, or c) point towards a posterior inferior iliac spine, or d) points toward a sacroiliac extra-articular region, or e) points towards a sacroiliac joint anterior boundary segment 3004, or f) points towards either superior boundary segment corner 3014 or 3012 or somewhere in-between; or, 2) the distal end of the implant generally lies within a) a caudal region of the sacroiliac joint articular region, or b) an extra-articular portion of the sacroiliac joint, or c) a cranial portion or cephalad region of the sacroiliac joint articular region.

Furthermore, in an aspect, an implant 12 may be inserted along a generally arcuate path. Accordingly, a surgical preparation technique and tools may be utilized while operating in an arcuate path. The implant arcuate path may follow and generally match the surgical preparation arcuate path and the path arc may include a radius of between approximately 3 cm to 6 cm. The portion of the path having an arcuate path including a radius of between approximately 3 cm to 6 cm may reside substantially in the plane of the sacroiliac joint or in a plane in close proximity and generally parallel thereto. Furthermore, the arcuate path may generally or substantially reside in sacroiliac joint articular region 1044. Additionally, an implant may be selected for use during the procedure which substantially matches the radius or curvature of the arcuate or curved insertion path or surgical preparation path.

According to a particular aspect, after drilling or otherwise producing an opening through an ilium (or sacrum) leading toward or into a sacroiliac joint, a sleeve may guide (alone or along with another cannulated tool, e.g., a needle) a bone paste, bone marrow aspirate, stem cells, allograft or any biocompatible material or substance into the sacroiliac joint space via a path with a trajectory which may be generally transverse to the plane of the sacroiliac joint. The sleeve may be caused to form a seal with a bone defining the sacroiliac joint, e.g. the ilium. The seal may be created by impacting a proximal end of sleeve which may, for example, cause the sleeve to slightly penetrate the cortex of the outer table of the ilium. Alternatively, a cannulated tool such as a large gauge needle or tube may either be interference fit within a hole in the ilium or the needle or tube may have a threaded distal end which may be threaded into the bore formed in the ilium. A plunger or bone tamp may be forced through a sleeve to advance the bone paste or other material into the sacroiliac joint space, adjacent/around the implant and/or into the bone graft window of the implant.

Subsequently, an anchor such as a bone screw may be advanced via the sleeve into engagement with an opening formed in the ilium and driven across the sacroiliac joint and further into the sacrum. Alternatively, a bone plug may positioned into the opening formed in the ilium in order to occlude the passageway between the outer cortex of the ilium and the implanted bone paste or other material positioned which had be positioned generally in the plane of the joint.

As such, the systems and methods described herein are directed to preparing the sacroiliac joint for surgical fusion procedures of this type and others.

II. System for Preparing the Sacroiliac Joint for Fusion

Various surgical preparation tools and assemblies will be discussed herein. These tools and assemblies may be used by themselves or in combination with each other. Additionally, features of a particular embodiment are non-limiting and may be incorporated into any or all other embodiments without departing from the teachings in this disclosure.

A. Joint Preparation Tool with Interchangeable Heads

Figure 6:
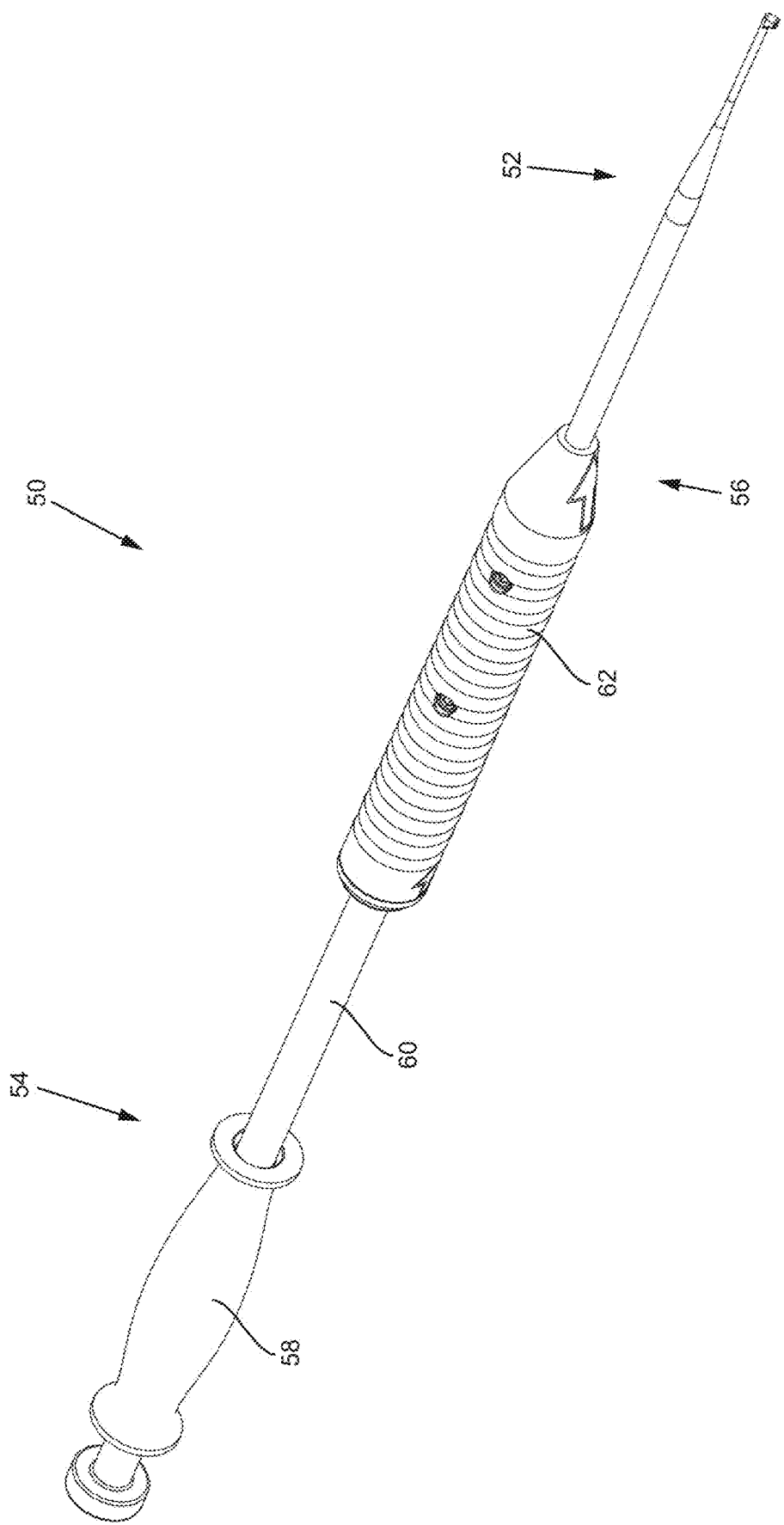
FIG. 6 is an isometric view of a first embodiment of a joint preparation tool.
Figure 7:
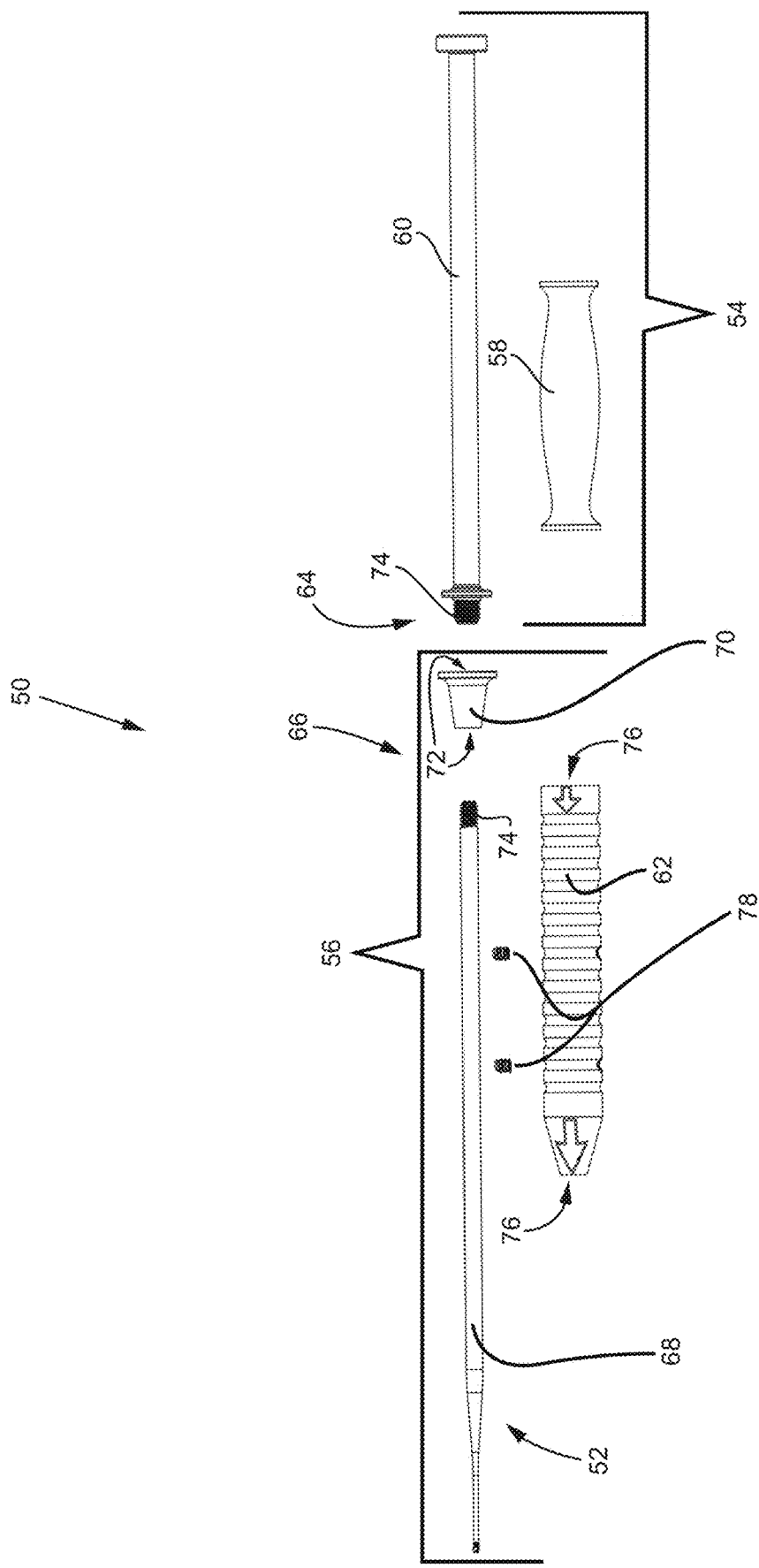
FIG. 7 is an exploded side view of the first embodiment of the joint preparation tool.

To begin a detailed discussion of the surgical preparation tools for preparing a sacroiliac joint for a fusion, reference is made to FIG. 6, which is an isometric view of a first embodiment of a joint preparation tool 50 with interchangeable tooling heads 52. Each of the tooling heads 52 described herein may be used by themselves, with one or more subcomponents of tool 50, with the completed tool 50, or with any other tool of the systems disclosed herein or incorporated herein. As seen in the figure, the joint preparation tool 50 includes a slap hammer assembly 54 and a cutting tool assembly 56. The slap hammer assembly 54 includes a proximal handle 58 that translates distal-proximal on a shaft 60. The cutting tool assembly 56 includes a distal handle 62. To better illustrate the components of the joint preparation tool 50, reference is made to FIG. 7, which is an exploded side view of the tool 50. As seen in the figure, a distal end 64 of the shaft 60 of the slap hammer assembly 54 is coupled to a proximal end 66 of a shaft 68 of the tooling head 52 via a connector 70 having dual-female threaded ports 72. The distal end 64 of the shaft 60 and the proximal end 66 of the shaft 68 have thread features 74 that correspond and engage with the dual-female threaded ports 72. In other embodiments, the connector 70 may include dual-male threaded ends and the shafts 60, 68 may include corresponding female threaded ports. The distal handle 62 includes a lumen 76 extending through the handle 62 that is slightly larger than an outer diameter of the shaft 68 of the tooling head 52. The distal handle 62 may be slidably positioned over the shaft 68 of the tooling head 52 and locked in place with a pair of set screws 78. Thus, the distal handle 62 may be positioned as far proximally such that it abuts the connector 70, as far distally so as not to interfere with the distal end of the tooling head 52, or at any point in between.

Figure 8:
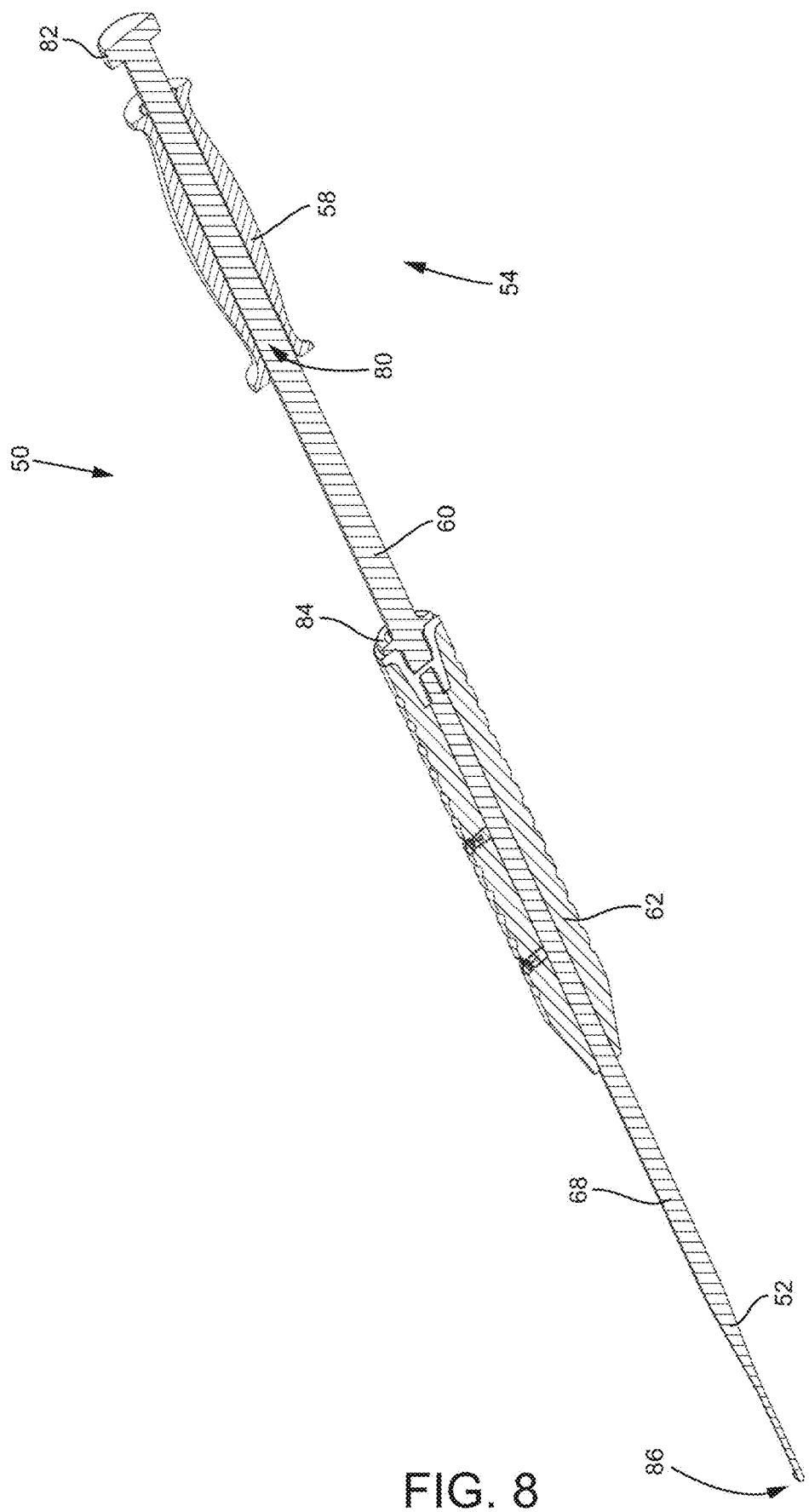
FIG. 8 is an isometric and cross-sectional view of the first embodiment of the joint preparation tool.

Reference is now made to FIG. 8, which is an isometric and cross-sectional view of the first embodiment of the joint preparation tool 50. As seen in the figure, the proximal handle 58 further includes a lumen 80 extending through the handle 58 that is slightly larger than an outer diameter of the shaft 60 of the slap hammer assembly 54. The proximal handle 58 is configured to slide or translate distal-proximal on the shaft 60 between a proximal stop feature 82 and a distal stop feature 84. In this way, a surgeon may grasp the distal handle 62 with one hand and the proximal handle 58 with the other hand. To facilitate distal driving of the tooling head 52, the surgeon may distally slide the proximal handle until it makes contact with the distal stop feature 84. The contact with the stop feature 84 will cause a force to be transmitted down the shaft 68 of the tooling head 52 such that head 52 will advance in the direction of the force. This type of driving of the tooling head 52 may be useful to advance a distal end 86 of the tooling head 52 into the sacroiliac joint.

Additionally, the proximal stop feature 82 may be configured such that an additional handle may be coupled to or integral with proximal stop feature 82. The additional handle may be in-line with shaft 60 and extend proximally from the proximal stop feature 82.

To facilitate backing-out of the tooling head 52, the surgeon may proximally slide the proximal handle until it makes contact with the proximal stop feature 82. This contact will cause a force to be transmitted proximally, which may aid in backing the tooling head 52 out from within the sacroiliac joint, for example.

As stated above, the first embodiment of the joint preparation tool 50 is configured to be used with a variety of interchangeable tooling heads 52. In certain embodiments and referring to FIGS. 9A-9B, the tooling head 52 may include a cutting element 88 at the distal end 86 of the tooling head 52. The cutting element 88 includes an aperture 90 at a distal most end of the tooling head 52 that extends between a distal edge 92 and a proximal edge 94. The distal edge 92 forms a boundary of the aperture 90 and, in this embodiment, the distal edge 92 is blunt. Opposite the distal edge 92 is the proximal edge 94, which, in this embodiment, is angled, sharp, and configured for cutting during "backing-out" of the preparation tool 50 from the sacroiliac joint.

In this embodiment, the aperture 90 is rectangular and is defined by a pair of generally parallel sidewall members 102 that extend generally tangentially from the surface of the shaft 68 of the tooling head 52. Adjacent and extending generally perpendicular between the parallel sidewall members 102 is a top wall member 104. Opposite the top wall member 104 is an inner wall member 106 that may communicate with an opened end of a lumen 108 that extends through the shaft 68 of the tooling head 52. Additional tooling (e.g., guidewire, suctioning device, irrigation, a (centerless/shaftless/flexible/etc.) screw conveyor, an auger, Archimedes' screw, or their various combinations) may communicate through the lumen 108 for interaction with the portion of the patient's body in contact with the distal end 86 of the tooling head 52.

A tooling head 52 with a cutting element 88 as described in FIGS. 9A-9B may be useful, for example, during the initial preparations of the sacroiliac joint. That is, the cutting element 88 may be initially and carefully advanced into the sacroiliac joint via the slap hammer assembly 54. Once at an appropriate depth into the caudal region of the joint, the cutting element 88 may be more aggressively backed-out by the application of force by the proximal handle 58 against the proximal stop feature 82. In this way, the force used to cut the articular cartilage is applied in the safer, proximal direction. Applying force distally requires care because advancement of the cutting element 88 too far (i.e., outside of the sacroiliac joint) can risk damage to, for example, the ventral sacroiliac joint ligament or the neurovascular structures in proximity to the joint.

Figure 10:
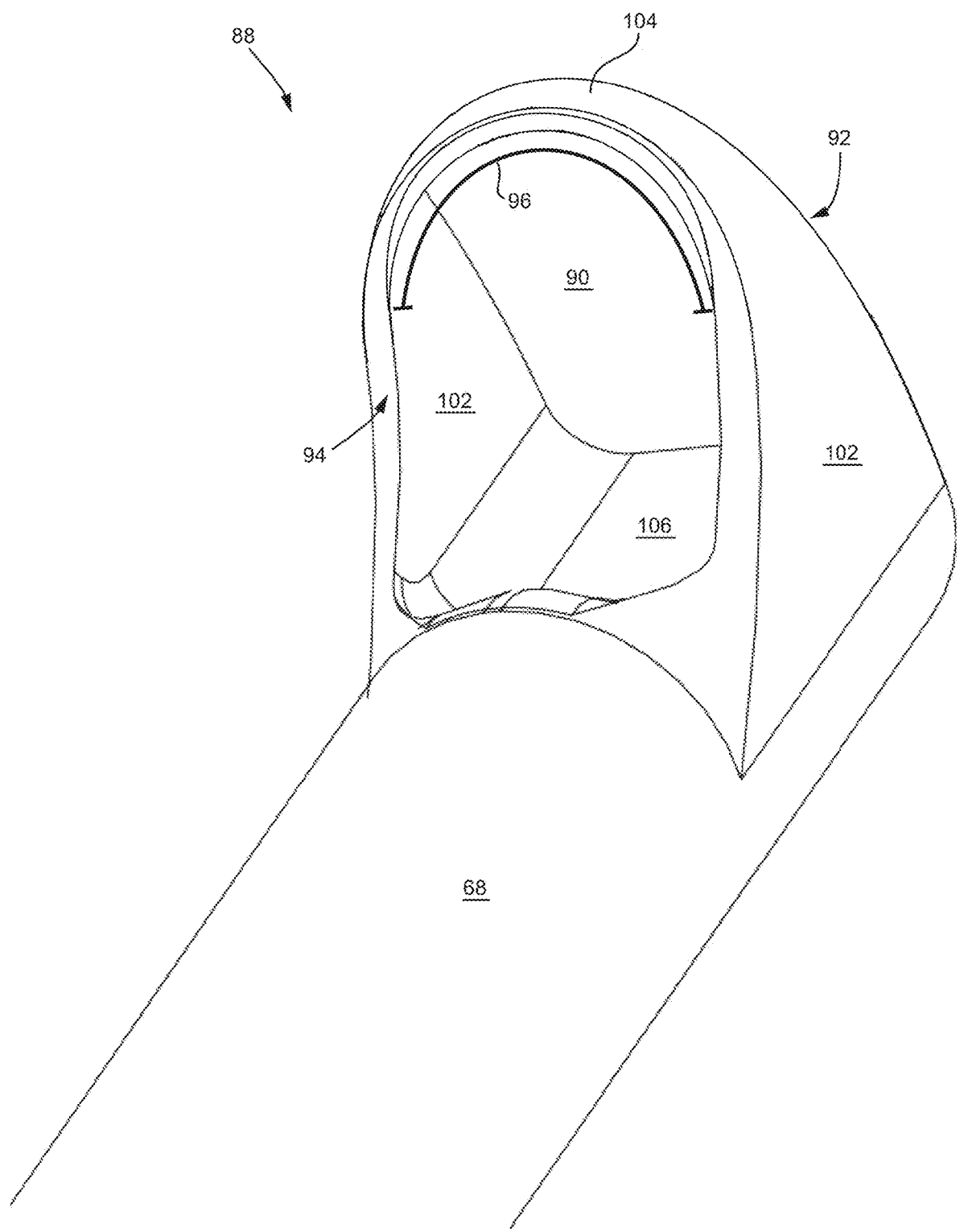
FIG. 10 is an isometric view of the proximal edge of the cutting element.

Other arrangements of the cutting element 88 are possible and contemplated by this disclosure. For example, the distal edge 92 may be sharp and configured for cutting, while the proximal edge 94 may be blunt. Additionally and as seen in FIG. 10, which is an isometric view of the proximal edge 94 of the cutting element 88, the side wall members 102 are parallel, but the top wall member 104 and, thus, the distal edge, 92, the proximal edge 94, and the aperture 90 are rounded. As seen in the figure, the proximal edge 94 is sharpened along its radial edge 96 and is configured to cut during a "backing-out" of the cutting element 88.

Other arrangements of the top wall member 104 and side wall members 102 are possible. For example, the side wall members 102 may converge to a blade-like point. The particular arrangement of the top wall member 104 and side wall members 102 may be chosen based on the density of the boney surface to be prepared. And, as will be discussed later, the tool 50 may be used oriented perpendicular to the articular surfaces of the sacroiliac joint in order to make "keel-cuts" into the bone of either or both of the sacrum or the ilium. Such keel-cuts may match or generally match a shape of an implant to be implanted into the joint. Alternatively, the keel-cuts may be sized smaller than portions of an implant to be implanted into the joint such that a portion of the implant when implanted may extend beyond the keel-cut void and further into the prepared bone. Alternatively, a keel-cut may be created in only one bone, for example, the ilium, and may generally match the shape of an implant to be implanted while the second bone, e.g., the sacrum, may have no keel-cut or a keel-cut which is significantly undersized in comparison to the shape or size of the feature of the implant which is to be implanted into the sacrum. Thus, the shape of the top wall member 104 and the side wall members 102 may be influenced by the type and configuration of the implant that is chosen for the fusion procedure.

Figure 12:
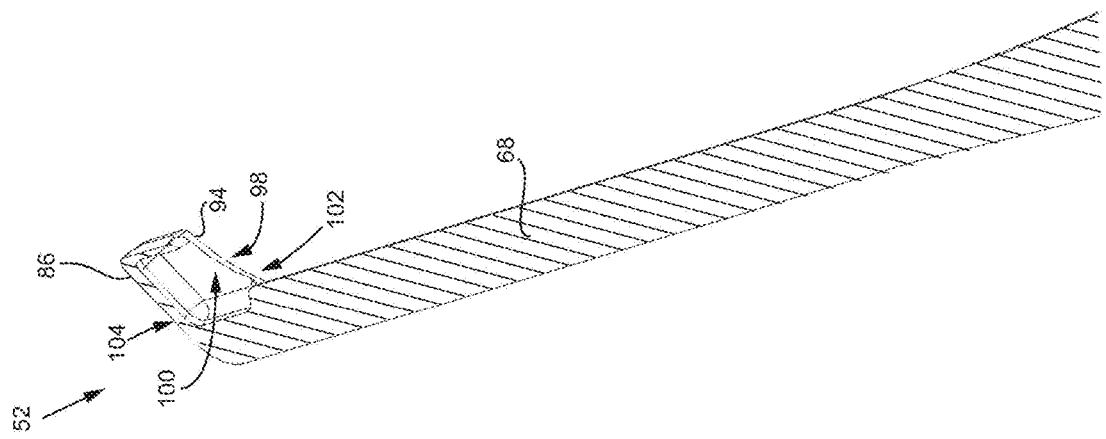
FIG. 12 is an isometric and cross-sectional view of the tooling head of FIG. 11.
Figure 11:
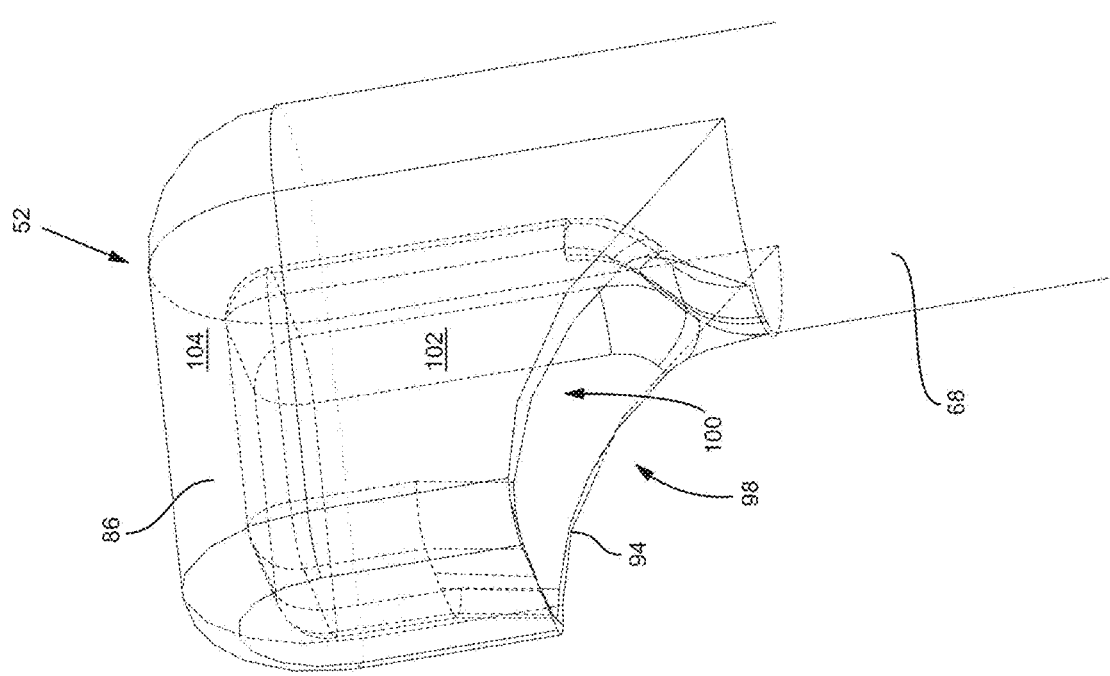
FIG. 11 is an isometric view of a tooling head with a closed distal end and an opened proximal end.

Referring now to FIG. 11, which is an isometric view of another embodiment of a tooling head 52, the head 52 may include a curette-type closed distal end 86 and an opened proximal end 98 that defines a cup-shape. The tooling head 52 may include a pair of generally parallel side wall members 102 and a rounded top wall member 104. A proximal edge 94 bounds the opened proximal end 98 and may or may not be sharpened. As best seen in FIG. 12, which is an isometric and cross-sectional view of the tooling head 52, the tooling head 52 defines an inner cavity 100 that is configured to gather cartilage or other material when scooping or backing the distal end 86 of the tooling head 52 out of the sacroiliac joint. While not depicted in this embodiment, the tooling head 52 may include an opening in the vicinity of the cavity 100 that communicates with a lumen that extends through the shaft 68 of the tooling head 52. In certain instances, it may be advantageous to use the cup-shaped tooling head 52 of FIGS. 11-12 to gather and remove biological material that was cut or abraded from the articular surfaces of the sacroiliac joint by the opened tooling head 52 of FIGS. 9-10. In other instances, however, the closed tooling head 52 of FIGS. 11-12 may be used without previous preparation of the joint.

Figure 13:
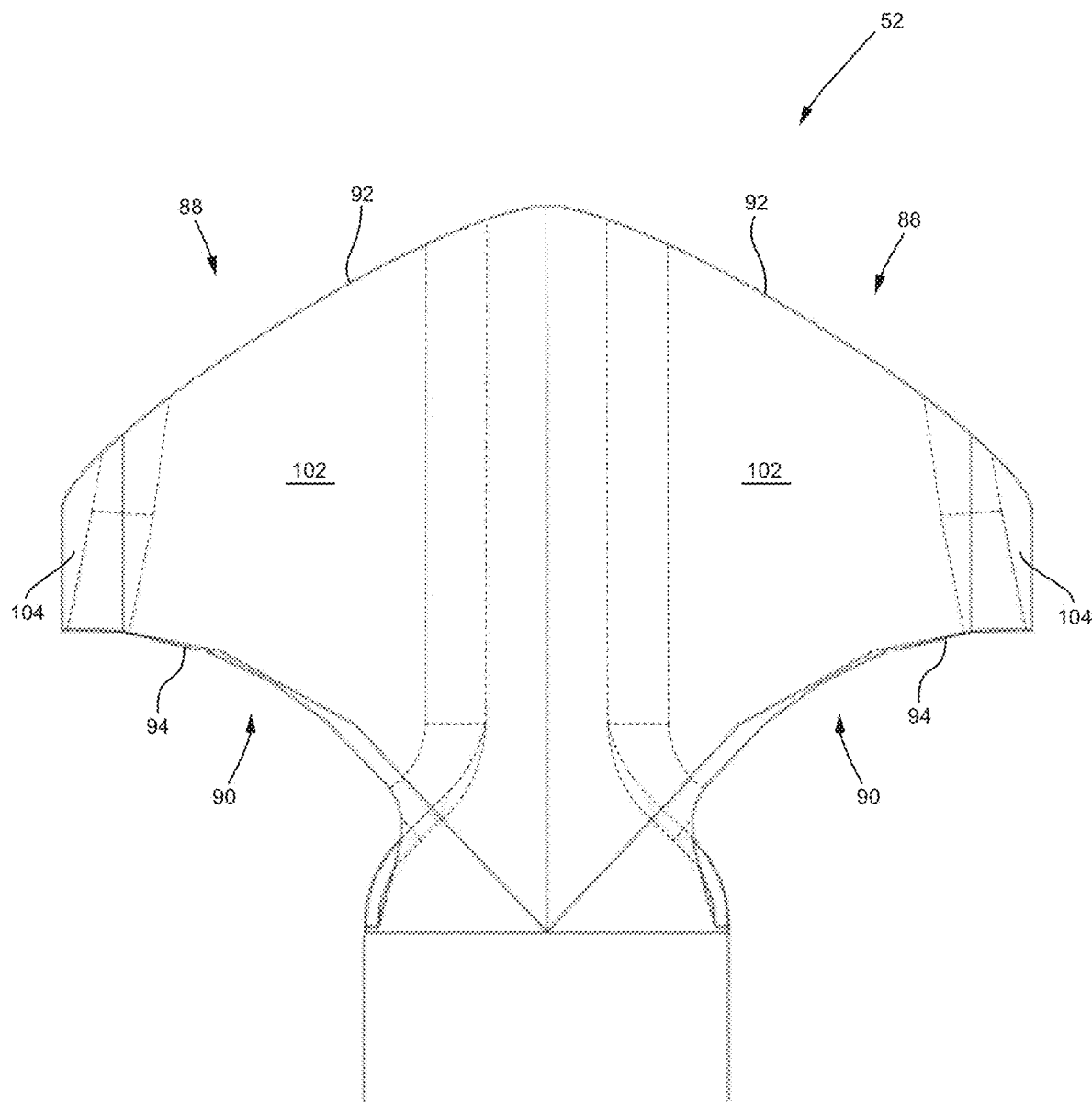
FIG. 13 is a side view of a tooling head with a pair of cutting elements opposite each other.
Figures 15C, 15D:
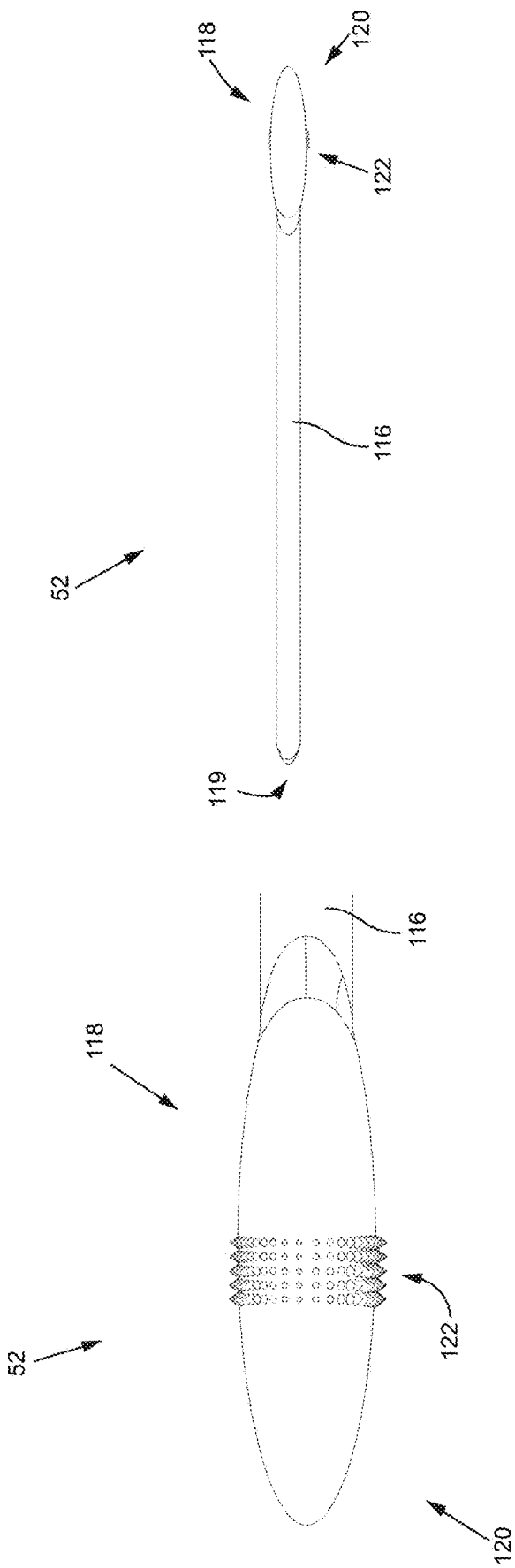
FIG. 15C is a close-up side view of the tooling head with the ellipsoidal head.
FIG. 15D is another side view of the tooling head with the ellipsoidal head.

Referring now to FIG. 13, which is a side view of another embodiment of the tooling head 52, the head 52 may include two cutting elements 88 opposite each other. Each cutting element 88 may be as described with reference to FIGS. 9A-9B, FIG. 10 or FIGS. 11-12. In particular, each cutting element 88 includes parallel side wall members 102, a top wall member 104 extending generally perpendicular between the parallel side wall members 102, a distal edge 92, a proximal edge 94 opposite the distal edge 92, and an aperture 90 extending between the distal and proximal edges 92, 94. In this embodiment, the distal edge 92 is blunt and the proximal edge 94 is sharpened such that the tooling head 52 is configured to cut or abrade cartilage or other material in the sacroiliac joint during backing-out of the tooling head 52 from the joint. An arrangement with two cutting elements as shown in FIG. 13 may be useful, for example, to prepare the plane of the joint as well as in making parallel side-cuts or keel-cuts into the surfaces of the ilium and sacrum. To prepare the plane of the joint, each of the cutting elements 88 may be oriented such that neither projects into the sacrum or the ilium. Rather, the cutting elements 88 are oriented vertically within the articular space. On the other hand, to prepare the sacrum and/or the ilium for a subsequent delivery of an implant, the cutting elements 88 may be oriented to project into the bone of the sacrum and ilium, and for example oriented perpendicularly with the plane of the joint such that the cutting elements protrude generally perpendicularly into the sacrum and the ilium to make cuts that match a shape of a portion of an implant that will be implanted in the joint.

Referring to FIG. 14A, which is a side view of a tooling head 52, the shaft 68 may include a gradual taper from the proximal end 66 of the tooling head 52 to the distal end 86. As seen in the figure, the shaft 68 extends along a straight longitudinal axis between the distal and proximal ends 86, 66. Other arrangements of the shaft 68, however, are possible. For example and as seen in FIG. 14A, the shaft 68 may include a dogleg 110 along the shaft 68. In this example, the distal and proximal ends 86, 66 of the shaft 68 extend along parallel axes, but a mid-portion 112 of the shaft 68 extends non-parallel to the distal and proximal ends 86, 66. The dogleg 110 at the mid-portion 112 of the shaft 68 defines an angle A between the proximal end 66 and the dogleg 110 and an angle B between the dogleg 110 and the distal end 86 of the shaft 68. Also, the proximal end 66 and distal end 86 may be offset by a distance D1, which, in certain instances, may be within a range of about 10 mm to about 25 mm or from about 15 mm to 70 mm. In certain embodiments, angle A may be within a range of about 90 degrees to about 165 degrees or from about 120 degrees and 150 degrees, and angle B may be within a range of about 90 degrees to about 165 degrees or from about 120 degrees and 150 degrees.

Referring to FIG. 14B, which is a close-up of the distal end 86 of the tooling head 52, a distance D2 is defined between the top wall member 104 and an opposite radial edge 114 of the shaft 68 of the tooling head 52. In certain instances, distance D2 may be within a range of about 4 mm to about 5.5 mm, from about 4.5 mm to about 6 mm, from about 5 mm to about 6.5 mm, from about 5.5 mm to about 8 mm, from about 7.5 mm to about 10 mm, from about 9 mm to about 11.5 mm and from about 11 mm to about 15 mm. A distance D3 is defined by a length of the top wall member and in certain instances D3 may be within a range of about 1.5 mm to about 2.5 mm, from about 2 mm to about 3.5 mm, from about 3 mm to about 4.75 mm, from about 4.25 mm to about 6 mm, from about 5 mm to about 6.75 mm, from about 5.5 mm to about 8 mm, from about 7.5 mm to about 10 mm, from about 9 mm to about 11.5 mm and from about 11 mm to about 15 mm. Angle C is defined between the shaft 68 of the tooling head 52 and the extension of the proximal edge 94 of the side wall member 102. In certain instances, angle C may be within a range of about 15 degrees to about 35 degrees, from about 30 degrees to about 45 degrees, from about 40 degrees to about 65 degrees, from about 60 degrees to about 75 degrees, from about 70 degrees to about 100 degrees, from about 90 degrees to about 135 degrees, from about 120 degrees to about 155 degrees, from about 150 degrees to about 170 degrees, from about 160 degrees to about 175 degrees, and from about 170 degrees to about 180 degrees (e.g., substantially in-line with shaft 68).

As stated above, the first embodiment of the joint preparation tool 50 is configured to be used with a variety of interchangeable tooling heads 52. Additionally, the tooling heads 52 may be used independently from the joint preparation tool 50. In certain embodiments and referring to FIGS. 15A-15D, the tooling head 52 may include an elongate shaft 116 coupled with an ellipsoidal head 118 at a distal end 120 of the tooling head 52. A proximal end 119 of the tooling head 52 may include threading (not shown) in order to couple with the connector 70 of the joint preparation tool 50 described previously. In this embodiment, the ellipsoidal head 118 is a triaxial ellipsoid shape (semi-axes lengths C>B>A), however, the head 118 may be other shapes without departing from the teachings of this disclosure. As seen in the figures, the ellipsoid head 118 includes a rasp band 122 around one half of the circumference of the ellipsoid head 118. The rasp band 122 may include a rough surface texture, or geometrically repeating or non-repeating pattern that is configured to abrade a boney surface of a patient (e.g., articular surface of the sacroiliac joint). In this particular embodiment, the rasp band 122 is a repeating cone-shaped pattern that is in the plane AB but is bounded on one side by axis A. While no rasp band 122 is depicted on the opposite side of the ellipsoid head 118, such a side may include a similar or different type of rasp band 122. For example, a less rough or "less aggressive" rasp band 122 may be included on the side opposite of the current rasp band 122 or simply on one half of the currently depicted rasp band 122. In this way, the tooling head 52 may be used to simultaneously rasp two surfaces with different rasp bands 122. In practice, such a tooling head 52 may be used to abrade the surfaces of the sacrum and the ilium in preparation for delivery of a joint implant. Since the sacrum is generally a softer bone than the ilium, the sacrum may require less abrasion than the ilium. Thus, the tooling head 52 with the ellipsoid head 118 having rasp bands 122 of differing roughness on opposite sides of the head 118 may be beneficial to rasp the ilium with a rasp band 122 having greater roughness and the sacrum with a rasp band 122 having less or no roughness.

Reference is now made to FIGS. 16-17, which are isometric views of tooling heads 52 with bisected ellipsoidal heads 124 and bisected shafts 126. The bisected ellipsoidal head 124 includes an ellipsoid shaped surface 128 on one side and a planar surface 130 opposite the ellipsoid shaped surface 128. The planar surface 130 extends a length of the shaft 126 from a distal end to a proximal end 120, 119. In FIG. 16, the bisected ellipsoidal head 124 includes a small rasp band 132 on a portion of the intersection of the planar surface 130 and the ellipsoidal shaped surface 128. In this embodiment, the small rasp band 132 includes a single row of teeth or other geometrically repeating pattern; however, the small rasp band 132 may include other surfaces configured to abrade or rasp a surface. In FIG. 17, the bisected ellipsoidal head 124 includes a rasp band 134 that is similar to that as described in FIGS. 15A-15D. That is, the rasp band 134 wraps around the entirety of the ellipsoid shaped surface 128 and includes a rough surface texture, or geometrically repeating or non-repeating pattern that is configured to abrade a boney surface of a patient (e.g., articular surface of sacroiliac joint). This type of tooling head 52 may be useful, for example, when a single surface of a pair of opposed surfaces requires rasping. As such, the tooling head 52 may be used, for example, to rasp the ilium only while orienting the planar surface 130 generally parallel with a plane defined by the sacrum. Alternatively, the tooling head 52 may be oriented to rasp the sacrum while orienting the planar surface 130 in-line with the ilium.

Moving on, the discussion will focus on FIGS. 18-23 and additional types and configurations of tooling heads 52 that are applicable for use with the joint preparation tool 50. Additionally and as discussed previously, the tooling heads 52 discussed herein may also be used independently from the joint preparation tool 50.

Reference is now made to FIGS. 18A-18D, which depict a tooling head 52 with a planar rasping head 136 at a distal end 138. The planar rasping head 136 is configured to prepare a joint or boney surface for subsequent delivery of an implant. More particularly, the planar rasping head 136 may be used to abrade or roughen a joint surface, such as the sacroiliac joint, by removing cartilage from the joint and causing the boney surface of the sacrum and the ilium to hemorrhage, which may contribute to subsequent bone growth and fusion of the sacrum and the ilium.

As seen in the FIGS. 18A-18B, the planar rasping head 136 is coupled to a shaft 140 that extends to a handle 142 at a proximal end 144 of the shaft 140. A proximal end 146 of the handle 142 includes an impact plate 148 that is configured to be struck with a hammer, mallet, or other device in order to drive the planar rasping head 136 distally. While this embodiment is depicted with a handle 142 attached to the proximal end 144 of the shaft 140, the shaft 140 could, alternatively, be coupled to the connector 70 of the joint preparation tool 50 described previously.

As seen FIGS. 18A-18D, the planar rasping head 136 is a planar member that includes a pair of planar surfaces 150 opposite of and generally parallel to each other. Alternatively, the pair of planar surfaces 150 may be non-parallel (not shown) and may taper. The planar surfaces 150 are disposed between a side edge 152 that wraps around the planar rasping head 136. A distal tip 158 of the planar rasping head 136 is rounded, although, in other embodiments, the distal tip may be pointed, flat, or otherwise. The planar rasping head 136 includes a rasping surface 154 on the planar surfaces 150 and the side edge 152. The rasping surface 154 may include ridges 156 in a chevron pattern, as seen in the figures, or other surfaces configured to roughen or abrade a biological surface. The rasping surface 154 may, for example, include geometrically repeating or non-repeating features (e.g., cones, pyramids, bubbles, spines, notches, teeth) formed by machining, surface treating, or otherwise.

As seen in FIG. 18A, the planar rasping head 136 may include a width W18 in a range of about 13 mm to about 19 mm. In certain instances, the width W18 may be 13 mm, 16 mm, or 19 mm. As seen in FIG. 18B, the planar rasping head 136 may include a thickness T18 between the planar surfaces 150 in a range of about 5 mm to about 7 mm. In certain instances, the thickness T18 may be 5 mm, 6 mm, or 7 mm.

Moving on, reference is made to FIGS. 19A-19D, which depict a tooling head 52 with a planar rasping head 160 at a distal end 162 of the tooling head 52 that includes a single perpendicularly extending cutting element 164. The planar rasping head 160 is a planar member that includes a planar top surface 166, a planar bottom surface 168 opposite the top surface 166, and a side edge 186 extending between the top and bottom surfaces 166, 168. The distal end 162 of the rasping head 160 includes a double chamfered tip 184. Both the top and bottom surfaces 166, 168 and the side edge 168 include a rasping surface 170 that is configured to abrade or roughen a boney surface or a joint. The rasping surface 170 may include a series of ridges 172 in a chevron pattern or otherwise, as described previously. The tooling head of this embodiment may also include a handle 142, an impact plate 148, and a shaft 140, among other features, as described in previous embodiments.

As seen in the figures, the cutting element 164 extends generally perpendicularly upward from a central portion of the top surface 166. The cutting element 164 is a planar member with opposite side surfaces 174 and a top surface 176 that includes a cutting element feature 178, which, in this embodiment, includes a series of teeth 180 with a rounded blade-tip 182 at the distal most end. The planar rasping head 136 is configured to prepare a joint or boney surface for subsequent delivery of an implant. More particularly, the bottom surface 168 of the planar rasping head 136 may be used to abrade or roughen a joint surface, such as the sacroiliac joint, by removing cartilage from the joint and causing the boney surface of the sacrum and the ilium to hemorrhage, which may contribute to subsequent bone growth within the joint space. The top surface 166 with the cutting element 164, on the other hand, may be used to cut into either the sacrum or the ilium in order to make way for a portion of an implant (e.g., keel or wing member) that will protrude into the bone of the sacrum or ilium. As previously described with reference to FIG. 5, an implant may include keels that extend generally perpendicularly into each of the ilium and the sacrum. Thus, a tooling head 52 such as seen in FIGS. 19A-19D may be useful in preparing a "keel-cut" into either or both of the sacrum or ilium such that when the implant 12 is delivered into the sacroiliac joint, the keels may be delivered and positioned within the keel-cuts made by the tooling head 52 with the planar rasping head 160 with the perpendicularly extending cutting element 164. While the tooling head 52 is described with a single perpendicularly extending cutting element 164, the head 52 may include a second cutting element (not shown) extending opposite the first cutting element 164 on the bottom surface 168 of the rasping head 160. In this way, the tooling head 52 may perform dual keel-cuts simultaneously in both the sacrum and the ilium. In such an embodiment, the cutting element feature 178 may be different for each cutting element 164 since the ilium is a generally harder bone than the sacrum, which is generally softer.

As seen in FIG. 19A, the planar rasping head 160 may include a width W19 in a range of about 11 mm to about 17 mm. In certain instances, the width W19 may be 11 mm, 14 mm, or 17 mm. Also seen in FIG. 19A, the cutting element 164 may include a thickness T19A of about 2.5 mm. As seen in FIG. 19B, the planar rasping head 160 may include a thickness T19B between the planar surfaces 166, 168 in a range of about 5 mm to about 7 mm. In certain instances, the thickness T19B may be 5 mm, 6 mm, or 7 mm. Also as seen in FIG. 19B, the planar rasping head 160 and the cutting element 164 may have a combined thickness TC19B in a range of about 5.5 mm to about 7.5 mm. In certain instances, the combined thickness TC19B may be about 5.5 mm, 6.5 mm, or 7.5 mm.

Moving on, reference is made to FIGS. 20A-20C, which depict a tooling head 52 with a planar rasping head 160 at a distal end 162 of the tooling head 52 that includes a single perpendicularly extending cutting element 164. This embodiment includes similar features to the tooling head 52 described in reference to FIGS. 19A-19D, except that the present embodiment includes a smooth surface 188 instead of a rasping surface on the top surface, bottom surface, and side edges 166, 168, 186. The present embodiment of the tooling head 52 may be useful in a surgical preparation when the articular surfaces of the sacroiliac joint need not be rasped, but merely require keel-cuts into the sacrum and/or the ilium in preparation for delivery of an implant.

Reference is now made to FIGS. 21A-21C, which depict a tooling head 52 with a planar rasping head 190 with a pair of perpendicularly extending cutting elements 192 extending from side edges 194 of the head 52. In this embodiment, the planar rasping head 190 is a planar member that includes a planar top surface 196, a planar bottom surface 198 opposite the top surface 196, both of which include a smooth surface texture 200. The planar rasping head 190 also includes a double chamfered tip 202 at a distal end 204 of the rasping head 190. Tip 202 may terminate distally in-line with the chamfered tip of cutting element 216. Alternatively, tip 202 may extend a distance distally beyond the distal most portion of the chamfered tip of cutting element 216, for example, said distance may be from about 1.5 mm to about 2.5 mm, from about 2 mm to about 3.5 mm, from about 3 mm to about 4.75 mm, from about 4.25 mm to about 6 mm, from about 5 mm to about 6.75 mm, from about 5.5 mm to about 8 mm, from about 7.5 mm to about 10 mm, from about 9 mm to about 11.5 mm and from about 11 mm to about 15 mm which may permit placement of a tip 202 within the plane of the joint thereby aligning cutting elements 192 to project toward or into the bone of the sacrum or ilium. Each of the cutting elements 192 includes an inner surface 206 that faces the smooth surface texture 200, an outer surface 208 opposite the inner surface 206 that is smooth and lies flush with the side edge 194, and a top surface 210 that includes a cutting element feature 212 that includes a series of teeth 214. A distal end of the cutting elements 192 includes a chamfered tip 216. Additionally, the tooling head 52 of the present embodiment may have similar features as described in the previous embodiments. The dimensions of the present embodiment may be similar to that as described in reference to FIGS. 19A-19D.

Such a tooling head 52 with a pair of cutting elements 192 may be used to perform dual keel-cuts in either or both of the ilium and sacrum for delivery of an implant with dual keels such as described in U.S. patent application Ser. No. 14/447,612, filed Jul. 31, 2014 and entitled SYSTEMS FOR AND METHODS OF FUSING A SACROILIAC JOINT, which is hereby incorporated by reference in its entirety. To prepare the sacroiliac joint for delivery of a dual keel implant, the tooling head 52 with the pair of cutting elements 192 may be inserted into the sacroiliac joint of a patient with the cutting elements oriented towards the ilium, for example, and the tooling head 52 may be advanced distally in the caudal region of the joint such that the cutting elements 192 cut into the boney surface of the ilium. Once at a far end of the caudal region, the tooling head 52 may be proximally withdrawn and repeated if desired. After sufficiently cutting into the ilium, the tooling head 52 may be withdrawn from the joint. Next, the tooling head 52 may be rotated one hundred and eighty degrees such that the cutting elements are oriented towards the sacrum. The tooling head 52 may then be advanced into the sacroiliac joint and make keel-cuts into the sacrum as described previously with reference to the ilium. Once the tooling head 52 is removed from the joint, the implant may then be delivered into the joint such that the implant keels are positioned within the keel-cuts made with the cutting elements 192 of the tooling head 52.

Continuing on, reference is made to FIGS. 22A-22D, which depict a tooling head 52 with a planar rasping head 190 at a distal end 204 of the tooling head 52 that includes a pair of perpendicularly extending cutting element 192. This embodiment includes similar features to the tooling head 52 described in reference to FIGS. 21A-21C, except that the present embodiment includes a rasping surface 218 instead of a smooth surface on the top and bottom surface 196, 198 of the rasping head 190. The rasping surface 218 may be as described previously and may include a series of ridges 220 in a chevron pattern. A planar rasping head 190 of this embodiment may be useful for simultaneously rasping the intra-articulating surfaces of the sacroiliac joint to remove cartilage or abrade the boney surfaces and make dual keel-cuts into either the sacrum or the ilium for the subsequent delivery of an implant having similarly featured keels.

Reference is now made to FIGS. 23A-23D, which depict a tooling head 52 with a box osteotome head 222. As seen in the figures, the box osteotome head 222 includes a planar top member 224, a planar bottom member 226 generally parallel to and opposite of the planar top member 224, a pair of side members 228 that extend generally perpendicularly between the top and bottom members 224, 226, and a pair of coaxially aligned openings 230 in the top and bottom members 224, 226. In this embodiment, the openings 230 are bounded by four edges 236; however, the configuration of the openings 230 may include a different number of edges 236 and shapes. The box osteotome head 222 defines a cavity 232 therein that is bounded by inner surfaces 242 of the top, bottom, and side members 224, 226, 228. The cavity 232 is open on a distal end 234 of the box osteotome head 222. A distal edge of the distal end 234 of each of the top, bottom, and side members 224, 226, 228 form a curved cutting edge 238 that includes an inward bevel 240 such that outer surfaces 244 of the members 224, 226, 228 extend further distally than the inner surfaces 242.

As seen in the figures, the tooling head 52 additionally includes a shaft 246 that is four-sided, a handle 248 coupled to a proximal end 250 of the shaft 246, and an impact plate 252 at a proximal end 254 of the handle 248. The tooling head 52 of this embodiment may additionally include features as described in the previous embodiments without limitation.

The box osteotome head 222 may be useful in a surgical procedure where a section of bone or cartilage is to be removed. The box osteotome head 222 may be distally advanced into the sacroiliac joint and bone and/or cartilage in contact with the cutting edge 238 will be cut and urged via the inward bevel 240 within the cavity 232. After an appropriate cut has been made, the box osteotome head 222 may be proximally removed from the joint space and the biological material within the cavity 232 may be removed through one or both of the coaxially aligned openings 230 in the top and bottom members 224, 226. The box osteotome head 222 may be used with the joint preparation tool 50, as described previously, or independently.

As seen in FIG. 23A, the box osteotome head 222 may include a width W23 in a range of about 13 mm to about 19 mm. In certain instances, the width W23 may be 13 mm, 16 mm, or 19 mm. As seen in FIG. 23B, the box osteotome head 222 may include a thickness T23 between the outer surfaces 244 of the top and bottom members 224, 226 in a range of about 5 mm to about 7 mm. In certain instances, the thickness T23 may be 5 mm, 6 mm, or 7 mm.

With reference to FIG. 23C, the shape of cavity 232 may generally match the shape of the implant which may be subsequently implanted into the void created by the head 222. In certain aspects, the cross sectional shape and dimensions of the cavity 232 may substantially match the corresponding cross sectional shape and dimensions of the implant to be implanted at the joint in the void created by head 222.

B. Joint Preparation Tool with Anchoring Arm

Figure 24A:
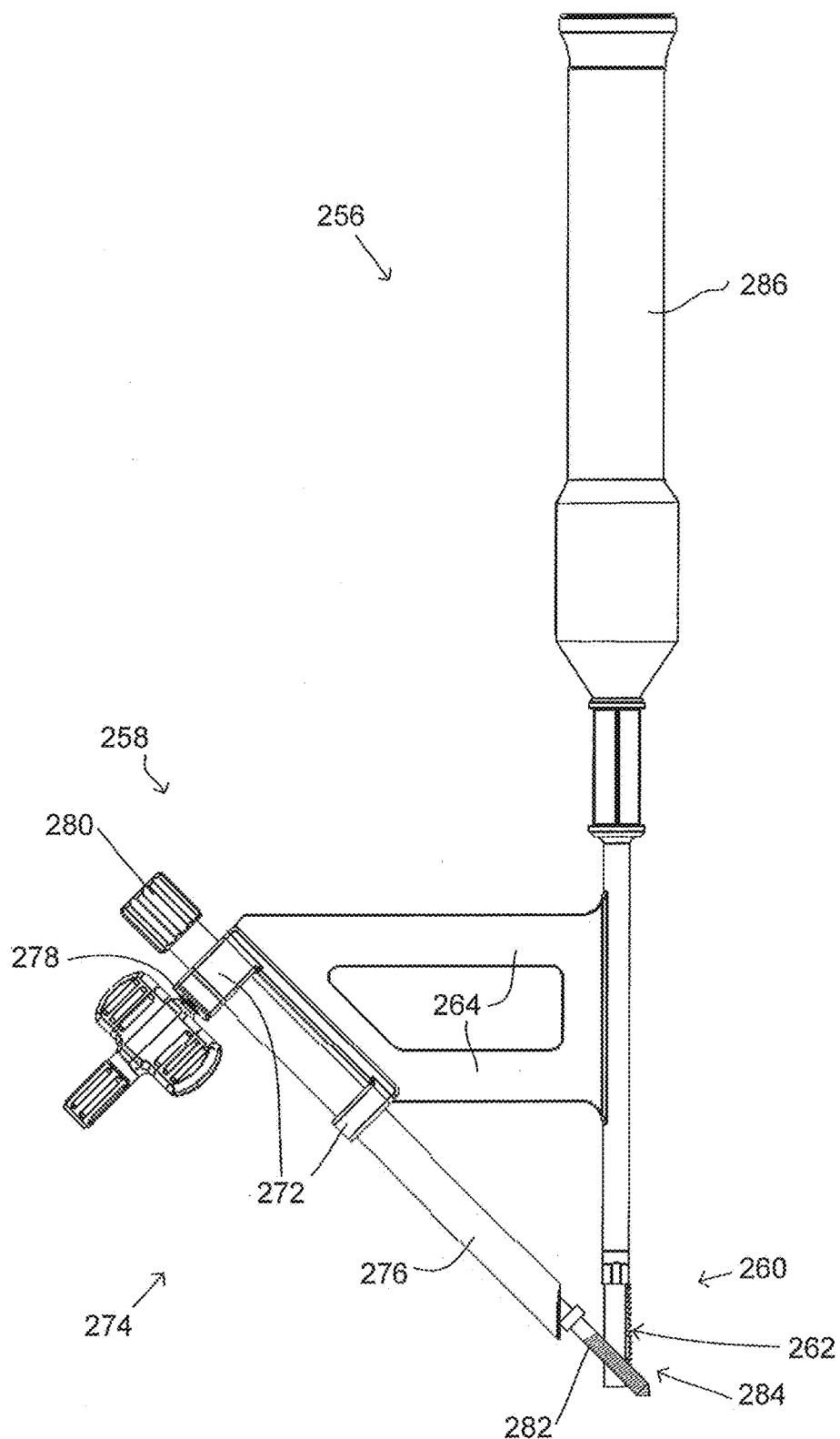
FIG. 24A is a side view of a surgical preparation tool attached to an anchor arm assembly.

Reference is now made to FIG. 24A, which is a side view of a first embodiment of a joint preparation tool 256 attached to an anchoring arm assembly 258. The anchoring arm assembly 258 may be similar to as described in U.S. patent application Ser. No. 14/447,612, mentioned previously, and hereby incorporated by reference in its entirety. The joint preparation tool 256 may be similar to those described previously and may include a tooling head 260 as also described previously. As seen in FIG. 24A, the tooling head 260 includes a rasping head 284 with a pair of perpendicularly extending cutting elements 262 extending from side edges of the head 260. The tooling head 260 is attached to a handle 286 at a proximal end of the tool 256. Regarding the anchoring arm assembly 258, it includes an extension member 264 that extends from the joint preparation tool 256. A distal portion of the extension member 264 includes a pair of guide collars 272 that are configured to securely support and position an anchoring tool 274. The anchoring tool 274 includes a tubular shaft 276 that is secured within the guide collars 272 via a set screw 278. The anchoring tool 274 further includes a rotationally engaged handle 280 at a proximal end of the tool 274 that is configured to rotationally extend and retract an anchoring element 282 that is coupled to a distal portion of the tool 274. The anchoring arm assembly 258 is configured to orient the anchoring element 282 in a single orientation relative to the rasping head 284. That is, the anchoring arm assembly 258 or, more particularly, the orientation of the guide collars 272 relative to the rasping head 284 is fixed and nonadjustable once the anchoring arm assembly 258 is affixed to the joint preparation tool. In this and other embodiments, the orientation of the anchoring element 282 may be such that, when delivered into the joint space, the anchoring element 282 will be positioned cranial (above) to the rasping head 284, caudal (below) to the rasping head 284, or in-line with and distally of the rasping head 284.

Figure 24B:
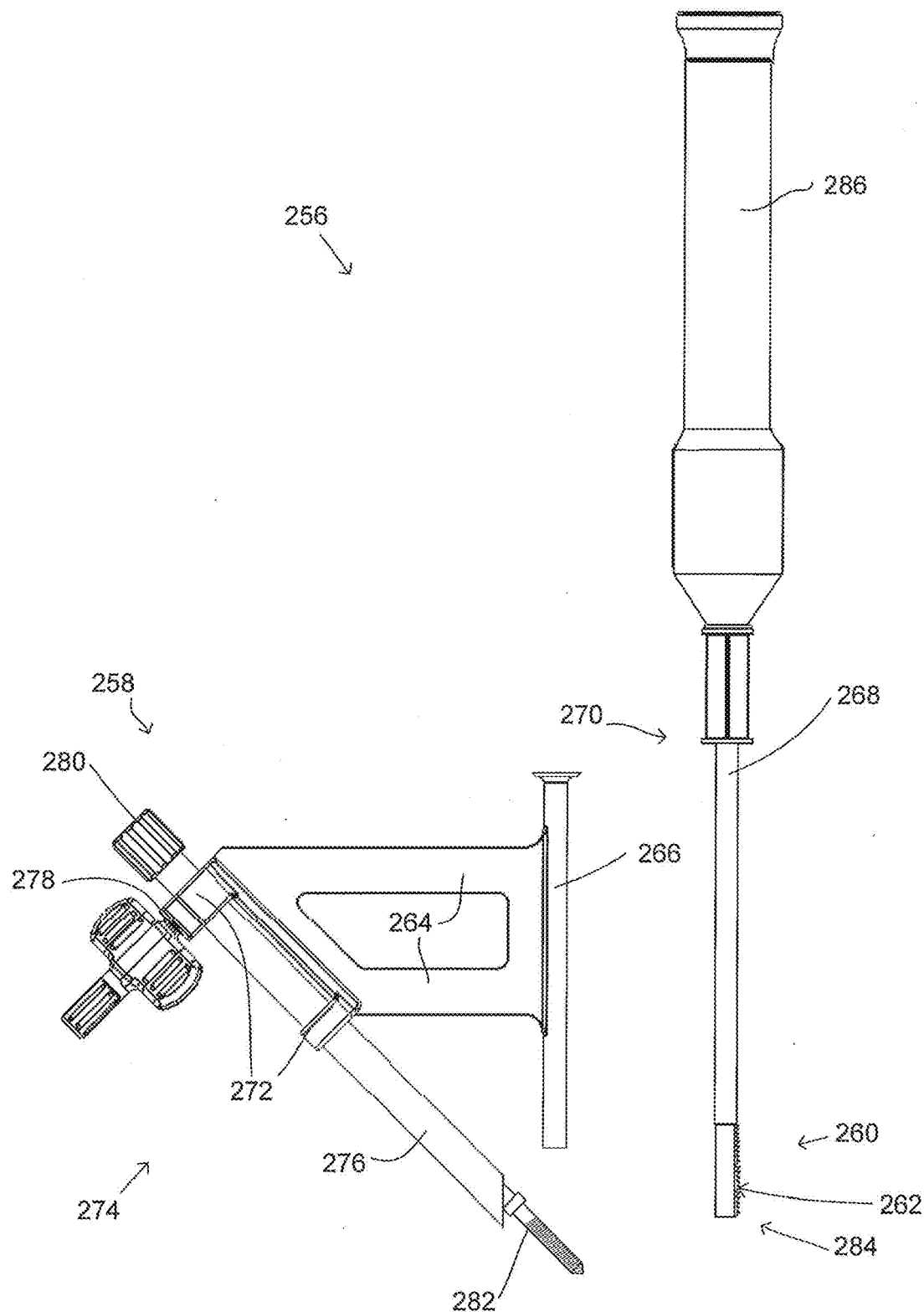
FIG. 24B is a side view of the surgical preparation tool and the anchor arm assembly of FIG. 24A in a pre-assembled state.

Turning to FIG. 24B, reference is made to a pre-assembled state of the joint preparation tool 256 and the anchoring arm assembly 258. As seen in the figure, the extension member 264 is coupled to and extends from a sleeve 266 that includes a lumen extending therethrough. The sleeve 266 is configured to receive a shaft 268 of the joint preparation tool 256 through the lumen. The sleeve 266 may be secured to the joint preparation tool 256 by any type of fastening mechanism such as, for example, corresponding threading on the sleeve 266 and a proximal portion 270 of the shaft 268 of the tool 256. The rasping head 284 may be fixed to the shaft 268 of the joint preparation tool 256 or the head 284 may be releasably coupled to the shaft 268.

Figure 25:
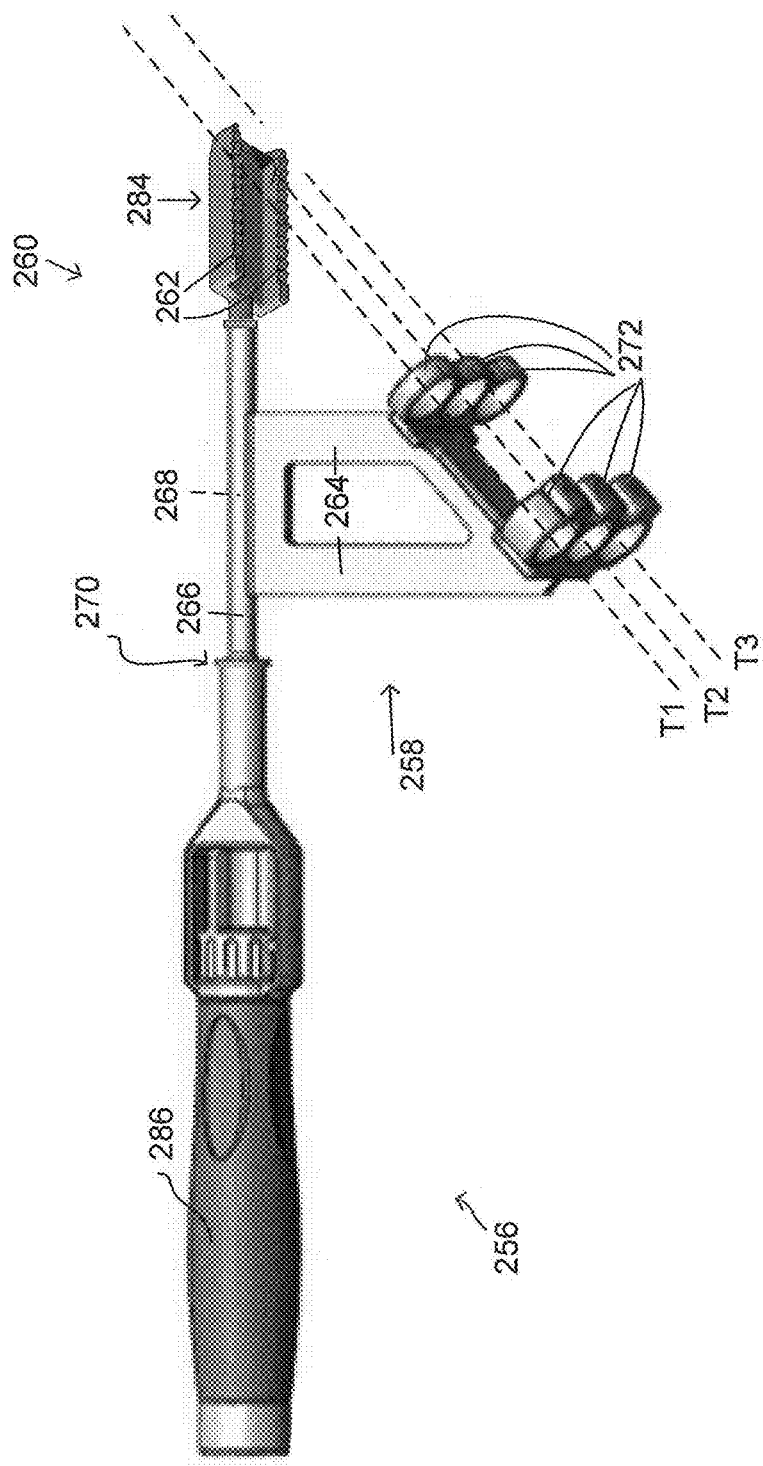
FIG. 25 is a side view of another surgical preparation tool attached to an anchor arm assembly.

Moving on to another embodiment of a joint preparation tool 256 attached to an anchoring arm assembly 258, reference is made to FIG. 25. The joint preparation tool 256 is identical to the tool 256 of FIGS. 24A-24B. The anchoring arm assembly 258 of the present embodiment is similar to the assembly 258 in FIGS. 24A-24B, except that the assembly 258 in the present embodiment includes a trio of guide collars 272. Each guide collar 272 is configured to orient a tool (not shown) in a specific trajectory T1, T2, T3 relative to the rasping head 284 of the joint preparation tool 256. T1 may, for example, orient an anchoring tool, as described previously, to deliver an anchor element cranial to the rasping head 284. T2 may, for example, orient an anchoring tool to deliver an anchor element distally, in-line with the rasping head 284. T3 may, for example, orient an anchoring tool to deliver an anchor element caudal to the rasping head 284. T2 may alternatively orient an anchoring tool to deliver an anchor element in-line with and towards a central portion of the rasping head 284. In such an orientation, the rasping head may include an opening (not shown) on its planar surface that extends proximally from a distal edge of the rasping head 284 such that the rasping head 284 is pronged or fork-shaped. While the anchoring arm assembly 258 is described as coupling to an anchoring tool that delivers an anchoring element that may be a screw, the assembly 258 may couple with other types of tools. For example, the guide collars 272 may couple with a syringe barrel that delivers a bone paste or other biomaterial into the joint space to facilitate fusion of the boney surfaces of the joint.

While the anchor arm assemblies 258 of the various embodiments are described with reference to a joint preparation tool with a shaft attached with a handle at a proximal end of the tool, the anchor arm assemblies 258 may be used with other embodiments of the joint preparation tool. For example, the anchor arm assemblies 258 may be coupled with the joint preparation tool 50 with the slap hammer assembly 54 as described previously.

In another aspect, for example as shown and described in U.S. Provisional Patent Application 61/860,185, the anchor arm assembly 258 may be provided in the form of two or more linked structural elements thereby providing an adjustable elongate shape. For example, anchor arm assembly 258 may be telescoping and may include a first section ending in the first arm end and a second section ending in the second arm end; both sections may have matched circular arc shapes with a common center.

Figure 56A:
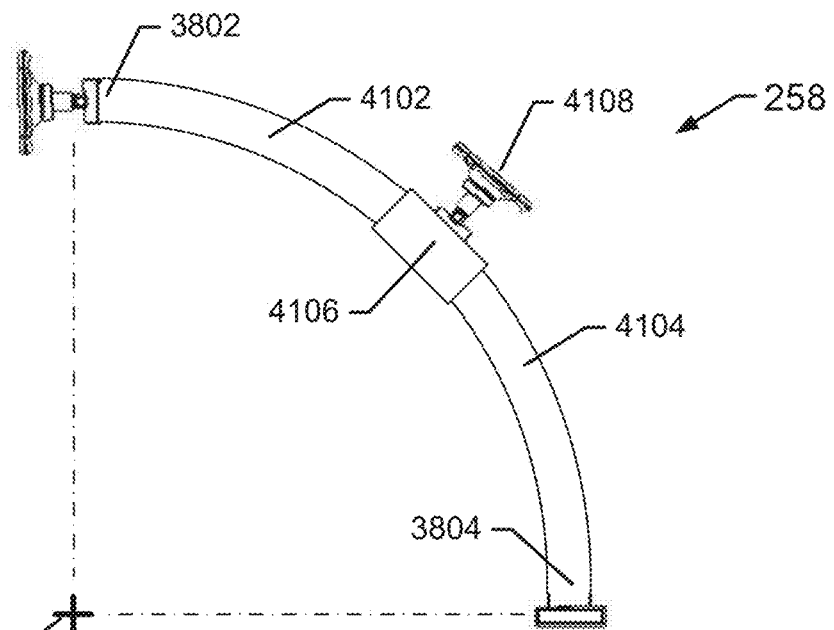
FIG. 56A is a side view of a telescoping anchor arm assembly.
Figure 56B:
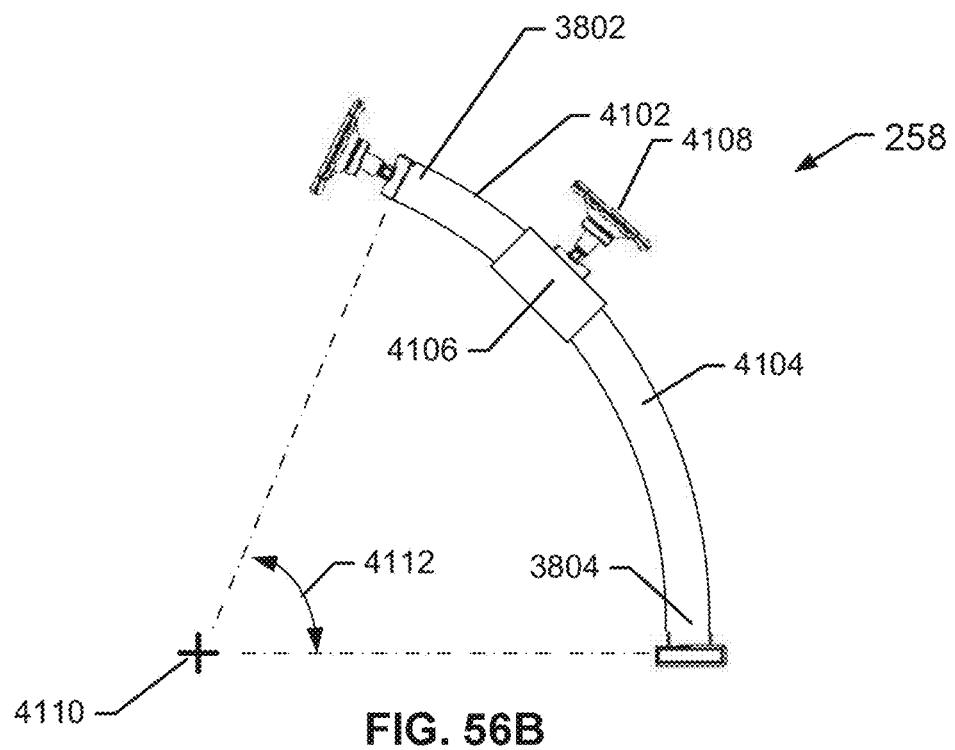
FIG. 56B is a side view of the telescoping anchor arm assembly of FIG. 56A, except with a portion of the first section nested within the central lumen of the second section, resulting in a shorter elongate shape.

For example, FIG. 56A and FIG. 56B are side views of a telescoping anchor arm assembly 258. Referring to FIG. 56A, the anchor arm assembly 258 may include a first section 4102 ending in a first arm end 3802 and a second section 4104 ending in a second arm end 3804; both sections 4102 and 4104 may have matched circular arc shapes with a common center 4110 as illustrated in FIG. 56A. In an aspect, the second section 4104 may have a hollow cross-section with a central lumen (not shown), and the first section 4102 may be shaped and dimensioned to fit within the central lumen by sliding along the arc length of the second section 4104. FIG. 56B illustrates the anchor arm assembly 258 with a portion of the first section 4102 nested within the central lumen of the second section 4104, resulting in a shorter elongate shape. The second section 4104 includes the second arm end 3804 as well as a sliding attachment fitting 4106 at an end of the second section 4104 opposite to the second arm end 3804. The sliding attachment fitting 4106 may slide along the first section 4102 to adjust the relative position of the first arm end 3802 and second arm end 3804 as illustrated in FIG. 56B. The elongate shape of the anchor arm assembly 258 and the sliding attachment fitting 4106 may be locked into a fixed position using a locking mechanism including, but not limited to, a set screw 4108 as illustrated in FIG. 56A. Any other known locking mechanism may be used to lock the adjustable anchor arm assembly 258 into a locked position including, but not limited to clamps, pegs, compression fittings, and any combination thereof. In this aspect, the shorter elongate shape illustrated in FIG. 56B may result in a change in the angle 4112 between the anchor element 18 and/or anchoring tool 274 and the implant 12 and/or tooling head 260. The adjustability of the anchor arm assembly 258 may further facilitate fine-tuning the entry paths of the various components during formation of the implant assembly 14, or delivery of the anchor element 18 relative to the tooling head 260, to account for variability in patient morphology and/or to avoid injury to vulnerable tissues including, but not limited to, nerves and/or blood vessels.

In an aspect, the second section may have a hollow cross-section with a central lumen, and the first section may be shaped and dimensioned to fit within the central lumen by sliding along the arc length of the second section. A portion of the first section may be nested within the central lumen of the second section, resulting in a shorter elongate shape. The second section includes the second arm end as well as a sliding attachment fitting at an end of the second section opposite to the second arm end. The sliding attachment fitting may slide along the first section to adjust the relative position of the first arm end and second arm end. The elongate shape of the anchor arm assembly 258 and the sliding attachment fitting may be locked into a fixed position using a locking mechanism including, but not limited to, a set screw. Any other known locking mechanism may be used to lock the adjustable anchor arm assembly 258 into a locked position including, but not limited to clamps, pegs, compression fittings, and any combination thereof. In this aspect, the shorter elongate shape may result in a change in the angle between the anchor and/or anchor guide and the implant body and/or implant guide. The adjustability of the anchor arm assembly 258 may further facilitate fine-tuning the entry paths of the various components during placement of the one or more anchors to account for variability in patient morphology and/or to avoid injury to vulnerable tissues including, but not limited to, nerves and/or blood vessels.

In other aspects, the anchor arm assembly 258 includes a straight horizontal segment and a straight vertical segment. The vertical segment includes the second arm end as well as a sliding attachment fitting at an end of the vertical segment opposite to the second arm end. The sliding attachment fitting may slide in a horizontal direction along the horizontal segment to adjust the relative position of the first arm end and second arm end. The position of the sliding attachment fitting may be locked into place using any known locking mechanism described previously above including, but not limited to, a set screw.

In various other aspects, the anchor arm assembly 258 may be made adjustable by the incorporation of any other adjustable elements known in the art. Non-limiting examples of suitable adjustable elements include: two or more hinged or jointed subsections of the anchor arm assembly 258, two or more telescoping subsections of the anchor arm assembly 258, one or more bendable subsections of the anchor arm assembly 258 having limited deformability, and any combination thereof. In other additional aspects, different sizes of fixed-geometry anchor arm assembly 258 may be used to provide a suitable range of installation tool geometries to account for differences in patient morphologies, differences in orthopedic surgical procedures, and any other variable factor governing the selection of an anchor arm assembly 258 geometry.

C. Joint Preparation Tool with Translating and Rotation Inhibiting Distal Handle Assembly Reference is now made to FIG. 26A, which is a side isometric view of a joint preparation tool 800 having a proximal handle 802 and a distal handle assembly 804 that is slidably attached to a shaft 806 of a tooling head 808. The distal handle assembly 804 is configured to translate on the shaft 806 along a set trajectory that inhibits rotation of the handle assembly 804 relative to the proximal handle 802 and shaft 806. The tooling head 808 may be similar to the various embodiments previously described and the joint preparation tool 800 may be configured to couple with any of the tooling heads described herein. In this embodiment, there is a cutting element 812 at a distal end 810 of the tooling head 808. Referring to the distal handle assembly 804, it includes a coupler member 816 that releasably secures to the shaft 806 of the tooling head 808. Proximal to the coupler member 816 is a handle 818 that is coupled to the coupler member 816 via an adjustable socket assembly 820.

With continuing reference to FIG. 26A, the joint preparation tool 800 may be further configured to have an indicator 803 coupled to or integral with a component (e.g., the proximal handle 802) of the joint preparation tool 800. The indicator 803 may indicate a position or orientation of the cutting element 812 when the cutting element is positioned out of view of the surgeon (e.g., in a joint space). Alternatively, an indicator 803 may be fixed to a portion of the patient's skeleton to act as a reference during the course of the procedure. The indicator 803 may be configured as a body visible to a human user during the course of employing the joint preparation tool 800 or one of its components. Additionally, the body may be configured to be visible to a user while using fluoroscopy or CT scan (e.g., the body may comprise a material which is radiopaque) or be identifiable by an O-Arm® Surgical Imaging System from Medtronic or similar device or a StealthStation® S7® surgical navigation system by Medtronic which has both optical and electromagnetic tracking options, or StealthStation i7™ also by Medtronic. The indicator 803 may be used as a reference guide when directly viewed by the human user or when identified by a computer, surgical robot or imaging system. According to an aspect, the indicator 803 may be a reference array and may include 3 or 4 balls supported in a predetermined spaced apart arrangement and connected to one another by a frame. The frame may be coupled to a component of the tool 800 or may be separately coupled to a portion of the patient's skeleton or may be coupled to a delivery tool 16 of a system 10.

In another aspect, the indicator 803 may indicate the position of the cutting element 812 supported by the tooling head 808 when the tooling head 808 may be obscured from view by the patient's soft tissues, by the positioning of the tooling head 808 within the joint, or by aspects of the operating environment which may otherwise obfuscate the arrangement or position of elements of the various components of the joint preparation tool 800. For example, the indicators 803 may be elongate cylinders extending radially from a proximal handle 802 (or shaft of a tooling head 806) longitudinal axis and projecting towards one or more outer cutting blades. In an aspect, the indicators 803 (when coupled to the tool 800) have a longitudinal axis which is parallel to a cutting element axis which is defined as being coincident with the tooling head axis and also coincident with a point along a tip of an outer cutting blade 856.

As such, the indicator 803 may permit a surgeon to align an outer cutting blade with the bone of an ilium and a second outer cutting blade with the bone of the sacrum. Alternatively or additionally, an indicator 803 may permit a surgeon to align an outer cutting blade 856 to be generally in-line with a plane of a sacroiliac joint.

As seen in FIG. 26B, which is a cross-sectional view of the coupler member 816 of the distal handle assembly 804 and the shaft 806 of the tooling head 808, the shaft 806 is hexagonal and includes six outer surfaces 840 that are configured to matingly slide within and against matching inner surfaces 814 of the coupler member 816. The inner surfaces 814 of the coupler member 816 are hexagonal and sized slightly larger than the six outer surfaces 840 of the shaft 806 in order to facilitate sliding of the distal handle assembly 804 relative to the shaft 806. As seen in the figure, the coupler member 816 includes two sections that are held together by fasteners (e.g., bolt, screw) 822. In this way, the coupler member 816 is releasably secured to the shaft 806 via the fasteners 822. And, when the coupler member 816 is secured to the shaft 806, the coupler member 816, along with the socket assembly 820 and the handle 818, are in a fixed position relative to the tooling head 808 and the proximal handle 802. That is, the distal handle assembly 804 may translate on the shaft 806 of the tooling head 808, but the distal handle assembly 804 may not rotate relative to the shaft 806.

In one aspect, coupler member 816 may be caused to disengage matching inner surfaces 814 from outer surfaces 840 of the shaft 806 such that rotation between shaft 806 and coupler member 816 may be permitted. For example, coupler member 816 may be distally displaced relative to shaft 806 such that surfaces 814 and 840 disengage and then coupler member 816 may be rotated relative to shaft 806 to a different desired position and then coupler member 816 may be proximally displaced relative to shaft 806 such that inner surfaces 814 reengage the outer surfaces 840.

Figure 26C:
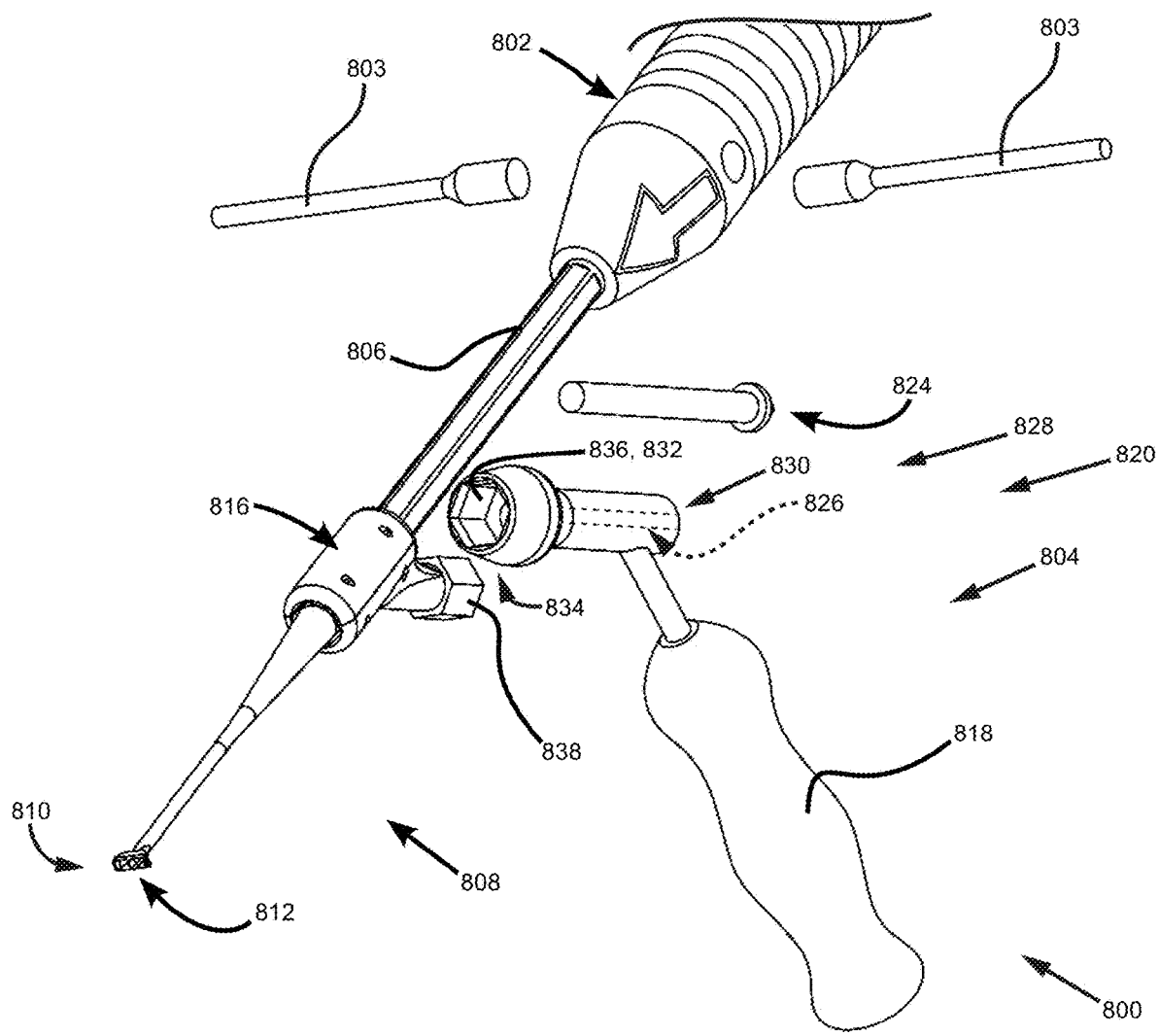
FIG. 26C is a front isometric view of the joint preparation tool of FIG. 26A with a socket assembly in an uncoupled state.

Reference is now made to FIG. 26C, which is an isometric front view of the joint preparation tool 800 with the distal handle assembly 804 in an exploded view. As seen in the figure, the socket assembly 820 is releasably secured to the coupler member 816 via a fastener 824 that is fitted within a passageway 826 through a socket member 828 of the socket assembly 820. The fastener 824 may be threaded and may engage with corresponding threads in the coupler member 816. The socket member 828 is coupled to the handle at a proximal end 830 of the socket member 828 and includes a socket opening 832 at a distal end 834 of the member 828. The socket opening 832 leads to the passageway 826 and includes a six-sided inner surface 836 that may be engaged with a matching male-end of a six-sided member 838 on the coupler member 816. As such, the socket member 828 may engage with and be secured to the six-sided member 838 in one of six orientations such that the handle 818 extends at differing orientations relative to the shaft 806 of the tooling head 808 and the proximal handle 802. This adjustability may be useful for a surgeon to appropriately position the handle 818 for a particular surgical procedure.

The present embodiment of the joint preparation tool 800 with a translating and rotation inhibiting distal handle assembly 804 may be useful to prevent inadvertent rotating of the cutting element 812 out of a desired cutting trajectory. For example, since the ilium is generally a harder bone than the sacrum, there may be a tendency for the cutting element 812 to deflect from being driven into the ilium by twisting into the joint space where this is less resistance. Such twisting of the tooling head 808 may be damaging to the patient and may inaccurately prepare the joint surfaces for fusion.

Figure 26D:
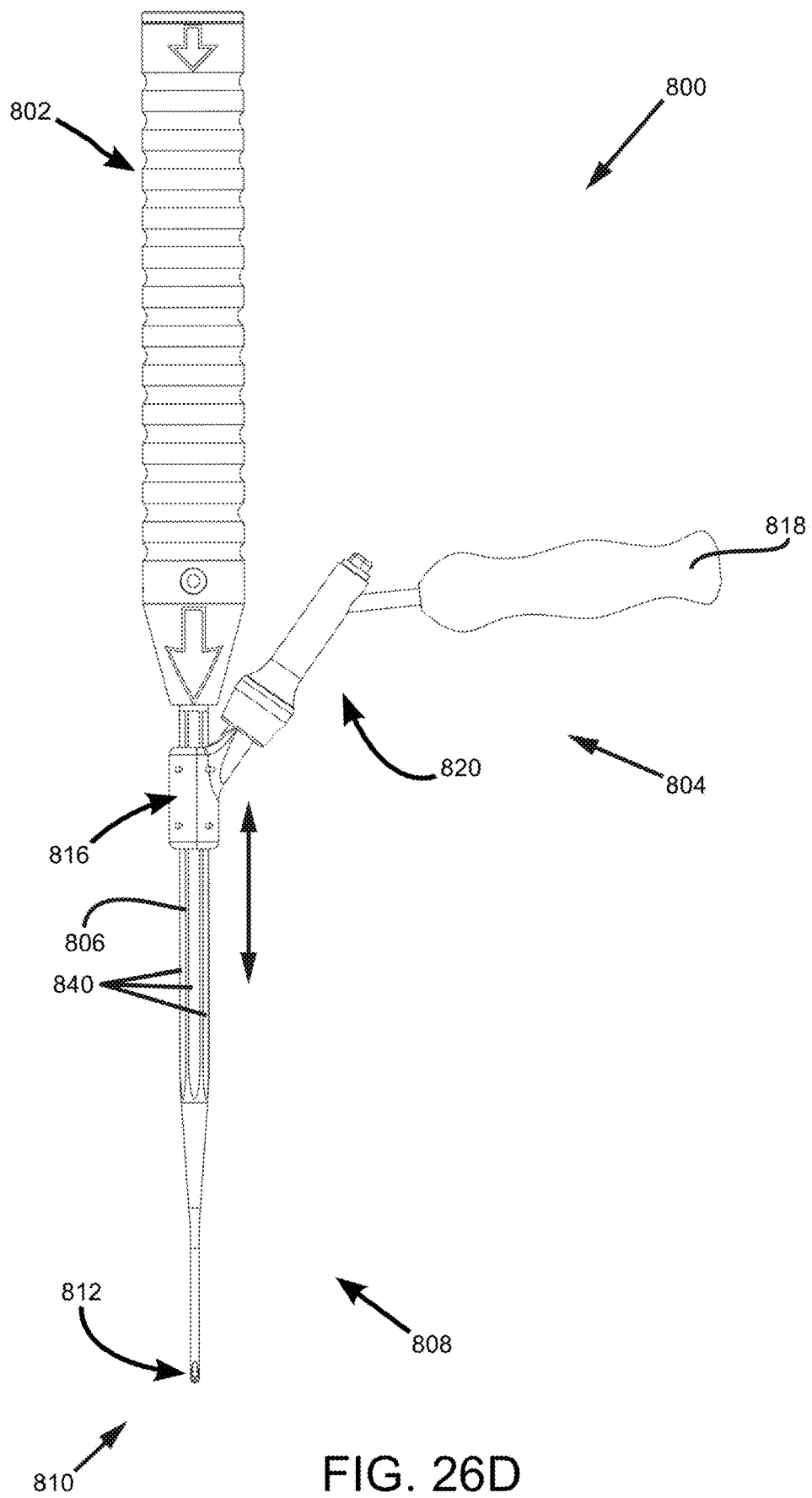
FIG. 26D is a side view of the joint preparation tool of FIG. 26A with the distal handle assembly in a proximal position.

In operation, the cutting element 812 at the distal end 810 of the tooling head 808 may be distally driven into a joint (e.g., sacroiliac joint) while a surgeon controls the trajectory of delivery. More particularly, a surgeon may grasp the handle 818 of the distal handle assembly 804 with one hand and the proximal handle 802 with the other hand. At this initial stage, the joint preparation tool 800 may be oriented as shown in FIG. 26A, which depicts the distal handle assembly 804 in a distal position. The surgeon may then urge the proximal handle 802 distally while maintaining a stabilizing force on the distal handle assembly 804. As the cutting element 812 is urged into the joint, the distal handle assembly 804 may displace proximally relative to the shaft 806 of the tooling head 808 as the surgeon maintains the stabilizing force on the assembly 804. At this stage of the procedure, the joint preparation tool 800 may be oriented as shown in FIG. 26D, which depicts the distal handle assembly 804 in a proximal position. In this way, the stabilizing force exerted on the distal handle assembly 804 ensures that the cutting element 812 is not caused to inadvertently rotate out of alignment during the delivery of the head 808 into the joint space.

Additionally, the coupler member may house a brake shoe which in turn may carry a brake block or pad. The brake shoe may be coupled to a brake caliper. The brake caliper may be manipulated by a user acting upon a lever which may be configured with an ergonomic lever handle and which may be coupled to the distal handle assembly 804. Such a braking system may resist longitudinal and rotational forces between shaft 806 and coupler member 816.

Figure 26E:
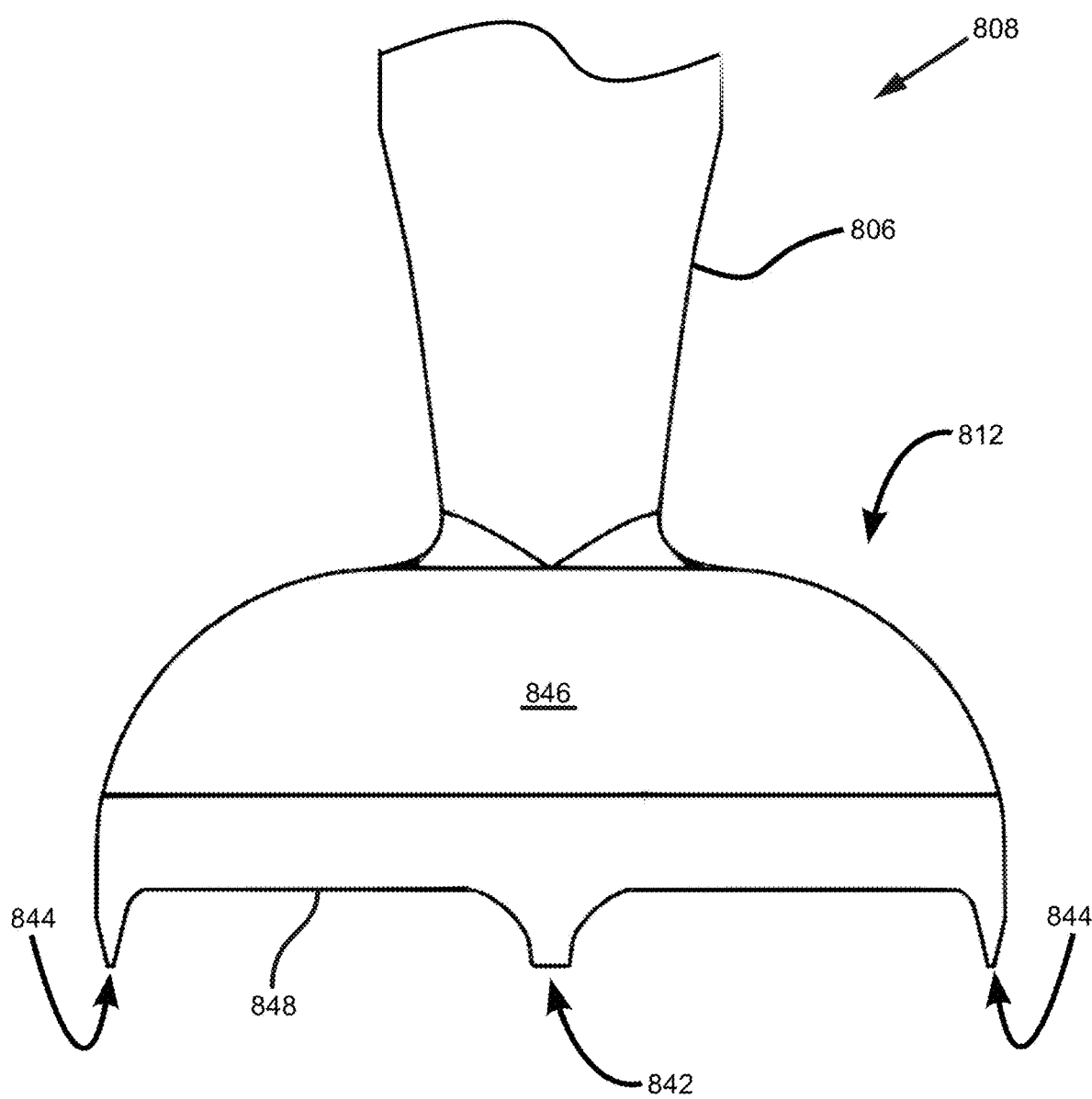
FIG. 26E is a close-up side view of a cutting element at a distal end of the tooling head of the joint preparation tool of FIG. 26A.

Moving on, reference is made to FIG. 26E, which is an up-close side view of the cutting element 812. As seen in the figure, the cutting element 812 includes a central cutting blade or central guide 842 and a pair of outer cutting blades 844. The cutting element 812 also includes a front and back wall member 846 that extends between and couples the outer cutting blades 844 with the central cutting blade 842. The front and back wall members 846 may include a distal beveled edge 848 extending between the outer cutting blades 844.

Figure 26F:
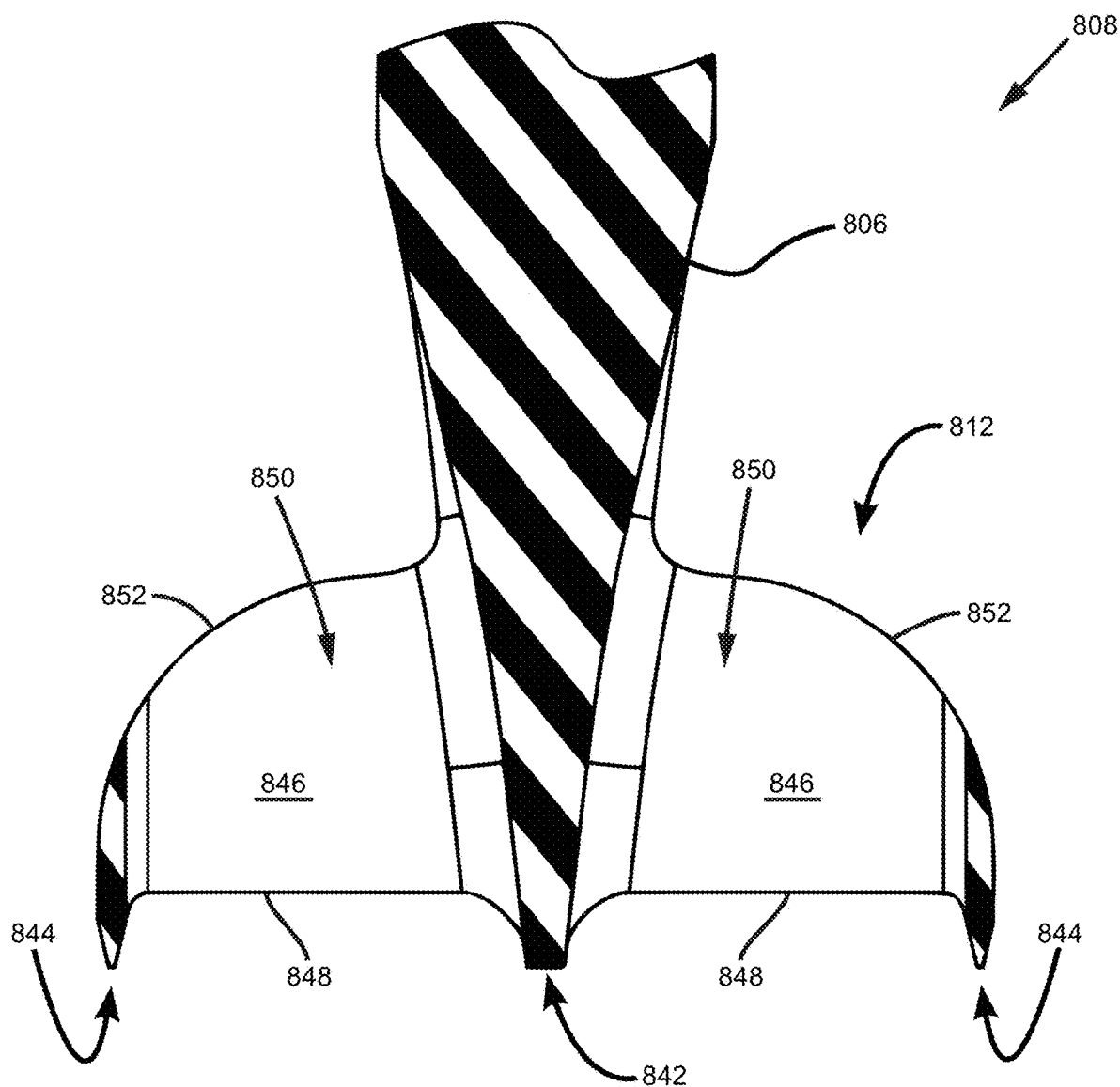
FIG. 26F is a cross-sectional view of the cutting element of FIG. 26E.

Referring to FIG. 26F, which is a cross-sectional side view of the cutting element 812, it can be seen that the shaft 806 of the tooling head 808 tapers into the central cutting blade 842. In between opposite sides of the central cutting blade 842 and the outer cutting blades 844 are passageways 850 that extend from the distal beveled edge to a proximal edge 852 of the cutting element 812. In operation, as the cutting element 812 is distally advanced within a joint space articular cartilage and/or bone may be cut with the distal beveled edge 848 and the central and outer cutting blades 842, 844 such that the severed bone/cartilage is caused to funnel through the passageway 850 to make way for additional bone/cartilage to be cut.

Such a cutting element 812 may be oriented within the joint plane or perpendicular to the joint plane. When oriented perpendicular to the joint plane, one of the outer cutting blades 844 may be positioned to cut the ilium and one of the outer cutting blades 844 may be positioned to cut the sacrum while the central cutting blade is positioned within the plane of the joint. Thus, as the tool 800 is distally advanced the cutting element 812 may make keel cuts into the sacrum and the ilium. The distal handle assembly 804, as discussed previously, may be useful to provide a stabilizing force that ensure the cutting element 812 does not inadvertently twist or rotate given the differences hardness of the sacrum and ilium.

Figure 26G:
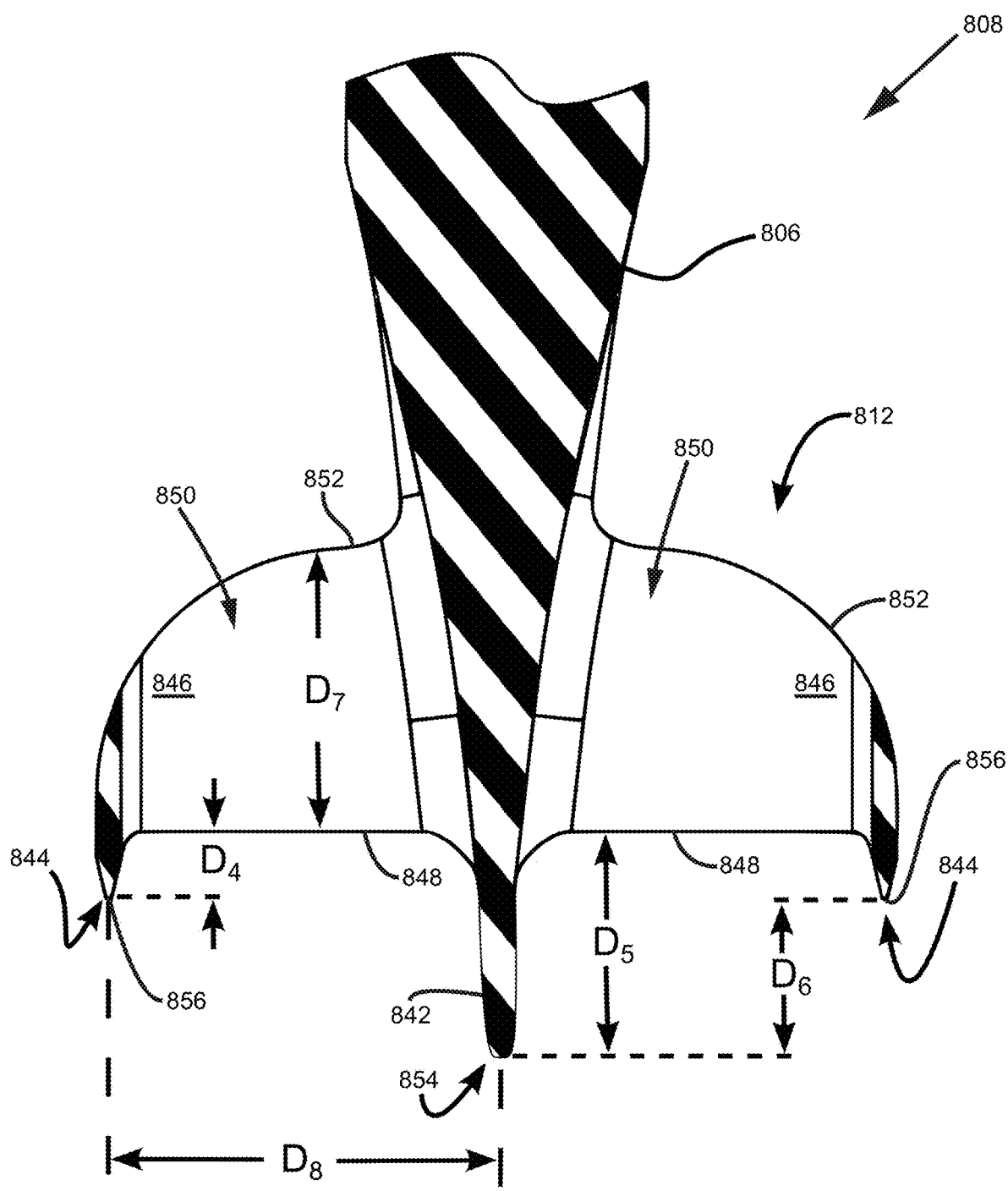
FIG. 26G is a cross-sectional view of another embodiment of a cutting element.

The cutting element 812 may be modified, as in FIG. 26G, to include an elongated central cutting blade 842. Such a cutting element 812 may be useful when the cutting element is oriented perpendicular to the joint plane, as described previously, in that the elongated central cutting blade 842 may urge the cutting element 812 to stay within the joint plane as opposed to easily cutting into one of the boney surfaces of the joint. The tip 854 of the elongated central cutting blade 842 may be blunt to further urge the central cutting blade 842 to remain within the joint plane.

As seen in FIG. 26G, sample dimensions of the cutting element 812 may be as follows. The outer cutting blades may extend a distance D4 from the distal edge 848 to a distal tip 856 of about 0 mm to about 1.75 mm, from about 1.5 mm to about 2.5 mm, from about 2 mm to about 3.5 mm, from about 3 mm to about 4.75 mm, from about 4.25 mm to about 6 mm, from about 5 mm to about 6.75 mm, from about 5.5 mm to about 8 mm, from about 7.5 mm to about 10 mm, from about 9 mm to about 11.5 mm, and from about 11 mm to about 13 mm. In certain embodiments, the distance D4 may be about 1 mm, 3 mm, or 5 mm. The elongated central portion 842 may extend a distance D5 from the distal edge 848 to the tip 854 of about 3 mm to about 4.75 mm, from about 4.25 mm to about 6 mm, from about 5 mm to about 6.75 mm, from about 5.5 mm to about 8 mm, from about 7.5 mm to about 10 mm, from about 9 mm to about 11.5 mm, from about 11 mm to about 13 mm, and from about 12.5 mm to about 15 mm. In certain embodiments, the distance D5 may be about 5 mm, 6.5 mm, or 8 mm. The elongated central portion 842 may extend a distance D6 beyond that of the distal tips 856 of the outer cutting blades by about 3 mm to about 15 mm. In certain embodiments, the distance D6 may be about 5 mm, 6.5 mm, or 8 mm. A distance D7 between the distal and proximal edges 848, 852 may be about 1.5 mm to about 2.25 mm, from about 2 mm to about 3.5 mm, from about 3 mm to about 4.75 mm, from about 4.25 mm to about 6 mm, from about 5 mm to about 6.75 mm, from about 5.5 mm to about 8 mm, from about 7.5 mm to about 10 mm, from about 9 mm to about 11.5 mm, from about 11 mm to about 13 mm, and may even range up to 40 mm-60 mm. In certain embodiments, the distance D7 may be 3.5 mm, 7.5 mm, 15 mm, 30 mm 40 mm or 45 mm. A distance D8 may be defined between one of the outer cutting blades 844 and the elongated central cutting blade 842. D8 may be in a range of about 2.25 mm to about 2.75 mm, from about 2 mm to about 3.5 mm, from about 3 mm to about 4.75 mm, from about 4.25 mm to about 6 mm, from about 5 mm to about 6.75 mm, from about 5.5 mm to about 8 mm, from about 7.5 mm to about 10 mm, from about 9 mm to about 11.5 mm, from about 11 mm to about 13 mm. In certain embodiments, the distance D8 may be about 6 mm, 8 mm, or 10 mm.

While the cutting element is shown in FIGS. 26E-26G as including a certain configuration of cutting blades, other arrangements are possible and contemplated herein. For example, a cutting element 812 may include serrated cutting blades and may include additional or fewer cutting blades than are depicted in the figures. In one aspect, there may be four passageways 850 arranged into two pairs. The first pair may be arranged such that the first and second passageways are positioned and aligned relative to one another similar to the configuration in FIGS. 26F-26G such that a back wall member 846 of the first passageway is generally coplanar with a back wall member 846 of the second passageway and forming a first plane. The second pair of passageways 850 may also have a relationship between each of the second pair passageways 850 similar to the first and second passageways of the first pair of passageways such that a back wall member 846 of the first passageway of the second pair is generally coplanar with a back wall member 846 of the second passageway of the second pair and forming a second plane. The second pair of passageways may be arranged relative to the first pair of passageways such that the first plane formed by the first pair of back wall members is generally perpendicular to the second plane formed by the second pair of back walls.

D. Joint Preparation Tool with Trial Fit Implant and Cutting Tool with Translating Cutting Element The discussion of preparing the sacroiliac joint, among other joints, for implant delivery will now focus on additional tools that may be used independently from or in combination with the previously mentioned tools.

1. Trial Fit Assembly and Cutting Tool with Offset Shafts

Figure 27:
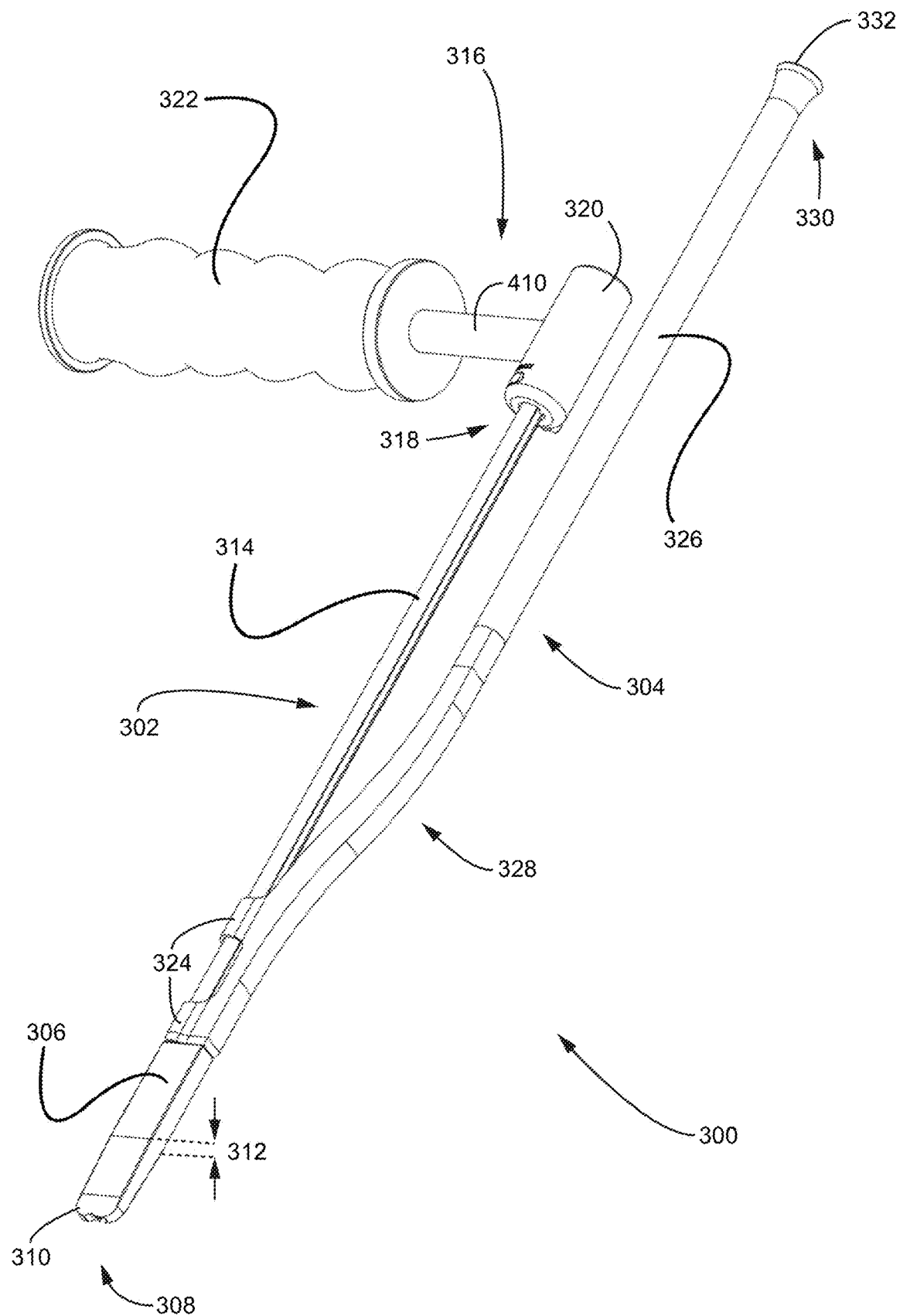
FIG. 27 is an isometric view of a bottom side of a surgical preparation tool assembly including a trial tool assembly and a cutting tool.

To begin, reference is made to FIG. 27, which is an isometric side view of a joint preparation tool assembly 300 that is configured to test-fit an implant size and make a transverse cut into either or both the sacrum and ilium to make way for a keel of an implant that is configured to extend into the bone. As seen in the figure, the joint preparation tool assembly 300 includes a trial tool assembly 302 and a cutting tool 304 that is configured to translate relative to the trial tool assembly 302 in order to make the transverse keel-cuts into the patient's bone.

The trial tool assembly 302 includes an implant trial 306 at a distal end 308 of the assembly 302. The implant trial 306 is a planar member with a tapered tip 310 that includes a width 312 that corresponds with a width of an implant that may be subsequently delivered into a joint. The implant trial 306 may be removably coupled with a shaft 314 that extends proximally. The shaft 314 is removably attached to a handle assembly 316 at a proximal end 318 of the shaft 314. The handle assembly 316 includes a coupler 320 configured to removably attach to the shaft 314 of the trial tool assembly 302. The coupler 320 is attached to a handle shaft 410 that extends to a gripping handle 322.

As mentioned previously, the implant trial 306 is used to gauge the size of the joint space so that an implant size may be chosen that best fits the joint space. Thus, the system described herein may include implant trials 306 of various sizes and configurations in order to gauge the size of the joint space. In operation, a surgeon may begin a surgical procedure by test-fitting the smallest size of implant trial 306 into the patient's joint to determine the fit. If the size of the implant trial 306 is too small, then the surgeon may remove the implant trial 306 and deliver a larger size implant trial 306 into the joint. Once an appropriate size of implant trial 306 is received within the joint, the surgeon may use the cutting tool 304 to deliver transverse keel-cuts into the boney surfaces in preparation for the implant delivery.

The cutting tool 304 is slidably coupled to the shaft 314 of the trial tool assembly 302 and configured to slide distal-proximal on the shaft 314. The cutting tool 304 is slidably coupled to the shaft 314 via a distal and a proximal collar 324 that extend around the shaft 314 of the trial tool assembly 302. The collars 324 are separated by a gap and are attached to a cutting tool shaft 326 that extends proximally. The cutting tool shaft 326 includes a curved mid-portion 328 such that the shaft 326 angles away from the shaft 314 of the trial tool assembly 302. A proximal end 330 of the cutting tool shaft 326 includes an impact plate 332 that is configured for being hit with a hammer or similar device to drive the cutting tool 304 distally. In this way, the surgeon may securely hold the handle 322 of the trial tool assembly 302 with one hand and strike the impact plate 332 with the other hand.

Figure 28:
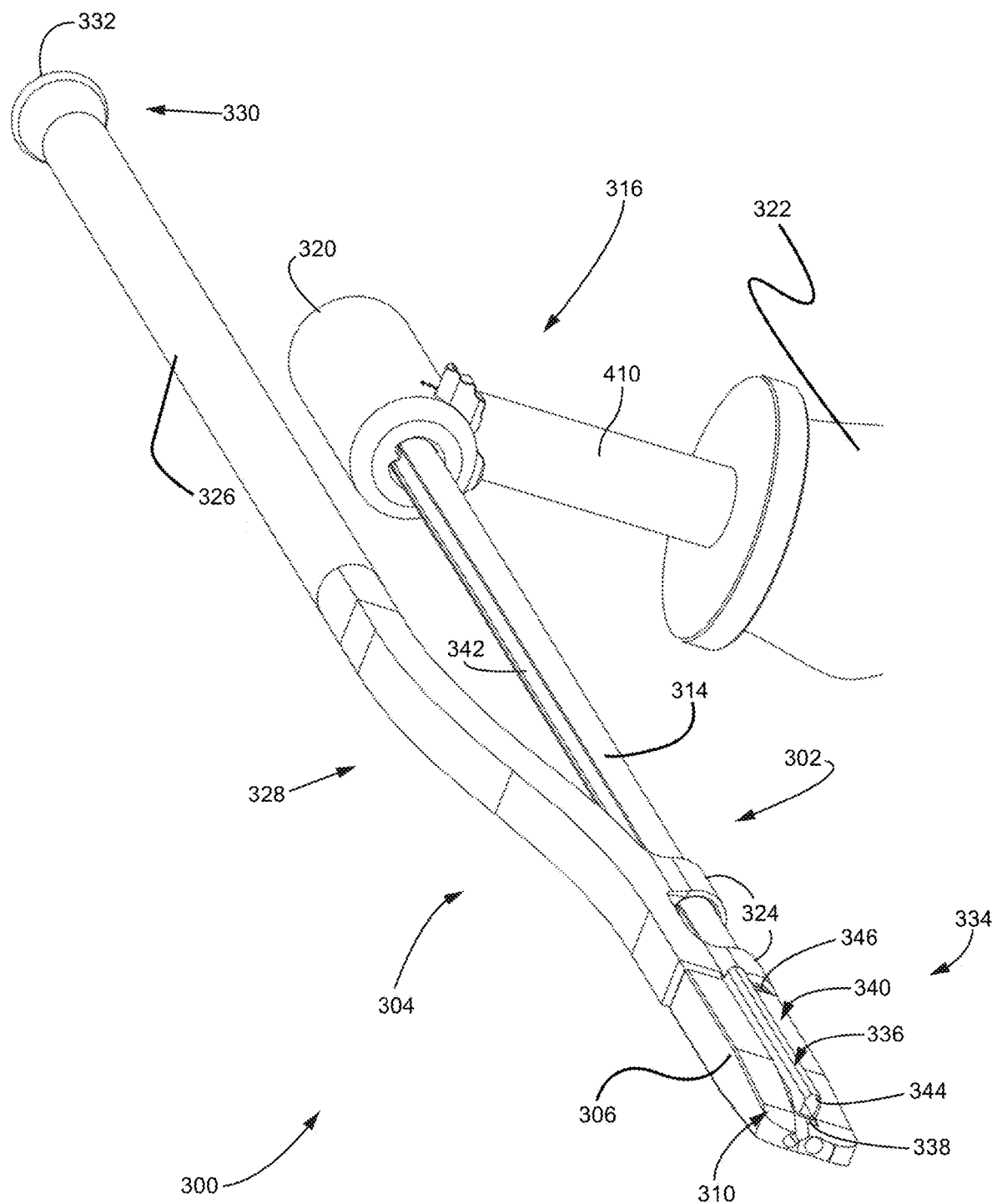
FIG. 28 is an isometric view of a top side of the surgical preparation tool assembly of FIG. 27.

Reference is now made to FIG. 28, which is an isometric view of an opposite side of the joint preparation tool assembly 300. As seen in the figure, a distal end 334 of the cutting tool 304 includes a cutting element 336 that extends within a guide 338 formed in a top surface 340 to the tapered tip 310 of the implant trial 306 when the cutting element 336 translates relative to the implant trial 306. A distal tip 344 of the cutting element extends to the tapered tip 310 of the implant trial 306 when the shaft 326 of the cutting tool 304 abuts a proximal end 346 of the implant trial 306. The cutting tool 304 is configured to maintain an orientation relative to the guide 338 when the cutting element 336 is proximally retracted or distally extended towards the guide 338 via a channel 342 formed in the shaft 314 of the trial tool assembly 302.

Figure 29:
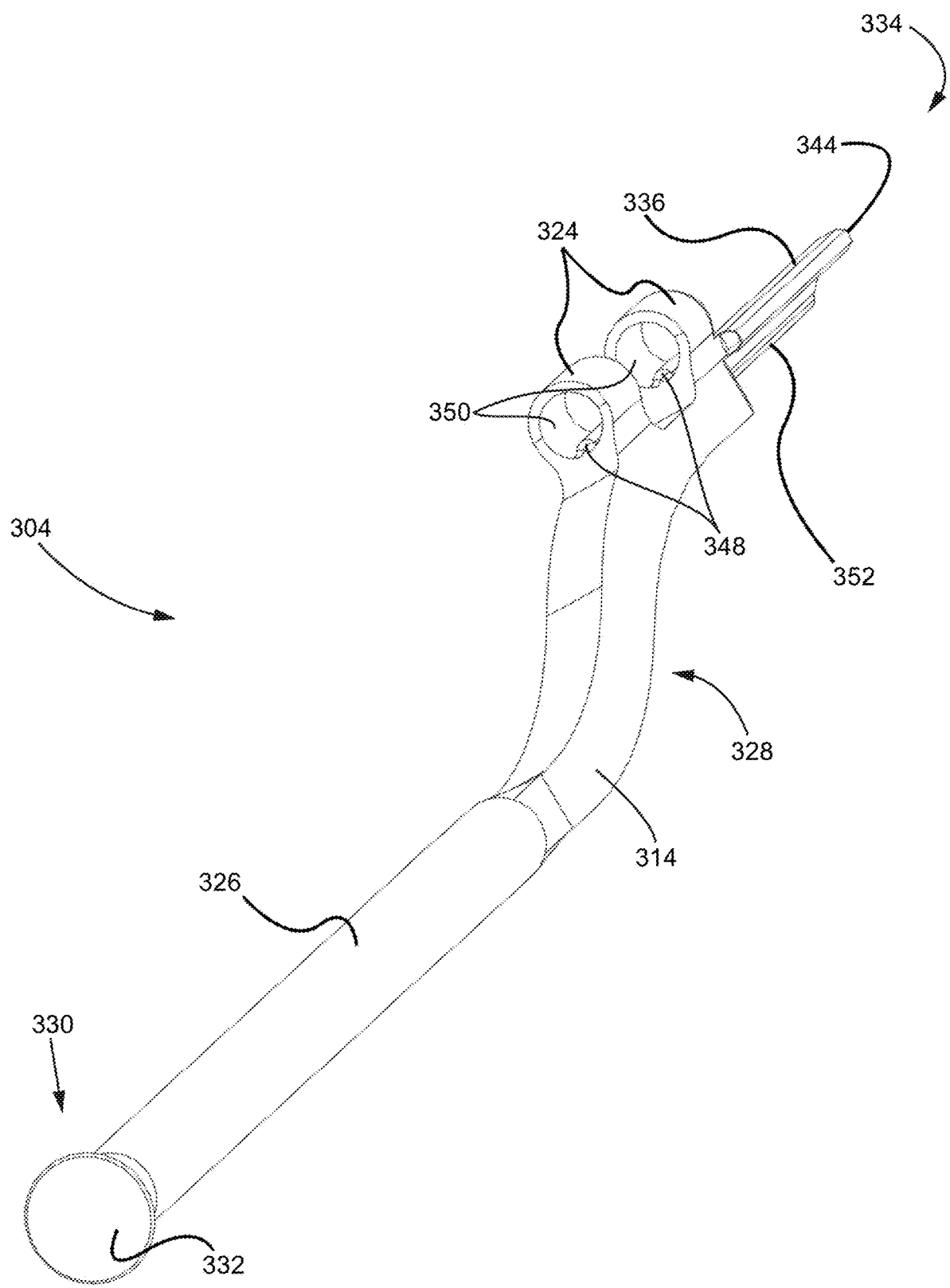
FIG. 29 is an isometric view of the cutting tool of the surgical preparation tool assembly of FIG. 27.
Figure 30:
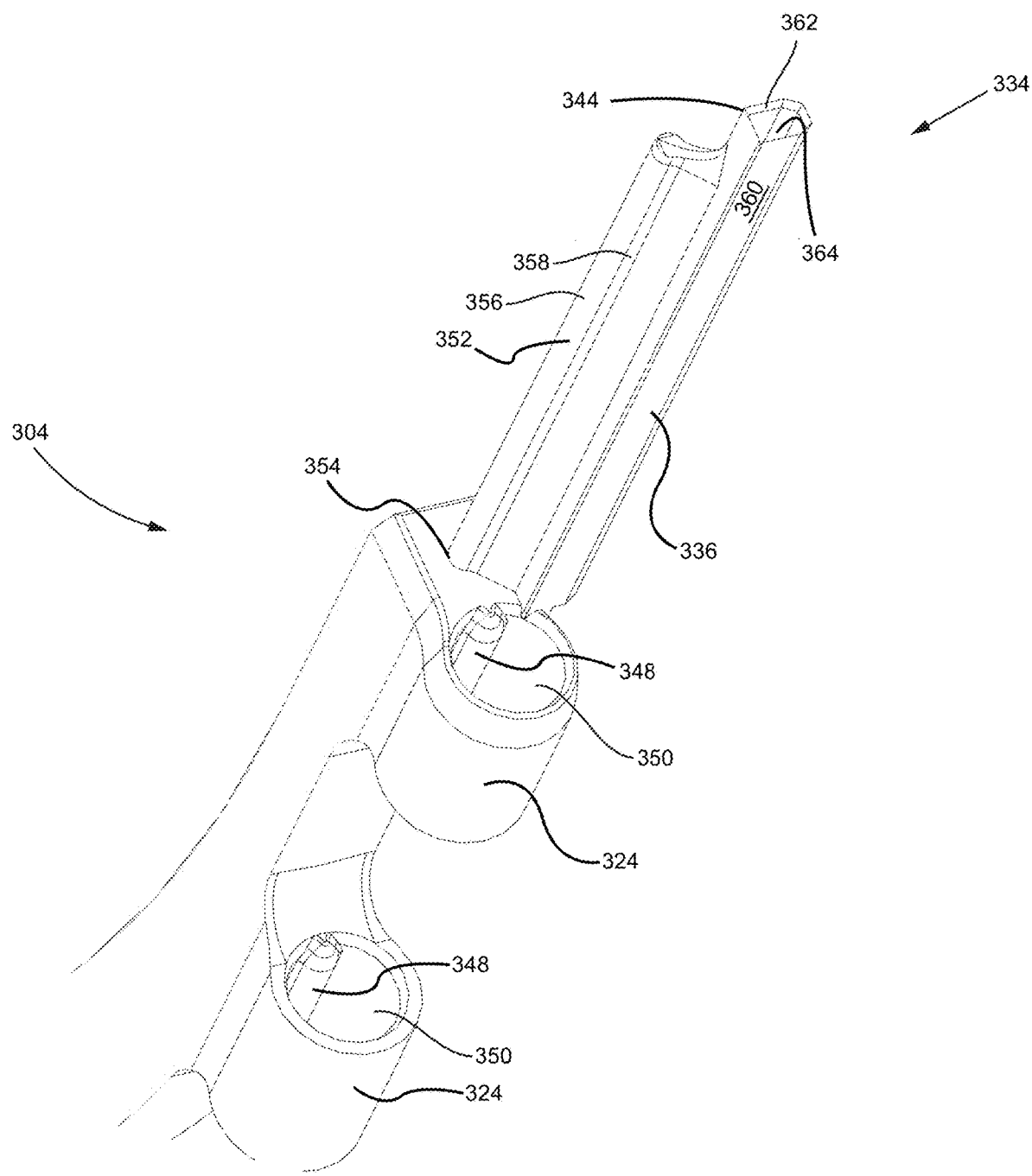
FIG. 30 is a close-up isometric view of a distal end of the cutting tool.

For a detailed discussion of the cutting tool 304, reference is made to FIGS. 29-30, which are isometric views of the cutting tool 304. As seen in FIG. 29, the cutting tool 304 includes a protrusion 348 on each inner surface 350 of the collars 324 that extend around the shaft 314 of the trial tool assembly 302. The protrusion 348 is configured to fit within the channel 342 formed in the shaft 314 of the trial tool assembly 302 such that the shaft 314 cannot rotate when the protrusion 348 is fitted within the channel 342. Reference is now made to FIG. 30, which is a close-up view of the distal end 334 of the cutting tool 304. As seen in this figure, the protrusion 348 is semi-hemispherical and extends a length of the collars 324. Other shapes for the protrusion 348 are possible and contemplated herein.

Turning to the distal end 334 of the cutting tool 304 and still referring to FIG. 30, the cutting element 336 is a six-sided, box-type chisel with planar outer surfaces 360 that distally terminates in a beveled cutting edge 362 that forms a distal opening 364 that extends to lumen extending through the cutting element 336. While this embodiment of the cutting element 336 includes a six-sided, box-type chisel, other arrangements and designs of cutting tool elements 336 are contemplated herein. For example, a rectangular, box-type chisel, knife blade, or saw may be used without departing from the teachings of the disclosure.

Figure 31:
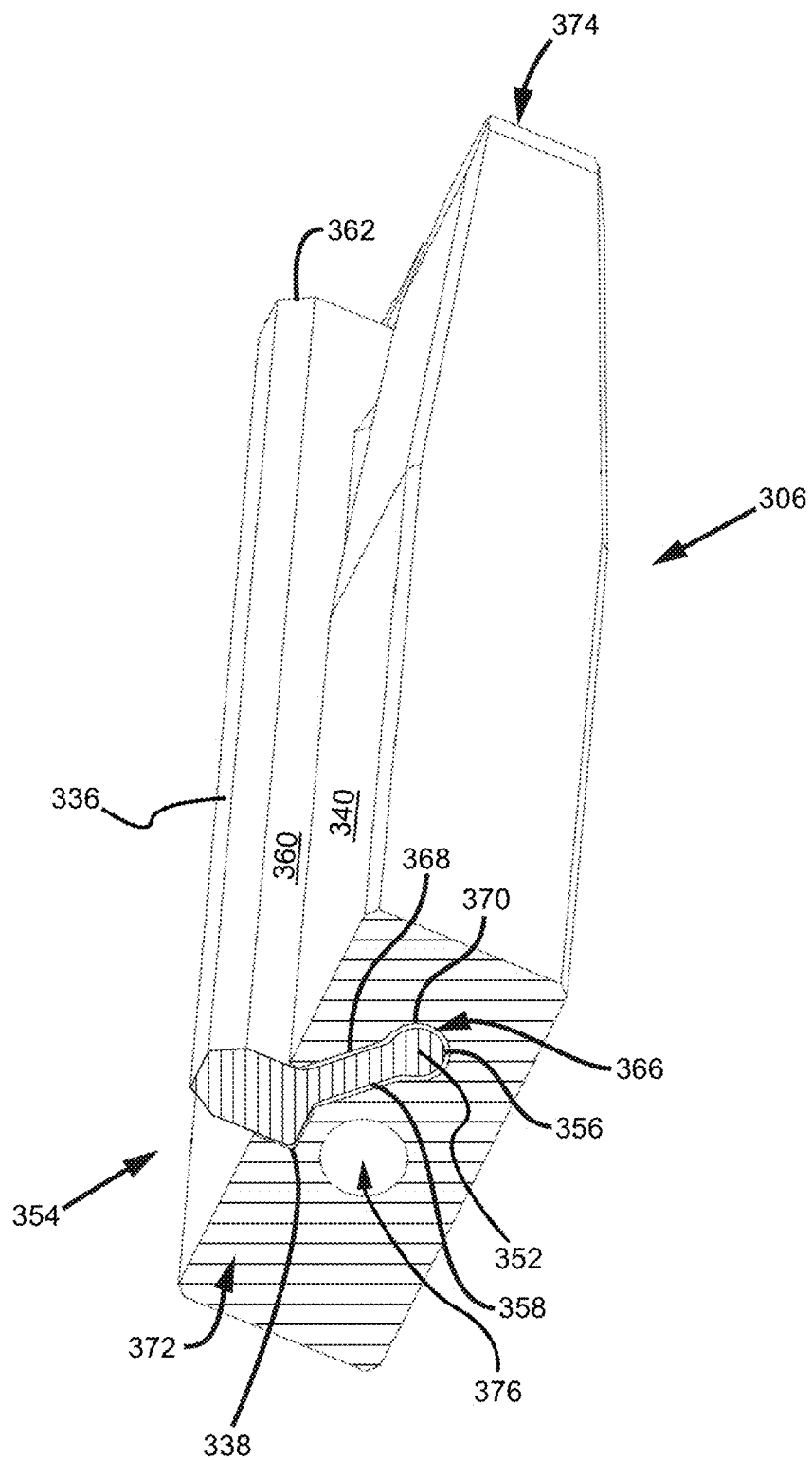
FIG. 31 is an isometric back view of the surgical preparation tool assembly with a cross-section at the proximal end of the implant trial.

Continuing with FIG. 30, the cutting element 336 further includes a cutting element guide 352 that extends off of the cutting element 336 and extends just proximally from the distal tip 334 of the cutting element 336 to a proximal end 354 of the cutting element 336. The cutting element guide 352 includes a rounded head 356 and a neck 358 that is thinner than a widest part of the head 356. Alternatively, cutting element guide 352 and guide channel 366 may have complementary dovetail or flaring tenon and mortise configurations. As seen in FIG. 31, which is an isometric view of the cutting element 336 and implant trial 306 with a cross-section at the proximal end 354 of the cutting element 336, the cutting element guide 352 is received within a guide channel 366 that is a corresponding shape to that of the cutting element guide 352. In particular, the guide channel 366 includes a neck region 368 and a head region 370 that are only slightly larger than the corresponding neck 358 and head 356 of the cutting element guide 352. The guide channel 366 extends from a proximal surface 372 to a distal surface 374 of the implant trial 306. In this way, as the cutting tool 304 and, more particularly, the cutting element 336 are translated distally, the cutting element guide 352 is received within the guide channel 366, which ensures that the cutting element 336 remains within the guide 338 on the top surface 340 of the implant trial 306 during a cutting operation. Stated differently, the guide channel 366 prevents rotation and other errant movement of the cutting element 336 during a cutting operation such that the cutting element 336 remains reliably within the guide 338 to perform repeatable and accurate cuts into the patient's bone.

Figure 32:
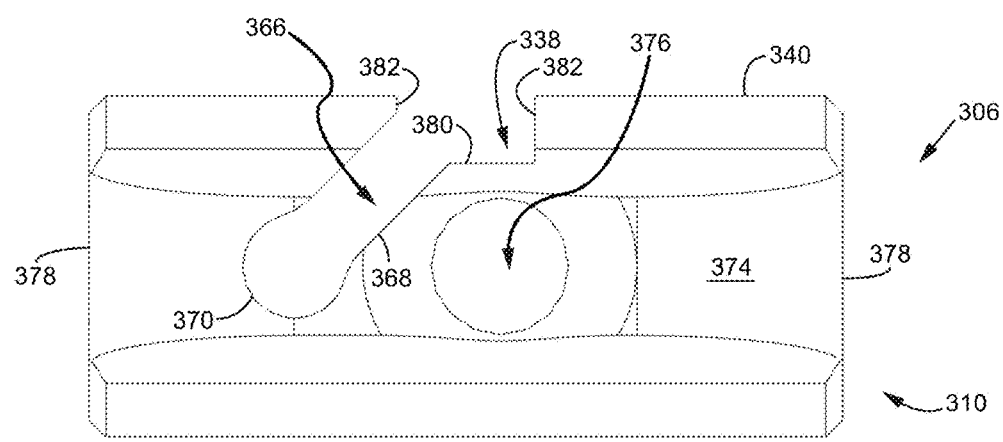
FIG. 32 is a front view of the trial tool assembly.
Figure 33:
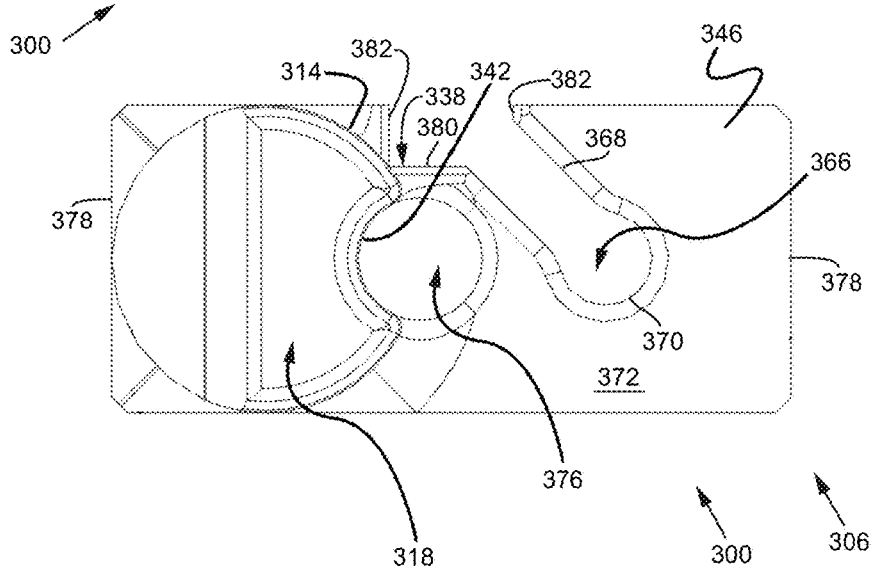
FIG. 33 is a back view of the trial tool assembly.

Still referring to FIG. 31 and also extending through the implant trial 306 from the proximal surface 372 to a distal surface 374 is a bore 376 that is configured receive a guidewire or similar device to guide the implant trial 306 into a joint space, for example. As best seen in FIGS. 32-33, which are respective front and back views of the implant trial 306, both the bore 376 and the guide channel 366 extend through the implant trial 306 parallel to a longitudinal axis of the implant trial 306. While shown in the figures as generally linear, the longitudinal axis of the implant trial 306 may be curved and may further include an arcuate portion with a radius between from about 3 cm and about 6 cm and may be about 2 cm, 2.5 cm, 3 cm, 3.5 cm, 4 cm, 4.5 cm, 5 cm, 5.5 cm, 6 cm, 6.5 cm and 7 cm. In one aspect, while shown in the figures as generally linear, the guide channel 366 may be curved and may further include an arcuate portion with a radius that matches the curved implant trial 306. The radius of the arcuate portion of the guide channel 366 may be between from about 3 cm and about 6 cm and may be about 2 cm, 2.5 cm, 3 cm, 3.5 cm, 4 cm, 4.5 cm, 5 cm, 5.5 cm, 6 cm, 6.5 cm and 7 cm. In another aspect, while shown in the figures as generally linear, the implant trial 306 may be curved and may further include an arcuate portion with a radius between from about 3 cm and about 6 cm and may be about 2 cm, 2.5 cm, 3 cm, 3.5 cm, 4 cm, 4.5 cm, 5 cm, 5.5 cm, 6 cm, 6.5 cm and 7 cm. In yet another aspect, the implant trial 306 and the guide channel 366 may both include a matching radius.

Still referring to FIGS. 32-33, while the guide 338 is centered between opposite side surfaces 378 of the implant trial 306, the bore 376 and the head region 370 of the guide channel 366 are offset from a center point between the opposite side surfaces 378. As seen in the figures, the guide 338 is an extrusion with a bottom surface 380 that is generally perpendicular to a pair of side surfaces 382. The bottom surface 380 adjoins one of the side surfaces 382 to form a perpendicular angle between the two surfaces while the opposite pair of surfaces are transected by the guide channel 366 extending about one hundred and thirty-five degrees from each of the bottom surface 380 and the side surface 382.

Reference is now made to FIG. 33 and the proximal end 346 of the implant trial 306. As seen in the figure, the channel 342 in the shaft 314 of the trial tool assembly 302 mirrors a portion of the circumference of the bore 376 extending through the implant trial 306. In this way, the trial tool assembly 302 may be delivered into a sacroiliac joint, or other joint, of a patient by way of a guidewire (not shown) being received through the bore 376 of the implant trial 306 which was previously delivered into the joint. The channel 342 in the shaft 314 provides a passageway for the guidewire when the trial tool assembly 302 is advanced into the joint. Subsequently, when it is appropriate to use the cutting tool 304 with the trial tool assembly 302, the channel 342 provides the function of guiding the cutting tool 304 in an appropriate orientation by aligning the protrusion 348 within the collars 324 of the cutting tool 304 within the channel 342 of the shaft 314 of the trial tool assembly 302.

Figure 43A:
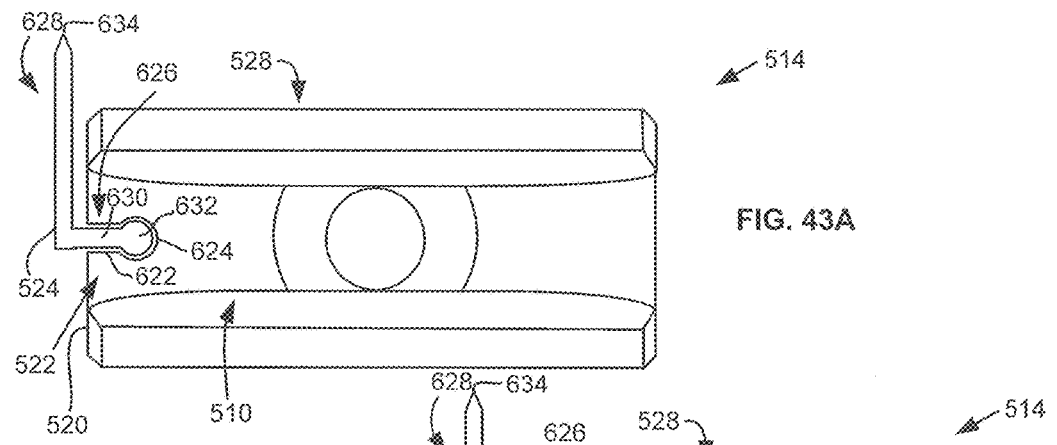
FIG. 43A-43D are front view of implant trials with differing configurations of cutting tools.
Figure 43B:
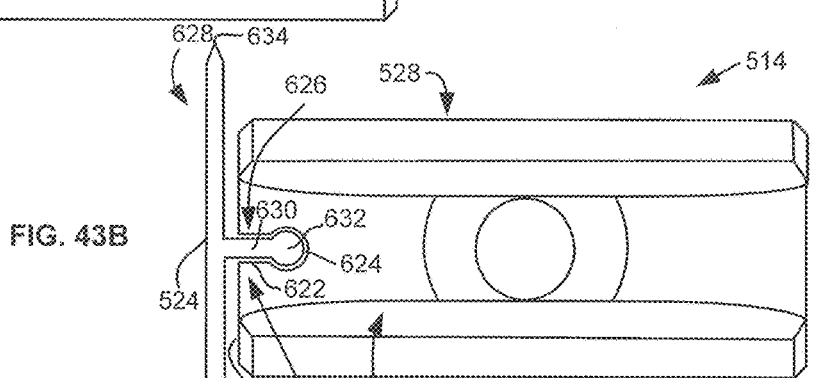
Figure 43C:
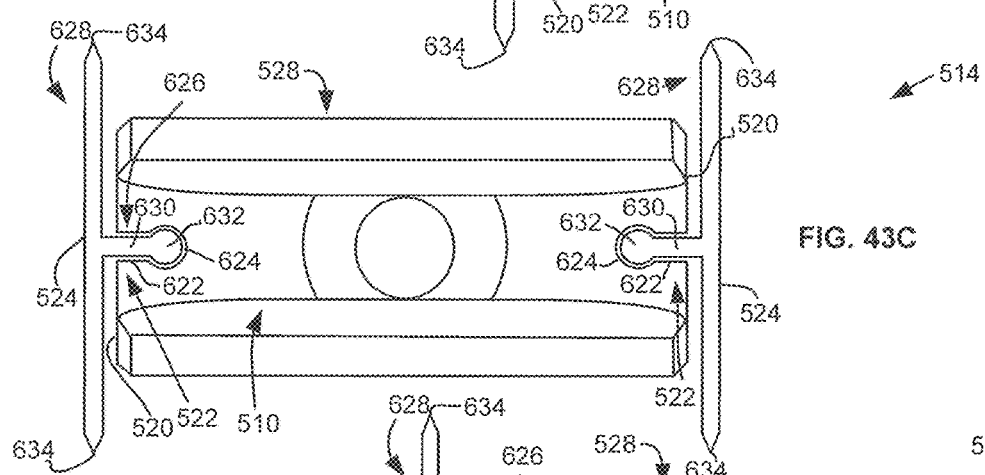
Figure 43D:
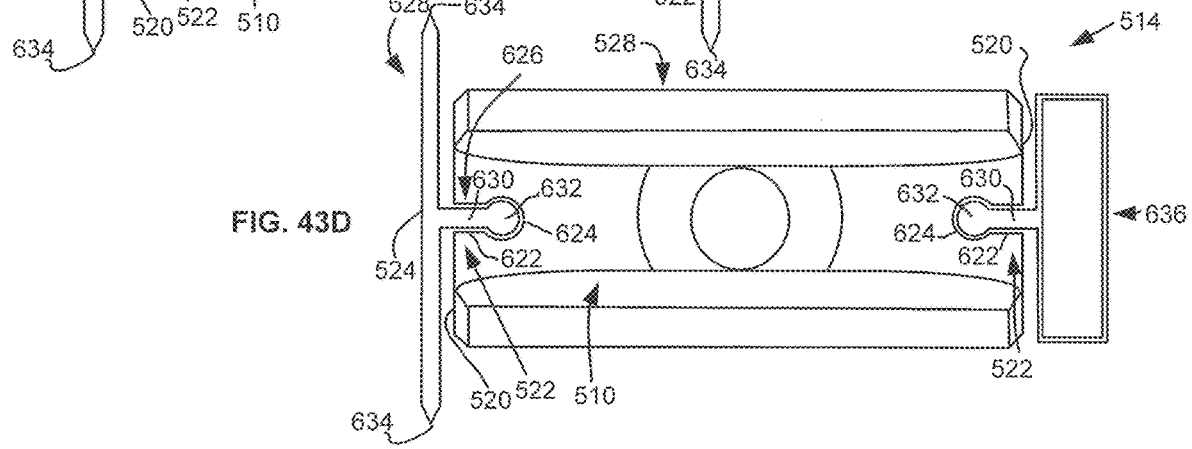
Figure 43E:
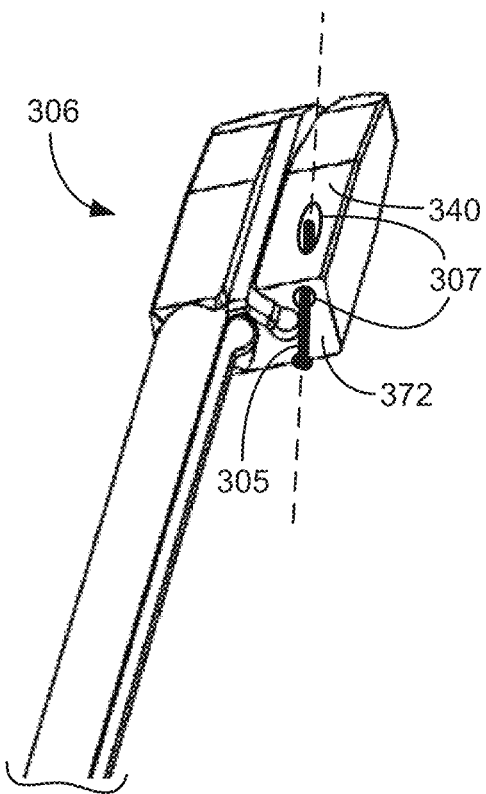
FIG. 43E is an isometric view of an implant trial and an anchor member in a recessed condition.
Figure 43F:
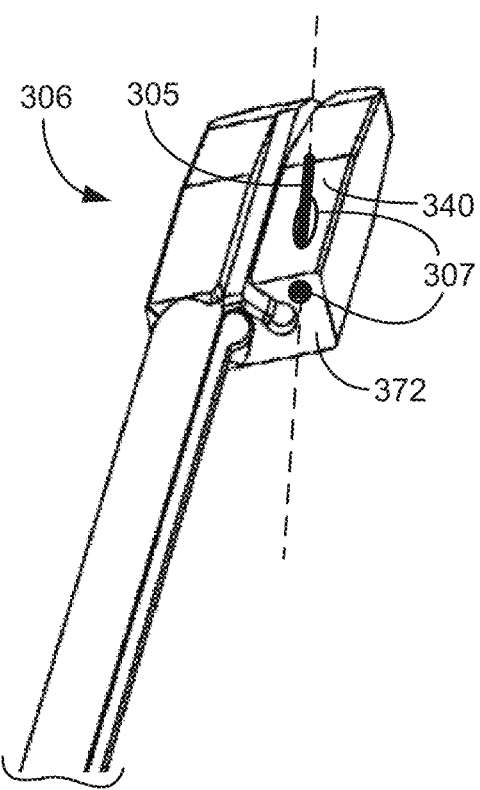
FIG. 43F is an isometric view of an implant trial and an anchor member in a deployed condition.

As seen in FIGS. 43E and 43F, the implant trial 306 may have a locking means which reversibly secures the trial 306 within the joint during certain steps in the procedure. For example, the proximal surface 372 of the implant trial 306 may have at least one passageway 307, which communicates with either a top of bottom surface 340, which is configured to receive an anchoring member 305 which may be proximally acted upon to reversibly transition from a recessed condition to a deployed condition. The recessed condition, as seen in FIG. 43E, is such that the anchoring member 305 is recessed within the passageway 307 or simply not extending beyond the top surface 340 and thereby not engaging a bone defining the joint and thereby not preventing movement of the implant trial 306 relative to the joint. The deployed condition, as seen in FIG. 43F, is such that the anchoring member 305 projects out of the passageway 307 from the top surface 340 thereby engaging a bone of the joint which may prevent or at least limit the movement of the implant trial 306 during the course of the procedure. The anchoring member 305 may be a spike, pin, dart, screw or other suitable locking or restraining member.

Figure 34:
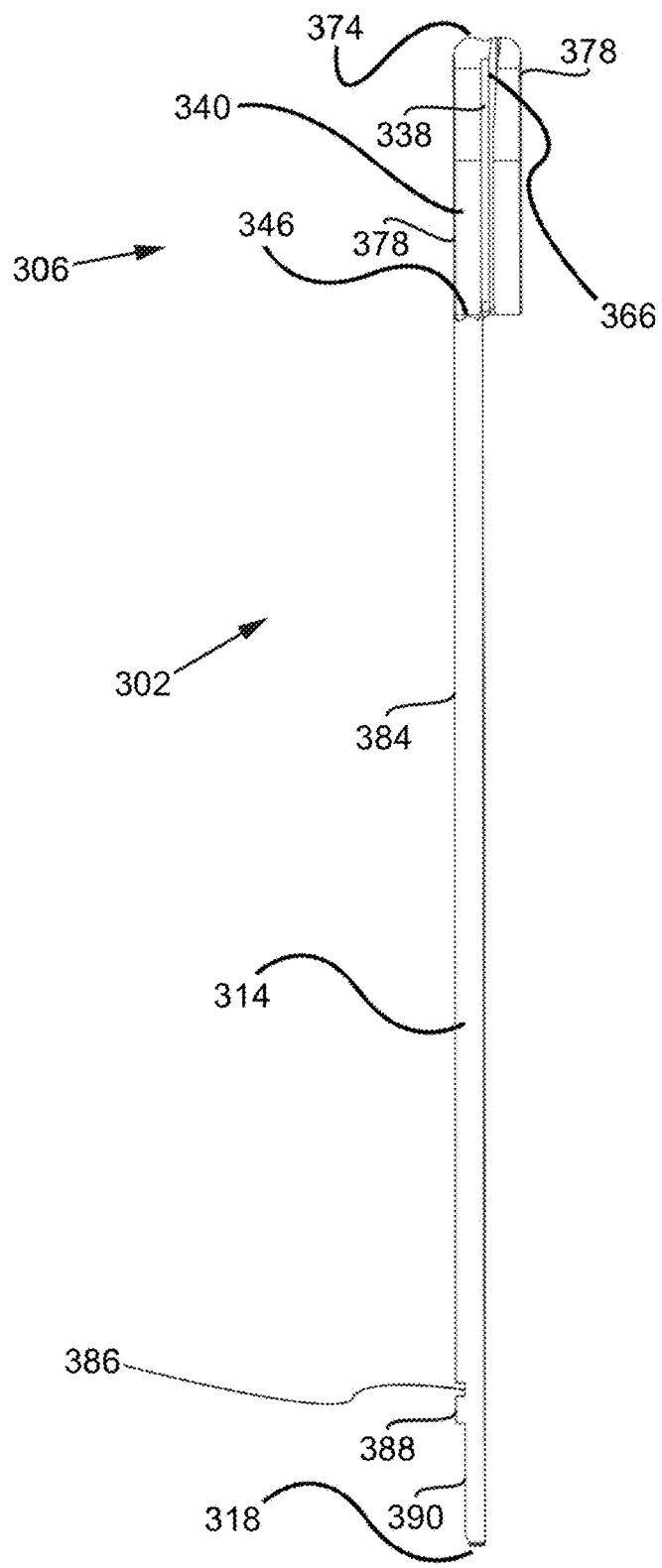
FIG. 34 is a side view of the trial tool assembly.

As further seen in FIG. 34, which is a front view of the trial tool assembly 302, an outer surface 384 of the shaft 314 of the trial tool assembly 302 lies flush with one of the outer surfaces 378 of the implant trial 306. As discussed previously, the proximal end 318 of the shaft 314 in configured to engage with a handle assembly 316. To facilitate the coupling of the shaft 314 and the handle assembly 316, the shaft 314 includes a notch or indent 386 within the outer surface 384 of the shaft 314. Proximally from the notch 386 is a stop feature 388 that defines a partial planar resection or flattening 390 of the outer surface 378 of the shaft 314.

Figure 35:
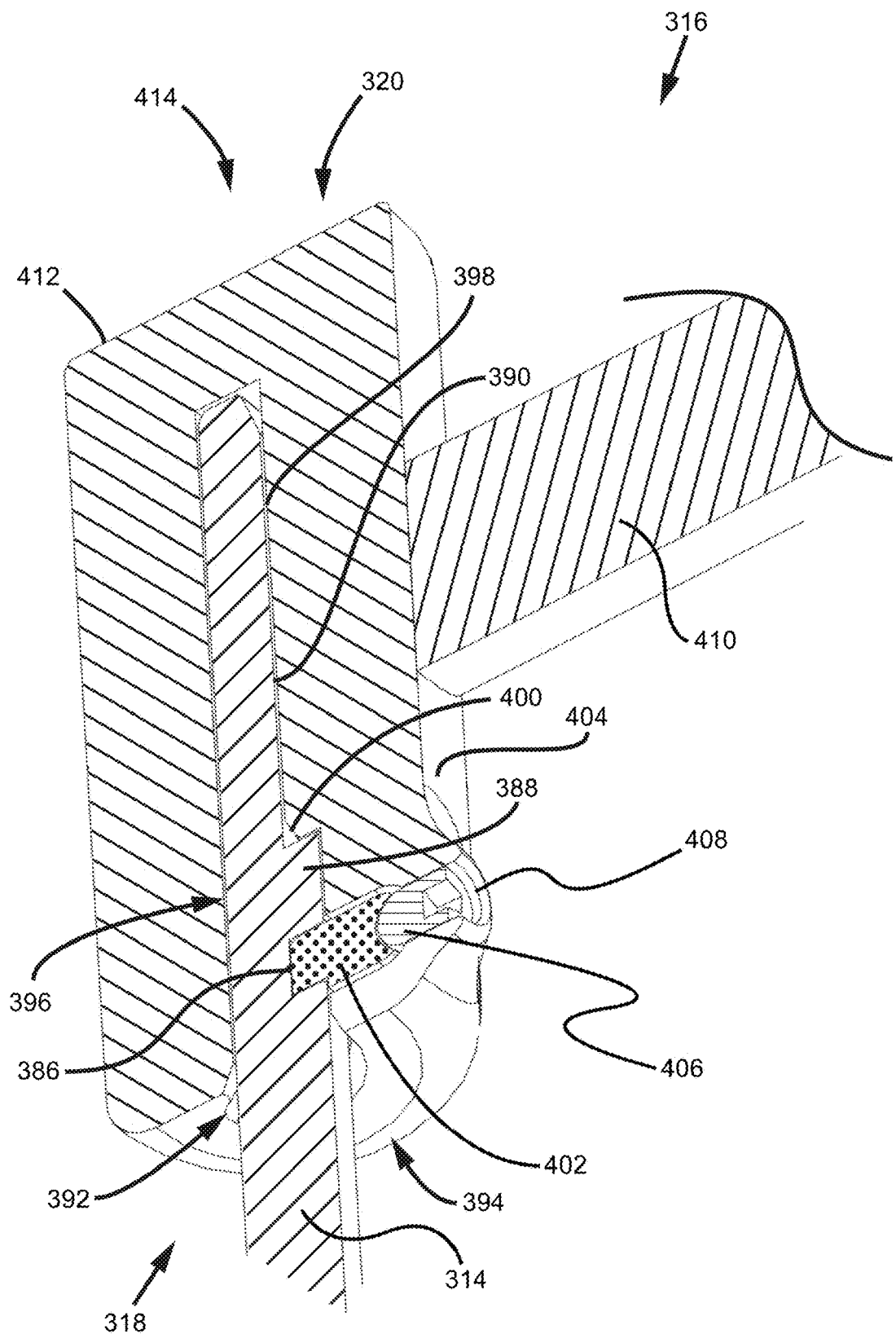
FIG. 35 is a cross-sectional isometric view of the handle assembly and the proximal end of the shaft of the trial tool.

For a discussion of the engagement of the handle assembly 316 with the shaft 314, reference is made to FIG. 35, which is a cross-sectional isometric view of the handle assembly 316 and the proximal end 318 of the shaft 314. As seen in the figure, the coupler 320 includes a cylindrical sidewall 404 and a flat impacting end 412 at a proximal end 414 of the coupler 320. Opposite the proximal end 414, a distal end 394 of the coupler 320 includes an opening 392 that is configured to receive the proximal end 318 of the shaft 314. The opening 392 includes a passageway that extend partially through the coupler 320 and includes a proximal inner surface 396 that is sized slightly larger than the proximal end 318 of the shaft 314. The inner surface 396 includes a planar inner surface portion 398 that matches the planar surface 390 of the shaft 314 such that when the shaft 314 is inserted into the opening 392, the planar surface 390 of the shaft 314 lies flush and opposed with the planar inner surface 398 of the opening 392 in a single orientation. When the shaft 314 is fully inserted into the opening 392, the stop feature 388 abuts a corresponding feature 400 on the inner surface 396 of the opening 392, which prevents further extension of the shaft 314 into the opening 392. Also, when the stop feature 388 abuts the corresponding feature 400, the notch 386 is aligned with a lock feature 402 that extends through a bore in the cylindrical sidewall 404 of the coupler 320. The lock feature 402 includes a tubular member that is configured to extend through the sidewall 404 and into the notch 386 while still being partially positioned in the sidewall 404 in order to lock the shaft 314 in place relative to the coupler 320. The lock feature 402 may be engaged and disengaged from within the notch 386 by activation of a set screw 406 or similar mechanism. In this embodiment, the set screw 406 is maintained within the sidewall 404 of the coupler by a retainer 408 that inhibits movement of the set screw 406 from full retraction outside of the sidewall 404. The function of the lock feature 402 and the set screw 406 may be accomplished with many different mechanisms and methods. For example, the set screw 406 may be substituted for a mechanical switch that forces the lock feature 402 into the notch 386 when the switch is engaged. This and other such mechanisms are possible and contemplated by this disclosure.

Figure 36A:
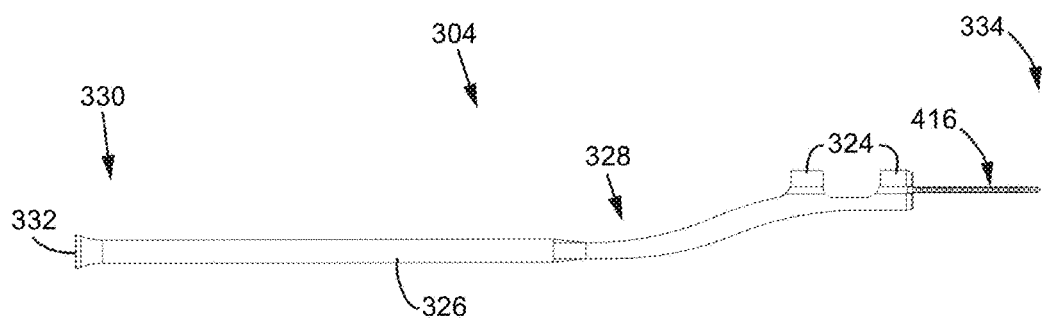
FIG. 36A is a side view of another embodiment of a cutting tool.
Figure 36B:
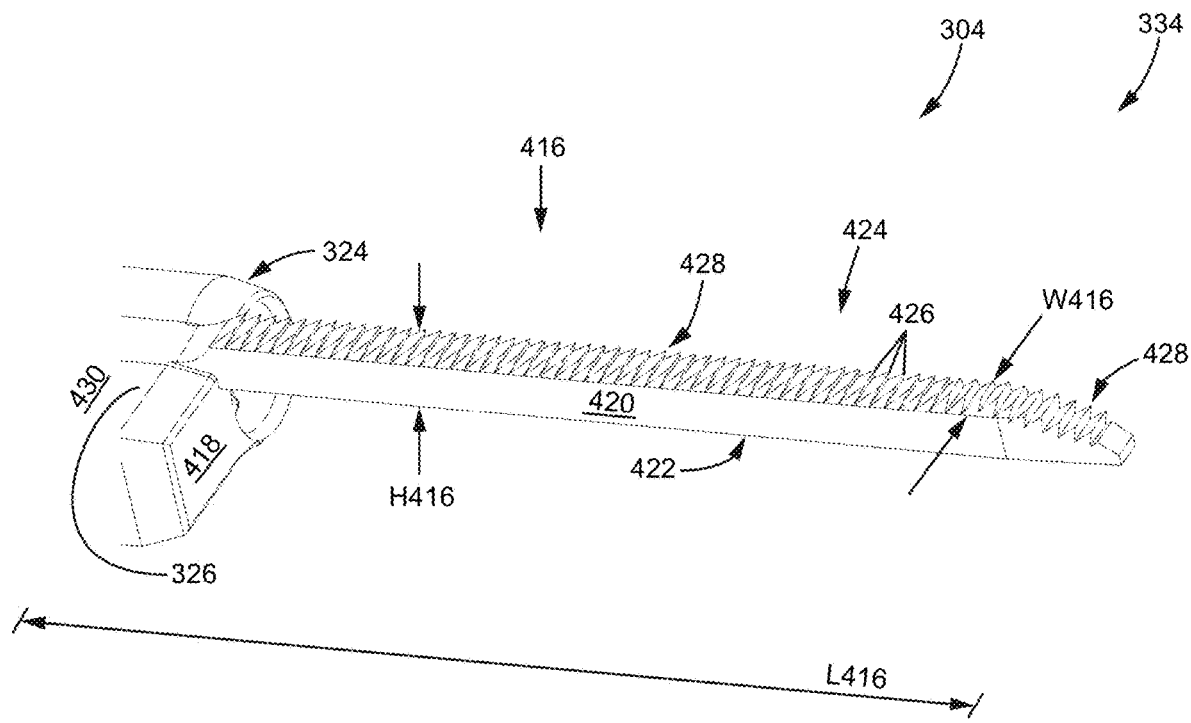
FIG. 36B is a close-up isometric view of the cutting tool of FIG. 35A.

Turning now to FIGS. 36A-36B, reference is made to another embodiment of the cutting tool 304. As seen in FIG. 36A, the cutting tool 304 include a similar shaft 326 with a curved mid-portion 328, distal and proximal collars 324 for receiving a shaft of a trial tool assembly, and an impact plate 332 at a proximal end 330 of the cutting tool 304 as described with reference to the previous embodiment of the joint preparation tool assembly 300. The present embodiment differs, however, from the previously described embodiment of the joint preparation tool assembly 300 in that it includes a saw-blade type cutting element 416 at a distal end 334 of the cutting tool 304. Referring to FIG. 36B, which is a close-up isometric view of the distal end 334 of the cutting tool 304, the cutting element 416 extends from a planar distal surface 418 of the tool 304 and includes opposite side surfaces 420, a bottom surface 422, and a top surface 424 that includes a series of teeth 426 arranged in a saw tooth shape that is configured to cut during a distal extension of the cutting tool 304. The series of teeth 426 extend generally perpendicularly from a top surface 430 of the shaft 326. At a distal end 334 of the cutting tool 304, the top surface 424 of the cutting element 416 tapers towards the bottom surface 422 to form a rounded, tapered distal tip 428.

In certain embodiments of the cutting tool 304, the cutting element 416 may include a width W416 between the opposite side surfaces within a range of about 1 mm to about 1.25 mm, from about 1 mm to about 1.75 mm, from about 1.5 mm to about 2.25 mm, from about 2 mm to about 2.75 mm, from about 2.5 mm to about 3 mm, from about 2.75 mm to about 4.25 mm, from about 4 mm to about 5 mm, from about 4.75 mm to about 6 mm, from about 5.75 mm to about 7 mm, and from about 6.5 mm to about 7.5 mm. In certain instances, the width W416 may be about 1.5 mm, 1.75 mm, 2 mm, 2.75 mm, 3 mm or 3.5 mm X. In certain embodiments, the cutting element 416 may include a length L416 from the planar distal surface 418 to the tapered distal tip 428 within a range of about 10 mm to about 15 mm, from about 13 mm to about 20 mm, from about 17.5 mm to about 30 mm, from about 25 mm to about 37.5 mm, from about 35 mm to about 40 mm, from about 37 mm to about 50 mm. In certain instances, the length L416 may be about 27 mm, 30 mm, 37 mm, or 40 mm. In certain embodiments, the cutting element may include a height H416 from the bottom surface 422 to the series of teeth 426 within a range of about 2.25 mm to about 2.65 mm, from about 2.5 mm to about 3 mm, from about 2.75 mm to about 4.25 mm, from about 4 mm to about 5 mm, from about 4.75 mm to about 6 mm, from about 5.75 mm to about 7 mm, from about 6.5 mm to about 7.5 mm, from about 7 mm to about 8.75 mm, from about 8.5 mm to about 9.75 mm and from about 9.5 mm to about 11.25 mm. In certain instances, the height H416 may be about 3.25 mm, 4 mm, 4.5 mm, 5 mm or 5.25 mm.

The cutting tool 304 of FIGS. 36A-36B is configured to be used with the trial tool assembly 302 as described previously. The cutting tool 304 in FIGS. 36A-36B may be useful, for example, in making a keel-cut into either the sacrum or the ilium after the implant trial of the trial tool assembly is delivered non-transversely into the sacroiliac joint. Since the cutting element 416 extends generally perpendicular from the shaft 326 of the cutting tool 304, when the implant trial is positioned non-transversely within the sacroiliac joint, the series of teeth 426 will be oriented generally perpendicularly to the sacrum/ilium such that a distal extension of the cutting tool 304 will provide a cut into the bone that may match a keel or wing member of an implant to be subsequently implanted into the joint space.

Figure 36E:
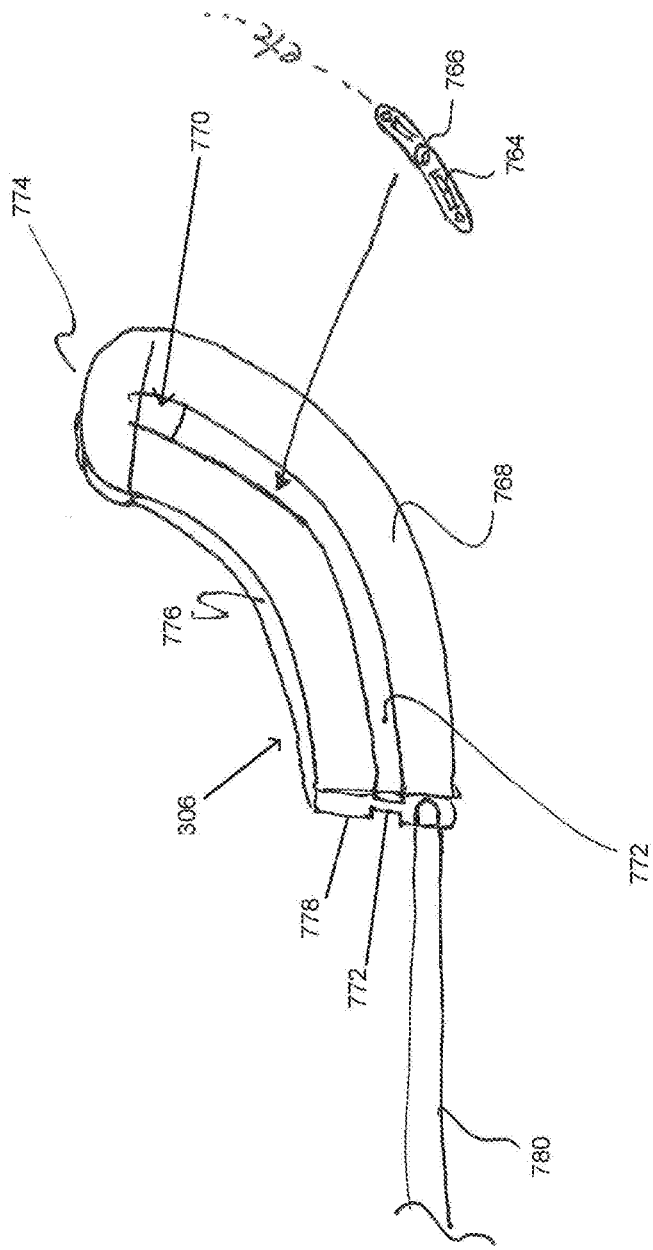
FIG. 36E is an isometric view of an arcuate implant trial configured to guide a cutting element formed of a chain of interconnected teeth.

Reference is now made to FIGS. 36C-36E, which depict an alternative implant trial 306 and cutting element 416. As seen in FIG. 36C, the cutting element 416 may include interconnected teeth 764 forming a chain that are configured to rotate around a portion of the implant trial 306. The interconnected teeth 764 may be segmented into individual teeth 764 and each segmented tooth 764 may be in-line and linked with one another via rivets 766 or similar mechanisms. The interconnected teeth 764 may be configured similar to a tooth on a chainsaw and dimensioned as herein described, however, the overall length of each tooth 764 will be a fraction of the total length L416 of the cutting element segment assembly. For example, if the assembly comprises three teeth 764, than the length of each tooth will be approximately one third of the overall length L416 of the cutting element segment assembly. In an aspect, an assembly comprises fifteen teeth 764 with each tooth approximately 2 mm in length. In one aspect, the teeth 764 are configured similar to chipper teeth or an OREGON no. 10 chipper chain, one of many STIHL saw chains or even a full-chisel chain. In other aspects, the teeth 764 may be configured as other linked-chains known in the art.

The interconnected teeth 764 may be configured to rotate through a portion of a length of the implant trial 306 such that a portion of the teeth 764 extend above a top surface 768 of the implant trial 306. Thus, in operation and during rotation, the interconnected teeth 764 are configured to deliver a cut (e.g., keel-cut) into a joint bone when the implant trial 306 is positioned within a joint space. The interconnected teeth 764 opposite the top surface 768, may extend outward from a bottom surface of the implant trial 306 such that rotation of the interconnected teeth 764 delivers simultaneous cuts to opposing bones in a joint space. Or, alternatively, the teeth 764 opposite the teeth 764 on the top surface 768 may remain housed within a passageway within the body of the implant trial 306 such that the teeth 764 only contact a joint bone that opposes the top surface 768.

Referring to FIG. 36D, which is a top view of an implant trial 306 that is suitable for use with the cutting element 416 described previously, the implant trial 306 may include a first guide or channel 338 formed in the top surface 768 and a second guide or channel (not shown) formed in the bottom surface of the implant trial 306, which is opposite the top surface 768 and not shown in FIG. 36D. And, at a distal end 774 of the implant trial 306, there may be a passageway 770 communicating between implant trial top and bottom surfaces 768. The passageway 770 may be configured and dimensioned to receive the interconnected teeth 764 as they run distal-proximal along the first and second guides 338 through the passageway 770. Such a configuration of the interconnected teeth 764 with the implant trial 306 having a passageway 770 at the distal end 774 may permit use of a rotating chain of teeth while protecting a patient's tissue that is distal to the distal end 774 of the implant trial 306.

Referring now to FIG. 36E, which is an isometric view of an arcuate implant trial 306 coupled with a shaft 780, the teeth 764 may be linked together such that they pivot relative to one another with a pivot axis which is generally perpendicular to the length of the trial guide 338 and perpendicular to the top surface 768 of the implant trial 306. Such a configuration would permit a saw chain of interconnected teeth 764 to travel an arcuate path via an arcuate trial guide path 772 formed on a generally planar implant trial top surface 768 where the opposite side surfaces 776 of implant trial 306 are curved and have a radius of approximately 2 cm to about 8 cm. In this arrangement a cutting tip of the interconnected teeth 764 remains oriented perpendicular to the top surface 768 of the implant trial 306; however, the orientation of the pivot 766 is altered from the previous embodiment. As described previously, the interconnected teeth 764 may travel along the arcuate trial guide path 772 until the teeth 764 enter the passageway 770 at the distal end 774 of the implant trial 306. The teeth 764 may then exit the passageway 770 and travel proximally on the arcuate trial guide path 772 formed on the bottom surface 778 of the implant trial 306. In this arrangement, the interconnected teeth 746 may include an additional pivot 766 oriented generally perpendicular to the previously described pivot 766 such that the additional pivot 766 enables movement of the chain of interconnected teeth 764 to travel through the passageway 770. Alternatively, the implant trial 306 may not include a passageway 770 and the teeth 764 may simply translate distally-proximally within the guide paths 772.

Other cutting elements 416 are possible and contemplated herein. For example, the cutting element 416 may include a serrated or smooth knife blade. And, the joint preparation tool assembly 300 may include a series of cutting tools 304, each cutting tool 304 with progressively larger (e.g., wider) blades that may or may not be used in succession to make larger and larger cuts until a desired cut size is made for subsequent implant delivery.

2. Trial Fit Assembly and Cutting Tool with Coaxially Aligned Shafts

Figure 37:
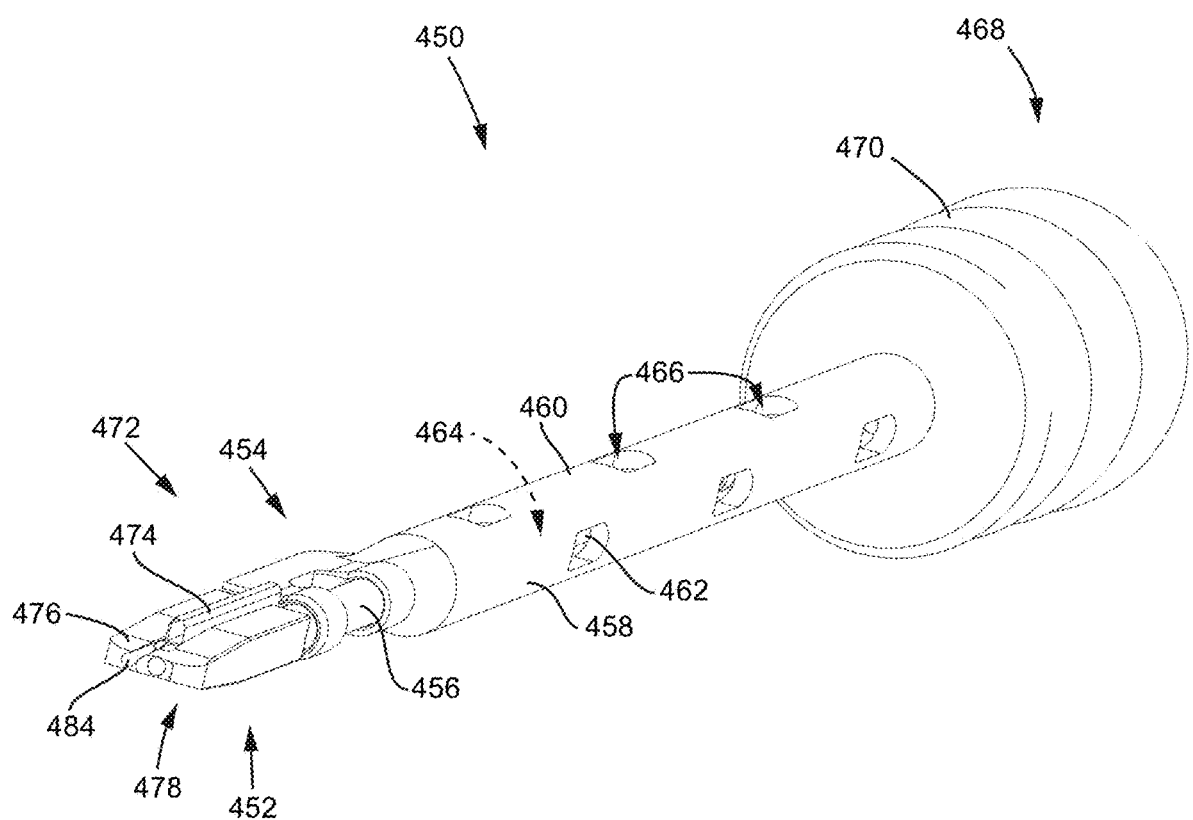
FIG. 37 is an isometric view of a joint preparation tool assembly with coaxially aligned shafts of a cutting tool and a trial implant tool assembly.

Turning now to another embodiment of a joint preparation tool assembly 450, reference is made to FIG. 37. As seen in the figure, the joint preparation tool assembly 450 includes a trial tool assembly 452 and a cutting tool 454 that translates on a shaft 456 of the trial tool assembly 452. The cutting tool 454 includes a tubular shaft 458 having an outer surface 460, an inner surface 462, and a hollow interior space 464. The tubular shaft 458 also includes a series of apertures 466 extending from the outer surface 460 to the inner surface 462 of the shaft 458. The apertures 466 provide for easier and improved steam cleaning compared with a tubular shaft without apertures. The apertures 466 also reduce weight of the assembly 450, among other benefits. The tubular shaft 458 or, more particularly, the hollow interior space 464 is configured to receive the shaft 456 of the trial tool assembly 452 such that the shafts 456, 458 are coaxially aligned. At a proximal end 468, the cutting tool 454 includes a handle 470. At a distal end 472, the cutting tool 454 includes a cutting element 474, which, in this embodiment, is a box-type chisel as described previously.

Figure 38:
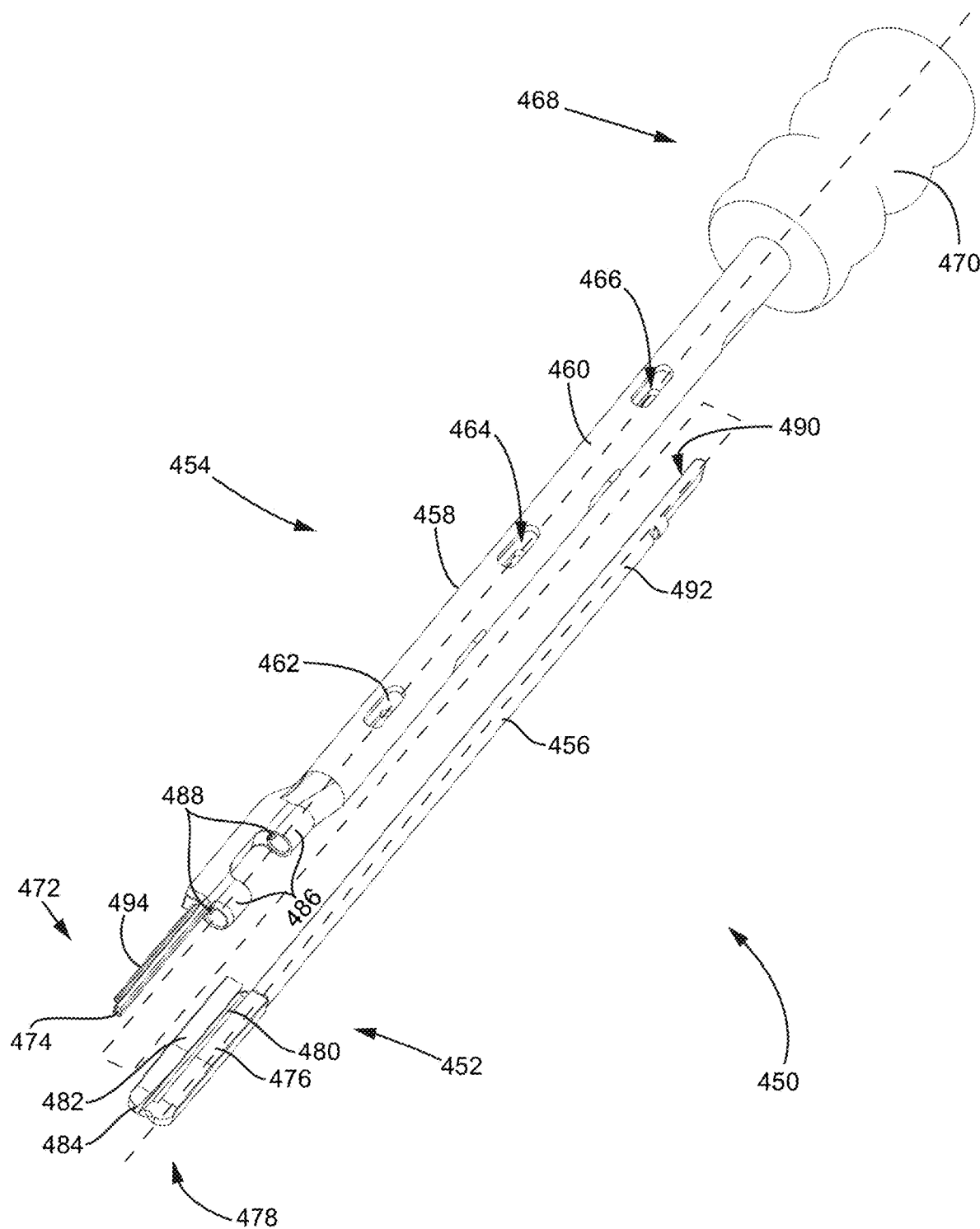
FIG. 38 is an isometric view of the joint preparation tool assembly of FIG. 37 with the cutting tool and the trial implant tool assembly in an uncoupled state.

Regarding the trial tool assembly 452, the assembly includes an implant trial 476 at a distal end 478 of the assembly. As seen in FIG. 38, which is an isometric view of the cutting tool 454 and the trial tool assembly 452 in an uncoupled state, it can be seen that the trial tool assembly 452 is similar to and may include the same or different features of the joint preparation tool assembly 300 discussed previously in FIGS. 27-35. That is, the trial tool assembly 452 includes the implant trial 476 at the distal end 478 of the assembly, a guide 480 on a top surface 482 of the implant trial 476, and a guide channel 484 that is configured to guide the cutting element 474 during translation of the cutting element 474 within the guide 480 of the implant trial 476.

To couple the trial tool assembly 452 and the cutting tool 454, the shaft 456 of the trial tool assembly 452 is received through a pair of collars 486 on the cutting tool and is translated proximally such that the shaft 456 is received within the tubular shaft 458 of the cutting tool 454. As seen in FIG. 38, the cutting tool 454 includes a protrusion 488 within each of the collars 486 that fit within a corresponding channel 490 formed within an outer surface 492 of the shaft 456 of the trial tool assembly 452. The interaction of the protrusion 488 and the corresponding channel 490 ensures that the trial tool assembly 452 maintains its orientation relative to the cutting tool 454 during distal-proximal movement. As the trial tool assembly 452 is proximally retracted within the tubular shaft 458 of the cutting tool 454, a cutting guide element 494 of the cutting tool 454 will engage with and be received within the guide 480 of the implant trial 476. The interaction of the cutting guide element 494 and the guide 480 and guide channel 484 further ensures that the orientation of the cutting tool 454 and the trial tool assembly 452 will be maintained during a cutting stroke of the cutting tool 454 during a surgical procedure.

3. Trial Fit Assembly, Cutting Tool, and Trial Impact Rod with Coaxially Aligned Shafts Turning now to another embodiment of a joint preparation tool assembly 500, reference is made to FIG. 39, which depicts the individual components of the assembly 500 in an uncoupled state. As seen in the figure, the joint preparation tool assembly 500 includes a trial tool assembly 502, a trial impact rod assembly 504, a handle assembly 506, and a cutting tool 508.

In one aspect, the trial impact rod assembly 504 is configured to be used in conjunction with the trial tool assembly 502 to provide stability during delivery of a distal end 510 of the trial tool assembly 502 into a joint of a patient. In particular, slidable coupling of the trial impact rod assembly 504 and the trial tool assembly 502 adds stability and rigidity to the assembly 500 by reducing potential bending, among other movements, of the trial tool assembly 502 shaft 512 during a striking of the handle assembly 506.

In another aspect, the cutting tool 508 is configured to be used in conjunction with the trial tool assembly 502 to deliver a transverse keel-cut into a bone of a joint. For example, the distal end 510 of the trial tool assembly 502 may be delivered non-transversely into a sacroiliac joint of a patient with stabilizing support from the trial impact rod assembly 504 and, then, once the trial impact rod assembly 504 is decoupled from the trial tool assembly 502, the cutting tool 508 may be may be slidably coupled with the trial tool assembly 502 and used to transversely cut into either or both of the sacrum and the ilium to make way for subsequent delivery of an implant having transversely extending members that match the cuts made into the sacrum/ilium. In each of the examples described above, the handle assembly 506 may be coupled to a proximal end of the trial impact rod 504 or the cutting tool 508 and a device (e.g., hammer, mallet) may be used to strike the handle assembly 506 in order to distally drive the assembly 500.

Figure 39:
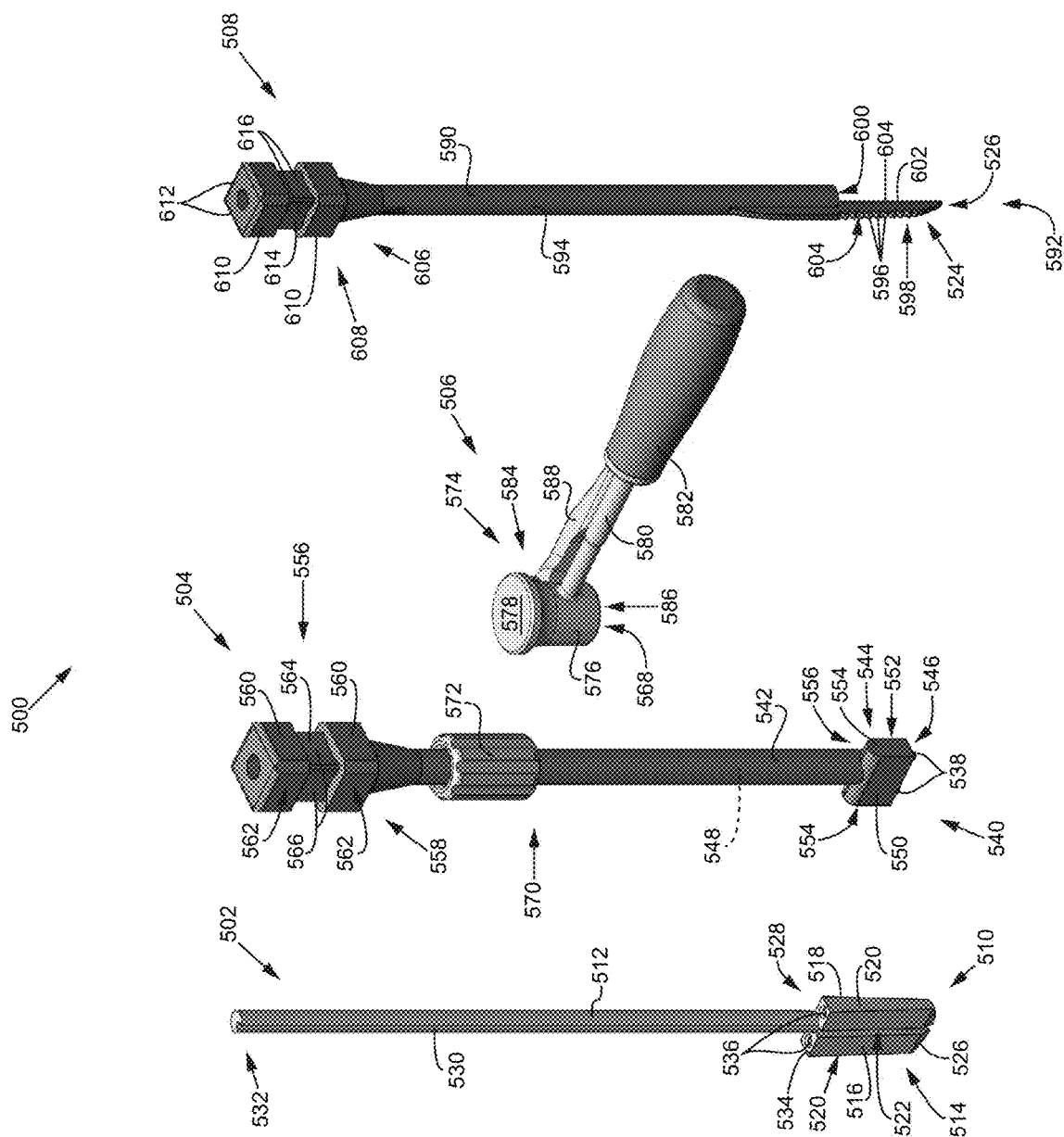
FIG. 39 is an isometric view of a joint preparation tool assembly with coaxially aligned shafts of a cutting tool, a trial implant tool assembly, and a trial impact rod assembly.

To begin the discussion of the components of the joint preparation tool assembly 500, reference is made to the trial tool assembly 502 in FIG. 39. As seen in the figure, the trial tool assembly 502 includes an implant trial 514 at the distal end 510 of the assembly 502. The implant trial 514 is a planar member with a top surface 516, a bottom surface 518 that is opposite the top surface 516, and opposite side surfaces 520. The top surface 516 includes a channel 522 that guides a cutting element 524 of the cutting tool 508. The channel 522 extends from a tapered distal tip 526 to a proximal end 528 of the implant trial 514 and is coaxial with a shaft channel 530 that extends the length of the shaft 512 from the proximal end 528 of the implant trial 514 to a proximal end 532 of the shaft 512. In this way, the cutting element 524 of the cutting tool 508 may be guided along the shaft channel 530 while the cutting element 524 is proximal of the implant trial 514. And, when the cutting element 524 is distally advanced it will also be guided by the channel 522 in the top surface 516 of the implant trial 514. Shaft channel 530 may simply be a planar surface along shaft 512 and aligned with a corresponding planar surface of channel 522.

As seen in FIG. 39, the shaft 512 of the trial tool assembly 502 is centrally positioned on a proximal surface 534 of the implant trial 514. On the proximal surface 534 of the implant trial 514 and on either side of the shaft 514 are bores 536 that extend distally through a portion of the implant trial 514. The bores 536 are configured to receive a corresponding pair of stud members 538 on a distal end 540 of the trial impact rod assembly 504. When the stud members 538 are received within the bores 536, the implant trial 514 is correctly aligned with the distal end 540 of the trial impact rod 504. Alternatively, the bores may be studs and the studs bores.

Now the discussion will focus on the trial impact rod assembly 504 of FIG. 39. As seen in the figure, the trial impact rod assembly 504 includes a tubular shaft 542 that couples or transitions to an implant trial extension member 544 at the distal end of the trial impact rod assembly 504. The implant trial extension member 544 is a planar member that includes the stud members 538 on a planar distal surface 546 of the member 544. The shaft 512 of the trial tool assembly 502 is configured to be received within an interior space 548 in the tubular shaft 542 and the stud members 538 are configured to be received within the bores 536 on the proximal surface 534 of the implant trial 514. In this arrangement, when the shaft 512 of the trial tool assembly 502 is fully received within the tubular shaft 542 of the trial impact rod assembly 504, the proximal surface 534 of the implant trial 514 and the distal surface 546 of the implant trial extension member 544 abut each other. The implant trial extension member 544 acts as a natural extension of the implant trial 514 such that when the implant trial 514 is delivered into a patient's joint, the distal end 540 of the trial impact rod assembly 504 may also be delivered into the joint space without stoppage. Stated differently, the implant trial extension member 544 includes top and bottom surfaces 550, 552 and opposite side surfaces 554 that align with and provide a smooth transition between (i.e., coplanar) the top, bottom, and opposite side surfaces 516, 518, 520 of the implant trial 514. Alternatively, implant trial extension member 544 may have a transition which intentionally interferes with a bone of the joint in order to act as a stop. The stop feature may be adjustable or fixed.

At a mid-portion 570 of the trial impact rod assembly 504, a screw-lock 572 is rotatably coupled to the tubular shaft 542 and configured to frictionally lock or support the shaft 512 of the trial tool assembly 502 when the shaft 512 is received within the tubular shaft 542 of the trial impact rod assembly 504. The screw-lock 572 may function to lock the shaft 512 in place in many ways. For example, the screw-lock 572 may rotationally advance on a pair of threaded push-locks (not shown) that extend through the tubular shaft 542 such that when the screw-lock 572 is rotationally engaged over the push-locks, the push-locks are caused to extend further through the tubular shaft 542 and into contact with the shaft 512 of the trial tool assembly 502. Such contact with the shaft 512 of the trial tool assembly 502 may cause sufficient friction to securely support the positioning of the shaft 512 within the tubular shaft 542.

Also as seen in FIG. 39, a proximal end 556 the trial impact rod assembly 504 includes a handle engagement mechanism 558 that includes a pair of block-like members 560 with four generally perpendicular sidewalls 562 separated by mid-section member 564 with four slightly concave sidewalls 566 that are generally coplanar with a pair of corresponding sidewall 562 of the pair of block-like members 560. The handle engagement mechanism 558 is configured to be received and secured within a distal opening 568 in the handle assembly 506. The distal opening 568 extends to a cavity 586 for housing and securing of the handle engagement mechanism 558.

Moving on, reference is made to the cutting tool 508 in FIG. 39. As seen in the figure, the tool 508 includes a shaft 590 that is coupled to the cutting element 524 at a distal end 592 of the cutting tool 508. The cutting element 524 is a planar member with generally parallel opposite sides and a top surface 598 that extends outward and distally from an outer surface 594 of the shaft 590. The cutting element 524 includes a series of teeth 596 on the top surface 598 of the cutting element 524. The cutting element in this embodiment is similar to as described in reference to FIGS. 36A-36B. Alternatively, the cutting element 524 may be as described in other portions of this disclosure. For example, the cutting element 524 may include a box chisel, serrated knife blade, etc.

The shaft 590 of the cutting tool 508 is tubular and includes an internal passageway 600 that is configured to receive the shaft 512 of the trial tool assembly 502. When the shaft 512 is fully received within the tubular shaft 590 of the cutting tool 508, the cutting element 524 or, more particularly, a bottom surface 602 and a portion of opposite sidewall surfaces 604 of the cutting element 524 are guided by and positioned within the channel 522 on the top surface 516 of the implant trial 514. The cutting tool 508 may include a protrusion (not shown) on the internal passageway 600 of the shaft 590 that is configured to engage with and be guided by the shaft channel 530 of the trial tool assembly 502. When the implant trial 514 is delivered into a joint of a patient, a distal stroke of the cutting element 524 relative to the implant trial 514 is configured to make a keel-cut perpendicular to a plane defined by the joint for the subsequent delivery of an implant having matching keels or wing members.

Referring to a proximal end 606 of the cutting tool 508, the shaft 590 is coupled or transitions to a handle engagement mechanism 608 that is similar to the mechanisms 558 on the trial impact rod assembly 504. The handle engagement mechanism 608 includes a pair of block-like members 610 with four generally perpendicular sidewalls 612 separated by a smaller mid-section member 614 with four slightly concave sidewalls 616 that are generally coplanar with a pair of corresponding sidewall 612 of the pair of block-like members 610. The handle engagement mechanism 608 is configured to be received and secured within the distal opening 568 in the handle assembly 506. As stated previously, the distal opening 568 extends to the cavity 586 for housing and securing of the handle engagement mechanism 608.

Referring to the handle assembly 506 in FIG. 39, the assembly 506 includes a coupler 574 that is configured to receive and support the handle engagement mechanisms 558, 608 on the trial impact rod assembly 504 and the cutting tool 508 within the distal opening 568. The coupler 574 includes a cylindrical sidewall 576 and a flat impact plate 578 that is opposite the distal opening 568 and configured to be struck with a hammer, mallet, or similar device in order to distally drive the joint preparation tool assembly 500 within a joint. Extending from and attached to the cylindrical sidewall 576 is a shaft 580 that further extends to a handle 582.

Still referring to the handle assembly 506 of FIG. 39, the coupler 574 includes a camming mechanism 584 that is configured to securely support the trial impact rod assembly 504 or the cutting tool 508 when the proximal end of the assembly 504 or tool 508 is positioned within the cavity 586 of the handle assembly 506. The camming mechanism 584 includes a handle 588 that transitions to a camming head having a cam-shaped surface. The camming head is coupled to the coupler 574 by an axle that extends through an aperture in the cylindrical sidewall 576 and is configured such that when the camming head is rotated about the axle, the cam-shaped surface contacts and locks against one of the concave sidewalls 566, 616 that is positioned adjacent the aperture. When the camming head is rotated in an opposite direction, the cam-shaped surface disengages with the concave sidewalls 566, 616 such that the trial impact rod assembly 504 or the cutting tool 508 may be removed from the cavity 586 in the coupler 574.

Figure 40C:
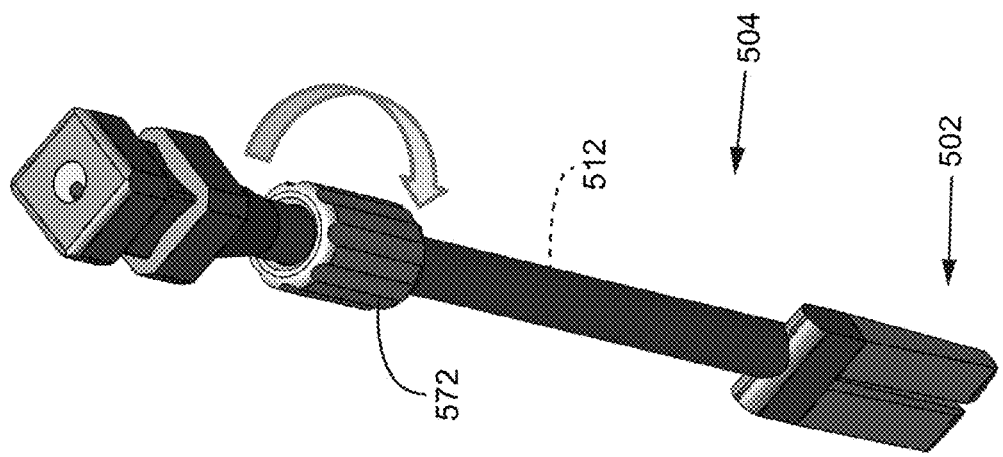
FIGS. 40A-40C are isometric views of the trial impact rod assembly and the trial tool assembly coupling together.
Figure 40B:
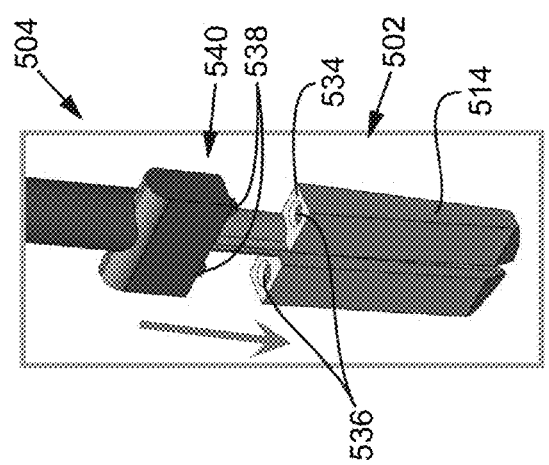
Figure 40A:
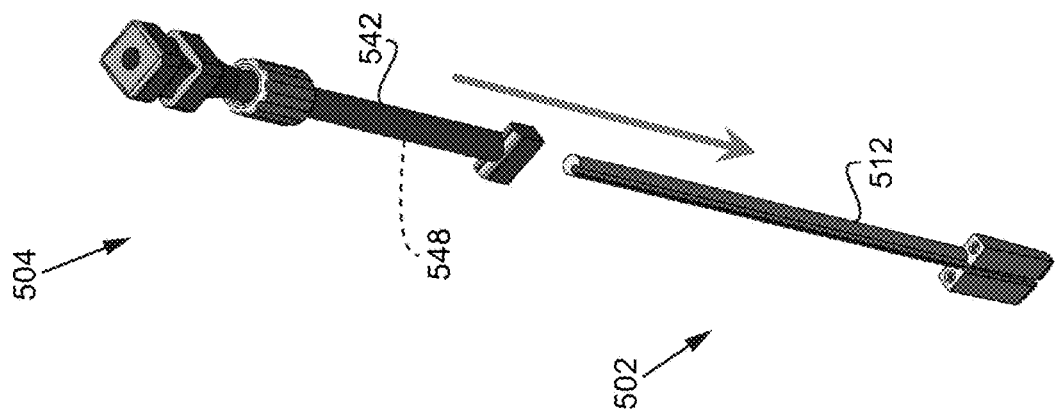

Reference is now made to FIGS. 40A-C, which are isometric views of the trial tool assembly 502 and the trial impact rod assembly 504 coupling together. As seen in FIG. 40A, the tubular shaft 542 of the trial impact rod assembly 504 is coaxially aligned with the shaft 512 of the trial tool assembly 502 such that the shaft 512 may be received within the interior space 548 of the tubular shaft 542. In this arrangement, as seen in FIG. 40B, which is a close-up view of the engagement of the implant trial 514 with the distal end 540 of the trial impact rod assembly 504, the stud members 538 on the trial impact rod 504 are aligned and configured to be received within the bores 536 on the proximal surface 534 of the implant trial 514. As seen in FIG. 40C, once the trial tool assembly 502 is received within the trial impact rod assembly 504, the screw-lock 572 may be rotationally engaged to frictionally support the shaft 512 of the trial tool assembly 502, which, in turn, securely supports the positioning of the trial tool assembly 502 relative to the trial impact rod assembly 504.

Figure 41:
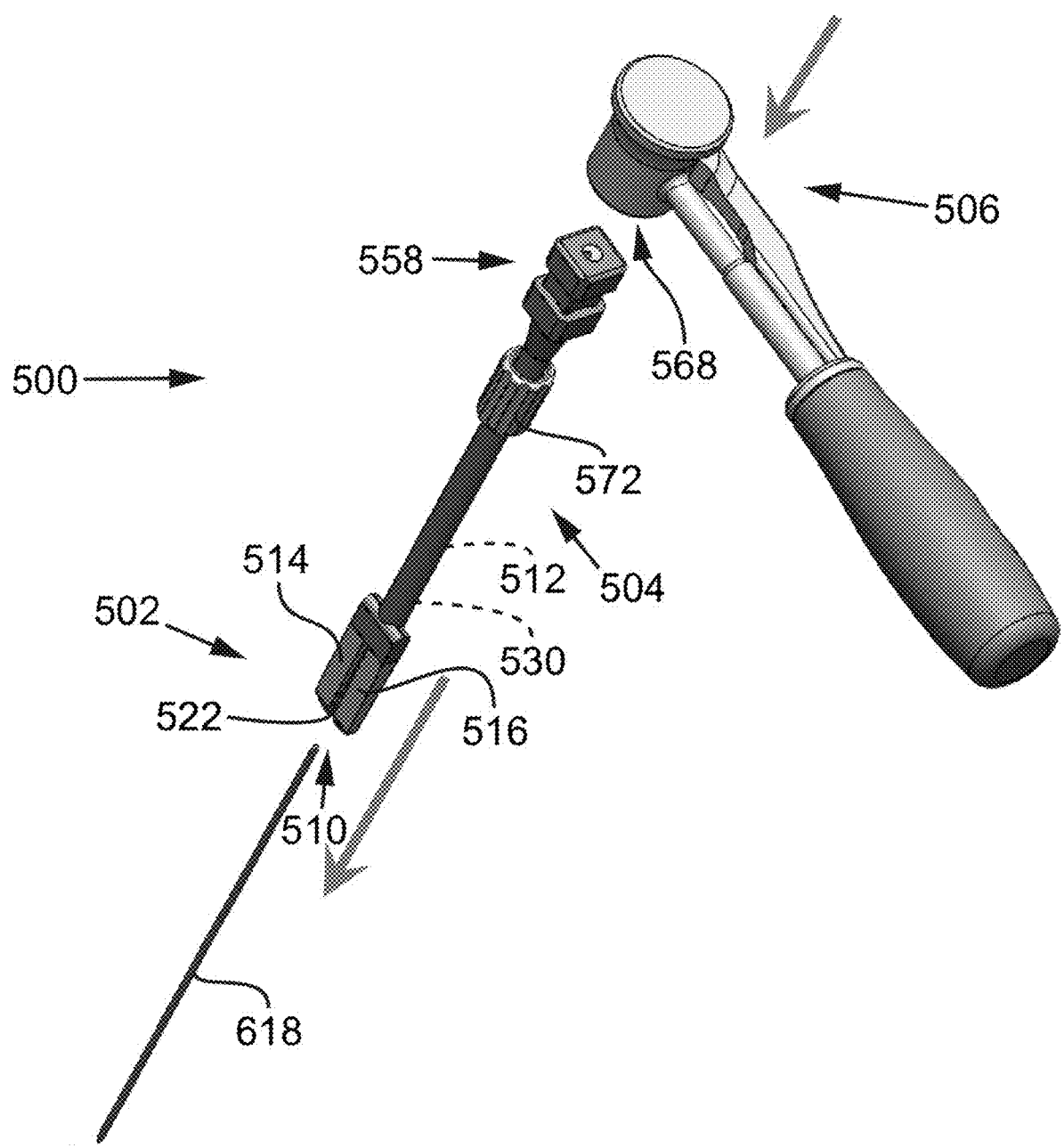
FIG. 41 is an isometric view of a handle assembly coupling with the trial impact rod assembly and the trial tool assembly.

Reference is now made to FIG. 41, which is an isometric view of the trial impact rod assembly 504 and the trial tool assembly 502 coupled together with the handle assembly 506 in close proximity. As seen in the figure, the handle engagement mechanism 558 is positioned to be received within the distal opening 568 in the handle assembly 506. Also, a guidewire 618 is positioned to be received within the channel 522 on the top surface 516 of the implant trial 514. After being received within the channel 522, the guidewire 618 may be further received within and guided by the shaft channel 530 in the shaft 512 of the trial tool assembly 502. In this way, the guidewire 618 may be delivered into a joint of a patient and the assembly 500 including the impact rod assembly 504 and the trial tool assembly 502 may be delivered into the joint via the guidewire 618 being received within the channel 522. Once the handle assembly 506 is coupled to the trial impact rod assembly 504, a mallet may be used to impact the handle assembly 506 in order to sufficiently drive the distal end 510 of the trial tool assembly 502 into the joint. And, once the implant trial 514 is sufficiently delivered within the joint space, the handle assembly 506 may be decoupled with the trial impact rod assembly 504. Next, the screw-lock 572 on the trial impact rod assembly 504 may be loosened so that the assembly 504 may be slidably removed from the trial tool assembly 502, which remains within the joint space. At this point, the guidewire 618 may be removed. Alternatively, the guide wire may be removed at any time during the procedure.

Figures 42A, 42B:
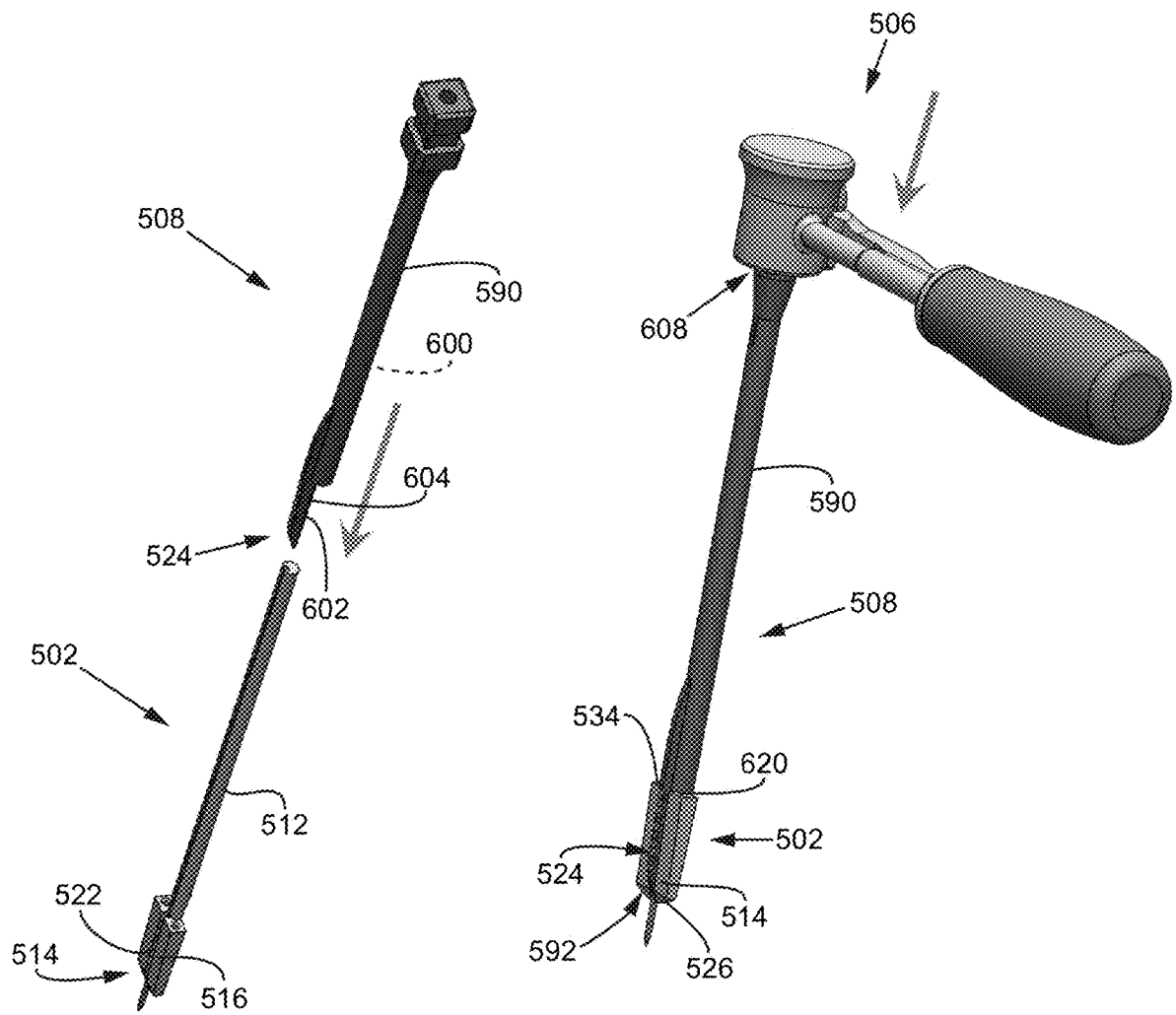
FIG. 42A is an isometric view of the cutting tool and the trial tool assembly coupling together.
FIG. 42B is an isometric view of the handle assembly coupling with the cutting tool and the trial tool assembly.

Reference is now made to FIGS. 42A-42B, which are isometric views of the trial tool assembly 502 and the cutting tool 508 coupling together. As seen in FIG. 42A, the shaft 512 of the trial tool assembly 502 is coaxially aligned with and configured to be received within the internal passageway 600 of the shaft 590 of the cutting tool 508. The cutting element 524 is aligned with and guided by the channel 522 on the top surface 516 of the shaft 512 as the cutting tool 508 is distally advanced relative to the trial tool assembly 502. That is, the bottom surface 602 and a portion of the opposite sidewall surfaces 604 are fitted and guided within the channel 522 such that rotation of the cutting tool 508 relative to the trial tool assembly 502 is restricted.

As seen in FIG. 42B, once the trial tool assembly 502 is coupled with the cutting tool 508, the handle assembly 506 may be coupled with the handle engagement mechanism 608 on the cutting tool 508. The handle assembly 506 may be struck with a mallet in order to distally drive the cutting element 524 relative to the implant trial 514 in order to make a keel-cut transverse to the joint. The cutting tool 508 may be distally driven relative to the implant trial 514 until a distal edge 620 of the shaft 590 abuts the proximal surface 534 of the implant trial 514. At this point, the distal end 592 of the cutting element 524 is positioned at the distal tip 526 of the implant trial 514.

Once the keel-cut has been made, the handle assembly 506 and the cutting tool 508 may be decoupled from the trial tool assembly 502 (either together or individually). Then, the trial tool assembly 502 may be removed from the joint space for subsequent delivery of an implant that matches the space that was cleared by the implant trial 514 and the cutting tool 508.

While the joint preparation tool assembly 500 as described in the previous figures includes an implant trial 514 with a single channel 522 and a cutting tool 508 with a single cutting element 524, the assembly 500 may include implant trials 514 and cutting tools 508 with multiple channels 522 and cutting elements 524. For example, a certain joint preparation tool assembly 500 may include an implant trial 514 with channels 522 on a top and bottom surface 516, 518 and a cutting tool 508 with cutting elements 524 on opposite sides of the shaft 590 such that the assembly 500 may deliver simultaneous, dual keel-cuts into a joint space (e.g., into both sacrum and ilium). As another example, a certain joint preparation tool assembly 500 may include an implant trial 514 with a pair of channels 522 on both a top and a bottom surface 516, 518 and a cutting tool 508 with a pair of cutting elements 524 on opposite sides of the shaft 590 in order to make quad keel-cuts into the bones defining the sacroiliac joint space to make way for an implant having an I-beam shape as described in U.S. patent application Ser. No. 14/447,612, mentioned previously, and hereby incorporated by reference in its entirety. Other embodiments of the assembly 500 are contemplated and within the scope of the present disclosure.

As further examples of alternative configurations of the implant trial 514 and cutting element 524, reference is made to FIGS. 43A-43D, which are respective front views of implant trials 514 with various configurations of cutting elements 524 channels 522. As seen in FIG. 43A, the channel 522 is formed by one of the side surfaces 520 that extends from the proximal end 528 of the implant trial 514 to the distal end 510 of the trial tool assembly. The channel 522 includes a neck portion 622 and a bulb-end portion 624 that is wider than the neck portion 622. In this way, once the cutting element 524 is received within the channel 522, the cutting element 524 is restrained from movement out of the channel 522 except by distal-proximal translation of the cutting element 524 relative to the implant trial 514.

Regarding the cutting element 524, it includes an implant trial engagement end 626 and a cutting end 628. The engagement end 626 includes a neck member 630 that extends to a bulb-member 632 that is slidingly and matingly received within the channel 522 by distally translating the cutting element 524 such that the engagement end 626 of the cutting element 524 is engaged and fitted within the channel 522 at the proximal end 528 of the implant trial 514. The channel 522 described herein may include additional mechanisms to restrain the cutting element 524 during distal-proximal translation. The description of a channel 522 having a neck portion 622 and a bulb portion 624 is illustrative and not intended to be limiting.

Regarding the cutting end 628 of the cutting element 524, as seen in FIG. 43A, the cutting end 628 transitions generally ninety degrees from the implant trial engagement end 626 and extends generally parallel with the side surface 520 of the implant trial 514. In particular, the cutting end 628 terminates in a cutting tip 634 that extends beyond the top surface 516 of the implant trial 514. In this way, as the cutting element 524 is distally translated, the patient's bone (e.g., sacrum or ilium) that abuts the top surface 516 of the implant 514 will be cut.

Referring to FIG. 43B, the cutting element 524 may be a T-shaped member and include a pair of cutting tips 634 where one cutting tip extends beyond the top surface 516 and one cutting tip extends beyond the bottom surface 518 of the implant trial 514. In this arrangement, the cutting element 524 may be used to deliver simultaneous cuts into opposing bones defining a joint (e.g., sacrum and ilium). And, referring to FIG. 43C, the cutting element 524 may include two T-shaped members wherein one T-shaped member is on each side surface 520 of the implant trial. In this arrangement, the cutting element 524 may be used to deliver dual-keel cuts into each of the sacrum and ilium. Such cuts may be useful for delivery of an implant having a pair of keels that are configured to extend into the sacrum and ilium.

And, while this discussion has focused on cutting elements 524 with cutting tips 634, other cutting devices that include a similar implant trial engagement end may be used with the implant trial 514 of the present discussion. For example and as seen in FIG. 43D, the cutting element 524 includes a T-shaped member with a cutting tip 634 as previously described on one side surface 520 and a box-chisel 636 on the opposite side surface 520. The box-chisel 636 may be useful, for example, to clear the plane of the joint while the T-shaped member with the cutting tips 634 may be useful for cutting into the sacrum and ilium to prepare for the subsequent delivery of a matching implant. Similarly, instead of the box chisel 636 as shown and positioned in FIG. 43D, a drill guide collar 710 may be positioned and arranged in place of the box chisel; however, the collar would be positioned adjacent the proximal surface of the implant trial as in FIG. 44 by aligned with one or both opposite side surfaces 520. In an aspect, the drill guide collar may have a slot like configuration similar to the collar shown in FIGS. 47A and 47B except that the slot length is positioned near the implant trial opposite side surface 520 as just described regarding the drill guide collar 710 in place of the box chisel of FIG. 43D. In an aspect with the slot length parallel to the implant trial opposite surface 520, a milling cutter bit may be passed immediately adjacent surface 520 while sweeping in a plane generally parallel to the surface 520 and in doing so the milling bit may be caused to project beyond top and bottom surfaces of the implant trial—effectively preparing a cut similar to that prepared by the cutting end 628 of FIG. 43B. In yet another aspect, a guide collar including a slot aperture may align a milling bit with an opposite surface 520 yet the slot length may extend generally perpendicularly away from the surface 520, thereby permitting preparation along the joint plane by safely milling from a reference surface 520 and perpendicularly directing the motion of the bit away from the surface 520 (e.g., the other opposite surface 520 may be facing the sciatic notch).

These are only some versions of alternative embodiments of the implant trial 514 and cutting element 524 that are applicable to all joint preparation tools described herein. Other arrangements of channels 522 on different surfaces of the implant trial 514 are possible and contemplated herein. Additionally and alternatively, the implant trial 514 and cutting element 524 described in reference to FIGS. 43A-43D may include other features described in reference to the previous embodiments. For example, the implant trial 514 of the present embodiment may additionally include a cutting element as described previously that extends over the top surface of the implant trial. Also, the cutting element 524 of the present embodiment may include a cutting element guide as described previously that is configured to fit within a reciprocally shaped opening in the implant trial.

4. Trial Fit Assembly and Cutting Tool with Drill Guiding System

Figure 44:
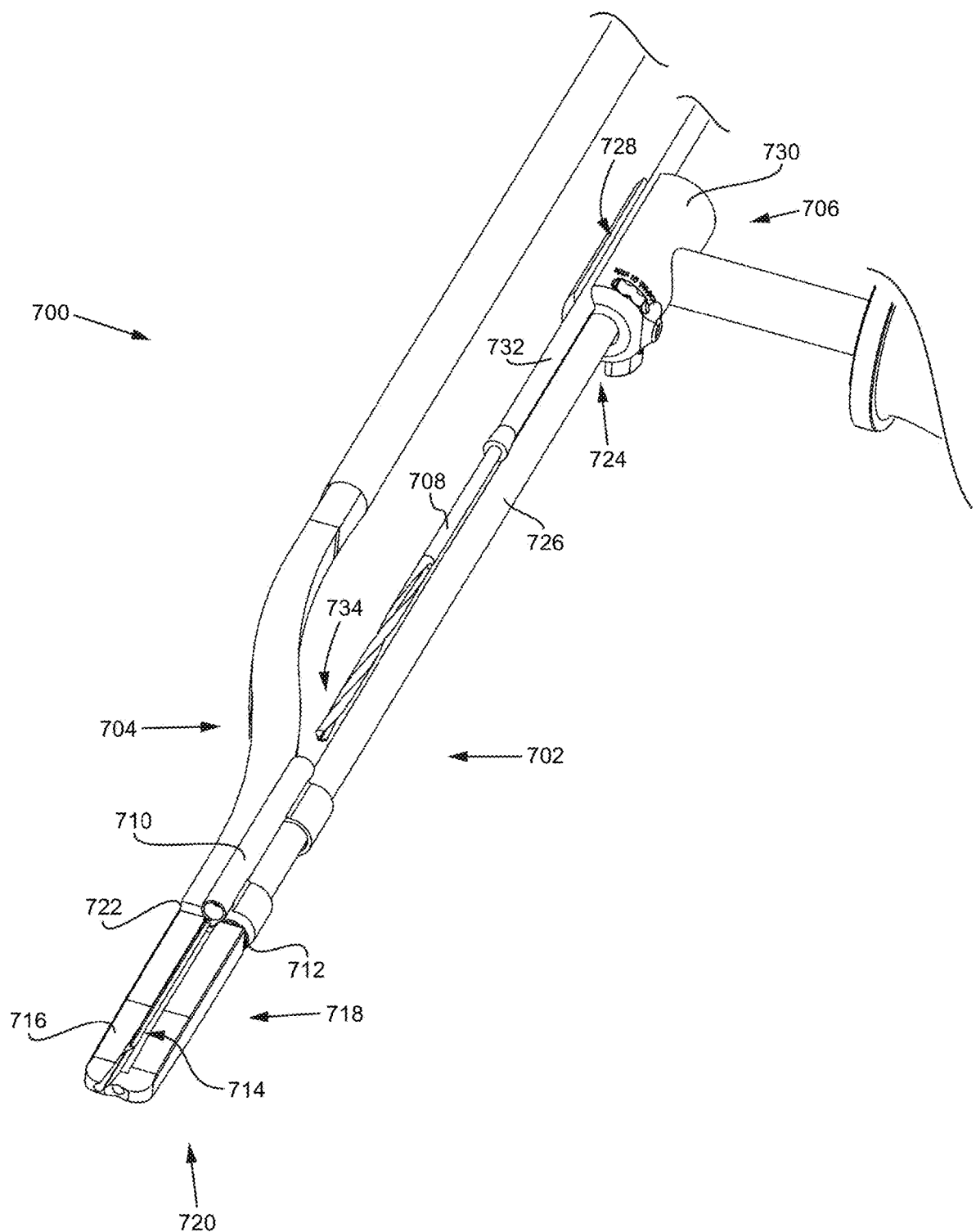
FIG. 44 is an isometric view of a joint preparation tool assembly with a trial tool assembly and a drill guide.

Turning now to FIGS. 44-47, reference is made to an additional embodiment of a joint preparation tool assembly 700. As seen in FIG. 44, the joint preparation tool assembly 700 includes a trial tool assembly 702, a drill guide 704, and a handle assembly 706.

In one aspect, the joint preparation tool assembly 700 is configured to guide a drill bit 708 during distal-proximal translation of the drill bit 708 relative to the drill guide 704 and trial tool assembly 702. In particular, the drill guide 704 is similar to as described previously with respect to the various embodiments of the cutting tool, except that the drill guide 704 includes a guide collar 710 at a distal end 712 of the drill guide 712 as opposed to a cutting element. The guide collar 710 is a tubular member that is positioned to guide the drill bit 708 above a channel 714 formed in a top surface 716 of an implant trial 718, which is located at a distal end 720 of the trial tool assembly 702, when the distal end 712 of the drill guide 704 abuts a proximal end 722 of the implant trial 718.

As seen in FIG. 44, the handle assembly 706 is releasably secured to a proximal end 724 of a shaft 726 of the trial tool assembly 702. The handle assembly 706 includes drill shank guide 728 that is formed within a body 730 of the handle assembly 706 and is configured to receive and guide a drill bit shank 732 during distal-proximal translation of the drill bit 708. The drill shank guide 728 is a cylindrical or partially cylindrical opening or cutout that is sized slightly larger than a diameter of the drill bit shank 732. In this way, as the drill bit shank 732 is translated distal-proximal a distal end 734 of the drill bit 708 is guided to be received within, and further guided by, an internal passageway 736 defined within the guide collar 710.

Figure 45:
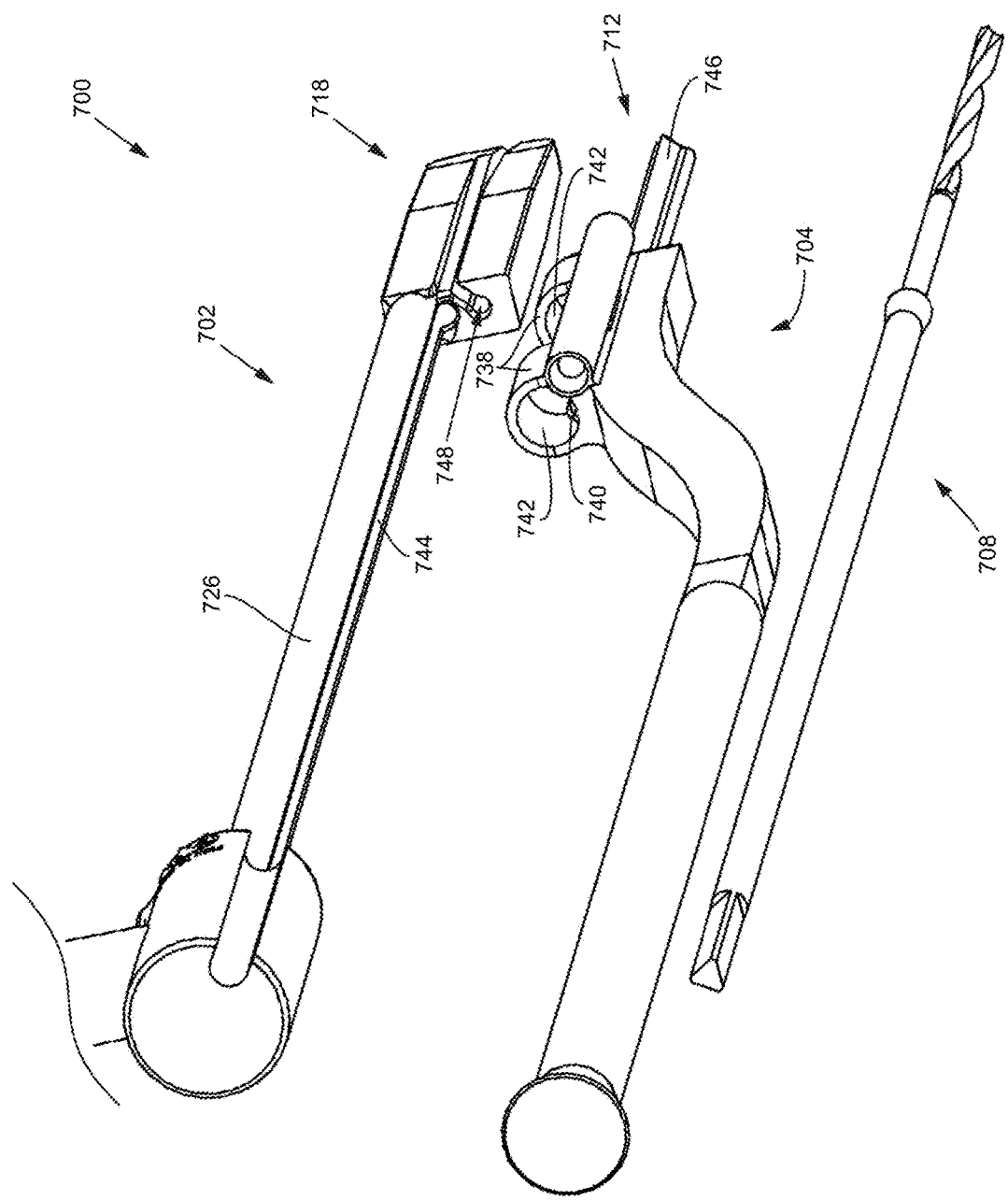
FIG. 45 is an isometric view of the joint preparation tool assembly of FIG. 44 with the various components in an uncoupled state.

Moving on to FIG. 45, reference is made to the various components of the joint preparation tool assembly 700 in an uncoupled state. As seen in the figure, the drill guide 704 is similar to previously described embodiments of the cutting tool in that it includes a pair of collars 738 with protrusions 740 extending radially inward from inner walls 742 of the collars 738. The protrusions 740 are configured to fit within and be guided by a groove 744 formed within the shaft 726 of the trial tool assembly 702. The drill guide 704 additionally includes a drill guide element 746 at distal end 712 of the drill guide 704 that is configured to slidingly engage with and be guided by a reciprocally shaped opening 748 formed within the implant trial 718.

Figure 46:
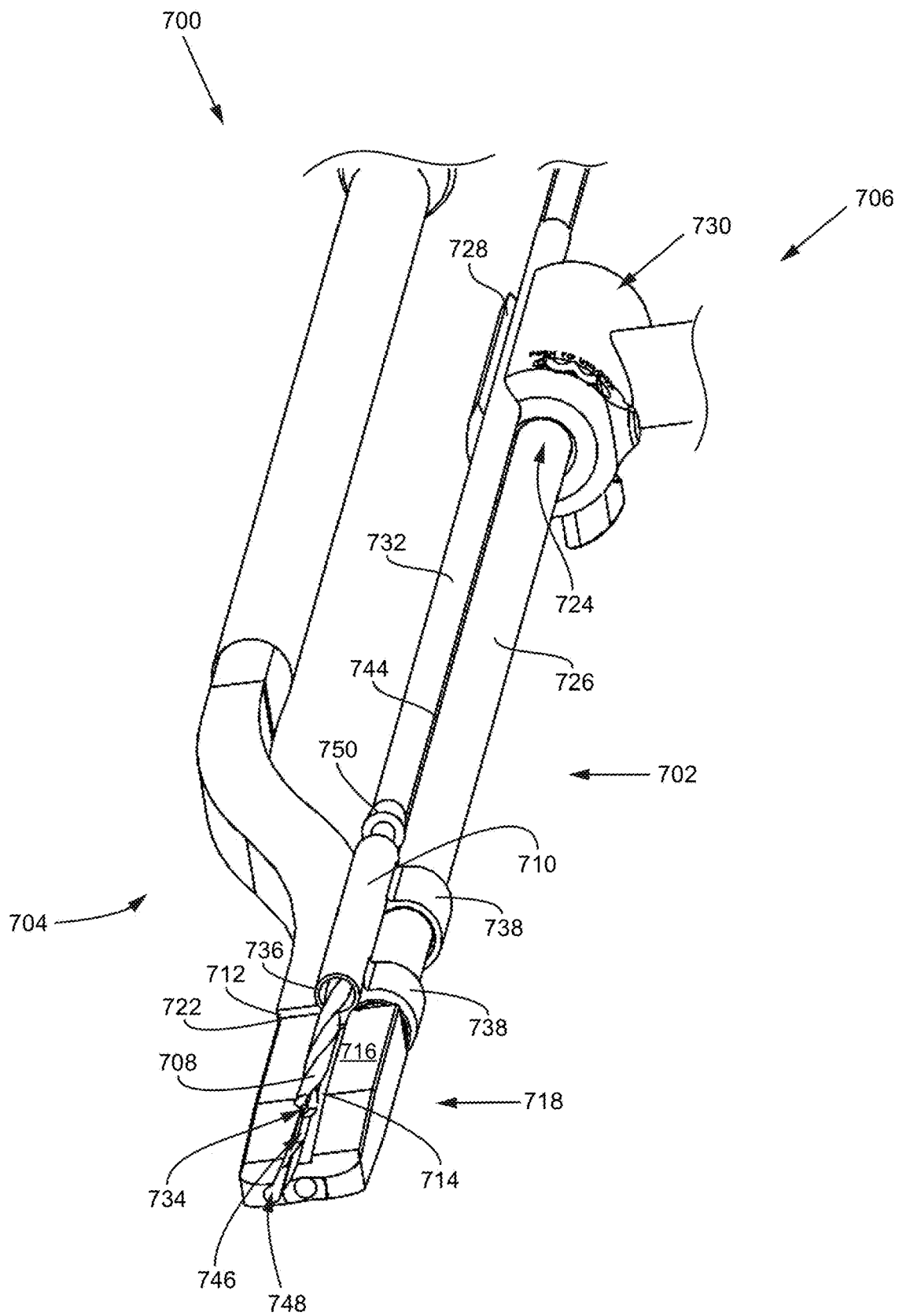
FIG. 46 is an isometric view of the joint preparation tool assembly of FIG. 44 with a drill bit positioned within a collar of the drill guide.

Turning now to FIG. 46, reference is made to the various components of the joint preparation tool assembly 700 in a coupled state. As seen in the figure, the drill bit 708 may include a stop feature 750 that limits a depth that the distal end 734 of the drill bit 708 may distally extend relative to the implant trial 718. The stop feature 750 may be permanently fixed (e.g., welded) or may be adjustable based on the needs of a particular surgical procedure.

In operation, the joint preparation tool assembly 700 may function as follows. The trial tool assembly 702 may be delivered into the sacroiliac joint of a patient with or without guidance by a guide wire. The drill guide 704 may be slidingly engaged with the shaft 726 of the trial tool assembly 702 by fitting the proximal end 724 of the shaft 726 within and through the collars 738 such that the protrusions 740 (not shown in FIG. 46) are fitted within the groove 744 of the shaft 726. The drill guide 704 may be translated distally while being guided by the collars 738 of the trial tool assembly 702. As the drill guide 704 approaches the implant trial 718, the drill guide element 746 will engage with, and be further guided by, the reciprocally shaped opening 748 formed in the implant trial 718. The drill guide 704 will continue its distal translation until the distal end 712 of the drill guide 704 abuts the proximal end 722 of the implant trial 718. At this point, the guide collar 710 is adjacent the channel 714 on the top surface 716 of the implant trial 718.

Next, the drill bit 708 or, more particularly, the drill bit shank 732 may be fitted within the drill bit shank guide 728 in the handle assembly 706. The drill bit 708 may then be distally advanced while being guided by the drill bit shank guide 728 until the distal end 734 of the drill bit 708 engages with and is caused to enter the internal passageway 736 of the guide collar 710. At this point the drill bit 708 may be further distally advanced to deliver a bore into a patient's bone or cartilage while being guided by the collar 710 on the drill guide 704 and by the drill bit shank guide 728 on the handle assembly 706.

Figures 47A, 47B:
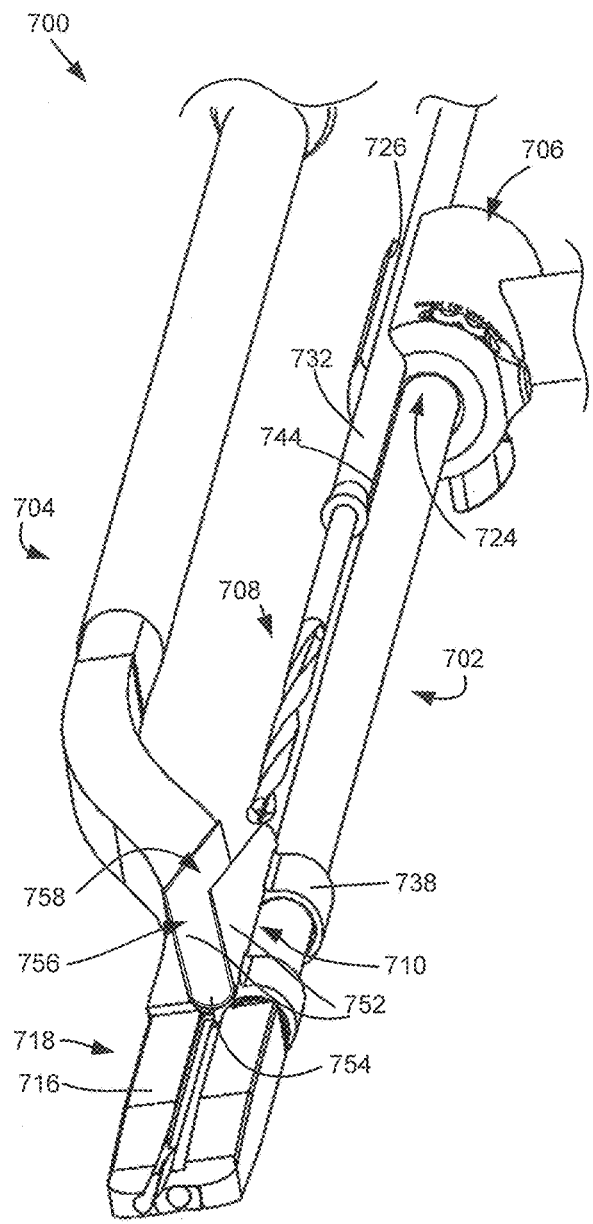
FIG. 47A-47B are differing configurations of the collar on the drill guide.

Reference is now made to FIGS. 47A-47B, which are alternative configurations for the guide collar 710. As seen in FIG. 47A, the guide collar 710 may include generally parallel sidewalls 752 that are generally perpendicular to a lower collar wall 754. Defined between the sidewalls 752 and the lower collar wall 754 is a slot or opening 756 that is open on a top side 758. Thus, as the drill bit 708 is distally translated relative to the guide collar 710, the sidewalls 752 prevent the drill bit 708 from angling laterally in a direction towards one of the side surfaces of the implant trial 718. The drill bit 708, however, is free to angle towards or away from the top surface 716 of the implant trial 718. In this way, the drill bit 708 (i.e., with a drill bit configured for milling) may be used to mill or machine a portion of a patient's bone that abuts the top surface 716 of the implant trial 718.

The guide collar 710 of FIG. 47B is similar to the collar of FIG. 47A, except that the guide collar 710 in FIG. 47B includes a top wall member 760 on the top side 758 of the guide collar 710. In this way, the guide collar 710 restrains the movement of the drill bit 708 as it angles away from the top surface 716 of the implant trial 718. Otherwise, the guide collar 710 functions very similarly to the collar of FIG. 47A. It is noted that a proximal opening 762 on the guide collar 710 may be sized larger than the drill bit 708 a particular amount such that the drill bit 708 may be angled slightly downward towards the implant trial 718. The exact size of the opening 762 may be chosen such that the drill bit 708 can angle somewhat downward towards the top surface 716 of the implant trial 718 without contacting the top surface 716.

Other mechanisms are possible to guide the drill bit 708 during distal-proximal movement in drilling or milling a patient's bone. The aforementioned embodiments are merely exemplary and are not intended to be limiting. Additionally and alternatively, the trial tool assembly 702 and drill guide 704 discussed in the present embodiment may include features described in previous embodiments. For example, while not discussed previously, the drill guide 704 may include an alignment guide that is similar to the cutting guide element discussed previously. The alignment guide may extend distally from the guide collar 710 and be received within a reciprocally shaped opening in the implant trial 718.

III. Methods of Preparing the Sacroiliac Joint for Fusion

The following discussion will focus on various methods of preparing a sacroiliac joint for a surgical fusion procedure utilizing the tools and devices discussed previously. While the discussion focuses on fusing the sacroiliac joint, the methods discussed herein are not limiting; rather, the methods are applicable to the preparation of other joints as well.

A. Preoperative Planning for a Surgical Fusion Procedure

Prior to any joint preparation, a surgeon or other medical person may select a suitable procedure to fuse the sacroiliac joint. The procedure may include fusing the joint with or without delivering an implant in the joint space. If the surgeon selects a procedure involving delivery of an implant within the joint space, the surgeon will select an implant configuration for delivery into the sacroiliac joint of the patient based on preoperative or intraoperative data. The data may be the result of post-processing of raw or other imaging data (e.g. CT or MRI DICOM files). The post-processing may include the use of a software program (e.g., 3DSLICER available from http://www.slicer.org) that may be used for medical image processing and 3D visualization of image data. Other data may include the patient's weight, activity level, and general health.

The preoperative or intraoperative data may assist in the planning and selecting of desirable anchor trajectories (e.g., starting and stopping points on patient's soft tissue and near or within bone tissue), anchor dimensions (e.g., length, diameter, head size, washer, thread pitch), implant types and dimensions, and joint preparation tool types, dimensions, and configurations. A particularly system for preparing and fusing the sacroiliac joint may be selected, for example, for a hypermobile joint, which may include an implant or fusion system that is resistant to the expected forces present at that particular patient's sacroiliac joint. The determination of fixation sufficiency may be calculated based on the patient's data and also on the performance results of various bench and/or finite element analysis ("FEA") tested implant assembly configurations. For example, a calculated anchor and/or implant trajectory may be considered and determined from certain patient imaging and post-processing data with an overlayed implant assembly. Further, the implant assembly footprint within the joint plane may be selected as a lower percent of total joint surface to permit sufficient boney fusion across the joint while maintaining a sufficient implant sacral and iliac face surface area to prevent implant subsidence.

Specific measurements and characteristics of the patient's anatomy may influence the selection of a particular joint fusion system. For example, the patient's bone density may be measured at numerous locations in proximity to and surrounding the elements of the implant assembly. Lower bone density (e.g., osteopenia, osteoporosis) corresponding to a T-score lower than −1, sacroiliac joint instability, or hypermobility may require the use of an implant assembly with a greater amount of keel (i.e., the material cross section as defined by thickness of the keel and its length along implant longitudinal axis and also keels extending a greater distance into both bones defining the sacroiliac joint) and anchor extending across the sacroiliac joint and into the ilium and sacrum. Additionally, the relative angles between the implant longitudinal axis and anchor or anchors, and also the relative angles between multiple anchors (e.g., parallel, divergent, convergent) may be preselected based on the patient's anatomy.

A comparison of the preoperative or intraoperative data (e.g., sacroiliac joint surface area, joint mobility, loading, bone density, desirable anatomic pathways) and the selected implant assembly and joint preparation tools may be conducted to ensure or validate compatibility before the manufacture ships the implant system and/or before the surgeon employs the system in a surgical procedure. After implant assembly and preparation tools validation, the selected assemblies may be shipped to the surgeon and the surgeon may proceed with the surgical fusion procedure utilizing the selected assemblies.

B. Fusion of the Sacroiliac Joint Via Implant Delivery

In order to fully understand the steps to prepare the sacroiliac joint for a fusion procedure, this section will detail one, among many, methods of fusion a sacroiliac joint for which the preparation tools discussed herein may be beneficial. To begin, reference is made to FIGS. 48A-48B, which depict various bone landmarks adjacent, and defining, the sacroiliac joint 1000 of a patient 1001.

Reference is first made to FIG. 48A, which is a right lateral view of a hip region 1002 of a patient 1001 lying prone, wherein the soft tissue 1003 surrounding the skeletal structure 1006 of the patient 1001 is shown in dashed lines. Delivery of an implant into the sacroiliac joint 1000 and, thus, preparing of the joint 1000 for delivery of the implant are via a posterior approach to the hip region 1002. FIG. 48B, which is an enlarged view of the hip region 1002 of FIG. 48A, depicts a lateral view of the patient's hip region 1002 reveals certain features of the ilium 1005, including the anterior superior iliac spine 2000, the iliac crest 2002, the posterior superior iliac spine 2004, the posterior inferior iliac spine 2006, the greater sciatic notch 2008 extending from the posterior inferior iliac spine 2006 to the ischial spine 2010, and the tubercle of iliac crest 2012.

The sacroiliac joint articular region 1044 is shown in dashed lines. A posterior inferior access region 2016 of the sacroiliac joint articular region 1044 has a superior end 2018 on the sacroiliac joint line 2019 that is between approximately 0 mm and approximately 40 mm inferior the posterior inferior overhang 2020 of the posterior superior iliac spine 2004. The posterior inferior access region 2016 of the sacroiliac joint articular region 1044 has an inferior end 2022 on the sacroiliac joint line that is at approximately the intersection of the posterior inferior iliac spine 2006 with the lateral anterior curved boundary 2024 of the sacrum 1004. In other words, the posterior inferior access region 2016 of the sacroiliac joint articular region 1044 has an inferior end 2022 on the sacroiliac joint line that is at approximately the superior beginning of the greater sciatic notch 2008.

Still referring to FIG. 48B, the sacroiliac joint articular region 1044 roughly defines an L-shape that includes a caudal region 1086 and a cranial region 1087. Access into the caudal region 1086 of the sacroiliac joint is via the posterior inferior access region 2016 that extends between corners defined by the superior end 2018 and the inferior end 2022. Access into the cranial region 1087 may be accomplished by continual, anterior travel in the caudal region 1086 until the articular region 1044 turns superiorly into the cranial region 1087.

To begin a discussion of implant delivery into the sacroiliac joint articular region 1044, reference is made to FIG. 48C, which is a close-up lateral side view of the hip region 1002 of a patient 1001 with a nearest ilium 1005 removed in order to show the sacroiliac joint boundary 3000 defined along the sacrum 1004 and outlining the sacroiliac joint articular region 1044, and an implant 25 positioned for implantation within the sacroiliac joint articular region 1044.

As seen in FIG. 48C, boundaries along the sacroiliac joint articular region 1044 include an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint. The posterior boundary segment 3008 separates articular region 1044 and extra-articular region 3007, which includes the sacral fossa on the sacrum 1004 and the corresponding iliac tuberosity on the ilium 1005 and defined by the extra-articular region boundary 3009.

In one aspect and as seen in FIG. 48C, the implant 25 may be delivered via an implant arm 111 of a delivery tool into the caudal region 1086 of the sacroiliac joint articular region 1044. As shown via the implant 25 and implant arm 110 shown in solid lines, in one embodiment, the implant 25 enters the posterior inferior access region 2016, and is further advanced into the caudal region 1086 of the sacroiliac joint articular region 1044, in an orientation such that the implant arm 110 and wide planar members 51 are in the joint plane and the longitudinally extending edge 3050 of the wide planar member 51 next to the inferior boundary segment 3002 is generally parallel to, and immediately adjacent to, the inferior boundary segment 3002. Thus, the distal end 43 of the implant is heading generally perpendicular to, and towards, the anterior boundary segment 3004.

As shown in FIG. 48C via the implant 25 and implant arm 110 shown in dashed lines, in one embodiment, the implant 25 enters the posterior inferior access region 2016, and is further advanced into the caudal region 1086 of the sacroiliac joint articular region 1044, in an orientation such that the implant arm 111 and wide planar members 51 are in the joint plane and the longitudinally extending edge 3050 of the wide planar member 51 next to the inferior boundary segment 3002 is somewhere between being generally parallel to the inferior boundary segment 3002 (as illustrated by the solid-lined implant 25 in FIG. 48C) or forming an angle AJ with the inferior boundary segment 3002 of up to approximately 50 degrees. Thus, the distal end 43 of the implant shown in dashed lines can be said to head anywhere from generally perpendicular to, and towards, the anterior boundary segment 3004 to heading generally towards the superior-anterior corner 3012, or points in between.

In one embodiment, the implant 25 may be first directed into the joint space as illustrated by the solid-lined implant 25 in FIG. 48C after which the implant 25 is rotated within the joint space to be positioned somewhere between, and including, angled position depicted by the dashed-lined implant 25. In other embodiments, the implant 25 may be first directed into the joint space as illustrated by the dashed-lined implant 25 in FIG. 48C after which the implant 25 is rotated within the joint space to be positioned somewhere between, and including, the parallel position depicted by the solid-lined implant 25. Thus, an implant 25 may be delivered non-transversely (i.e., within the joint and not across the joint) into the caudal region 1086, the cranial portion 1087, or partially within each of the caudal and cranial regions 1086, 1087 of the sacroiliac joint articular region 1044. Further details of the implant delivery can be found in related applications, mentioned previously, such as U.S. patent application Ser. No. 12/998,712, which is incorporated by reference herein in its entirety.

C. Utilization of the Tools and Assemblies Described Herein to Prepare the Sacroiliac Joint for Fusion Now that an overview of the relevant anatomical landmarks and an example fusion procedure has been described, the discussion may now focus on preparing the sacroiliac joint for a fusion procedure. In doing so, reference will be made to FIGS. 49A-49D, among additional figures, which are steps in the methodology and illustrated in the same transverse cross section taken in along a plane extending medial-lateral and anterior posterior. In this cross section, articular surfaces 1016 are covered by a thick layer of articular cartilage with a joint space existing between them, the FIGS. 49A-49D are simplified for illustrative purposes and do not show these features to scale.

Figure 49B:
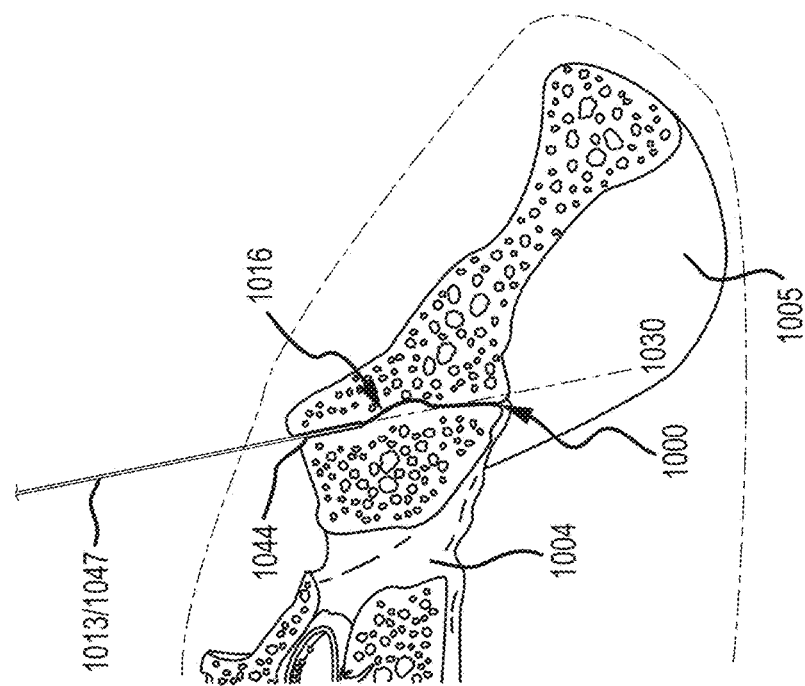
Figure 49A:
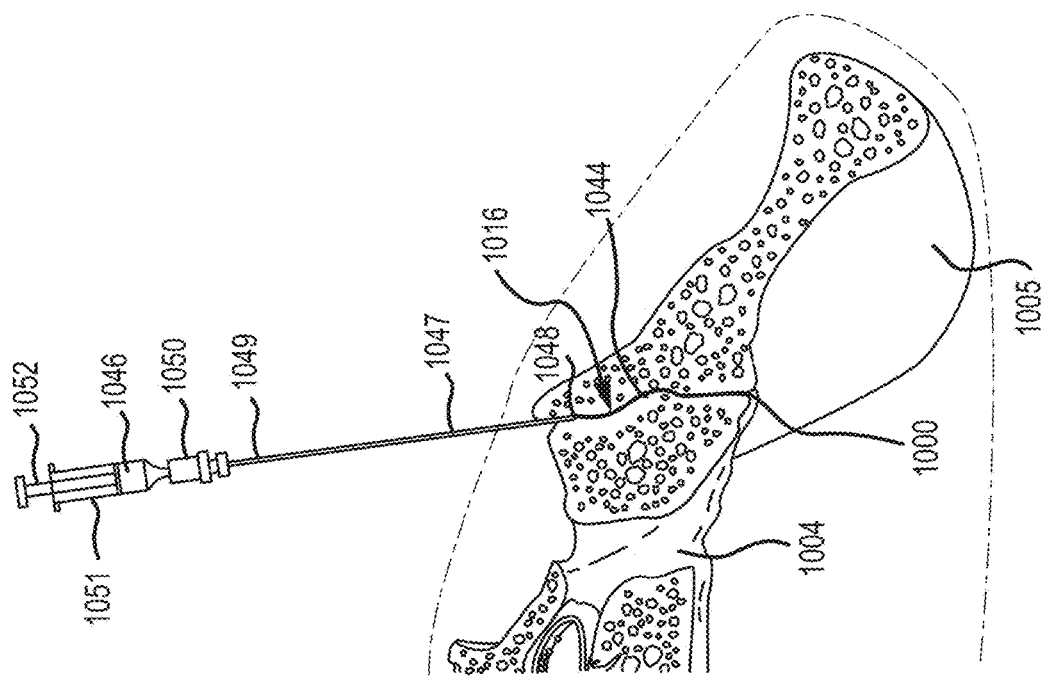

Now referring primarily to FIG. 49A, an embodiment of the method can include the step of placing a patient under sedation prone on a translucent operating table (or other suitable surface). The sacroiliac joint 1000 can be locally anesthetized to allow for injecting a radiographic contrast 1046 (as a non-limiting example, Isoview 300 radiographic contrast) under fluoroscopic guidance into the inferior aspect of the sacroiliac joint 1000 to outline the articular surfaces 1016 of the sacroiliac joint 1000) defined between the sacrum 1004 and ilium 1005, the sacroiliac joint 1000 having an interarticular region 1044. Injection of the radiographic contrast 1046 within the sacroiliac joint 1000 can be accomplished utilizing a tubular member 1047 (e.g., a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 or other device to contain and deliver an amount of radiographic contrast 1046. In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy. A plunger 1052 can be slidingly received within the barrel 1051 to deliver the radiographic contrast 1046 through the tubular member 1047 into the sacroiliac joint 1000. The tubular member 1047 can have a gauge in the range of about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

Now referring primarily to FIG. 49B, once the first tubular member end 1048 has been sufficiently advanced into the sacroiliac joint 1000 and the articular surfaces 1016 of the sacroiliac joint 1000 have been sufficiently visualized, the hub 1050 can be removed from the tubular member 1047 leaving the tubular member 1047 fixed within the sacroiliac joint 1000 as an initial guide for tools subsequently used to locate or place the sacroiliac joint implant non-transversely between the articulating surfaces 1016 of the sacroiliac joint 1000 (e.g., locate the implant non-transversely to the joint plane 1030 generally defined by the articulating surfaces 1016 of the interarticular region 1044 of the sacroiliac joint 1000) or in removal of a portion of the sacroiliac joint 1000 within the region defined by the articular surfaces 1016 to generate an implant receiving space 1029. Alternately, one or more guide pins 1013 can be inserted along substantially the same path of the tubular member 1047 for fixed engagement within the sacroiliac joint 1000 and used in subsequent steps as a guide(s).

Now referring primarily to FIG. 49C, a small incision 1053 can be made in the skin at the posterior superior, or as to certain embodiments inferior, aspect of the sacroiliac joint 1000, extending proximal and distal to the tubular member 1047 along the line of the sacroiliac joint 1000 to provide a passage to access the interarticular space between the articulating surfaces 1016 (see FIG. 49B) of the sacroiliac joint 1000. More specifically, the small incision 1053 can be made along the joint line of the sacroiliac joint 1000 in the tissue covering the posterior inferior access region 2016 of the sacroiliac joint articular region 1044. A cannulated probe 1054 can be slidingly engaged with the tubular member 1047 (or guide pin 1013) extending outwardly from the sacroiliac joint 1000 (while the sacroiliac joint may be shown in the figures as being substantially linear for illustrative purposes, it is to be understood that the normal irregular features of the sacroiliac joint have not been removed). The cannulated probe 1054 can have a probe body 1054 of generally cylindrical shape terminating in a spatulate tip 1055 at the end advanced into the sacroiliac joint 1000. A removable cannulated probe handle 1056 couples to the opposed end of the probe body 1054. The spatulate tip 1055 can be guided along the tubular needle 1047 or guide wire 1013 into the posterior portion of the sacroiliac joint 1000 and advanced to the anterior portion of the sacroiliac joint 1000 under lateral fluoroscopic visualization. The cannulated probe handle 1056 can then be removed providing the generally cylindrical probe body 1054 extending outwardly from the sacroiliac joint 1000 through the incision 1053 made in the skin.

Alternatively, the probe 1054 can be used to guide, advance or place a needle, guide wire or other instrument up to, near, or into the joint.

Additionally, in particular embodiments, probe handle 1056 or the opposed end of the probe body 1054, or both, can be configured to have an interference fit or a luer lock hub to communicate with a syringe barrel 1051 in order to advance contrast, in situ curable biocompatible materials, stem cells, or etc. through the cannulated probe 1054 or cannulated probe handle 1056.

Now referring primarily to FIG. 49D, a passage from the incision 1053 (see FIG. 49C) to the sacroiliac joint 1000 can be generated by inserting a cannula 1057 into the incision. A soft tissue dilator 1058 having a blunt end 1059 can be advanced over the probe body 1054, or a plurality of soft tissue dilators of increasing size, until the blunt end 1059 of the soft tissue dilator 1058 and the corresponding cannula end contact the posterior aspect of the sacroiliac joint 1000. More specifically, in one embodiment, the ends of the dilator 1058 and cannula 1057 contact the joint line 2019 of the sacroiliac joint 1000 at the posterior inferior access region 2016 of the sacroiliac joint articular region 1044. The soft tissue dilator 1058 can be removed from within the cannula 1057. The external surface of the cannula 1057 can be sufficiently engaged with the surrounding tissue to avoid having the tissue locate with in the hollow inside of the cannula 1057. A non-limiting embodiment of the cannula 1057 provides a tubular body having substantially parallel opposed side walls which terminate in a radius at both ends (lozenge shape) into which a plurality of different jigs can be inserted. Alternatively, as a non-limiting example, according to particular embodiments, cannula 1057 and corresponding dilators 1058 and alignment jigs 1060 can be configured to have tubular bodies with an elliptical or circular cross section.

In some embodiments, the cannula 1057 may be additionally configured to have within or near its walls a light source such as, for example, a fiberoptic or a LED light source to assist in visualization of the working area. Also, in some embodiments, irrigation and suction tubing may communicate with the inside passage of cannula 1057.

At this stage, additional tools and methods may be employed to provide access to the sacroiliac joint 1000 as described in U.S. patent application Ser. No. 13/475,695 filed May 18, 2012 entitled "SYSTEMS FOR AND METHODS OF FUSING A SACROILIAC JOINT," which is hereby incorporated by reference in its entirety. For example, drill jigs may be further advanced over the probe body 1054 to align a drill or other joint preparation tool. Accordingly, the discussion will now focus on employing the tools and devices described in previous sections of this application.

In certain embodiments of the method, an amount of articular cartilage or other tissues from between the articular surfaces of the sacroiliac joint 1000 can be removed sufficient to allow embodiments of the sacroiliac joint implant to be implanted in replacement of the removed articular cartilage or tissue. Because the method removes the degenerative articular cartilage or tissue between the articular surfaces of the sacroiliac joint 1000, the articular surfaces of the sacroiliac joint 1000 can remain intact or substantially intact allowing the sacroiliac joint implant to be non-transversely located between the articular surfaces of the sacroiliac joint 1000.

Figure 49E:
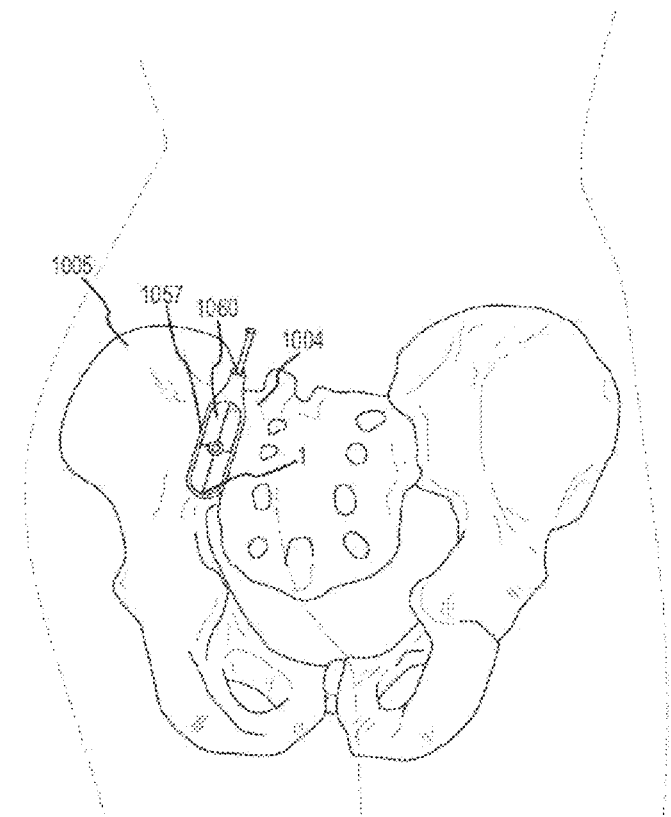
FIG. 49E is a posterior view of the pelvic region showing fixed placement of the cannula in relation to the sacroiliac joint having inserted within a cannula alignment jig.
Figure 49F:
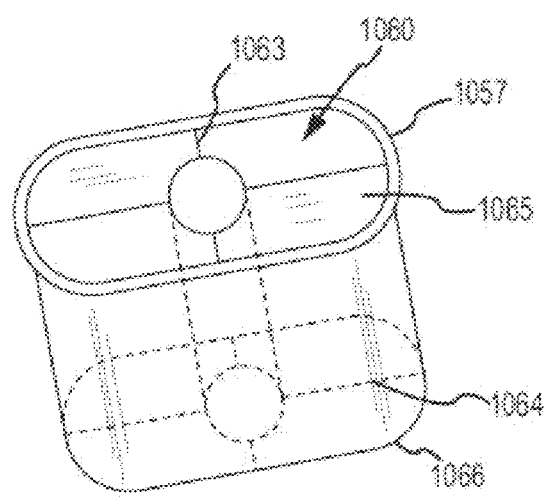
FIG. 49F is a perspective view of the cannula jig insert shown in FIG. 49E having cross hairs.
Figure 49G:
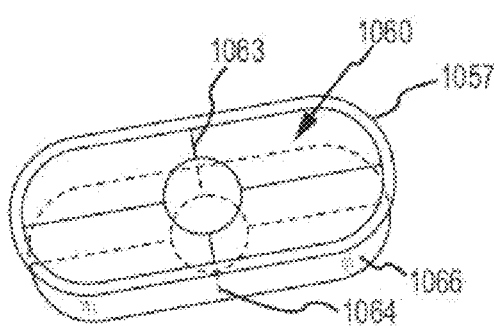
FIG. 49G is a perspective view of the cannula shown in FIG. 49F having a cannula alignment jig inserted within having alignable cross hairs.

Now referring primarily to FIGS. 49E-49G, a cannula alignment jig 1060 can be advanced over the probe body 1054 (or guide pins 1013) and received within the cannula 1057. Substantially, identical cross hairs 1063, 1064 can be disposed on the upper jig surface 1065 and the lower jig surface 1066. Alignment of the cross hairs 1063, 1064 under x-ray with the sacroiliac joint 1000 can confirm that the cannula 1057 has proper orientation in relation to the paired articular surfaces 1016 of the sacroiliac joint 1000. The cannula 1057 properly oriented with the paired articular surfaces 1016 can then be disposed in fixed relation to the sacroiliac joint by placement of fasteners through the cannula 1057 into the sacrum 1004 or the ilium 1005.

Figure 49H:
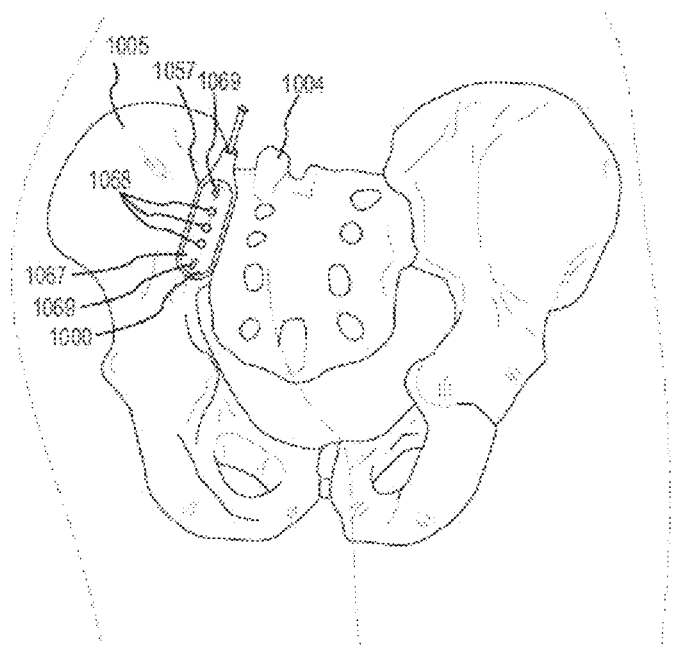
FIG. 49H is a posterior view of the pelvic region showing fixed placement of the cannula in relation to the sacroiliac joint having within a first drill jig.
Figure 49I:
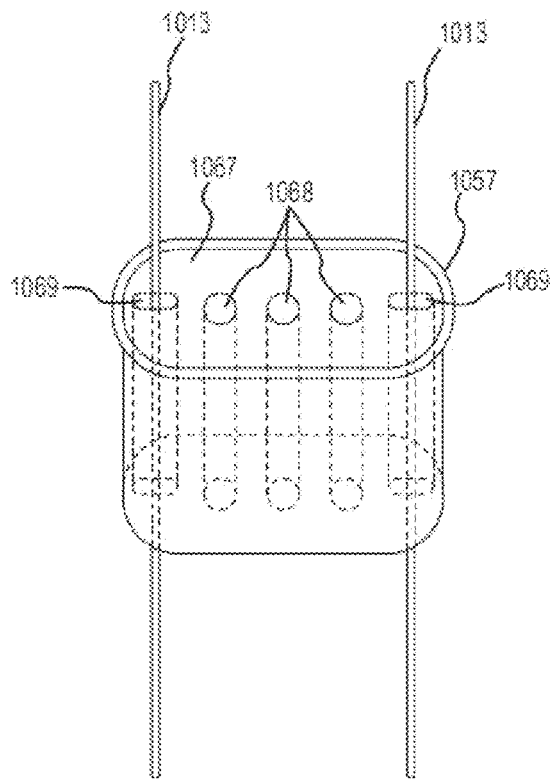
FIG. 49I is a perspective view of the cannula of FIG. 49H having within the first drill jig.

Now referring to FIGS. 49H and 49I, a first drill jig 1067 can be advanced over the probe body 1054 (or guide pins 1013) and received within the cannula 1057. The probe body 1054 (or guide pins 1013) extending outwardly from the sacroiliac joint 1000 passes through a drill guide hole 1068 of the first drill jig 1067 (or a plurality of guide pins 1013 can extend through a corresponding plurality of guide pin holes 1069). The drill guide hole 1068 can take the form of a circular hole as shown in the Figures, a slot, or other configuration to restrict the movement of a drill bit 1062 within the drill jig 1067 and provide a guide for a drill bit 1062 in relation to the sacroiliac joint 1000. Guide pin holes 1069 can receive guide pins which can be positioned between the articular surfaces 1016 of the sacroiliac joint 1000 to demarcate the zone of desired treatment or safe working zones while using, for example, lateral fluoroscopy. As a non-limiting example, a first guide pin 1013 can be advanced through a first guide pin hole 1069, or alternatively a guide pin 1013 is first inserted into the sacroiliac joint 1000 and subsequently a guide jig 1067 is advanced over the guide pin 1013, the first guide pin 1013 can enter near inferior end 2022 of the posterior inferior access region 2016 of the sacroiliac joint articular region 1044 via the sacroiliac joint line 2019 to border a portion of the greater sciatic notch 2008 thereby allowing a medical person, computer guided surgical system, or other observer to more easily highlight under x-ray a border which should not be crossed during the procedure due to the presence of nerve and other structures. Additionally, as a non-limiting example, first guide pin 1013 can configured as an electrode, insulated from the operator and the patient's soft tissues, and may be connected to a monitor to signal to an operator or surgeon when implant 12, configured with a stimulating electrode (NM), e.g., as shown and described in U.S. Provisional Patent Application 61/860, 185, comes into contact with first guide pin. Similarly, a second guide pin 1013 can be placed in another guide pin hole 1069 to demarcate a second limit to a desired zone of treatment, or safe working zone. For example, a second guide pin 1013 can enter near the superior end 2018 of the posterior inferior access region 2016 of the sacroiliac joint articular region 1044 via the sacroiliac joint line 2019 to be positioned to border an area of the sacroiliac joint 1000 such as a transition zone between the extra-articular 3007 and the interarticular region 1044 which, for example, has been highlighted by contrast material as above described.

Referring to FIGS. 49J-49R, a cannula 1057 may be used to facilitate access to the surgical region during a procedure to implant the implant assembly 14 (not shown). In one embodiment, the cannula 1057 may be used in conjunction with a sacroiliac joint repair procedure via a known surgical access region including, but not limited to, the posterior inferior access region 2016 as illustrated in FIGS. 49J-49R. The cannula 1057 may include a cannula body 1057H forming a wall enclosing an internal volume 1057J, which opens to a proximal opening 1057A and a distal opening 1057B. Upon insertion of the cannula 1057 within the surgical access region, the internal volume 1057J may be maintained, thereby functioning as an opening through which surgical instruments, appliances, fasteners, and any other associated surgical equipment or supplies may be inserted or removed and through which the surgical procedure may be visually monitored.

The outer surface of the cannula body 1057H may include one or more contoured regions or projections to enhance the close fit of the cannula 1057 between the skeletal structures surrounding the surgical access region 2016. The outer surface of the body 1057H may form a cannula sacral contour 1057C on one side and may additionally form a cannula iliac contour 1057D on a side opposite to the cannula sacral contour 1057C. The cannula 1057 may also include a distal projection 1057E which extends distally beyond the cannula sacral contour 1057C and may be shaped to fit within a portion of the greater sciatic notch 2008 (see FIG. 49P). In addition, the outer distal surface of the cannula body 1057H may form a PSIS contact area 1057F to enhance the fit of the portion of the cannula 1057 contacting the posterior superior iliac spine (PSIS) 2004 (see FIG. 49N).

Figure 49J:
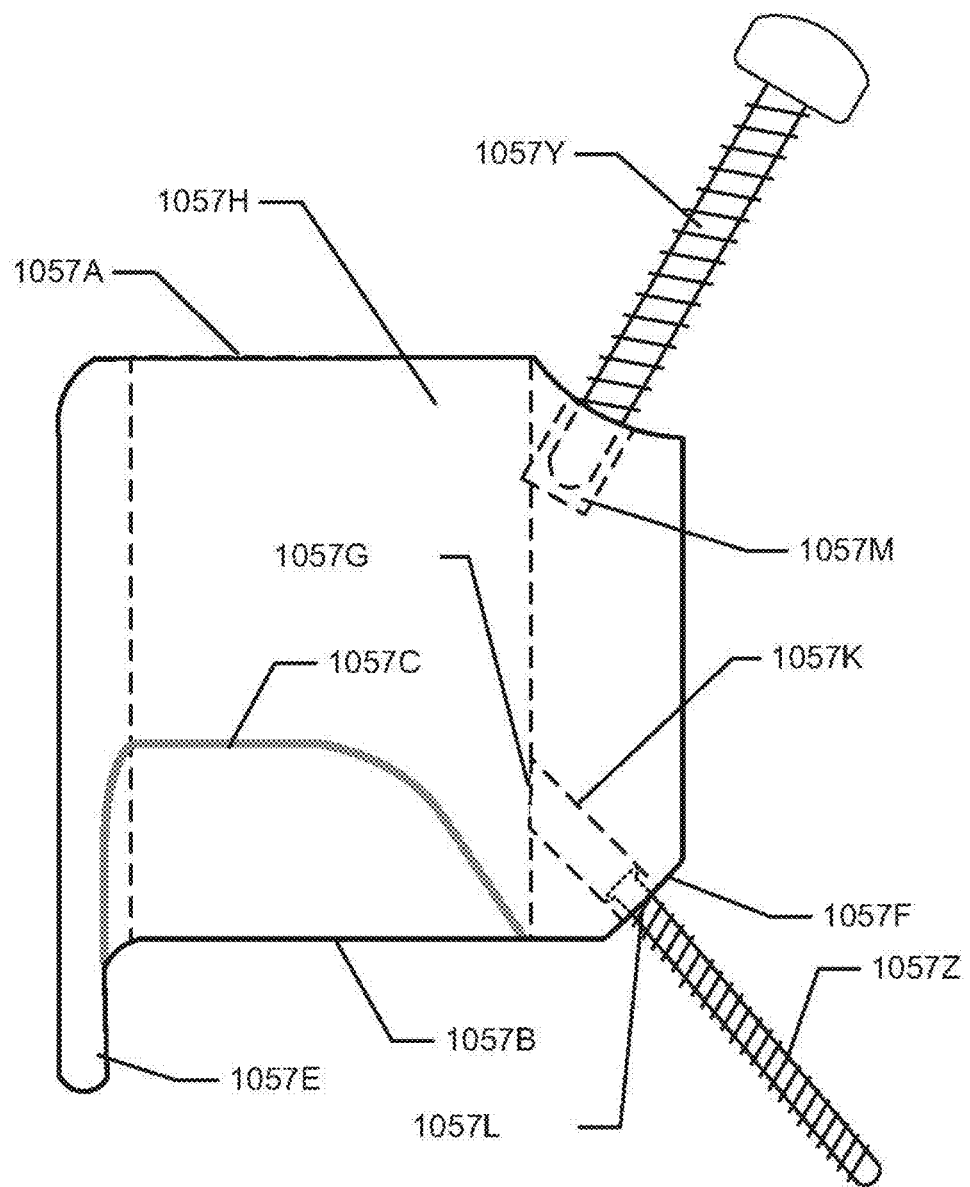
FIG. 49J is a side view of a cannula, in one embodiment.
Figure 49K:
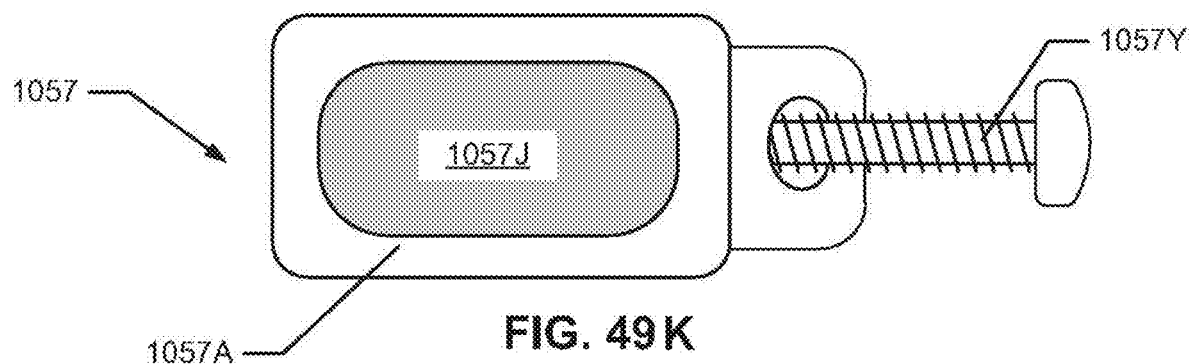
FIG. 49K is a top view of the cannula of FIG. 49J.
Figure 49L:
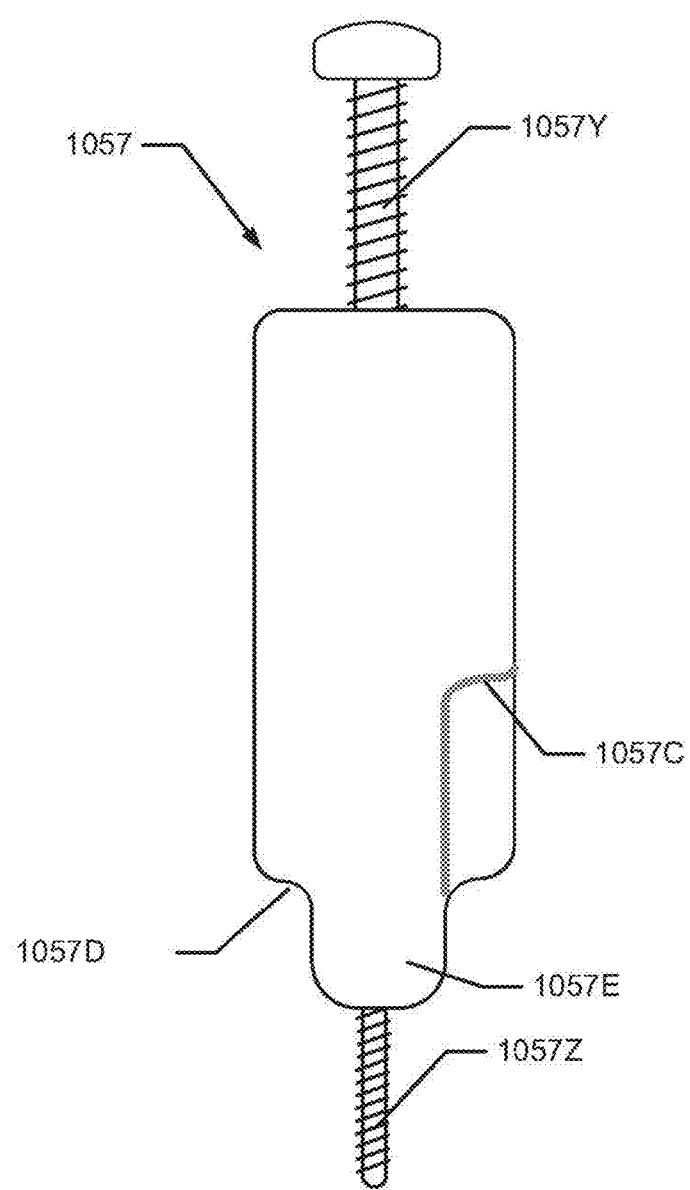
FIG. 49L is a front view of the cannula of FIG. 49J.
Figure 49M:
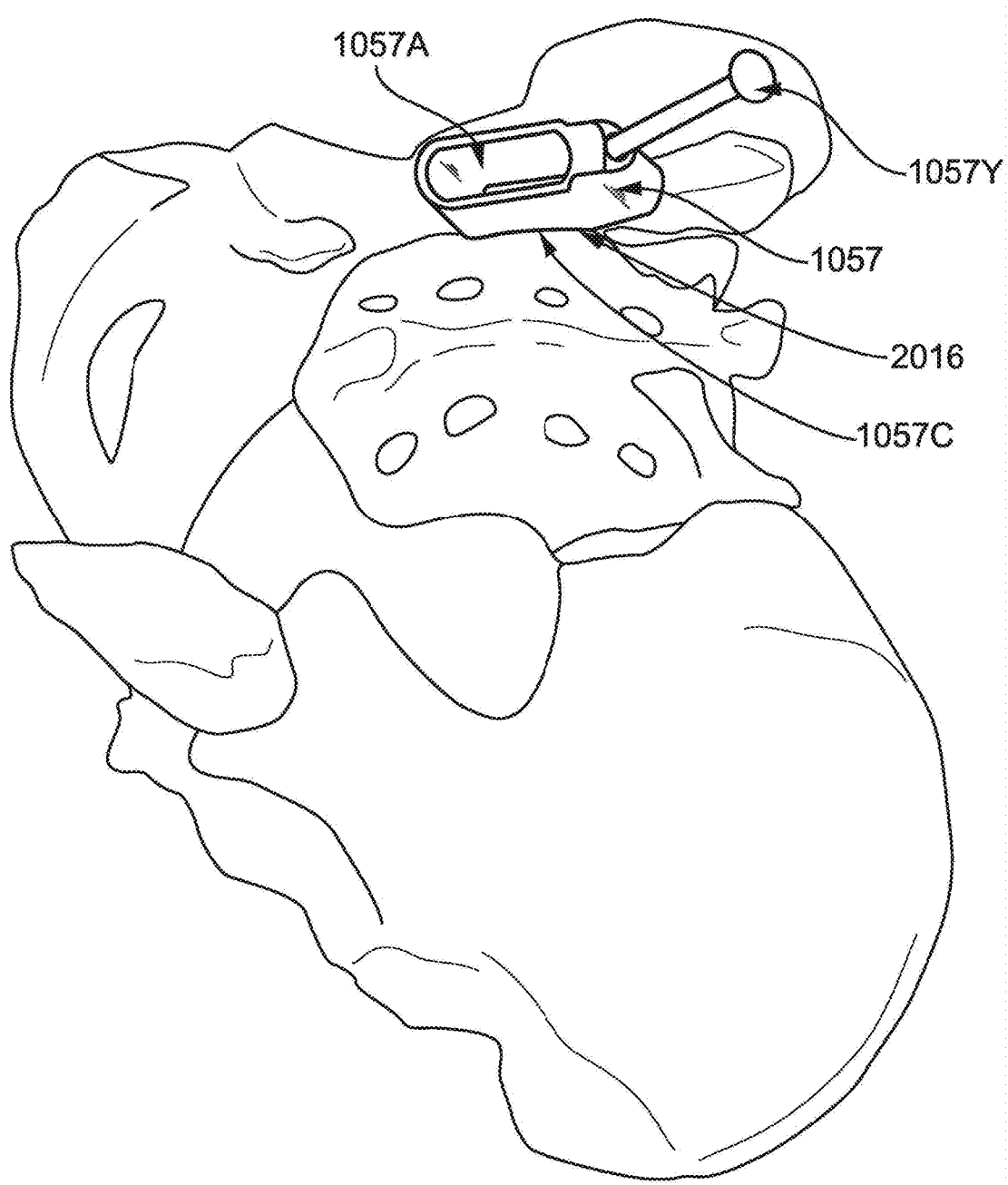
FIG. 49M is a posterior lateral view of the pelvic region showing the cannula of FIG. 49J positioned in relation to the sacroiliac joint.

The cannula body 1057H may further define one or more additional bores configured to reversibly receive handles and/or fasteners used to situate the cannula within the surgical region and/or to reversibly receive fasteners used to fix the cannula in place within the surgical region during the surgical procedure. The cannula body 1057H may define a fastener bore 1057K passing through the cannula body 1057H from the outer surface into the internal volume 1057J of the cannula 1057. The cannula bore may open at one end to a cannula fastener bore proximal opening 1057G, which may be in communication with the internal volume 1057J of the cannula 1057. The cannula bore may also open at an opposite end to a cannula fastener bore distal opening 1057L which may be further configured to permit a fastener 1057Z to i) extend generally perpendicular to the cannula PSIS contact area 1057F; and/or, ii) be in a divergent relation relative to distal projection 1057E. Furthermore, the cannula 1057 may have a handle 1057Y extending from the cannula body 1057H for inserting, removing, and/or otherwise manipulating the cannula 1057 during a surgical procedure. As illustrated in FIG. 49J, the handle 1057Y may be reversibly attached to the cannula body 1057 via a handle bore 1057M formed with the cannula body 1057H. The handle bore 1057M may be provided with fastener features including, but not limited to, threads, that may cooperatively engage corresponding fastener features at a distal end 1057N of the handle 1057Y in order to implement the reversible attachment of the handle 1057Y to the cannula 1057.

Figure 49N:
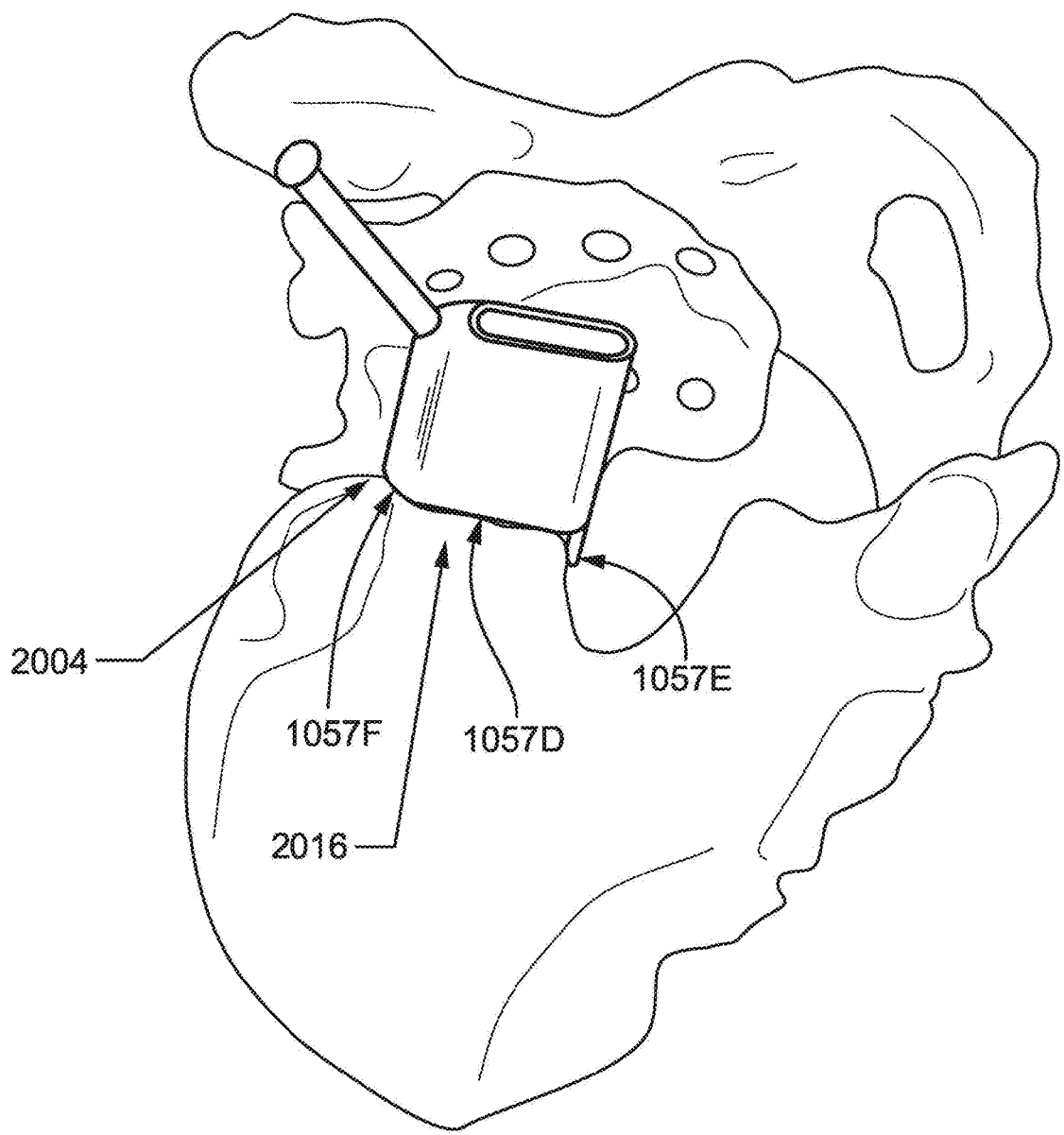
FIG. 49N is another posterior lateral view of the pelvic region showing the cannula of FIG. 49J positioned in relation to the sacroiliac joint.
Figure 49O:
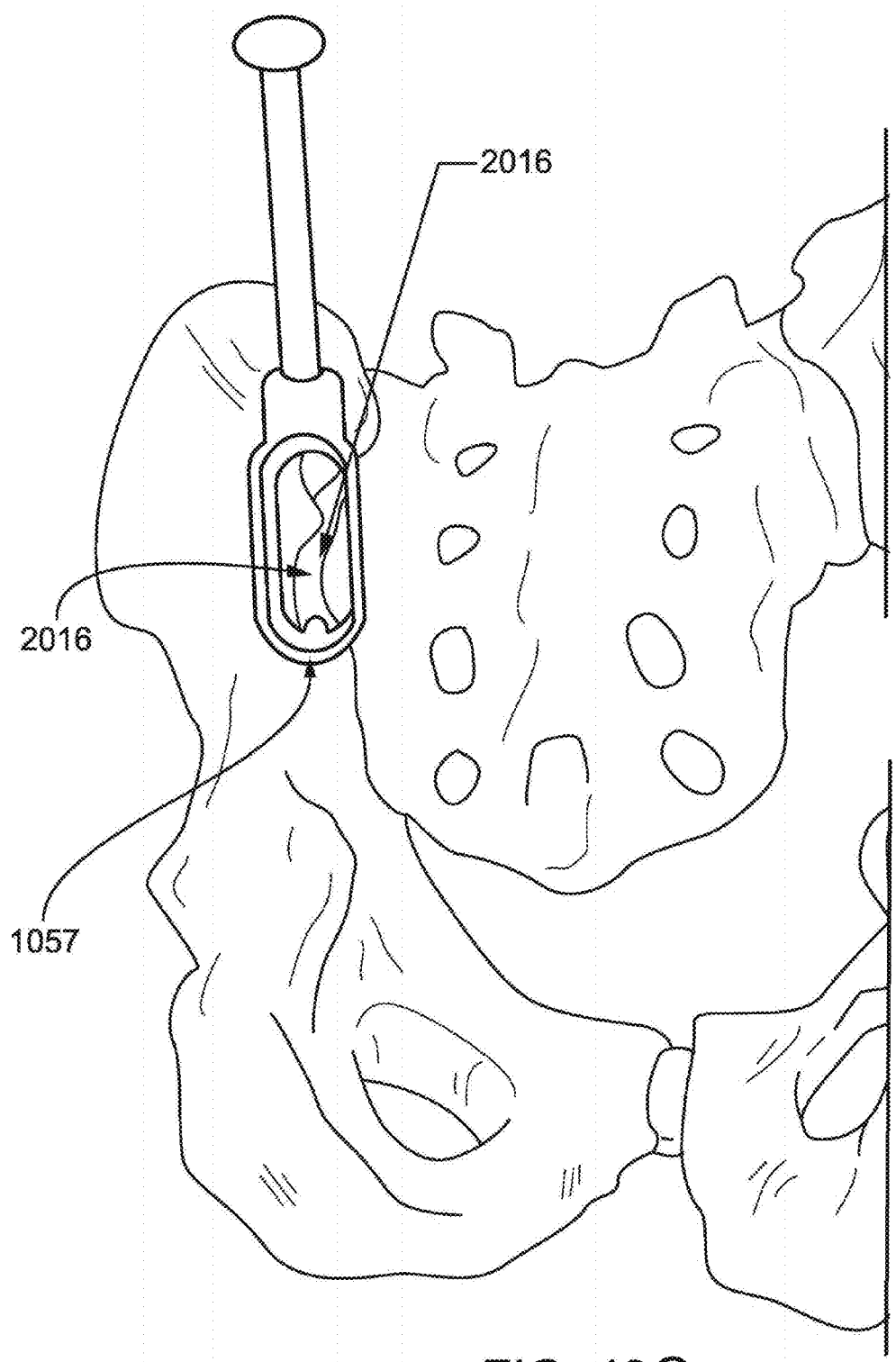
FIG. 49O is a posterior view of the pelvic region showing the cannula of FIG. 49J positioned in relation to the sacroiliac joint.
Figure 49P:
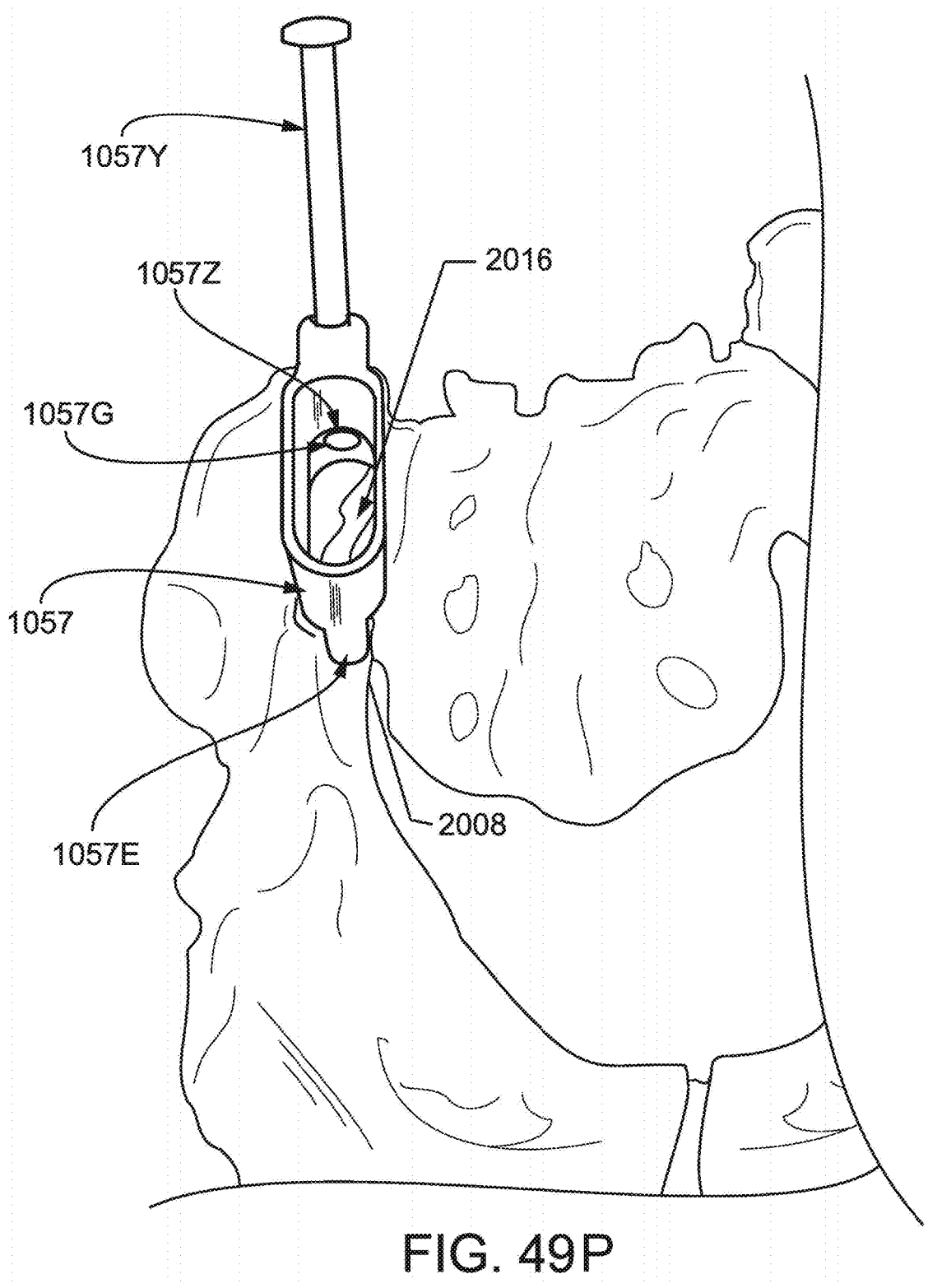
FIG. 49P is a posterior inferior view of the pelvic region showing the cannula of FIG. 49J positioned in relation to the sacroiliac joint.
Figure 49Q:
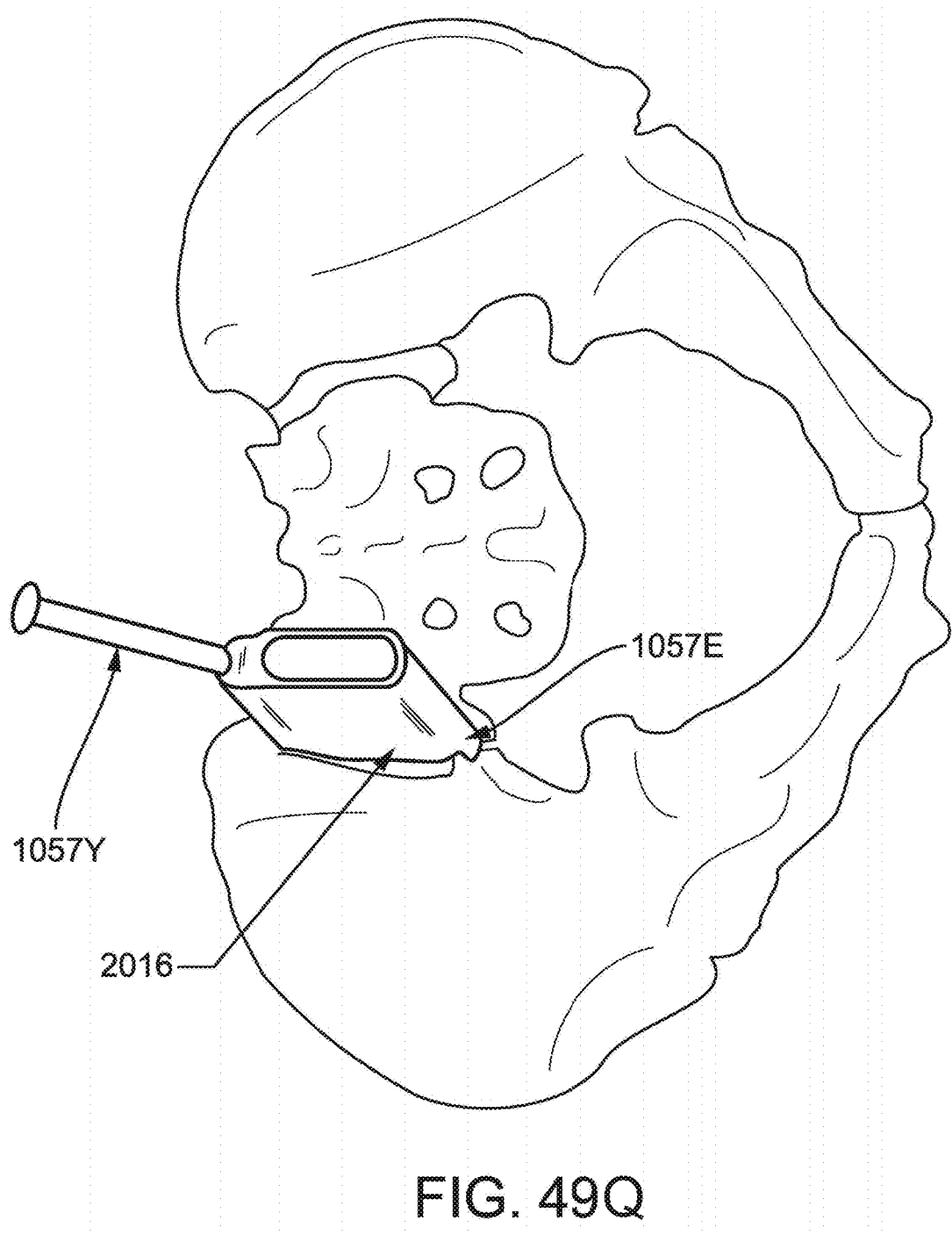
FIG. 49Q is a posterior view of the pelvic region showing the cannula of FIG. 49J positioned in relation to the sacroiliac joint.
Figure 49R:
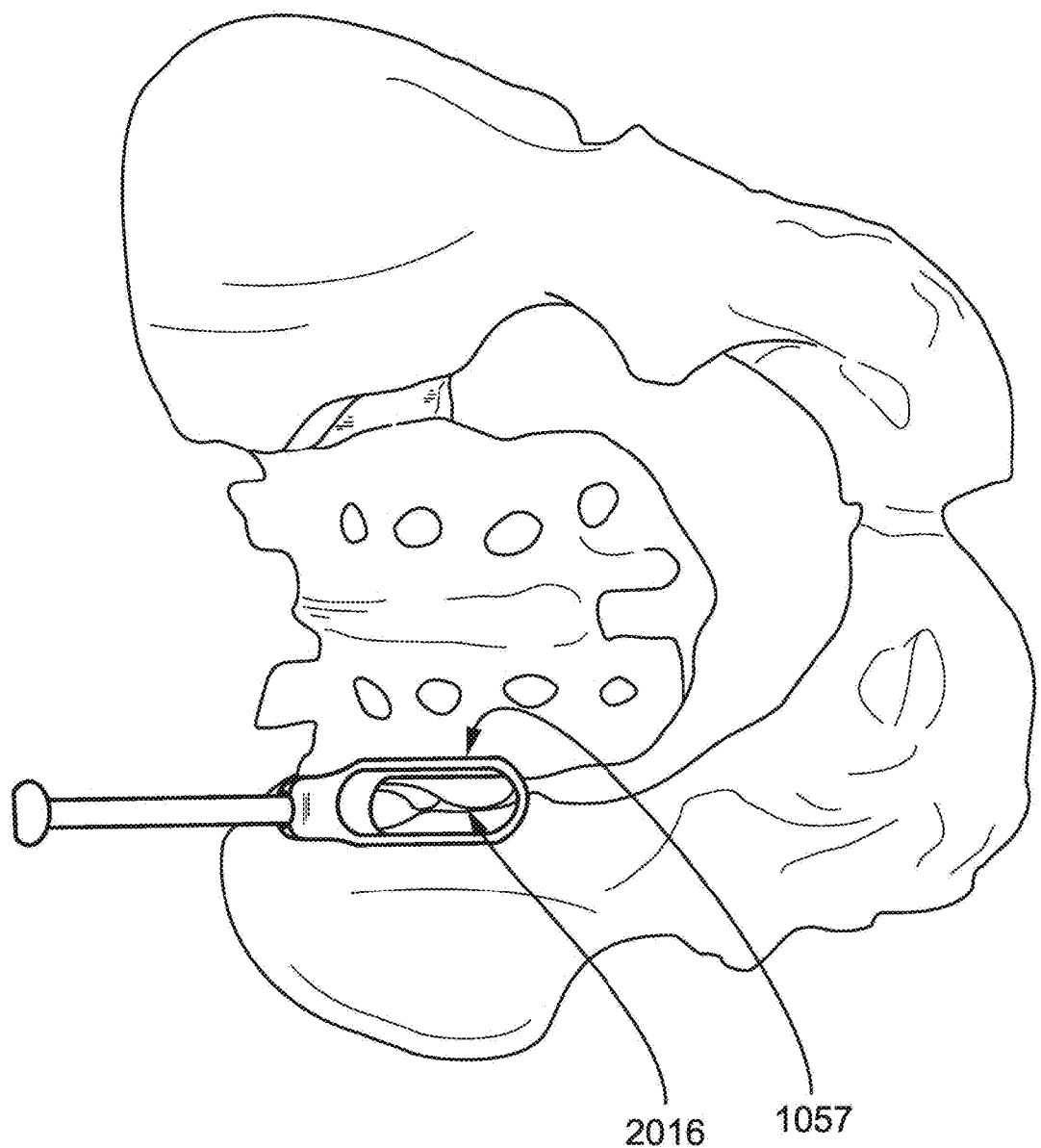
FIG. 49R is another posterior view of the pelvic region showing the cannula of FIG. 49J positioned in relation to the sacroiliac joint.

Referring again to FIGS. 49J to 49R, a surgical procedure employing the cannula 1057 may be conducted using a method described herein below. A cannula 1057 may be positioned near a sacroiliac joint line 2019 and in an area including the posterior inferior access region 2016 such that the sacroiliac joint line 2019 may be visible and/or accessible via a cannula proximal opening 1057A, as illustrated in FIG. 49O. The cannula 1057 may be further positioned to align the distal extension 1057E with a portion of the greater sciatic notch 2008, as illustrated in FIG. 49P. The cannula 1057 may be further positioned to align the cannula PSIS contact area 1057F with a portion of a posterior superior iliac spine 2004 as illustrated in FIG. 49N. The cannula 1057 may then be disposed in fixed relation to the sacroiliac joint by placement of fasteners 1057Z through the cannula 1057 into the sacrum 1004 or the ilium 1005, as illustrated in FIG. 49P.

Figure 50A:
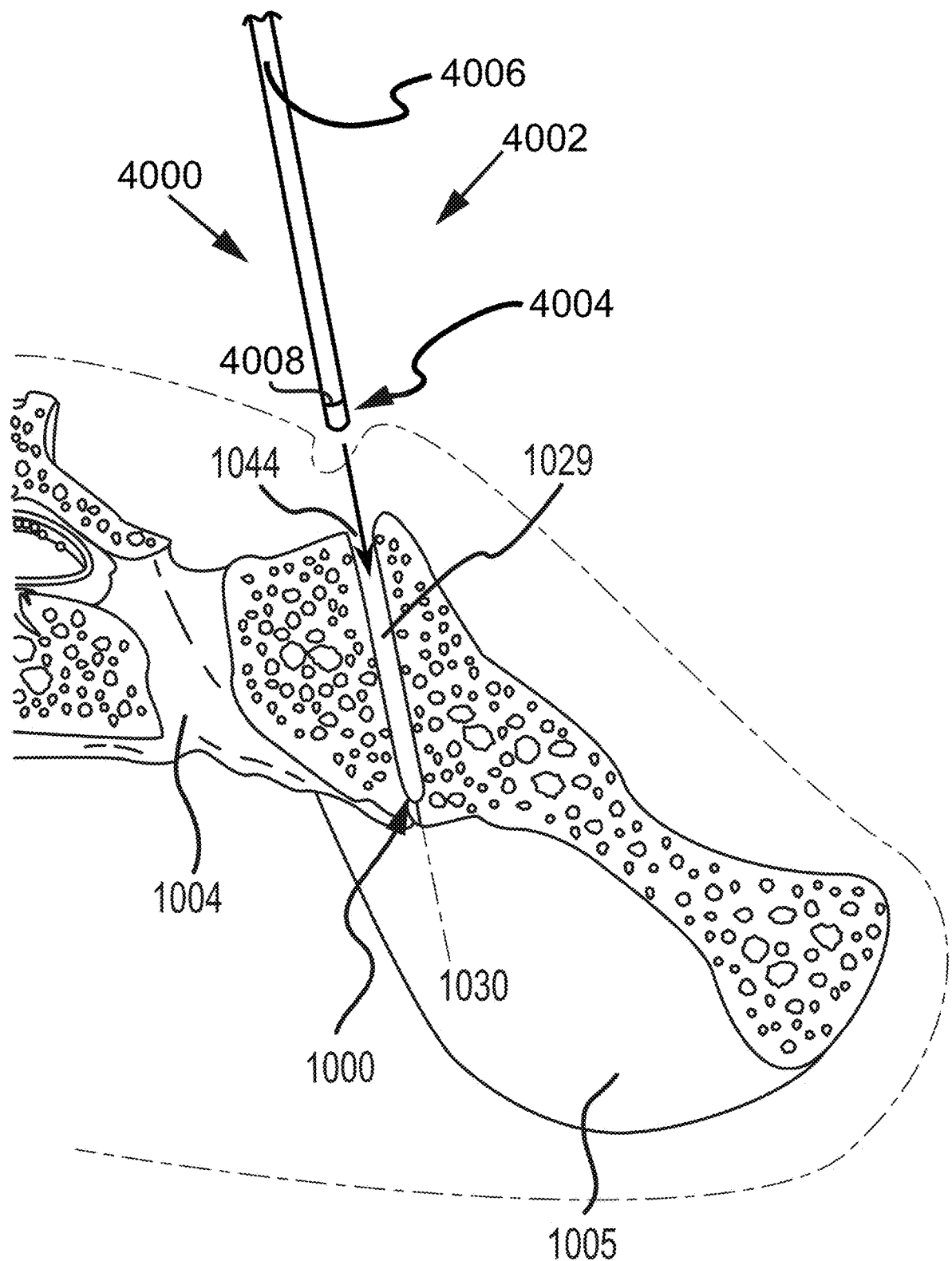
FIGS. 50A-50B are steps in the methodology of preparing the sacroiliac joint for fusion utilizing a tooling head, e g., of FIGS. 9-10, and illustrated in the transverse cross section of FIGS. 49A-49D.

Reference is now made to FIG. 50A, which depicts a joint preparation tool 4000 including a tooling head 4002, as described in FIGS. 9-10, approaching the sacroiliac joint 1000. The joint preparation tool 4000, in particular, includes a cutting element 4004 that outwardly extends from a shaft 4006 at the distal end of the tooling head 4002. The cutting element 4004 includes a sharpened proximal edge 4008 such that a cutting stroke occurs with a proximal retraction of the joint preparation tool 4000.

Figure 50B:
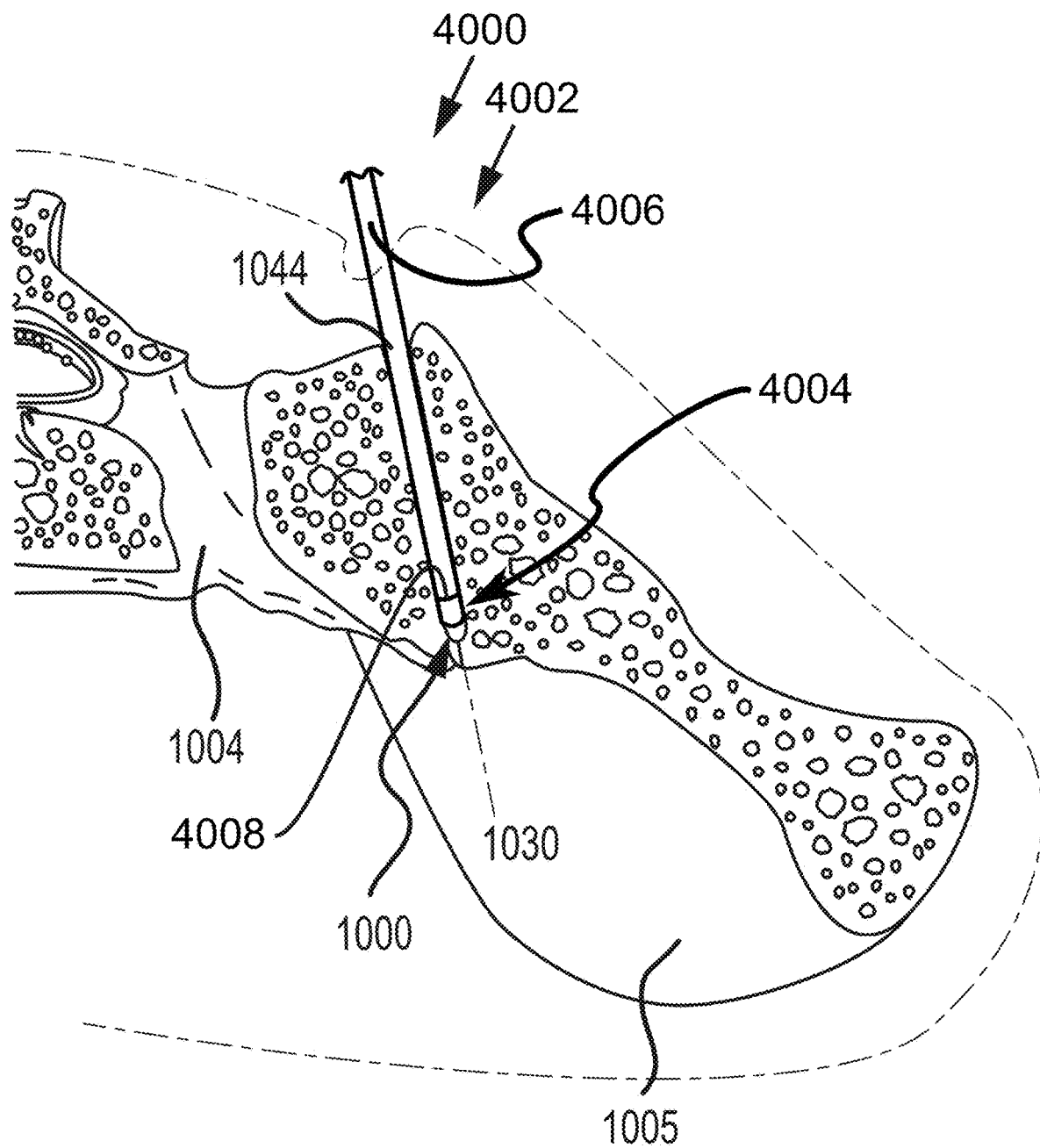

As seen in FIG. 50A, the joint preparation tool 4000 is oriented relative to sacroiliac joint articular region 1044 such that the outwardly extending cutting element 4004 is positioned parallel to the joint plane 1030. That is, each of the side walls the cutting element 4004 is oriented between the articular surfaces of the joint 1000 and the proximal edge 4008 is, initially, oriented transversely across the joint plane 1030. As illustrated in FIG. 50B, the joint preparation tool 4000 is advanced into the sacroiliac joint articular region 1044 in the previously described orientation.

Figure 50C:
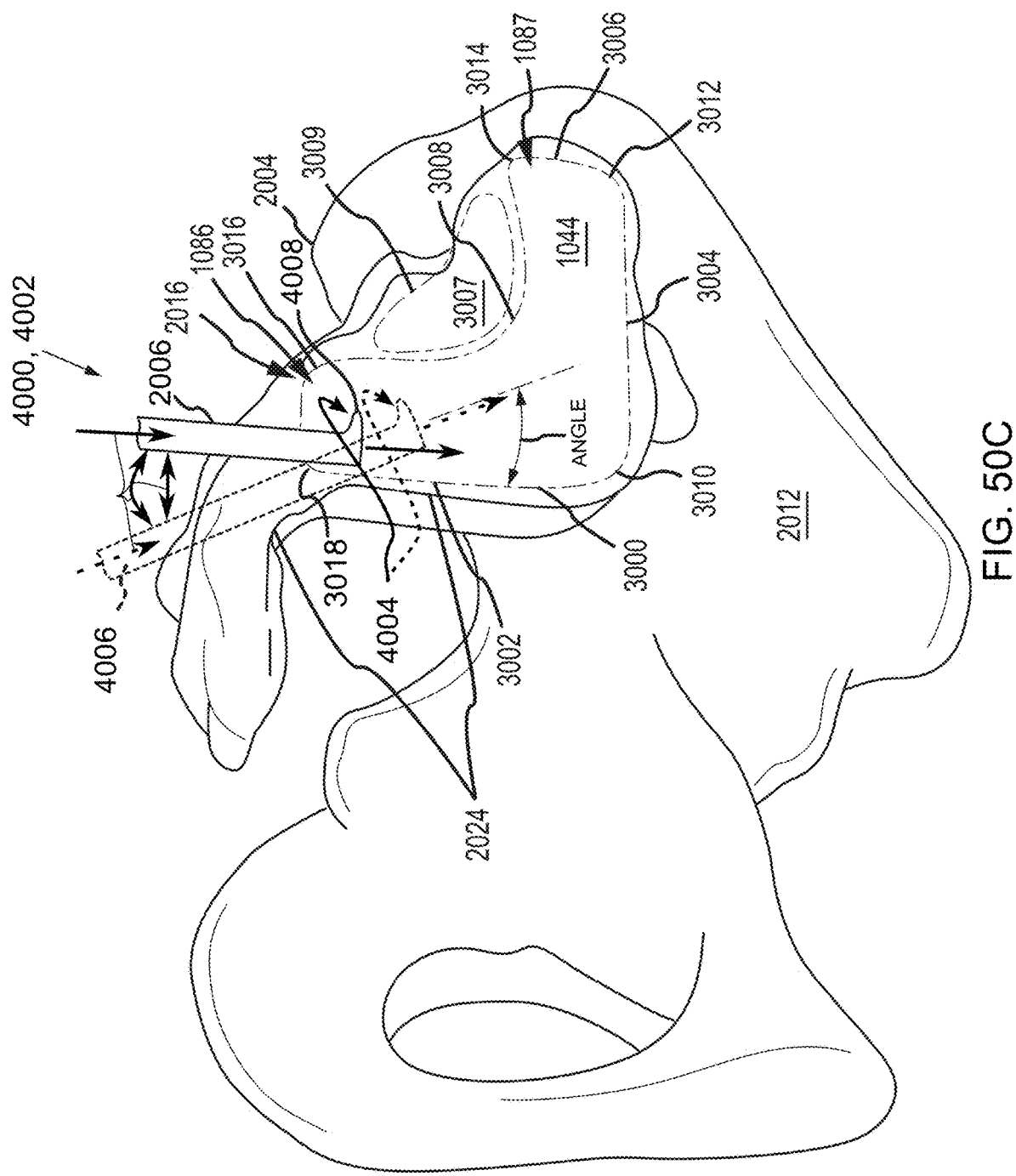
FIGS. 50C-50F are additional steps in the methodology that continue from those described in reference to FIGS. 50A-50B, except that the view is of the sacroiliac joint from the perspective in FIG. 48C.

Now reference is made primarily to FIG. 50C, which is a similar view to that of FIG. 48C, except that instead of an implant being delivered into the sacroiliac joint 1000, the joint 1000 is being prepared for implant delivery. As seen in the figure, the distal end of the tooling head 4002 may enter the posterior inferior access region 2016 and extend into the caudal region 1086 of the sacroiliac joint articular region 1044. As an example and as seen by the solid line depiction of the tooling head 4002, the head 4002 may be delivered into the caudal region 1086 such that the shaft 4006 is generally adjacent and parallel to the inferior boundary segment 3002. At a sufficient depth, the joint preparation tool 4000 may be rotated within the joint plane (as seen by the broken line depiction of the joint preparation tool 4000) such that the shaft 4006 angles the cutting element 4004 towards the cranial region 1087 of the articular region 1044. This and other movements will cause the proximal edge 4008 of the cutting element 4004 to cut into or shear the articular cartilage from the articular surfaces of the sacroiliac joint articular region 1044.

Figure 50D:
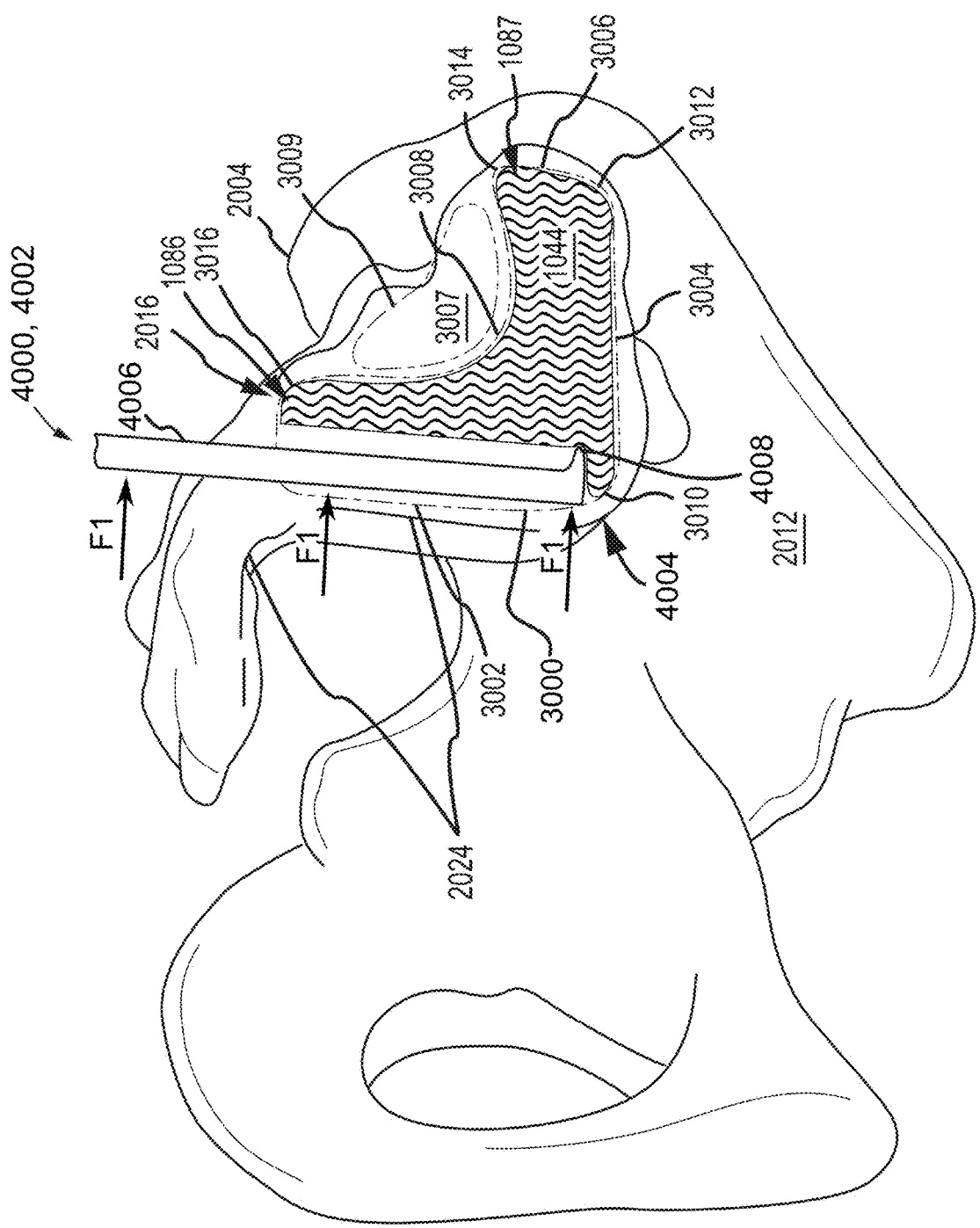
Figure 50E:
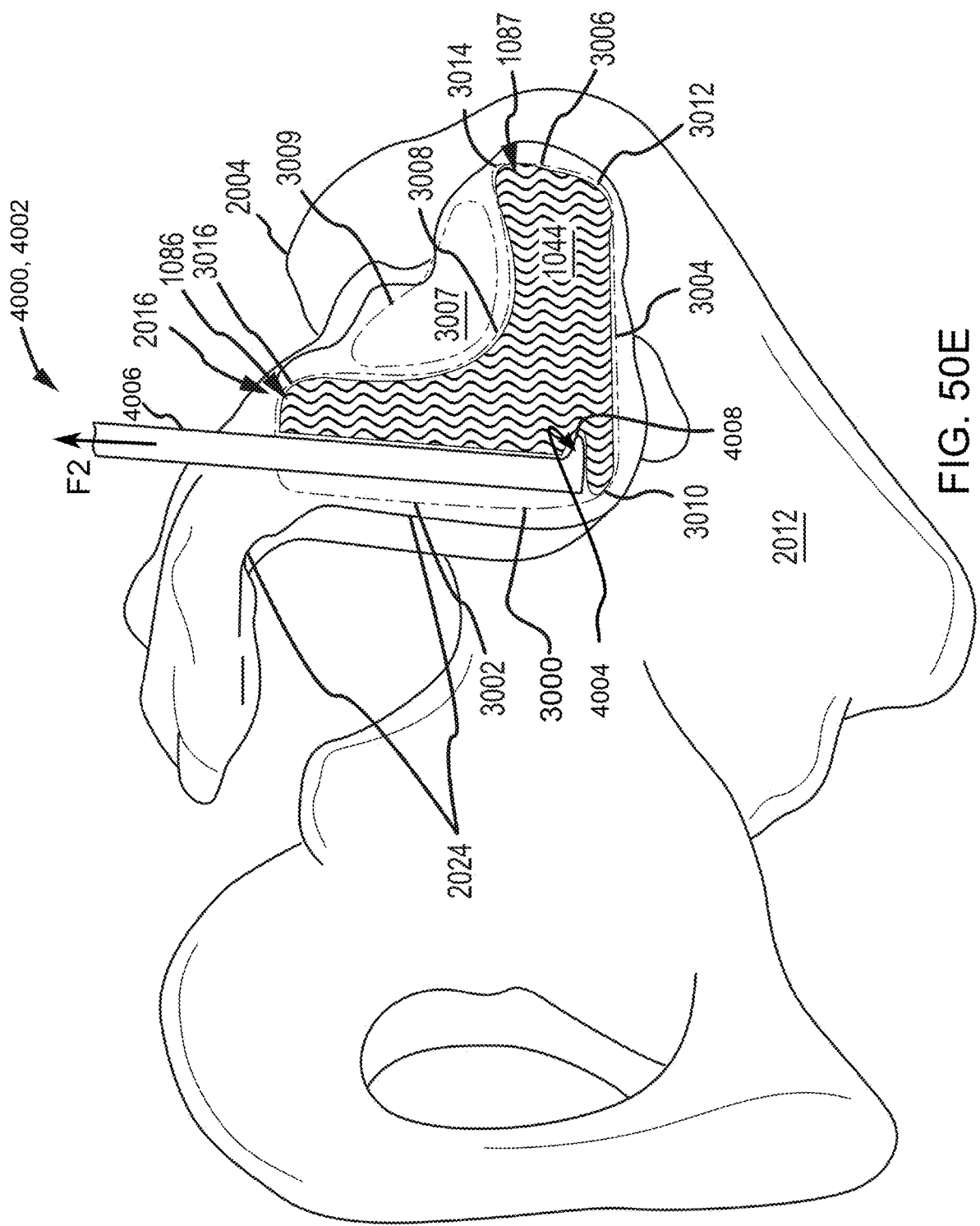

As another example of preparing the articular region 1044 once the tool 4000 is positioned within the articular region 1044, reference is made to FIG. 50D, which depicts the joint preparation tool 4000 fully in into the articular region 1044 such that the shaft 4006 of the tooling head 4002 is adjacent and parallel to the inferior boundary segment 3002 and the cutting element 4004 is adjacent the anterior-inferior corner 3010. In this orientation, the cutting element 4004 extends from the shaft 4006 towards the cranial region 1087 of the articular region 1044. It is noted that insertion of the tool 4000 into the articular region 1044 causes an initial abrasion to the articular cartilage in the portions of the articular region 1044 where the tool 4000 is inserted. To further prepare the articular region 1044, a force F1 may be applied to joint preparation tool 4000 in a direction perpendicular to the extension of the shaft 4006 and in a direction towards the cranial region 1087. As seen in FIG. 50E, which depicts the joint preparation tool 4000 moved superiorly according to the applied force F1, the cutting element 4004 is now in contact with additional articular cartilage that was not previously abraded by the insertion of the tool 4000 into the articular region 1044. At this point, a force F2 may be applied proximally on the joint preparation tool 4000.

Figure 50F:
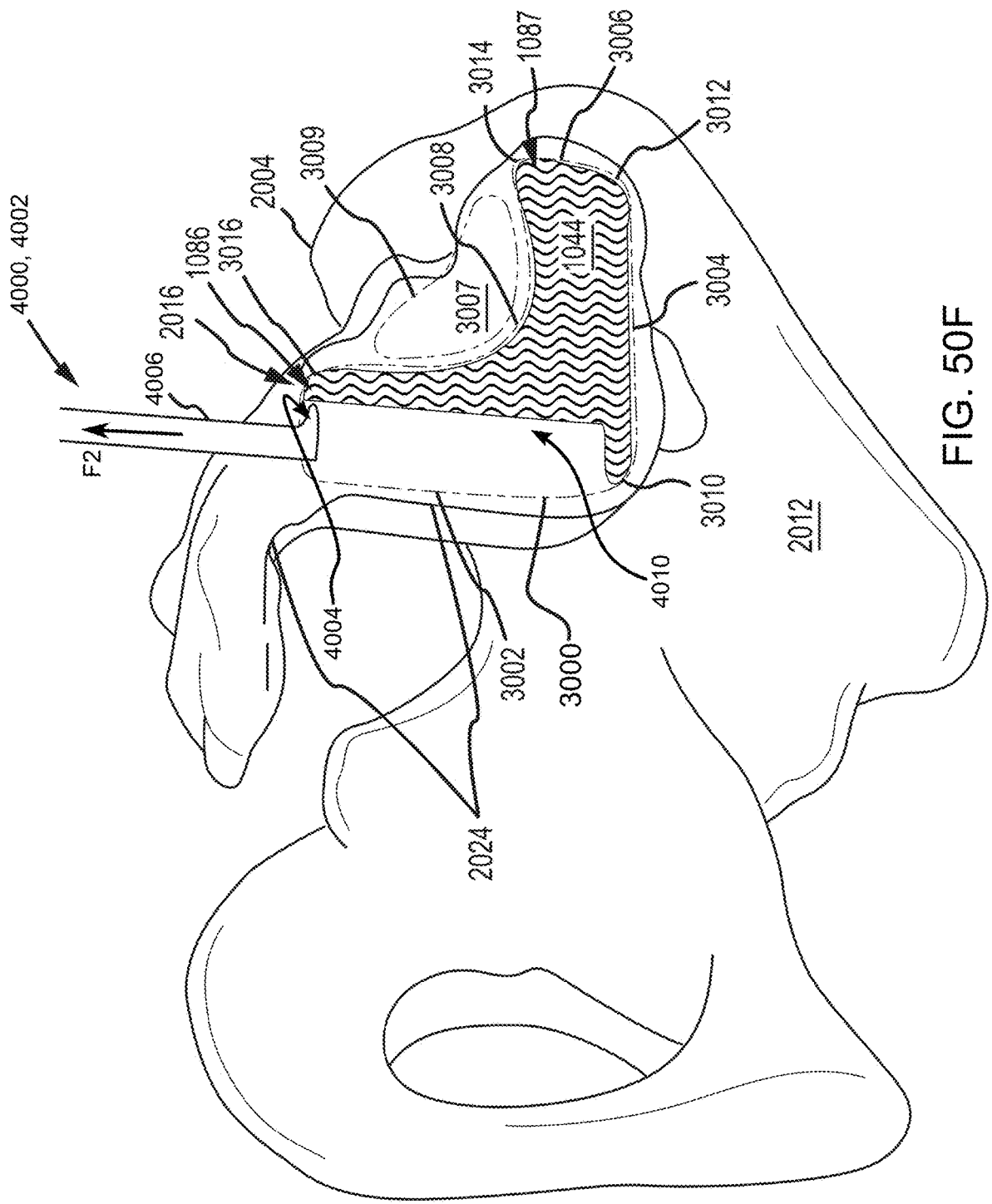

As seen in FIG. 50F, the force F2 and the proximal retraction of the tooling head 4002 from the articular region 1044 will cause articular cartilage in-line with the cutting element 4004 to be cut or otherwise sheared from the articular surfaces of the articular region 1044 leaving a prepared joint surface 4010. At this point, the joint preparation tool having a curette-type tooling head may be used to remove the abraded articular cartilage in the joint space by any number of methods.

The previously mentioned steps may be repeated in order to increase the size of the prepared joint surface 4010 as may be needed for a particular surgical procedure. For example, a joint preparation tool 4000 having a tooling head 4002 with a larger outwardly extending cutting element 4004 may be subsequently used to prepare an even larger joint surface 4010.

Figure 51A:
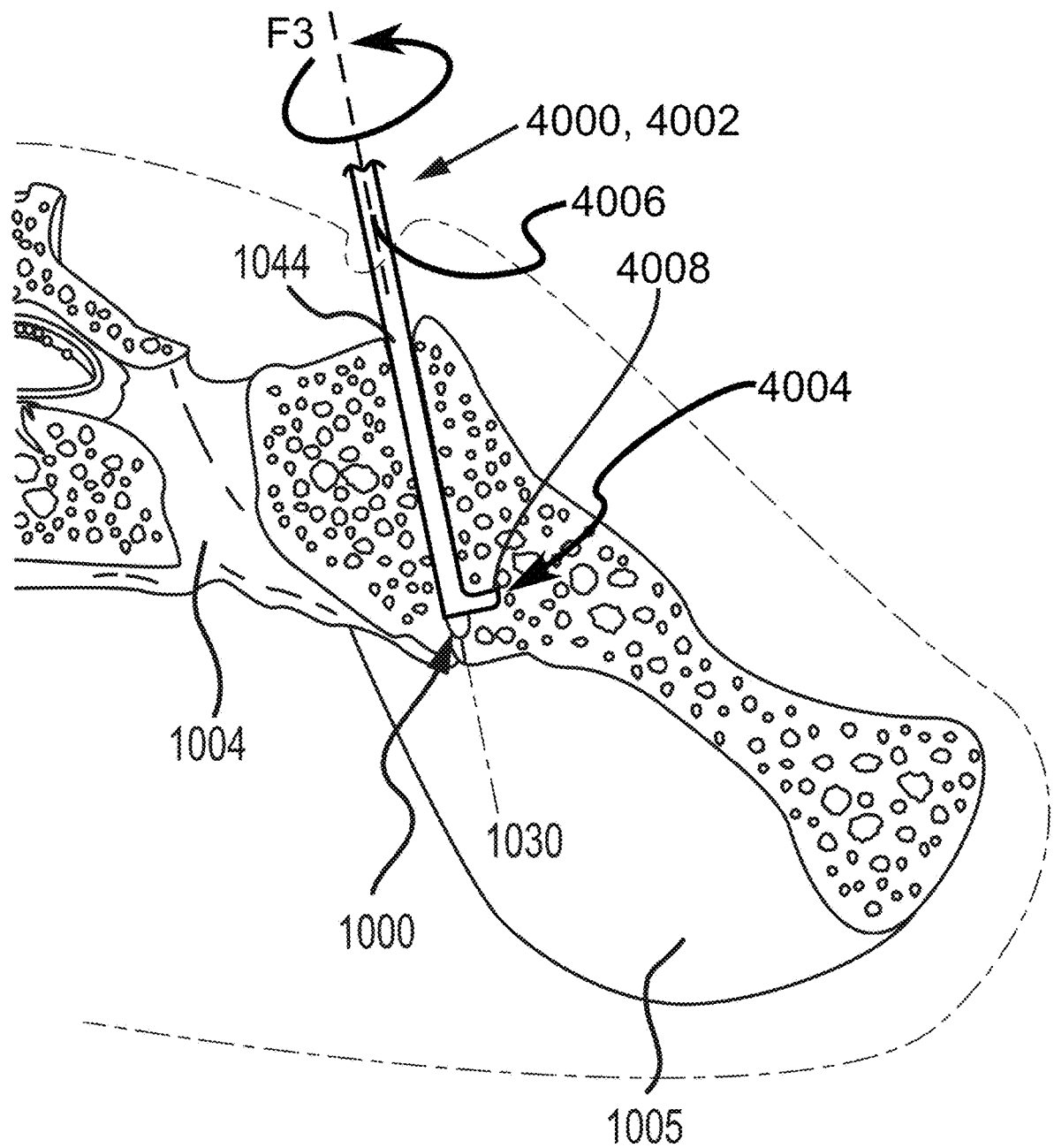
FIGS. 51A-51E are additional steps in the methodology of preparing the sacroiliac joint for fusion including utilizing a tooling head, e.g., of FIGS. 9-10, and illustrated in the transverse cross section of FIGS. 50A-50B.
Figure 51B:
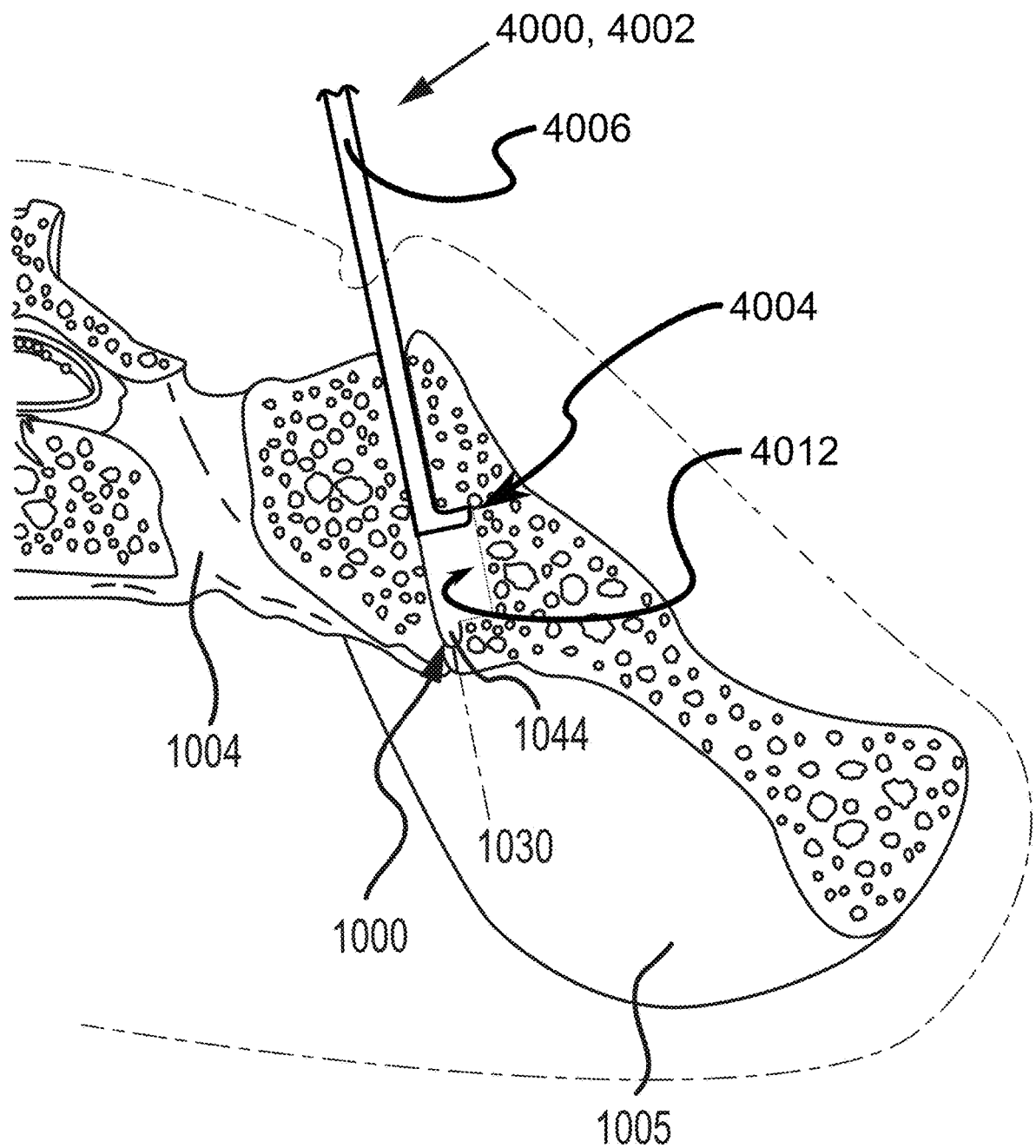

Now primarily referring to FIG. 51A, the joint preparation tool 4000 previously described may be used to make keel-cuts generally perpendicularly into the sacrum 1004 and/or the ilium 1005. As seen in the figure, which is a transverse cross section of the sacrum 1004 and the ilium 1005 taken in along a plane extending medial-lateral and anterior posterior, the joint preparation tool 4000 may be delivered into the sacroiliac joint articular region 1044, as described previously in FIGS. 50A-50B, such that the cutting element 4004 extends from the shaft 4006 of the tooling head 4002 parallel to the joint plane 1030. In this orientation, the proximal edge 4008 of the cutting element 4004 extends across the joint plane 1030. Once the joint preparation tool 4000 is at a sufficient depth within the articular region 1044, as seen in FIG. 51A, the shaft 4006 of the tool 4000 may be rotated such that the cutting element extends within either the sacrum 1004 or the ilium 1005 (cutting element extends within ilium 1005 in FIG. 51A) and is oriented perpendicular to the joint plane 1030. Next, a force F3 may be proximally applied (e.g., via a slap hammer assembly) to the joint preparation tool 4000 such that the proximal edge 4008 of the cutting element 4004 cuts a channel, groove, or other feature as defined by the shape of the proximal edge 4008 into the bone of the ilium 1005. As seen in FIG. 51B, the proximal retraction of the joint preparation tool 4000 forms a receiving space 4012 within the bone of the ilium 1005 for use in a particular fusion procedure. While FIG. 51B depicts the cutting element 4004 only partially retracted from the articular region 1044, the cutting element 4004 may be fully retracted such that the keel-cuts forming the receiving space 4014 extend to the proximal end of the joint line 1030.

Figure 51C:
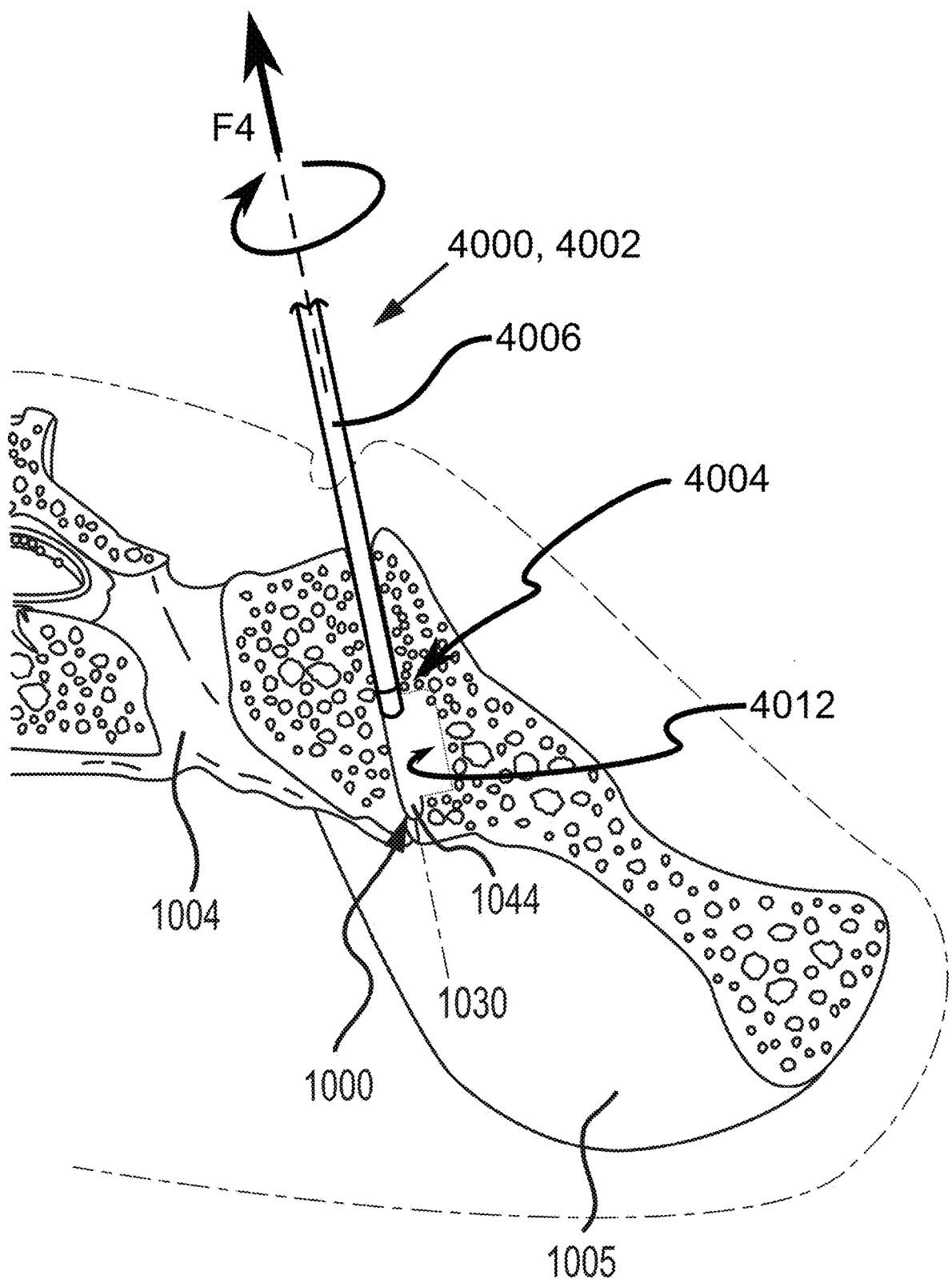
Figure 51D:
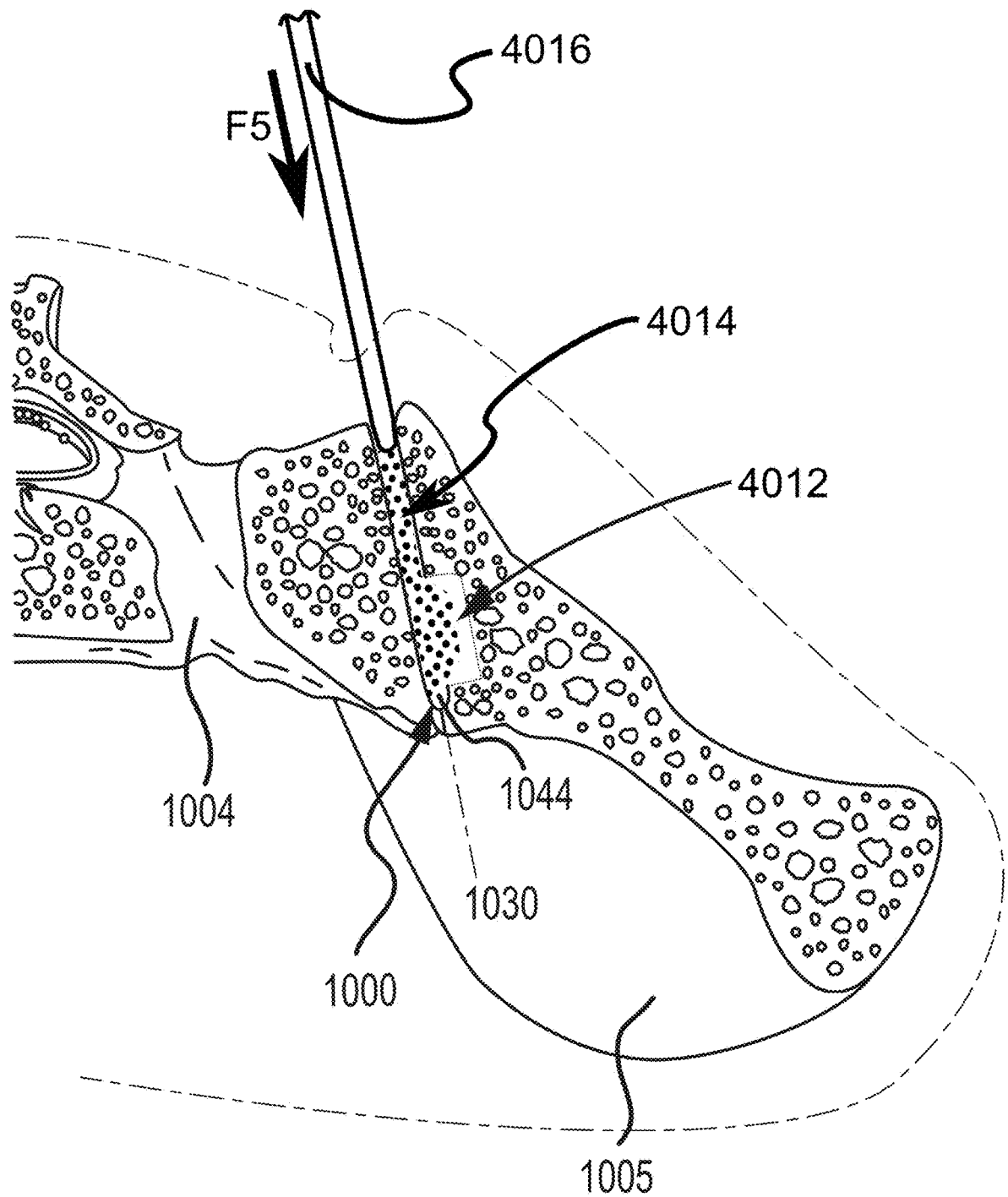
Figure 51E:
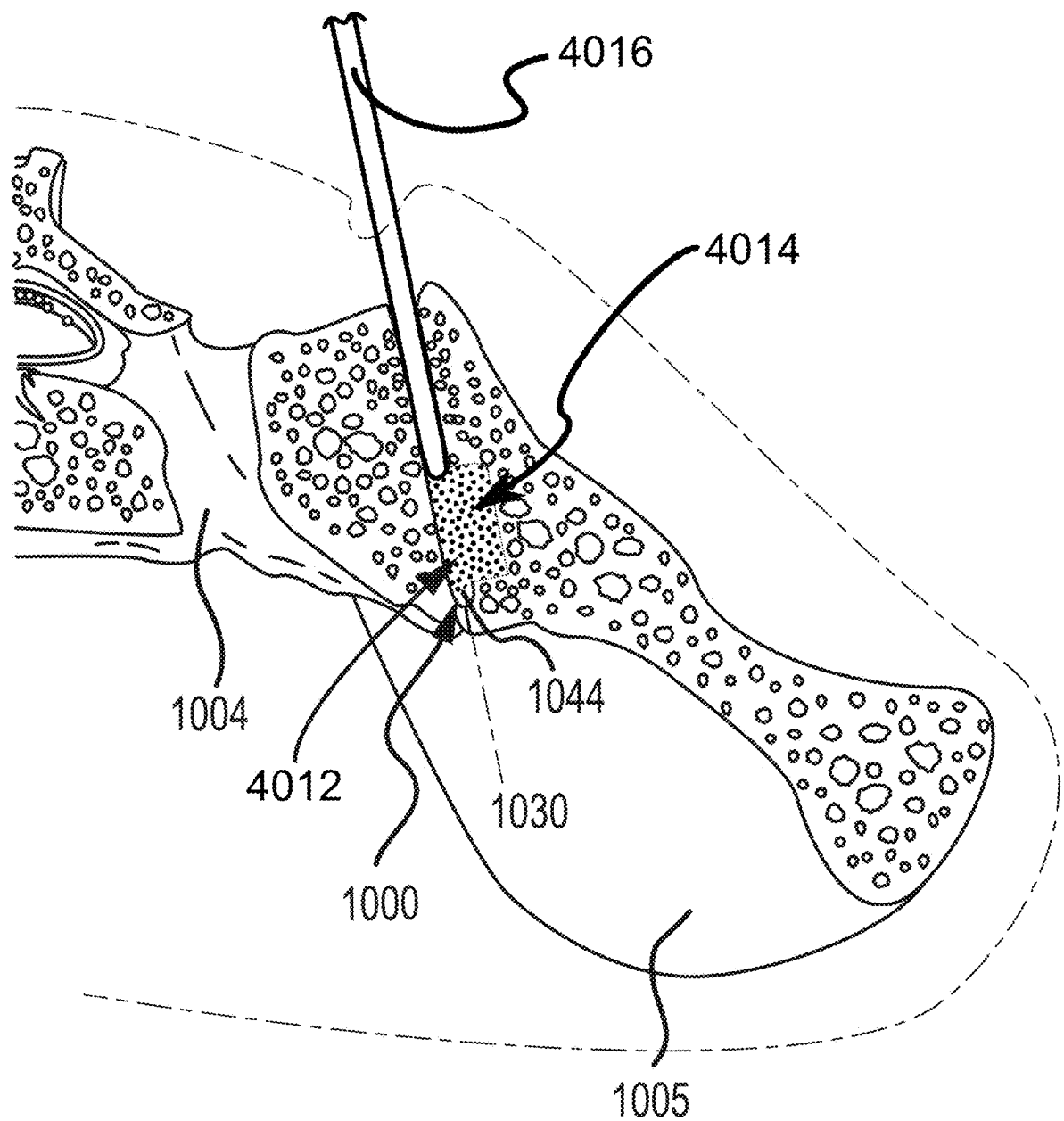

Alternatively and as seen in FIG. 51C, which is the same as FIG. 51B except the shaft 4006 of the joint preparation tool 4000 is rotated about ninety degrees, the tooling head 4002 may be removed from the articular region 1044 after the ninety degree rotation by a proximal force F4. Thus, the tooling head 4002 is removed from the joint without performing a full keel-cut that would extend the receiving space 4012 to the proximal end of the joint line 1030. Turning to FIG. 51D, which depicts the receiving space 4012 after the joint preparation tool 4000 has been proximally withdrawn; the receiving space 4012 may be filled with a biological material 4014 such as an allo/auto-graft, synthetic biologic, or scaffold, among other materials. Next, a bone tamp 4016 or other device may be used to apply a distal force F5 along the joint line 1030 so as to compress the biological material 4014 into the receiving space 4012. As seen in FIG. 51E, the bone tamp 4016 may be compressed along the joint line 1030 up to a depth of the keel-cut, among other possible depths, such that the biological material 4014 may compress across the articular surface of the sacrum 1004 and the groove formed in the receiving space 4012.

Figure 52A:
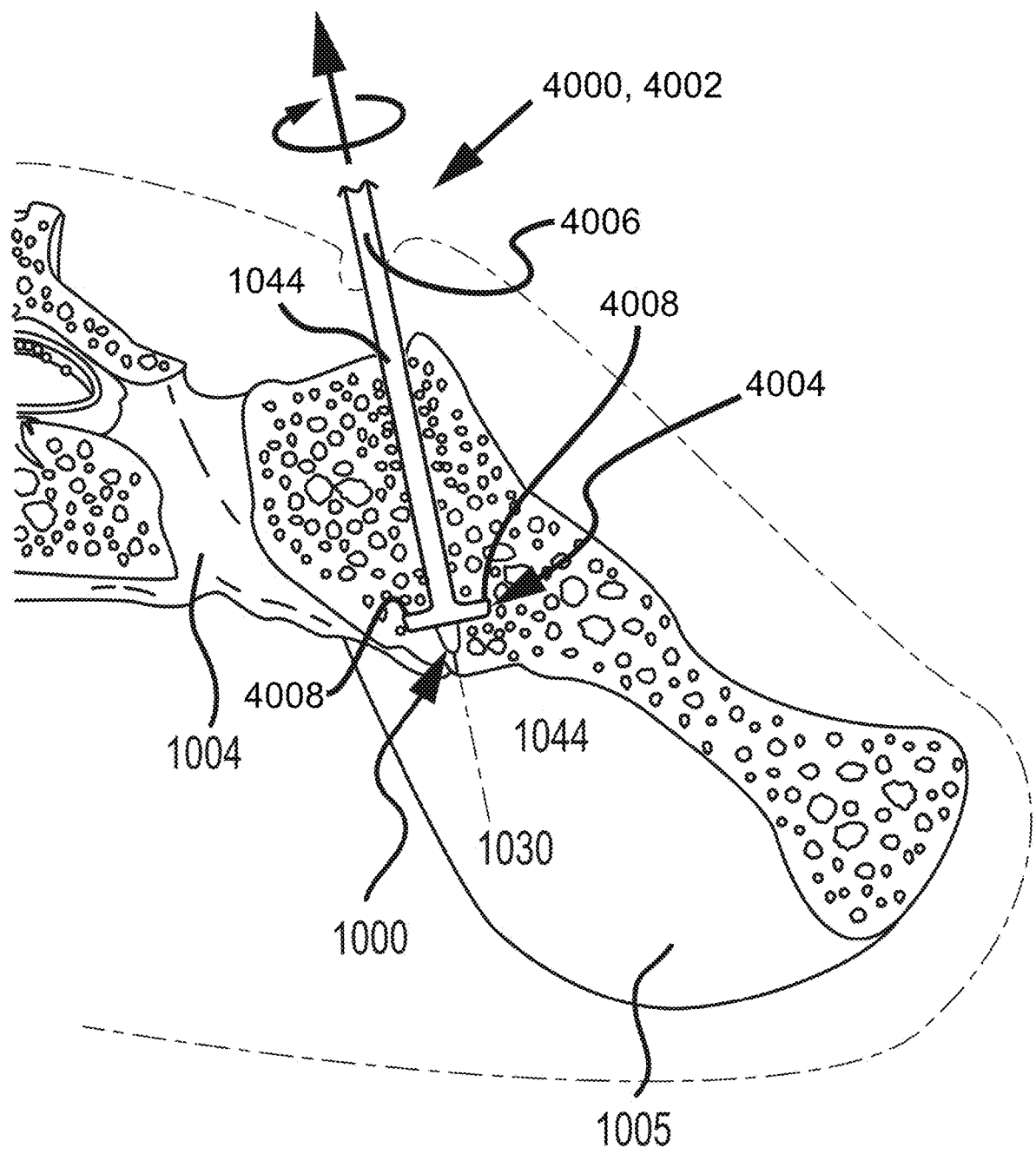
FIGS. 52A-52B are steps in the methodology of preparing a sacroiliac joint for fusion utilizing a tooling head with dual cutting elements, e.g., as seen in FIG. 13, and shown in the transverse cross section of FIGS. 49A-49D.
Figure 52B:
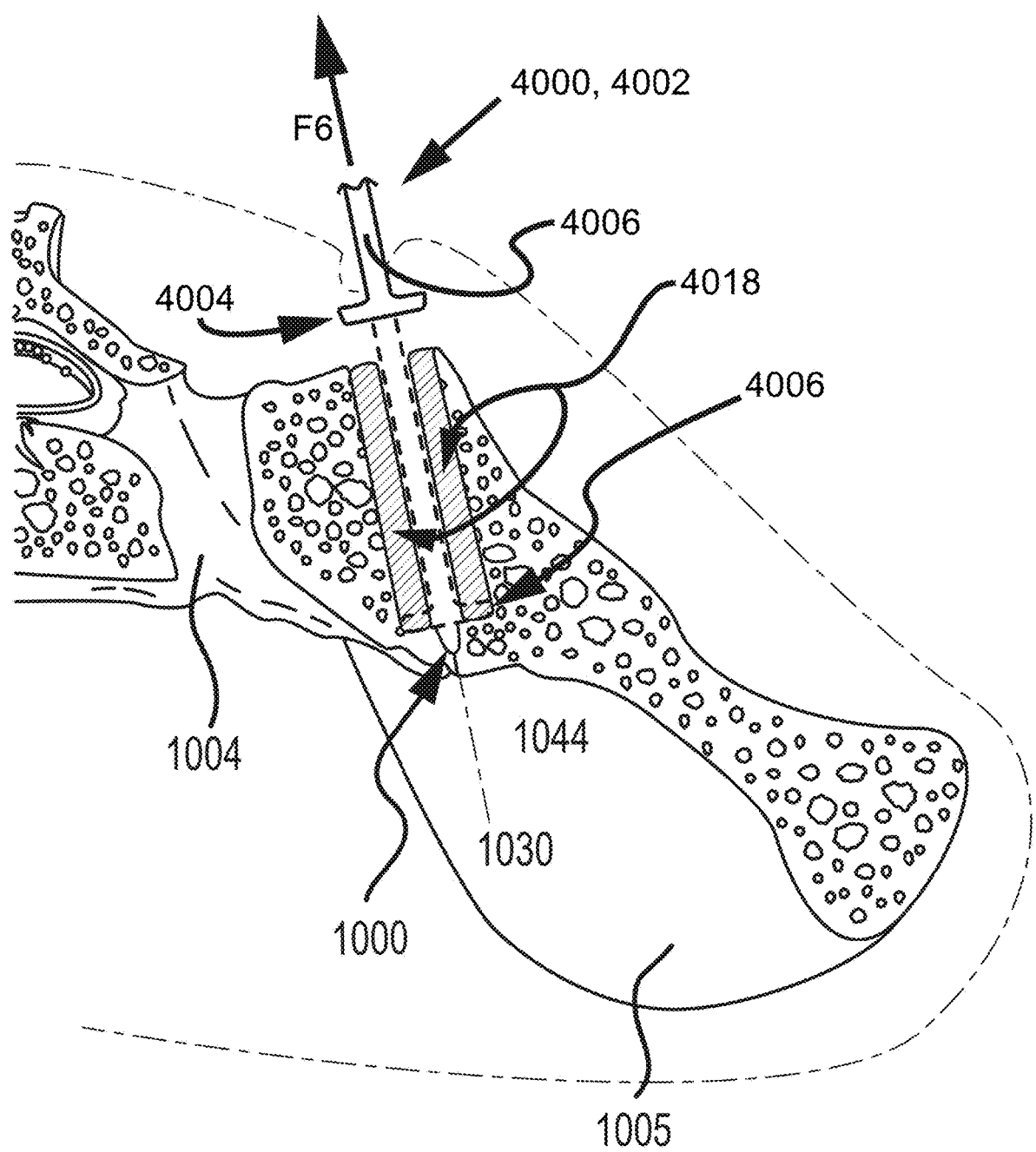

In certain embodiments of the method, keel-cuts can be made in either or both of the sacrum 1004 and the ilium 1005 and such a decision will be based on the particular fusion procedure and the type and configuration of an implant to be delivered into the joint. For example, an implant having a coplanar wing member may require dual keel-cuts where both the sacrum 1004 and the ilium 1005 are cut for the subsequent delivery of the implant. In such an example and referring to FIG. 52A, a joint preparation tool 4000 having a tooling head 4002 with dual-cutting elements 4004, as described in reference to FIG. 13, may be employed. Similar to as discussed previously, the joint preparation tool 4000 having dual-cutting elements 4004 may be delivered into the sacroiliac joint articular region 1044 with the outwardly extending cutting elements 4004 positioned within the joint plane 1030 such that the proximal edges 4008 extend across the joint line 1030. Once the joint preparation tool 4000 is delivered into the articular region 1044 at an appropriate depth, as seen in FIG. 52A, the tool 4000 may be rotated about ninety degrees such that the cutting elements extend generally perpendicularly into the sacrum 1004 and the ilium 1005. Next, as seen in FIG. 52B, the joint preparation tool 4000 may be proximally retracted by a force F6 (e.g., via a slap hammer) such that the dual-cutting elements 4004 form opposing channels 4018 in the sacrum 1004 and the ilium 1005 that match the shape of an implant to be delivered in the surgical procedure.

In certain embodiments, the dual-cutting elements 4004 are identical in shape and size. In other embodiments, the dual-cutting elements 4004 may be differently configured based on the physical characteristics of the bone type to be cut, the implant to be delivered, etc. That is, since the ilium 1005 is generally a harder bone than the sacrum, a different type of cutting edge configuration may be used on one of the cutting elements 4004.

Now the discussion will focus on methods of preparing the sacroiliac joint 1000 for a surgical fusion procedure with a joint preparation tool assembly including a trial tool assembly and a cutting tool as described in reference to FIGS. 27-47.

Figure 53A:
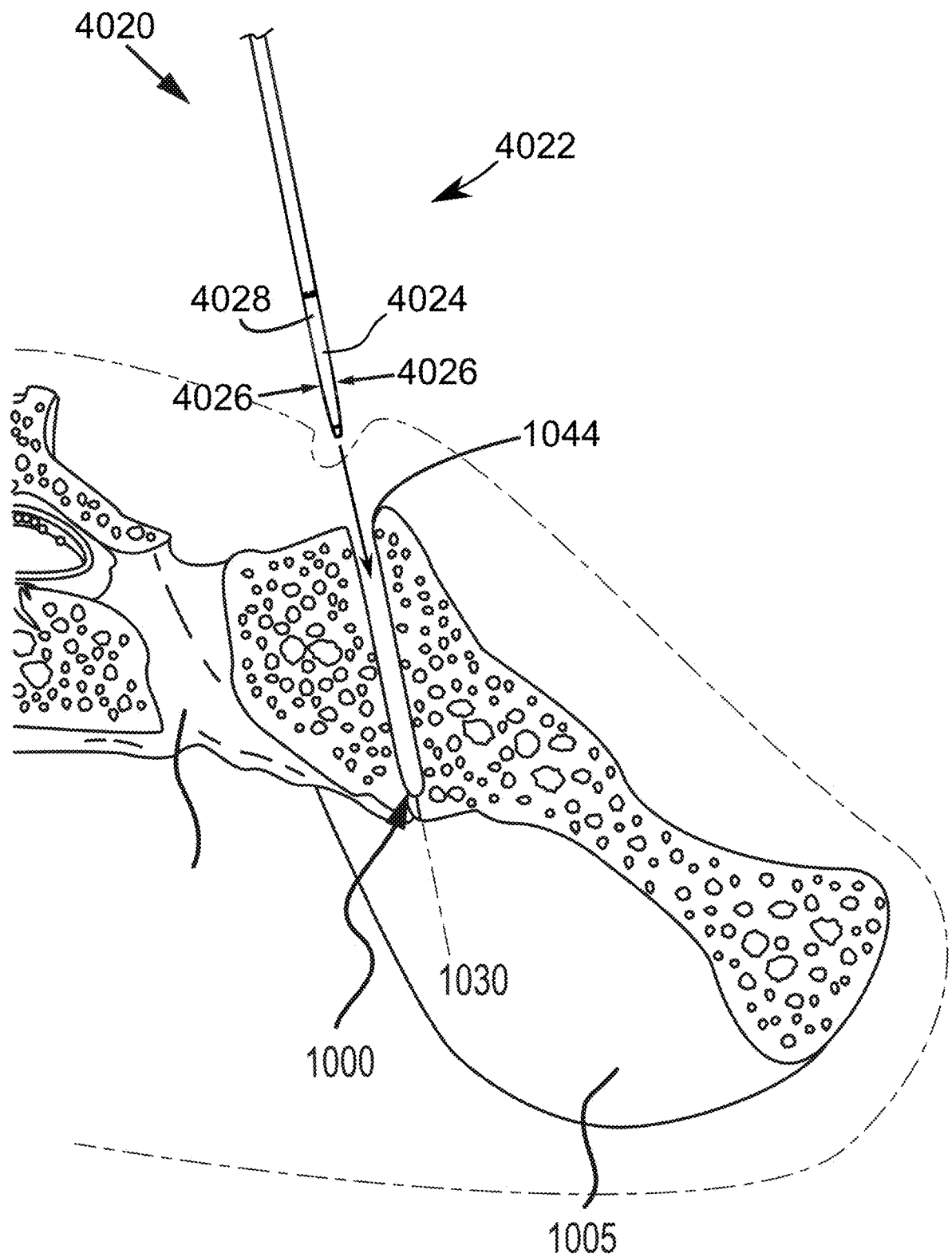
FIGS. 53A-53D are steps in the methodology of preparing a sacroiliac joint for fusion utilizing the joint preparation tool assemblies described in FIGS. 27-47.

Referring primarily to FIG. 53A, a trial tool assembly 4022 having an implant trial 4024 at a distal end of the assembly 4022 may be delivered into the sacroiliac joint articular region 1044 of a patient. The trial tool assembly 4022 may be guided into the articular region 1044 by a guide wire (not shown) that was previously delivered into the joint by previously described methods. In particular, the guide wire may be received within a bore that extends from a distal end to a proximal end of the implant trial 4024. The implant trial 4024 may be delivered within the joint plane 1030 such that the planar top and bottom surfaces 4026 are parallel to the joint plane 1030 and the opposite side surfaces 4028 of the implant trial 4024 are perpendicular to the joint plane 1030.

The implant trial 4024 may be forcibly delivered into the articular region 1044 by using a hammer or mallet to strike an impact plate (not shown) at a proximal end of the joint preparation tool assembly 4020. And, in certain embodiments, a trial impact rod assembly (not shown) may be used in conjunction with the trial tool assembly 4022 to provide stiffness during the forceful delivery of the implant trial 4024 within the articular region 1044.

The implant trial 4024 is used to determine an appropriate fit of an implant. So, implant trials 4024 of increasingly larger size may be delivered into the articular region 1044 until an implant trial 4024 is chosen that appropriately fits the top and bottom surfaces 4026 of the implant trial 4024 against the articular surfaces of the articular region 1044.

Figure 53B:
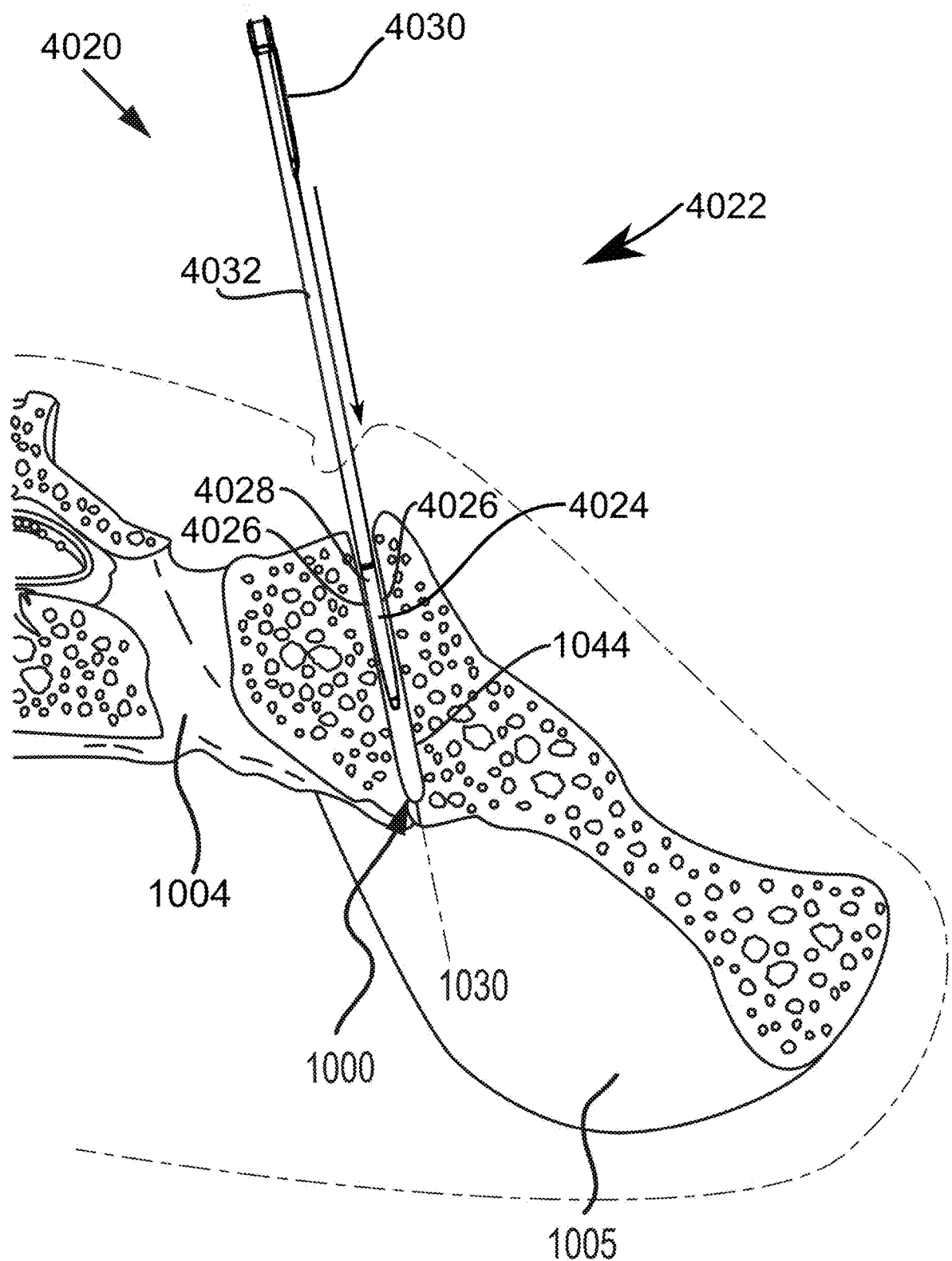
Figure 53C:
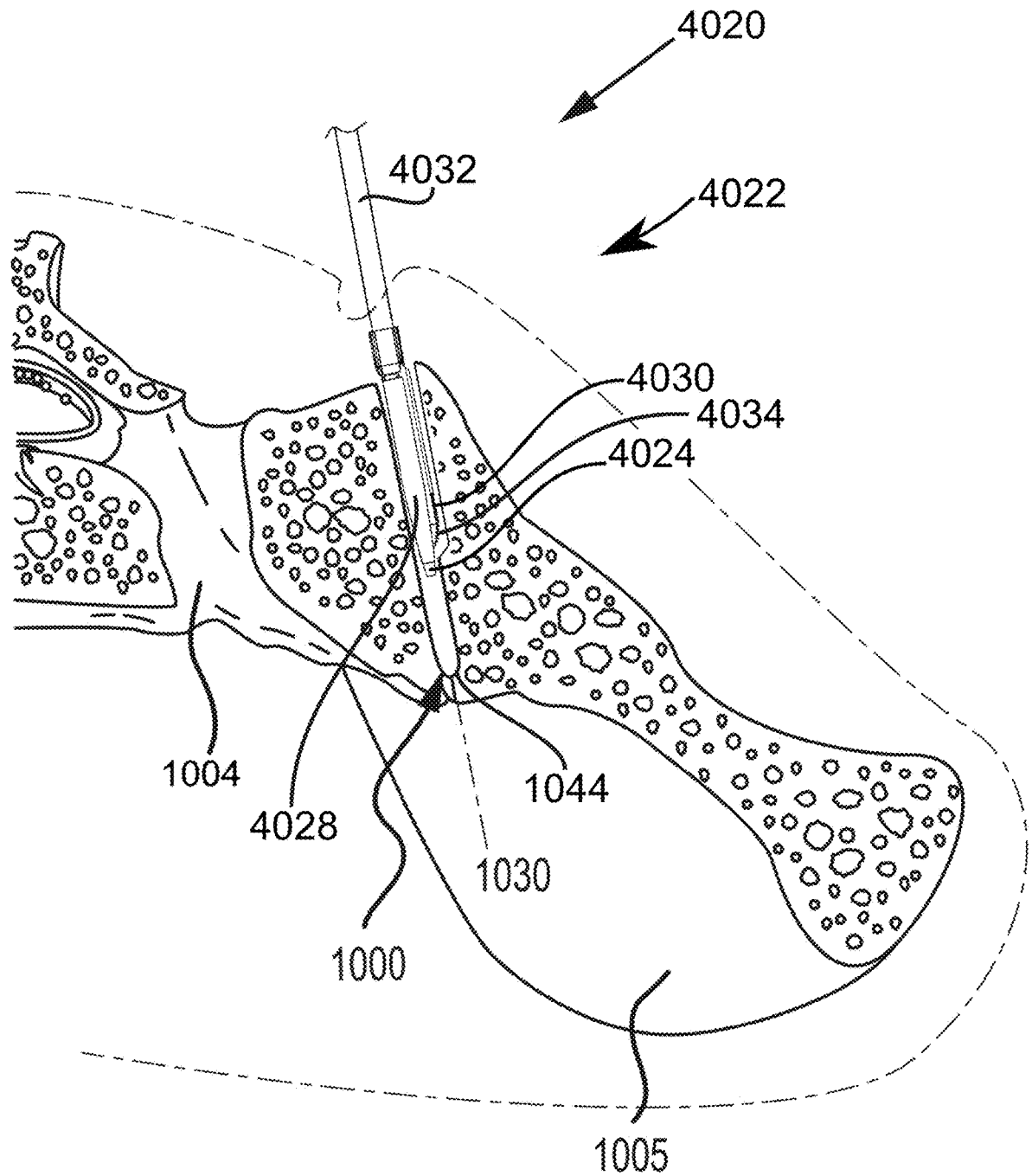

Referring primarily to FIG. 53B, which depicts the implant trial 4024 positioned within the articular region 1044, a cutting tool 4030 may be slidingly engaged with a shaft 4032 of the trial tool assembly 4022 and translated distally on the shaft 4032. As seen in FIG. 53B and as described previously, the cutting tool 4030 is guided along the shaft 4032 in a single orientation such that it will be guided within a channel (not shown) on the top surface 4026 of the implant trial 4024. The channel is configured to guide the cutting tool 4030 such that a cutting element 4034 of the cutting tool 4030 extends generally perpendicular to the top surface 4026 of the implant trial 4024. Thus, as seen in FIG. 53C, as the cutting element 4034 advances distally into the channel of the implant trial 4024 and within the articular region 1044, the cutting element 4034 extends and cuts into the articular surface of either the sacrum 1004 or the ilium 1005. A reciprocating motion may be employed.

While, as seen in FIG. 53C, the cutting element 4034 extends and cuts into the ilium 1005 during a distal stroke of the cutting tool 4030, the process may be similarly performed with respect to the sacrum 1004. Alternatively, a cutting tool 4030 with dual-cutting elements 4034 may be employed to deliver simultaneous and opposing cuts into both the sacrum 1004 and the ilium 1005. In such an embodiment of the joint preparation tool assembly 4020 with dual-cutting elements 4034 (and, thus, dual-channels in the implant trial 4024) the individual cutting elements 4034 may be the same or different. The individual cutting elements 4034 may, for example, be different types and configurations of cutting elements 4034 since the ilium 1005 is a generally harder bone than the sacrum 1004. Additionally, cutting tools 4030 with increasingly larger cutting elements 4034 may be employed such that initial cuts are smaller and of a shallower depth into the articular surfaces while subsequent cuts are larger and of a deeper depth into the articular surfaces of the sacrum 1004 and ilium 1005.

Figure 53D:
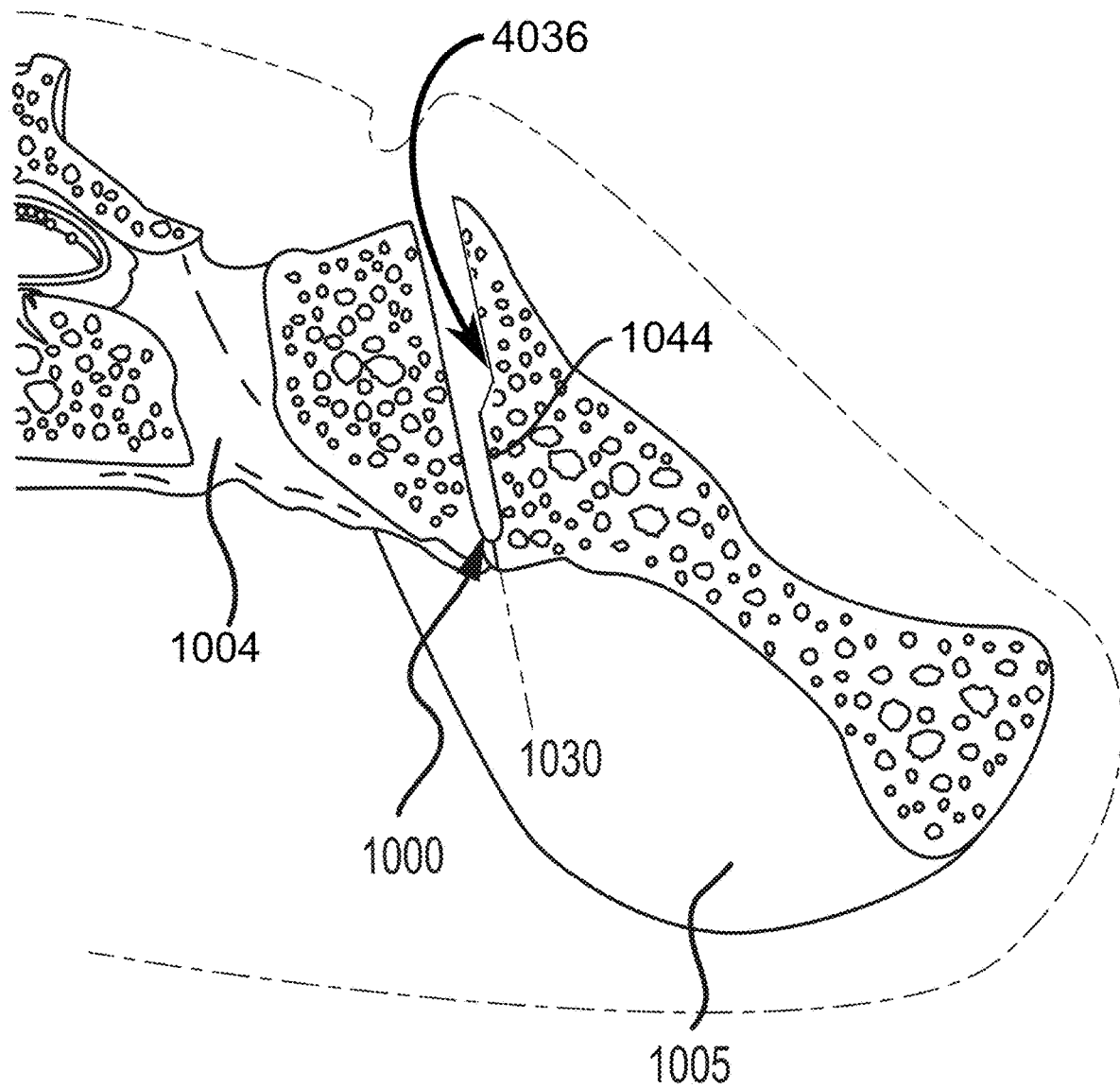
Figure 54A:
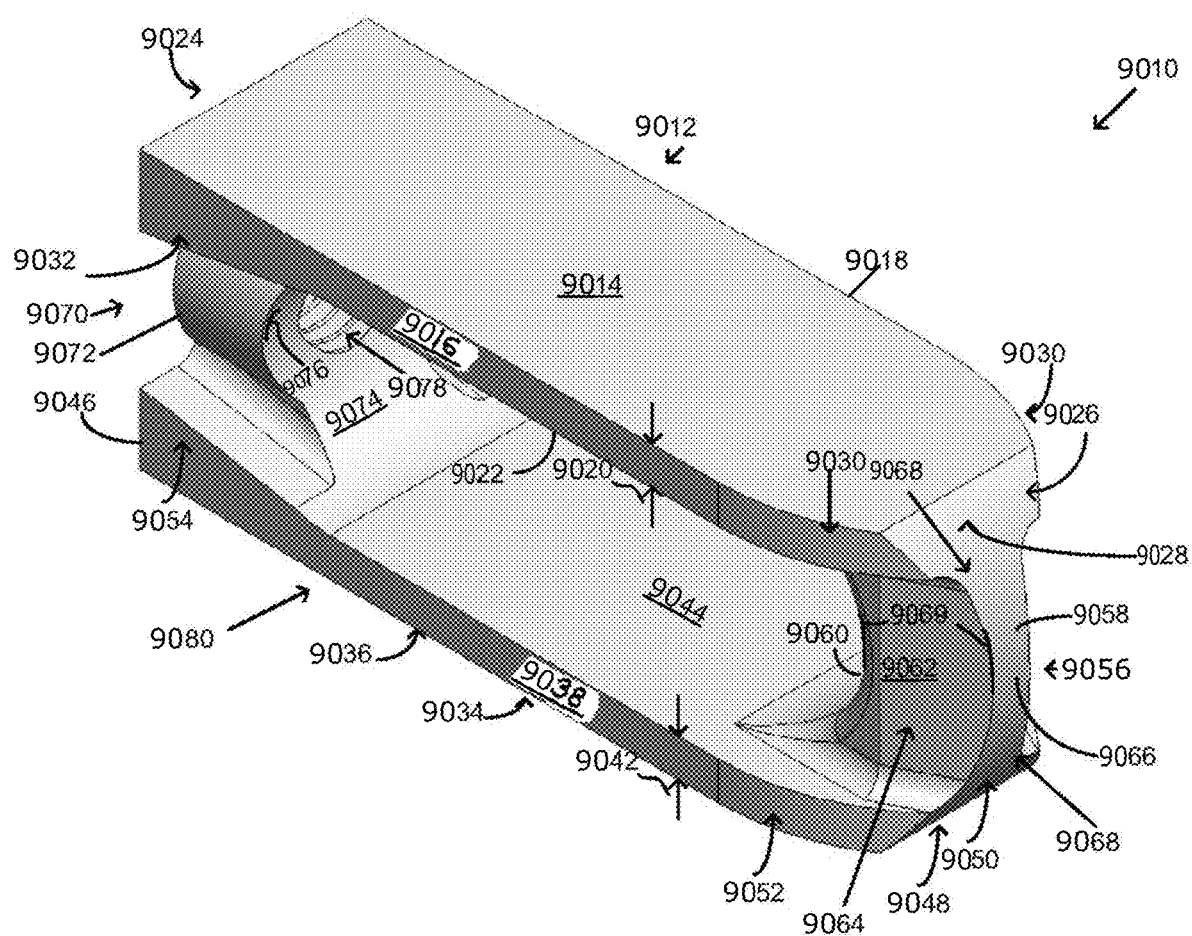
FIG. 54A-54E depict, respectively, an isometric view, top view, side view, back view, and front view of a joint implant, in one embodiment. The side view being the same as an opposite side view, and the top view being the same as the bottom view.
Figure 54D:
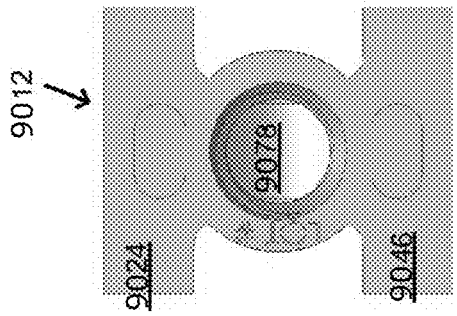
Figure 54E:
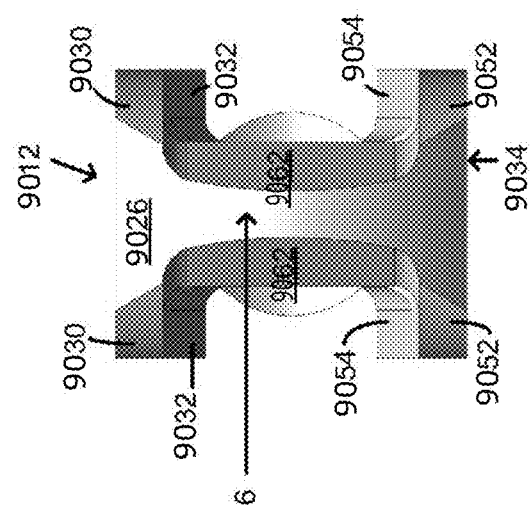
Figure 54B:
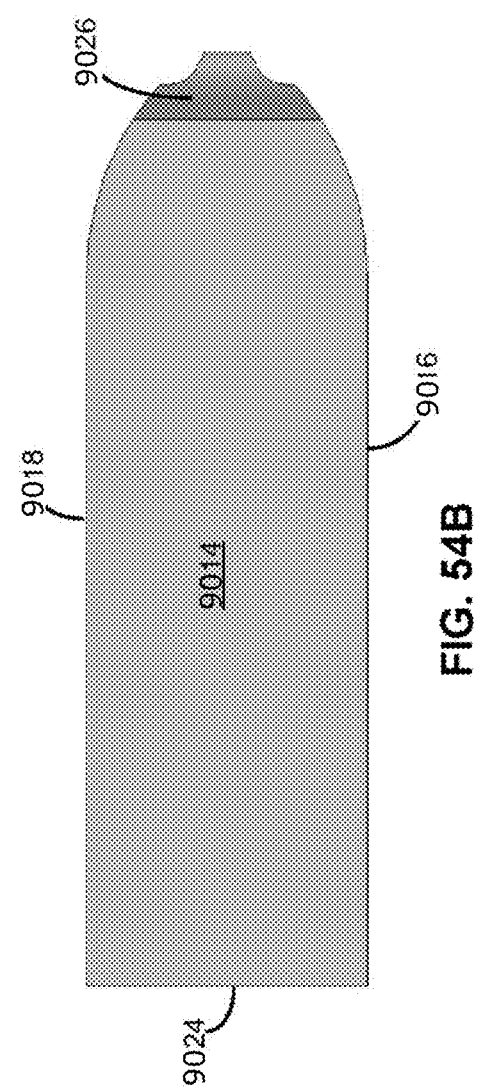
Figure 54C:
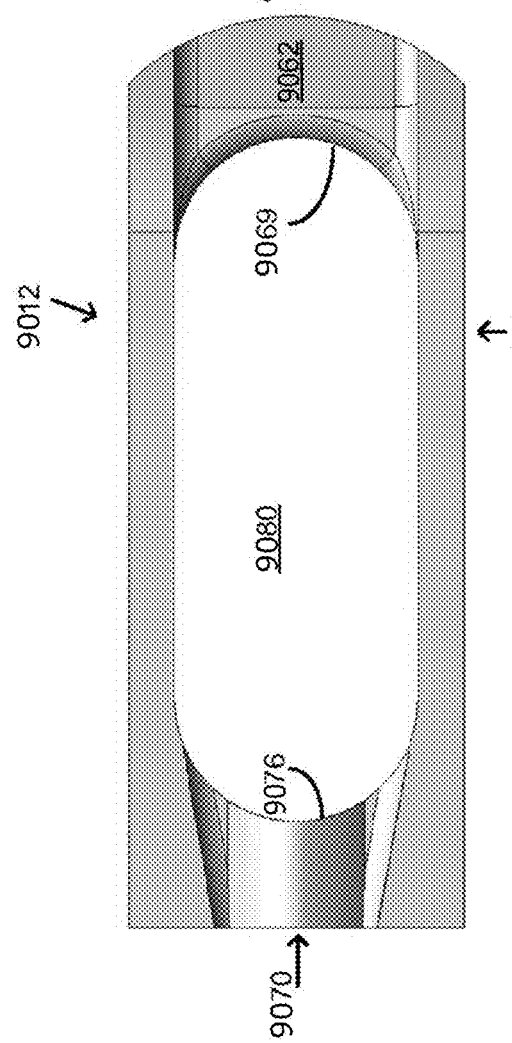
Figure 55A:
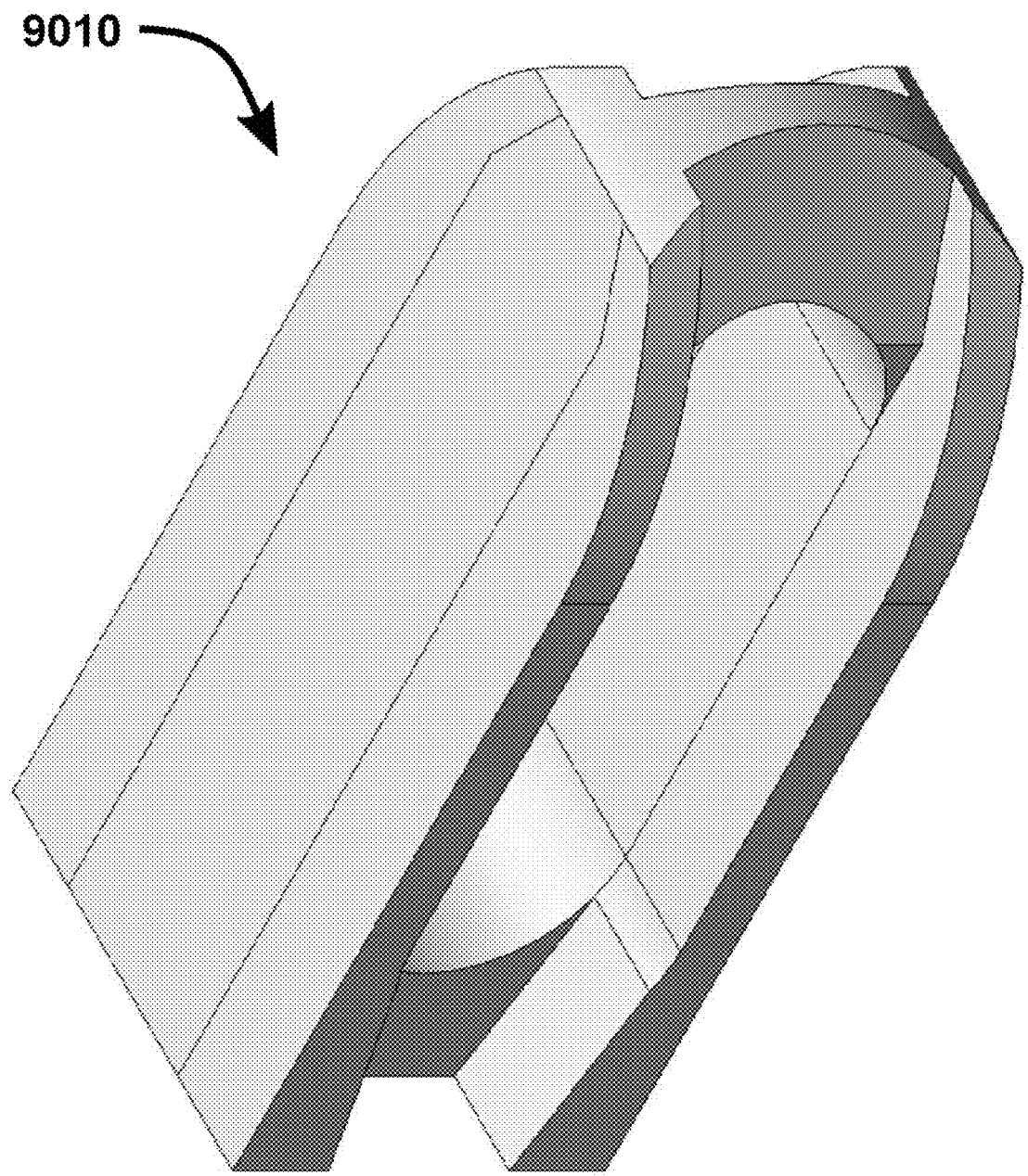

After employing the joint preparation tool 4020 to make appropriate keel-cuts, as seen in FIG. 53D, the tool 4020 may be removed from the articular region 1044 leaving one or more channels 4036 that match an implant to be delivered into the joint 1000.

As stated previously, the various tools and assemblies discussed herein may be used independently or in combination with each other. Thus, in certain embodiments and at various steps within the methodology the anchor arm assembly 258, as discussed in reference to FIGS. 24-25, may be employed with any of the joint preparation tools to deliver an anchoring element 282 across the sacroiliac joint. The anchoring arm assembly 258 may, for example, orient the anchoring element 282 to be delivered first through the ilium, transversely across the joint line of the sacroiliac joint, and then through the sacrum. Alternatively, the anchoring arm assembly 258 may orient the anchoring element 282 to be delivered first through the sacrum, transversely across the joint line of the sacroiliac joint, and then through the ilium.

Understandably, other instruments can be utilized separately or in combination during the course of any of the steps of the methodology, e.g., for the removal of articular cartilage or tissue between articular surfaces, such as any of the tools previously described or any of: endoscopy tools, box chisels, side cutting router bits, burs, flexible burs and bits, hole saws, key hole saw, medical bone chainsaw osteotome, curettes, lasers (e.g., CO2, Neodymium/Y AG (yttrium-aluminum-garnet), argon, and ruby), electrosurgical equipment employing electromagnetic energy (the cutting electrode can be a fine micro-needle, a lancet, a knife, a wire or band loop, a snare, an energized scalpel, or the like) where the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

The foregoing merely illustrates the principles of the embodiments described herein. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the embodiments described herein and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A method of surgically preparing a sacroiliac joint having a sacrum, an ilium, and a sacroiliac joint space defined therebetween for a surgical fusion procedure, the method comprising:
   a) approaching the sacroiliac joint space with a joint preparation tool comprising: a proximal end, a distal end, a cutting element supported at the distal end, and a shaft extending proximally from the cutting element, the cutting element comprising a length extending between a proximal cutting element end and a distal cutting element end, a first surface extending the length, and a second surface opposite the first surface extending the length;
   b) delivering at least a portion of the cutting element non-transversely into the sacroiliac joint space, the cutting element being oriented in the sacroiliac joint space such that the first surface opposes the sacrum and the second surface opposes the ilium;
   c) delivering an anchor into the sacrum, the sacroiliac joint space, and the ilium along a delivery trajectory provided by an anchoring arm assembly; and
   d) removing the cutting element from the sacroiliac joint space.

2. The method of claim 1, wherein the delivery trajectory is fixed and non-adjustable.

3. The method of claim 1, wherein the anchoring arm assembly comprises a tubular guide, and at least one guide collar for supporting the tubular guide in an orientation that provides the delivery trajectory for the anchor.

4. The method of claim 1, wherein, upon being delivered into the sacrum and the ilium, the anchor is positioned cranial to the cutting element.

5. The method of claim 1, wherein, upon being delivered into the sacrum and the ilium, the anchor is positioned caudal to the cutting element.

6. The method of claim 1, wherein, upon being delivered into the sacrum and the ilium, the anchor is positioned distal to the cutting element.

7. The method of claim 1, wherein delivering the at least a portion of the cutting element non-transversely into the sacroiliac joint space at least partially forms an implant receiving space, and wherein the method further comprises: delivering a joint implant into the implant receiving space.

8. The method of claim 7, wherein the joint implant comprises a distal end, a proximal end, at least two planar members extending between the distal and proximal ends, and a window positioned between the at least two planar members, the window positioned intermediate the distal and proximal ends.

9. The method of claim 8, wherein upon delivery of the joint implant into the implant receiving space, the window is positioned within the sacroiliac joint space and the at least two planar members bridge across the sacroiliac joint space.

10. The method of claim 1, wherein the cutting element comprises a box-chisel, a drill bit, a rasp, or a saw blade.

11. The method of claim 1, further comprising attaching the anchoring arm assembly to the joint preparation tool.

12. The method of claim 1, wherein removing the cutting element from the sacroiliac joint space occurs subsequent to step c).

13. A method of surgically preparing a sacroiliac joint having a sacrum, an ilium, and a sacroiliac joint space defined therebetween for a surgical fusion procedure, the method comprising:
   a) aligning a trajectory of an anchor for delivery into the sacrum and the ilium, the trajectory being provided by an anchor arm assembly which is coupled to a joint preparation tool, the joint preparation tool comprising: a proximal end, a distal end, a cutting element supported at the distal end, and a shaft extending proximally from the cutting element, the cutting element configured to remove tissue from at least one of the sacrum, the ilium, or the sacroiliac joint space, the cutting element comprising a longitudinal axis extending between a proximal cutting element end and a distal cutting element end, a first surface extending along the longitudinal axis, and a second surface opposite the first surface extending along the longitudinal axis; and
   b) removing the tissue from at least one of the sacrum, the ilium, or the sacroiliac joint space with the cutting element.

14. The method of claim 13, wherein step b) further comprises inserting the cutting element non-transversely into the sacroiliac joint space.

15. The method of claim 14, wherein the cutting element is inserted non-transversely into the sacroiliac joint space such that the first surface opposes the sacrum and the second surface opposes the ilium.

16. The method of claim 14, wherein the trajectory of the anchor is along a trajectory axis that intersects the longitudinal axis distal to the cutting element.

17. The method of claim 14, further comprising delivering the anchor into the sacrum and the ilium.

18. The method of claim 17, wherein the anchor is positioned distal to the cutting element.

19. The method of claim 17, wherein the anchor is positioned caudal to the cutting element.

20. The method of claim 17, wherein the anchor is positioned cranial to the cutting element.

21. The method of claim 13, further comprising positioning a cannula adjacent the sacroiliac joint space; and passing at least a portion of the joint preparation tool through the cannula.

22. A method of surgically preparing a sacroiliac joint having a sacrum, an ilium, and a sacroiliac joint space defined therebetween for a surgical fusion procedure, the method comprising:
   a) approaching the sacroiliac joint space with a joint preparation tool comprising: a proximal end, a distal end, a cutting element supported at the distal end, and a shaft extending proximally from the cutting element, the cutting element comprising a length extending between a proximal cutting element end and a distal cutting element end, a first surface extending the length, and a second surface opposite the first surface extending the length;
   b) delivering at least a portion of the cutting element non-transversely into the sacroiliac joint space along a cutting axis, the cutting element being oriented in the sacroiliac joint space such that the first surface opposes the sacrum and the second surface opposes the ilium; and
   c) delivering an anchor into at least one of the sacrum and the ilium along an anchor axis via guidance by an anchoring arm assembly, the anchoring arm assembly being adjustable so as to provide multiple trajectories for the anchor axis relative to the cutting axis, wherein the anchor axis and the cutting axis converge at a common axis for the multiple trajectories.

23. The method of claim 22, wherein the anchor is delivered through the sacroiliac joint space.

24. The method of claim 22, further comprising removing the cutting element from the sacroiliac joint space.

25. The method of claim 22, further comprising positioning a cannula adjacent the sacroiliac joint space; and passing at least a portion of the joint preparation tool through the cannula.

26. The method of claim 22, wherein the anchor axis and the cutting axis converge at a coincident point on the common axis for the multiple trajectories.

27. The method of claim 22, wherein the anchor arm assembly is coupled to the joint preparation tool.

\* \* \* \* \*